US006455295B1

(12) United States Patent
Brode, III et al.

(10) Patent No.: US 6,455,295 B1
(45) Date of Patent: Sep. 24, 2002

(54) SUBTILISIN CARLSBERG VARIANTS HAVING DECREASED ADSORPTION AND INCREASED HYDROLYSIS

(75) Inventors: Philip Frederick Brode, III; Bobby Lee Barnett; Donn Nelton Rubingh, all of Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/400,698

(22) Filed: Mar. 8, 1995

(51) Int. Cl.[7] .......................... C12N 9/56; C12N 15/57; C12N 15/74; C11D 3/386

(52) U.S. Cl. ................... 435/221; 435/69.1; 435/252.3; 435/320.1; 435/471; 510/392; 536/23.2

(58) Field of Search ................................. 435/221, 220, 435/69.1, 477; 536/23.2; 510/320, 350

(56) References Cited

U.S. PATENT DOCUMENTS

| 4,760,025 A | 7/1988 | Estell et al. ................. 435/222 |
| 4,908,773 A | 3/1990 | Pantoliano et al. ......... 364/496 |
| 4,914,031 A | 4/1990 | Zukowsky et al. ......... 435/222 |

(List continued on next page.)

FOREIGN PATENT DOCUMENTS

| AU | 8772281 | 11/1987 |
| EP | 0 251 446 A2 * | 4/1987 |
| EP | 0 260 105 | 3/1988 |
| EP | 0 328 229 | 8/1989 |
| EP | 0 328 229 A1 * | 8/1989 |
| EP | 0 357 157 A1 * | 3/1990 |
| EP | 0 380 362 | 8/1990 |
| EP | 0 398 539 | 11/1990 |
| EP | 0 405 901 A1 | 1/1991 |
| EP | 0 405 902 A1 | 1/1991 |
| WO | 87/04461 | 7/1987 |
| WO | 87/05050 | 8/1987 |
| WO | WO 88/08033 A1 * | 10/1988 |
| WO | 89/06279 | 1/1989 |
| WO | 89/09830 | 10/1989 |
| WO | 91/00345 | 1/1991 |
| WO | WO 91/14420 A1 * | 11/1991 |
| WO | WO 92/02615 A1 * | 2/1992 |
| WO | WO 92/08778 A1 * | 5/1992 |
| WO | 92/11357 | 7/1992 |
| WO | WO 92/11357 A1 * | 7/1992 |
| WO | WO 94/02618 A1 * | 2/1994 |
| WO | 94/02618 | 2/1994 |
| WO | WO 95/07991 A2 * | 3/1995 |
| WO | 95/07991 | 3/1995 |
| WO | WO 95/30010 A1 * | 4/1995 |
| WO | WO 95/30011 A1 * | 4/1995 |
| WO | WO 88/08028 A1 * | 10/1998 |

OTHER PUBLICATIONS

Thomas, P. G., et al., 1985, "Tailoring the pH dependence of enzyme catalysis using protein engineering to change a single amino acid at BPN' position 99: D99S reduces pKa", Nature, vol. 318, pp. 375–376.*
Russell, A. J. & Fersht, A. R., 1987, "Rational modification of enzyme catalysis by engineering surface charge", Nature, vol. 328, pp. 496–500.*
Jacobs, M., et al., Nucleic Acids Research, vol. 13, "Cloning, sequencing and expression of subtilisin Carlsberg from *Bacillus licheniformis*", pp. 8913–8926, 1985.*
Abrahmsèn, L., J. Tom, J. Burnier, K. A. Butcher, A. Kossiakoff and J. A. Wells, "Engineering Subtilisin and its Substrates for Efficient Ligation of Peptide Bonds in Aqueous Solution", Biochemistry, vol. 30, No. 17, pp. 4151–4159 (no month identified 1991).
Arnold, F.H., "Engineering Enzymes for Non–aqueous Solvents", TibTech, vol. 8, pp. 244–249 (Sep. 1990).
Braxton, S. and J. A. Wells, "The Importance of a Distal Hydrogen Bonding Group in Stabilizing the Transition State in Subtilisin BPN'", The Journal of Biological Chemistry, vol. 266, No. 18, pp. 11797–11800 (Jun. 1991).
Brode, P. F., III and D. S. Rauch, "Subtilison BPN': Activity on an Immobilized Substrate", Langmuir, vol. 8, No. 5, pp. 1325–1329 (no month identified 1992).
Brode, P.F. III, C.R. Erwin, D.S. Rauch, E.S. Wang, J.M. Armpriester, B.L. Barnett, M.D. Bauer, P.R. Green, D.A. Thaman, and D.N. Rubingh, "Surface Active Variants of Subtilisin BPN': Interfacial Hydrolysis", Abstract, Keystone Symposium (Mar. 6–11, 1994).
Carter, P., L. Abrahmsèn and J. A. Wells, "Probing the Mechanism and Improving the Rate of Substrate–Assisted Catalysis in Subtilisin BPN'", Biochemistry, vol. 30, No. 25, pp. 6142–6148 (no month identified 1991).
Carter, P. and J. A. Wells, "Functional Interaction Among Catalytic Residues in Subtilisin BPN'", Proteins: Structure, Function, and Genetics, vol. 7, pp. 335–342, (no month identified 1990).

(List continued on next page.)

Primary Examiner—Charles L. Patterson, Jr.
Assistant Examiner—William W. Moore
(74) Attorney, Agent, or Firm—Frank Taffy; C. Brant Cook; Kim W. Zerby

(57) ABSTRACT

The present invention relates to subtilisin Carlsberg variants having a modified amino acid sequence of wild-type subtilisin Carlsberg amino acid sequence, the wild-type amino acid sequence comprising a first loop region, a second loop region, a third loop region, a fourth loop region, a fifth loop region and a sixth loop region; wherein the modified amino acid sequence comprises different amino acids than that occurring in wild-type subtilisin Carlsberg (i.e., substitution) at specifically identified positions in one or more of the loop regions whereby the subtilisin Carlsberg variant has decreased adsorption to, and increased hydrolysis of, an insoluble substrate as compared to the wild-type subtilisin Carlsberg. The present invention also relates to the genes encoding such subtilisin Carlsberg variants. The present invention also relates to compositions comprising such subtilisin Carlsberg variants for cleaning a variety of surfaces.

65 Claims, No Drawings

U.S. PATENT DOCUMENTS

| | | | | |
|---|---|---|---|---|
| 4,980,288 A | | 12/1990 | Bryan et al. | 435/222 |
| 4,990,452 A | | 2/1991 | Bryan et al. | 435/222 |
| 5,013,657 A | | 5/1991 | Bryan et al. | 435/172.3 |
| 5,116,741 A | | 5/1992 | Bryan et al. | 435/87 |
| 5,118,623 A | * | 6/1992 | Boguslawski et al. | 510/374 |
| 5,155,033 A | * | 10/1992 | Estell et al. | 435/221 |
| 5,182,204 A | * | 1/1993 | Estell et al. | 435/222 |
| 5,185,258 A | * | 2/1993 | Caldwell et al. | 435/220 |
| 5,208,158 A | * | 5/1993 | Bech et al. | 435/219 |
| 5,217,878 A | * | 6/1993 | van Eekelen et al. | 435/69.1 |
| 5,240,632 A | * | 8/1993 | Brumbaugh | 252/95 |
| 5,244,791 A | * | 9/1993 | Estell | 435/68.1 |
| 5,246,849 A | | 9/1993 | Bryan et al. | 435/220 |
| 5,260,207 A | * | 11/1993 | Pantoliano et al. | 435/221 |
| 5,275,945 A | * | 1/1994 | Hsiao et al. | 435/221 |
| RE34,606 E | * | 5/1994 | Estell et al. | 510/392 |
| 5,310,675 A | * | 5/1994 | Estell et al. | 435/320.1 |
| 5,316,941 A | * | 5/1994 | Estell et al. | 435/252.3 |
| 5,324,653 A | * | 6/1994 | van Eekelen et al. | 435/221 |
| 5,336,611 A | * | 8/1994 | van Eekelen et al. | 435/221 |
| 5,346,823 A | * | 9/1994 | Estell et al. | 435/221 |
| 5,352,603 A | * | 10/1994 | Vetter et al. | 435/221 |
| 5,371,008 A | * | 12/1994 | Carter et al. | 435/222 |
| 5,371,190 A | * | 12/1994 | Carter et al. | 530/350 |
| 5,389,307 A | * | 2/1995 | Lindegaard et al. | 510/320 |
| 5,403,737 A | * | 4/1995 | Abrahmsen et al. | 435/252.3 |
| 5,441,882 A | * | 8/1995 | Estell et al. | 435/222 |
| 5,453,372 A | * | 9/1995 | Vetter et al. | 435/222 |
| 5,470,733 A | * | 11/1995 | Bryan et al. | 435/222 |
| 5,472,855 A | * | 12/1995 | Carter et al. | 435/68.1 |
| 5,482,849 A | * | 1/1996 | Branner et al. | 435/222 |
| 5,500,364 A | * | 3/1996 | Christianson et al. | 435/221 |
| 5,567,601 A | * | 10/1996 | Bryan et al. | 435/222 |
| 5,629,173 A | * | 5/1997 | Abrahmsen et al. | 435/68.1 |
| 5,631,217 A | * | 5/1997 | Branner et al. | 510/320 |
| 5,652,136 A | * | 7/1997 | Carter et al. | 435/252.3 |
| 5,665,587 A | * | 9/1997 | Aaslyng et al. | 435/221 |
| 5,677,272 A | * | 10/1997 | Ghosh et al. | 510/306 |
| 5,679,630 A | * | 10/1997 | Baeck et al. | 510/305 |
| 5,700,676 A | * | 12/1997 | Bott et al. | 435/221 |
| 5,707,848 A | * | 1/1998 | Bryan et al. | 435/6 |
| 5,736,512 A | * | 4/1998 | Abrahmsen et al. | 514/12 |
| 5,741,664 A | * | 4/1998 | Ballinger et al. | 435/221 |
| 5,741,694 A | * | 4/1998 | Hastrup et al. | 435/221 |
| 5,763,257 A | * | 6/1998 | Bott et al. | 435/221 |
| 5,801,038 A | * | 9/1998 | Bott et al. | 435/221 |
| 5,801,039 A | * | 9/1998 | Maurer et al. | 435/221 |
| 5,955,340 A | * | 9/1999 | Bott et al. | 435/221 |
| 5,972,682 A | * | 10/1999 | Bott et al. | 435/221 |
| 5,985,639 A | * | 11/1999 | Christianson et al. | 435/221 |
| 6,197,567 B1 | * | 3/2001 | Aaslyng et al. | 435/221 |
| 6,197,589 B1 | * | 3/2001 | Maurer et al. | 435/471 |
| 6,271,012 B1 | * | 8/2001 | van Eekelen et al. | 435/221 |
| 6,287,841 B1 | * | 9/2001 | Mulleners et al. | 435/221 |

OTHER PUBLICATIONS

Cunningham, B. C, and J. A. Wells, "Improvement in the Alkaline Stability of Subtilisin Using an Efficient Random Mutagenesis and Screening Procedure", Protein Engineering, vol. 1, No. 4, pp. 319–325 (no month identified 1987).

Egmond, M. R., W. P. Antheunisse, P. Ravestein, A. T. A. Mooren and J. de Vileg, "Engineering Surface Charges in a Subtilisin", First International Symposium on Subtilisin Enzymes, Hamburg, Germany, (Sep. 1992).

Estell, D.A. "Engineering Enzymes for Improved Performance in Industrial Applications", Journal of Biotechnology, vol. 28, No. 1, pp. 25–30 (Jan. 1993).

Hopp, T. P. and K. R. Woods, "Prediction of Protein Antigenic Determinants From Amino Acid Sequences", Proc. Natl. Acad. Sci. USA, vol. 78, No. 6, pp. 3824–3828 (Jun. 1981).

Mitchinson, C. and J.A. Wells, "Protein Engineering of Disulfide Bonds in Subtilisin BPN", Biochemistry, vol. 28, No. 11, pp. 4807–4815 (no month identified 1989).

Mizushima, N., D. Spellmeyer, S. Hirono, D. Pearlman and P. Kollman, "Free Energy Perturbation Calculations on Binding and Catalysis after Mutating Threonine 220 in Subtilisin", Journal of Biological Chemistry, vol. 266, No. 18, pp. 11801–11809 (Jun. 1991).

Pantoliano, M.W., M. Whitlow, J.F. Wood, S.W. Dodd, K.D. Hardman, M.L. Rollence and P.N. Bryan, "Large Increases in General Stability for Subtilisin BPN' through Incremental Changes in the Free Energy of Unfolding", Biochemistry, vol. 28, No. 18, pp. 7205–7213 (no month identified 1989).

Russell, A. J. and A. R. Fersht, "Rational Modification of Enzyme Catalysis by Engineering Surface Charge", Nature, vol. 328, pp. 496–500 (Aug. 1987).

Siezen, R.J., W.M. de Vos, J.A.M. Leunissen and B.W. Dijkstra, "Homology Modelling and Protein Engineering Strategy of Subtilases, the Family of Subtilisin–like Serine Proteinases", Prot. Eng., vol. 4, No. 7, pp. 719–737 (no month identified 1991).

Sternberg, M. J. E., F. R. F. Hayes, A. J. Russell, P. G. Thomas and A. R. Fersht, "Prediction of Electrostatic Effects of Engineering of Protein Charges", Nature, vol. 330, pp. 86–88 (Nov. 1987).

Wells, J.A., B.C. Cunninghma, T.P. Graycar and D.A. Estell, "Recruitment of Substrate–specificity Properties from One Enzyme into a Related One by a Protein Engineering", Proc. Natl. Acad. Sci., USA,, vol. 84, pp. 5167–5171 (Aug. 1987).

Wells, J.A. and D.A. Estell, "Subtilisin–An Enzyme Designed to be Engineered", Tibs 13, pp. 291–297 (Aug. 1988).

Wong, C.–H., S.–T. Chen, W. J. Hennen, J. A. Bibbs, Y.–F. Wang, J. L.–C. Liu, M. W. Pantoliano, M. Whitlow and P. N. Bryan, "Enzymes in Organic Synthesis: Use of Subtilisin and a Highly Stable Mutant Derived from Multiple Site–Specific Mutations", J. Am. Chem. Soc., vol. 112, No. 3, pp. 945–953 (no month identified 1990).

* cited by examiner

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 274 amino acids
      (B) TYPE: amino acid
      (C) STRANDEDNESS: single
      (D) TOPOLOGY: linear -continued (xi) SEQUENCE DESCRIPTION: SEQ ID NO:1:

```
Ala Gln Thr Val Pro Tyr Gly Ile Pro Leu Ile Lys Ala Asp Lys Val
1               5                  10                  15

Gln Ala Gln Gly Phe Lys Gly Ala Asn Val Lys Val Ala Val Leu Asp
                20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
        50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
                100                 105                 110

Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
        130                 135                 140

Gly Val Val Val Ala Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
                180                 185                 190

Ala Glu Leu Glu Val Met Ala Pro Gly Ala Gly Val Tyr Ser Thr Tyr
            195                 200                 205

Pro Thr Asn Thr Tyr Ala Thr Leu Asn Gly Thr Ser Met Ala Ser Pro
        210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln
```

SUBTILISIN CARLSBERG VARIANTS HAVING DECREASED ADSORPTION AND INCREASED HYDROLYSIS

TECHNICAL FIELD

The present invention relates to novel enzyme variants useful in a variety of cleaning compositions, and the genes encoding such enzyme variants.

BACKGROUND

Enzymes make up the largest class of naturally occurring proteins. Each class of enzyme generally catalyzes (accelerates a reaction without being consumed) a different kind of chemical reaction. One class of enzymes known as proteases, are known for their ability to hydrolyze (break down a compound into two or more simpler compounds with the uptake of the H and OH parts of a water molecule on either side of the chemical bond cleaved) other proteins. This ability to hydrolyze proteins has been taken advantage of by incorporating naturally occurring and protein engineered proteases as an additive to laundry detergent preparations. Many stains on clothes are proteinaceous and wide-specificity proteases can substantially improve removal of such stains.

Unfortunately, the efficacy level of these proteins in their natural, bacterial environment, frequently does not translate into the relatively unnatural wash environment. Specifically, protease characteristics such as thermal stability, pH stability, oxidative stability and substrate specificity are not necessarily optimized for utilization outside the natural environment of the enzyme.

The amino acid sequence of the protease determines the characteristics of the protease. A change of the amino acid sequence of the protease may alter the properties of the enzyme to varying degrees, or may even inactivate the enzyme, depending upon the location, nature and/or magnitude of the change in the amino acid sequence. Several approaches have been taken to alter the wild-type amino acid sequence of proteases in an attempt to improve their properties, with the goal of increasing the efficacy of the protease in the wash environment. These approaches include altering the amino acid sequence to enhance thermal stability and to improve oxidation stability under quite diverse conditions.

Despite the variety of approaches described in the art, there is a continuing need for new effective variants of proteases useful for cleaning a variety of surfaces.

OBJECTS OF THE PRESENT INVENTION

It is an object of the present invention to provide subtilisin Carlsberg enzyme variants having improved hydrolysis versus the wild-type of the enzyme.

It is also an object of the present invention to provide cleaning compositions comprising these subtilisin enzyme variants.

SUMMARY

The present invention relates to subtilisin Carlsberg variants having a modified amino acid sequence of wild-type subtilisin Carlsberg amino acid sequence, the wild-type amino acid sequence comprising a first loop region, a second loop region, a third loop region, a fourth loop region and a fifth loop region; wherein the modified amino acid sequence comprises different amino acids than that occurring in wild-type subtilisin Carlsberg (i.e., substitution) at specifically identified positions in one or more of the loop regions whereby the subtilisin Carlsberg variant has decreased adsorption to, and increased hydrolysis of, an insoluble substrate as compared to the wild-type subtilisin Carlsberg. The present invention also relates to the genes encoding such subtilisin Carlsberg variants. The present invention also relates to compositions comprising such subtilisin Carlsberg variants for cleaning a variety of surfaces.

DESCRIPTION

I. Subtilisin Variants

This invention pertains to subtilisin enzymes, in particular subtilisin Carlsberg, that have been modified by mutating the various nucleotide sequences that code for the enzyme, thereby modifying the amino acid sequence of the enzyme. The modified subtilisin enzymes (hereinafter, "subtilisin Carlsberg variants") of the present invention have decreased adsorption to and increased hydrolysis of an insoluble substrate as compared to the wild-type subtilisin. The present invention also pertains to the mutant genes encoding for such subtilisin Carlsberg variants.

The subtilisin enzymes of this invention belong to a class of enzymes known as proteases. A protease is a catalyst for the cleavage of peptide bonds. One type of protease is a serine protease. A serine protease is distinguished by the fact that there is an essential serine residue at the active site.

The observation that an enzyme's rate of hydrolysis of soluble substrates increases with enzyme concentration is well documented. It would therefore seem plausible that for surface bound substrates, such as is encountered in many cleaning applications, the rate of hydrolysis would increase with increasing surface concentration. This has been shown to be the case. (Brode, P.F. III and D. S. Rauch, LANGMUIR, "Subtilisin BPN': Activity on an Immobilized Substrate", Vol. 8, pp. 1325–1329 (1992)). In fact, a linear dependence of rate upon surface concentration was found for insoluble substrates when the surface concentration of the enzyme was varied. (Rubingh, D. N. and M. D. Bauer, "Catalysis of Hydrolysis by Proteases at the Protein-Solution Interface," in POLYMER SOLUTIONS, BLENDS AND INTERFACES, Ed. by I. Noda and D. N. Rubingh, Elsevier, p. 464 (1992)). Surprisingly, when seeking to apply this principle in the search for variant proteases which give better cleaning performance, we did not find that enzymes which adsorb more give better performance. In fact, we surprisingly determined the opposite to be the case: decreased adsorption by an enzyme to a substrate resulted in increased hydrolysis of the substrate (i.e., better cleaning performance).

While not wishing to be bound by theory, it is believed that improved performance, when comparing one variant to another, is a result of the fact that enzymes which adsorb less are also less tightly bound and therefore more highly mobile on the surface from which the insoluble protein substrate is to be removed. At comparable enzyme solution concentrations, this increased mobility is sufficient to outweigh any advantage that is conferred by delivering a higher concentration of enzyme to the surface.

The mutations described herein are designed to change (i.e., decrease) the adsorption of the enzyme to surface-bound soils. In subtilisin Carlsberg, certain amino acids form exterior loops on the enzyme molecule. For purposes of discussion, these loops shall be referred to as first, second, third, fourth and fifth loop regions. Specifically, positions 5845 form the first loop region; positions 94–106 form the second loop region; positions 125–132 form the third loop region; positions 153–166 form the fourth loop region; positions 186–190 form the fifth loop region; and positioins 199–219 form the sixth loop region (position numbering analagous to positions in the amino acid sequence for wild-type subtilisin subtilisin Carlsberg (SEQ ID NO:1)).

It believed that these loop regions play a significant role in the adsorption of the enzyme molecule to a surface-bound peptide, and specific mutations in one or more of these loop regions will have a significant effect on this adsorption. While not wishing to be bound by theory, it is believed that the loop regions are important to the adsorption of the subtilisin Carlsberg molecule for at least two reasons. First, the amino acids which comprise the loop regions can make close contacts with any surfaces to which the molecule is exposed. Second, the proximity of the loop regions to the active-site and binding pocket of the subtilisin Carlsberg molecule gives them a role in the catalytically productive adsorption of the enzyme to surface-bound substrates (peptides/protein soils).

As used herein, "variant" means an enzyme having an amino acid sequence which differs from that of wild-type.

As used herein, "mutant subtilisin Carlsberg gene" means a gene coding for a subtilisin Carlsberg variant.

As used herein, "wild-type subtilisin Carlsberg" refers to a subtilisin enzyme represented by SEQ ID NO:1. The amino acid sequence for subtilisin Carlsberg is further described by Smith, E. L., Delange, R. J Evans, W. H., is Landon, M., and Markland, F. S., J. BIOL. CHEM., Vol. 243, pp. 2184–2191 (1968), incorporated herein by reference.

As used herein, the term "subtilisin Carlsberg wild-type amino acid sequence" encompasses SEQ ID NO:1 as well as SEQ ID NO:1 having modifications to the amino acid sequence other than at any of positions 58–65, 94–106, 125–132, 153–166, 186–190 and 199–219.

As used herein, "more hydrophilic amino acid" refers to any other amino acid having greater hydrophilicity than a subject amino acid with reference to the hydrophilicity table below. The following hydrophilicity table (Table 1) lists amino acids in descending order of increasing hydrophilicity (see Hopp, T. P., and Woods, K. R., "Prediction of Protein Antigenic Determinants from Amino Acid Sequences", PROCEEDINGS OF THE NATIONAL ACADEMY OF SCIENCE USA, Vol. 78, pp. 3824–3828, 1981, incorporated herein by reference).

TABLE 1

| Amino Acid | Hydrophilicity Value |
| --- | --- |
| Trp | −3.4 |
| Phe | −2.5 |
| Tyr | −2.3 |
| Leu, Ile | −1.8 |
| Val | −1.5 |
| Met | −1.3 |
| Cys | −1.0 |
| Ala, His | −0.5 |
| Thr | −0.4 |
| Pro, Gly | −0.0 |
| Gln, Asn | 0.2 |
| Ser | 0.3 |
| Arg$^+$, Lys$^+$, Glu$^-$, Asp$^-$ | 3.0 |

Table 1 also indicates which amino acids carry a charge (this characteristic being based on a pH of from about 8–9). The positively charged amino acids are Arg and Lys, the negatively charged amino acids are Glu and Asp, and the remaining amino acids are neutral. In a preferred embodiment of the present invention, the substituting amino acid is either neutral or negatively charged, more preferably negatively charged (i.e., Glu or Asp).

Therefore, for example, the statement "substitute Gln with an equally or more hydrophilic amino acid which is neutral or has a negative charge" means Gln would be substituted with Asn (which is equally hydrophilic to Gln), or Ser, Glu or Asp (which are more hydrophilic than Gln); each of which are neutral or have a negative charge, and have a greater hydrophilicity value as compared to Gln. Likewise, the statement "substitute Pro with a more hydrophilic amino acid which is neutral or has a negative charge" means Pro would be substituted with Gln, Asn, Ser, Glu or Asp.

In one embodiment of the present invention, the subtilisin Carlsberg variant has a modified amino acid sequence of subtilisin Carlsberg wild-type amino acid sequence, wherein the wild-type amino acid sequence comprises a substitution at one or more positions in one or more of the first loop region, the second loop region, the third loop region, the fourth loop region, the fifth loop region or the sixth loop region; whereby the subtilisin Carlsberg variant has decreased adsorption to, and increased hydrolysis of, an insoluble substrate as compared to the wild-type subtilisin Carlsberg.

In a preferred embodiment of the present invention, the substituting amino acid for one or more of the positions in one or more of the loop regions is, with reference to Table 1, neutral or negatively charged and equally or more hydrophilic, preferably more hydrophilic, than the amino acid at the subject position in the wild-type amino acid sequence.

A. Substitutions in the First Loop Region

When a substitution occurs in the first loop region, the substitution occurs at one or more of positions 58, 59, 60, 61, 62, 64 or 65.

When a substitution occurs at position 58, the substituting amino acid is Asn, Asp, Gln, Glu, Gly, Pro or Ser.

When a substitution occurs at position 59, the substituting amino acid is Glu.

When a substitution occurs at position 60, the substituting amino acid is Asn, Asp, Gln, Glu, Pro or Ser.

When a substitution occurs at position 61, the substituting amino acid is Asp, Gln, Glu or Ser.

When a substitution occurs at position 62, the substituting amino acid is Asn, Asp, Gln, Glu, Pro or Ser.

When a substitution occurs at position 64, the substituting amino acid is Asn, Asp, Gln, Glu, Pro or Ser.

When a substitution occurs at position 65, the substituting amino acid is Asn, Asp, Gln, Glu, Gly, Pro or Ser.

B. Substitutions in the Second Loop Region

When a substitution occurs in the second loop region, the substitution occurs at one or more of positions 94, 95, 96, 97, 98, 99, 100, 101, 102, 103, 104, 105 or 106.

When a substitution occurs at position 94, the substituting amino acid is Ala, Asn, Asp, Cys, Gln, Glu, Gly, His, Met, Pro, Ser or Thr.

When a substitution occurs at position 95, the substituting amino acid is Ala, Asn, Asp, Cys, Gln, Glu, Gly, His, Ile, Met, Pro, Ser, Thr or Val.

When a substitution occurs at position 96, the substituting amino acid is Asp, Gln, Glu, Ser.

When a substitution occurs at position 97, the substituting amino acid is Asp or Glu.

When a substitution occurs at position 98, the substituting amino acid is Asp or Glu.

When a substitution occurs at position 99, the substituting amino acid is Asn, Asp, Gln, Glu, Pro or Ser.

When a substitution occurs at position 100, the substituting amino acid is Asp or Glu.

When a substitution occurs at position 101, the substituting amino acid is Asn, Asp, Gln, Glu, Pro or Ser.

When a substitution occurs at position 102, the substituting amino acid is Asp or Glu.

When a substitution occurs at position 103, the substituting amino acid is Ala, Asn, Asp, Cys, Gln, Glu, Gly, His, Ile, Leu, Met, Pro, Ser, Thr or Val.

When a substitution occurs at position 104, the substituting amino acid is Asp or Glu.

When a substitution occurs at position 105, the substituting amino acid is Asn, Asp, Gln, Glu, Pro or Ser.

When a substitution occurs at position 106, the substituting amino acid is Ala, Asn, Asp, Cys, Gln, Glu, Gly, His, Leu, Met, Pro, Ser, Thr or Val.

C. Substitutions in the Third Loop Region

When a substitution occurs in the third loop region, the substitution occurs at one or more of positions 125, 126, 127, 128, 129, 130, 131 or 132.

When a substitution occurs at position 125, the substituting amino acid is Ala, Asn, Asp, Cys, Gln, Glu, Gly, His, Ile, Met, Pro, Ser, Thr or Val.

When a substitution occurs at position 126, the substituting amino acid is Asn, Asp, Gln, Glu, Pro or Ser.

When a substitution occurs at position 127, the substituting amino acid is Asn, Asp, Gln, Glu, Pro or Ser.

When a substitution occurs at position 128, the substituting amino acid is Asn, Asp, Gln, Glu, Gly, His, Pro, Ser or Thr.

When a substitution occurs at position 129, the substituting amino acid is Asp or Glu.

When a substitution occurs at position 130, the substituting amino acid is Asn, Asp, Gln, Glu, Pro or Ser.

When a substitution occurs at position 131, the substituting amino acid is Asp or Glu.

When a substitution occurs at position 132, the substituting amino acid is Asn, Asp, Gln, Glu, Gly, Pro or Ser.

D. Substitutions in the Fourth Loop Region

When a substitution occurs in the fourth loop region, the substitution occurs at one or more of positions 153, 154, 155, 156, 157, 158, 159, 160, 161, 162, 163, 164, 165 or 166.

When a substitution occurs at position 153, the substituting amino acid is Asn, Asp, Gln, Glu, Pro or Ser.

When a substitution occurs at position 154, the substituting amino acid is Asp, Gln, Glu or Ser.

When a substitution occurs at position 155, the substituting amino acid is Asp or Glu.

When a substitution occurs at position 156, the substituting amino acid is Asn, Asp, Gln, Glu, Pro or Ser.

When a substitution occurs at position 157, the substituting amino acid is Asp, Gln, Glu, Ser.

When a substitution occurs at position 158, the substituting amino acid is Asp or Glu.

When a substitution occurs at position 159, the substituting amino acid is Asn, Asp, Gln, Glu, Pro or Ser.

When a substitution occurs at position 160, the substituting amino acid is Asp or Glu.

When a substitution occurs at position 161, the substituting amino acid is Asn, Asp, Gln, Glu, Gly, Pro or Ser.

When a substitution occurs at position 162, the substituting amino acid is Asp, Gln, Glu or Ser.

When a substitution occurs at position 163, the substituting amino acid is Asn, Asp, Gln, Glu, Gly, Pro or Ser.

When a substitution occurs at position 164, the substituting amino acid is Ala, Asn, Asp, Cys, Gln, Glu, Gly, His, Met, Pro, Ser, Thr or Val.

When a substitution occurs at position 165, the substituting amino acid is Asn, Asp, Gln, Glu, Pro or Ser. and When a substitution occurs at position 166, the substituting amino acid is Ala, Asn, Asp, Cys, Gln, Glu, Gly, His, Ile, Leu, Met, Pro, Ser, Thr or Val.

E. Substitutions in the Fifth Loop Region

When a substitution occurs in the fifth loop region, the substitution occurs at one or more of positions 186, 187, 188, 189 or 190.

When a substitution occurs at position 186, the substituting amino acid is Asn, Asp, Gln, Glu, Gly, His, Pro, Ser and Thr.

When a substitution occurs at position 187, the substituting amino acid is Asp or Glu.

When a substitution occurs at position 188, the substituting amino acid is Ala, Asn, Asp, Cys, Gln, Glu, Gly, His, Ile, Leu, Met, Pro, Ser, Thr, Tyr or Val.

When a substitution occurs at position 189, the substituting amino acid is Asp or Glu.

When a substitution occurs at position 190, the substituting amino acid is Asp or Glu.

F. Substitutions in the Sixth Loop Region

When a substitution occurs in the sixth loop region, the substitution occurs at one or more of positions 199, 200, 201, 202, 203, 204, 205, 206, 207,208, 209, 210,211, 212,213,214,215, 216,217,218 or 219.

When a substitution occurs at position 199, the substituting amino acid is Asn Asp, gin, Glu, Gly, His, Pro, Ser or Thr.

When a substitution occurs at position 200, the substituting amino acid is Asn, Asp, Gln, Glu, Gly or Ser.

When a substitution occurs at position 201, the substituting amino acid is Asn, Asp, Gln, Glu, Pro or Ser.

When a substitution occurs at position 202, the substituting amino acid is Asn, Asp, Gln, Glu, Gly, His, Pro, Ser or Thr.

When a substitution occurs at position 203, the substituting amino acid is Asn, Asp, Gln, Glu, Pro or Ser.

When a substitution occurs at position 204, the substituting amino acid is Ala, Asn, Asp, Cys, Gln, Glu, Gly, His, Met, Pro, Ser or Thr.

When a substitution occurs at position 205, the substituting amino acid is Ala, Asn, Asp, Cys, Gln, Glu, Gly, His, Ile, Leu, Met, Pro, Ser, Thr or Val.

When a substitution occurs at position 206, the substituting amino acid is Asp or Glu.

When a substitution occurs at position 207, the substituting amino acid is Asn, Asp, Gln, Glu, Gly, Pro or Ser.

When a substitution occurs at position 208, the substituting amino acid is Ala, Asn, Asp, Cys, Gln, Glu, Gly, His, Ile, Leu, Met, Pro, Ser, Thr or Val.

When a substitution occurs at position 209, the substituting amino acid is Asn, Asp, Gln, Glu, Gly or Ser.

When a substitution occurs at position 210, the substituting amino acid is Asn, Asp, Gln, Glu, Gly, Pro or Ser.

When a substitution occurs at position 211, the substituting amino acid is Asp, Gln, Glu or Ser.

When a substitution occurs at position 212, the substituting amino acid is Asn, Asp, Gln, Glu, Gy, Pro or Ser.

When a substitution occurs at position 213, the substituting amino acid is Ala, Asn, Asp, Cys, Gln, Glu, Gly, His, Ile, Leu, Met, Pro, Ser, Thr or Val.

When a substitution occurs at position 214, the substituting amino acid is Asn, Asp, Gln, Glu, Gly, His, Pro, Ser or Thr.

When a substitution occurs at position 215, the substituting amino acid is Asn, Asp, Gln, Glu, Gly, Pro or Ser.

When a substitution occurs at position 216, the substituting amino acid is Ala, Asn, Asp, Cys, Gln, Glu, Gly, His, Ile, Met, Pro, Ser, Thr or Val.

When a substitution occurs at position 217, the substituting amino acid is Asp, Gln, Glu or Ser.

When a substitution occurs at position 218, the substituting amino acid is Asn, Asp, Gln, Glu, Pro or Ser.

When a substitution occurs at position 219, the substituting amino acid is Asn, Asp, Gln, Glu, Gly, Pro or Ser.

G. Preparation of enzyme variants

EXAMPLE 1

Mutant subtilisin Carlsberg Genes

A phagemid ("CP") containing the wild type subtilisin Carlsberg gene is constructed. The 2.8 Kbp Pvu II restriction enzyme fragment of plasmid pUC119, (Vieira, J. and Messing, J., "Production of Single-Stranded Plasmid DNA", 153 METHODS IN ENZYMOLOGY 3–11 (1989)) is cloned into the Pvu II site of plasmid pUB110 (Bacillus Genetic Stock Center, Columbus, Ohio 1 E9). The pUC119-pUB110 hybrid plasmid is named pJMA601. Into the Bam H1 restriction site of pJMA601 is cloned the polymerase chain reaction-amplified subtilisin Carlsberg gene giving CP. Phagemid CP is transformed into *Escherichia coli* ung-strain CJ236 and a single stranded uracil-containing DNA template is produced using the VCSM13 helper phage (Kunkel, T.A., J. D. Roberts and R. A. Zakour, "Rapid and efficient site-specific mutagenesis without phenotypic selection", METHODS IN ENZYMOLOGY, Vol. 154, pp. 367–382, (1987); as modified by Yuckenberg, P. D., F. Witney, J. Geisselsoder and J. McClary, "Site-directed in vitro mutagenesis using uracil-containing DNA and phagemid vectors", DIRECTED MUTAGENESIS—A PRACTICAL APPROACH, ed. M. J. McPherson, pp. 27–48, (1991); both of which are incorporated herein by reference). A single primer site-directed mutagenesis modification of the method of Zoller and Smith (Zoller, M. J., and M. Smith, "Oligonucleotide-directed mutagenesis using M13-derived vectors: an efficient and general procedure for the production of point mutations in any fragment of DNA", NUCLEIC ACIDS RESEARCH, Vol. 10, pp. 6487–6500, (1982), incorporated herein by reference) is used to produce all mutants (basically as presented by Yuckenberg, et al., 1991, above). Oligonucleotides are made using an Applied Biosystem Inc. 380B DNA synthesizer. Mutagenesis reaction products are transformed into Escherichia coli strain MM294 (American Type Culture Collection *E. Coli.* 33625). All mutants are confirmed by DNA sequencing and the isolated DNA is transformed into the *Bacillus subtilis* expression strain BG2036 (Yang, M. Y., E. Ferrari and D. J. Henner, (1984), "Cloning of the Neutral Protease Gene of Bacillus subtilis and the Use of the Cloned Gene to Create an In Vitro-derived Deletion Mutation", JOURNAL OF BACTERIOLOGY, Vol. 160, pp. 15–21). For some of the loop mutants a modified CP with a frameshift-stop codon mutation in the corresponding loop is used to produce the uracil template. Oligonucleotides are designed to restore the proper reading frame and to encode for random substitutions at positions 58, 59, 60, 61, 62, 64, 65, 94, 95, 96, 97, 98, 99, 100, 101, 102, 103, 104, 105, 106, 125, 126, 127, 128, 129, 130, 131, 132, 153, 154, 155, 156, 157, 158, 159, 160, 161, 162, 163, 164, 165, 166, 186, 187, 188, 189, 190, 199, 200, 201, 202, 203, 204, 205, 206, 207, 208, 209, 210, 211, 212, 213, 214, 215, 216, 217, 218 and/or 219 (equimolar and/or variable mixtures of all four nucleotides for all three bases at these codons). Mutations that correct for the frameshift-stop and produce a functional enzyme are identified by their ability to digest casein. The random substitutions are determined by DNA sequencing.

EXAMPLE 2

Fermentation

The *Bacillus subtilis* cells (BG2036) containing a subtilisin mutant of interest are grown to mid-log phase in a one liter culture of LB-lucose broth and inoculated into a Biostat ED fermenter (B. Braun Biotech, Inc., Allentown, Pennsylvania) in a total volume of 10 liters. The fermentation media contains Yeast Extract, starch, antifoam, buffers and trace minerals (see FERMENTATION: A PRACTICAL APPROACH, Ed. B. McNeil and L. M. Harvey, 1990). The broth is kept at a constant pH of 7.0 during the fermentation run. Chloramphenical is added for antibiotic selection of mutagenized plasmid. The cells are grown overnight at 37° C. to an $A_{600}$ of about 60 and harvested.

EXAMPLE 3

Purification

The fermentation broth is taken through the following steps to obtain pure enzyme. The broth is cleared of *Bacillus subtilis* cells by centrifugation, and clarified by removing fine particulates with a 100K cutoff membrane. This is followed by concentration on a 10K cutoff membrane, and flow dialysis to reduce the ionic strength and adjust the pH to 5.5 using 0.025M MES buffer (2-(N-morpholino) ethanesulfonic acid). The enzyme is further purified by loading it onto either a cation exchange chromatography column or an affinity adsorption chromatography column and eluting it from the column with a NaCl or a propylene glycol gradient (see Scopes, R. K., PROTEIN PURIFICATION PRINCIPLES AND PRACTICE, Springer-Verlag, New York (1984), incorporated herein by reference).

The pNA assay (DelMar, E.G., C. Largman, J.W. Brodrick and M.C. Geokas, ANAL. BIOCHEM., Vol. 99, pp. 316–320, (1979), incorporated herein by reference) is used to determine the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm are used to determine the total protein concentration. The active enzyme/total-protein ratio gives the enzyme purity, and is used to identify fractions to be pooled for the stock solution.

To avoid autolysis of the enzyme during storage, an equal weight of propylene glycol is added to the pooled fractions obtained from the chromatography column. Upon completion of the purification procedure the purity of the stock enzyme solution is checked with SDS-PAGE (sodium dodecyl sulfate polyacrylamide gel electrophoresis) and the absolute enzyme concentration is determined via an active site titration method using trypsin inhibitor type II-T: turkey egg white purchased from Sigma Chemical Company (St. Louis, Mo.). The measured conversion factors will show which changes made in the enzyme molecule at the various positions result in the enzyme variant having increased activity over the wild-type, against the soluble substrate pNA.

In preparation for use, the enzyme stock solution is eluted through a Sephadex-G25 (Pharmacia, Piscataway, N.J.) size exclusion column to remove the propylene glycol and exchange the buffer. The MES buffer in the enzyme stock solution is exchanged for 0.1 M Tris buffer (Tris (hydroxymethyl-aminomethane) containing 0.01M $CaCl_2$ and pH adjusted to 8.6 with HCl. All experiments are carried out at pH 8.6 in Tris buffer thermostated at 25° C.

H. Characterization of enzyme variants

EXAMPLE 4

Model Surface Preparation

Aminopropyl controlled pore glass (CPG) purchased from CPG Inc. (Fairfield, N.J.) is used as a support for covalently attaching the sAAPF-pNA substrate purchased from Bachem, Inc. (Torrence, California). The reaction is carried out in dimethyl sulfoxide and (1-ethyl-3-[3-(dimethylamino)propyl] carbodiimide hydrochloride) (EDC) is used as a coupling agent. Upon completion (monitored by pNA assay), the excess solvent is removed, and the CPG:sAAPF-pNA is rinsed with dimethyl sulfoxide (DMSO) and doubly-distilled water. This is followed by oven drying with a $N_2$ purge at about 70° C. The reaction scheme and preparation of the immobilized substrate are conducted as described by Brode, P.F. III, and D. S. Rauch, "Subtilisin BPN': Activity on an Immobilized Substrate," LANGMUIR, Vol. 8, p. 1325–1329, (1992), incorporated herein by reference.

The CPG surface will have 62,000±7,000 pNA molecules/$\mu m^2$. The surface area will remain unchanged from the value of 50.0 $m^2/g$ reported by CPG Inc. for the CPG as received. This suggests that the procedure used to add sAAPF-pNA to CPG does not damage the porous structure (mean diameter is 486 Å).

EXAMPLE 5

Surface Hydrolysis Assay

Using CPG:sAAPF-pNA, adsorption of an enzyme variant and hydrolysis of a CPG-bound peptide can be measured in a single experiment. A small volume of enzyme variant stock solution is added to a flask containing Tris buffer and CPG:sAAPF-pNA which has been degassed. The flask is shaken on a wrist-action shaker for a period of 90 minutes during which the shaker is stopped at various time intervals (for example, every 2 minutes during the early stages of adsorption hydrolysis—e.g., the first 20 minutes—and every 10 minutes towards the end of the experiment). The CPG:sAAPF-pNA is allowed to settle and the solution is sampled. Both the experimental procedure and the calculation of the adsorption and hydrolysis are conducted as described by Brode et al., 1992, above.

All enzymes are monitored for stability against autolysis and should show no appreciable autolytic loss over the time course of this experiment. Therefore, enzyme adsorption can be determined by measuring solution depletion. The difference between the initial enzyme variant concentration and the concentration measured at each individual time point gives the amount of enzyme variant adsorbed. The amount of pNA hydrolyzed from the surface is measured by taking an absorbance reading on an aliquot of the sample at 410 nm. The total amount of pNA hydrolyzed is calculated by adding the amount sampled and the amount remaining in the flask. This value is corrected by subtracting the amount of pNA that is hydrolyzed by Tris buffer at pH 8.6 when no enzyme is present. This base-hydrolysis ranges from 7–29% of the total hydrolysis depending on the efficiency of the enzyme.

EXAMPLE 6

Soluble Substrate Kinetic Analysis

The rates of hydrolysis of the soluble substrate sAAPF-pNA are monitored by measuring the adsorbance increase as a function of time at 410 nm on a DU-70 spectrophotometer. The enzyme concentration is held constant and is prepared to be in the range of 6–10 nanomolar while the substrate concentration is varied from 90–700 $\mu$M sAAPF-pNA for each kinetic determination. An adsorbance data point is taken each second over a period of 900 seconds and the data are transferred to a LOTUS™ spreadsheet (Lotus Development Corporation, Cambridge, Mass.). Analysis for kinetic parameters is conducted by the standard Lineweaver Burk analysis in which the data in the initial part of the run (generally the first minute) are fit to a linear regression curve to give $v_o$. The $v_o$ and $s_o$ data are plotted in the standard inverse fashion to give $K_M$ and $k_{cat}$.

I. Example subtilisin Carlsberg variants

Subtilisin Carlsberg variants of the present invention which have decreased adsorption to and increased hydrolysis of surface bound substrates are exemplified in Tables 3–36, below. In describing the specific mutations, the original amino acid occurring in wild-type is given first, the position number second, and the substituted amino acid third.

TABLE 2

Loop 1 – Single Mutation Variants

Thr58Asn
Thr58Asp
Thr58Gln
Thr58Glu
Thr58Gly
Thr58Pro
Thr58Ser
Asp59Glu
Gly60Asn
Gly60Asp
Gly60Gln
Gly60Glu
Gly60Pro
Gly60Ser
Asn61Asp
Asn61Gln
Asn61Glu
Asn61Ser
Gly62Asn
Gly62Asp
Gly62Gln
Gly62Glu
Gly62Pro
Gly62Ser
Gly64Asn
Gly64Asp
Gly64Gln
Gly64Glu
Gly64Pro
Gly64Ser
Thr65Asn
Thr65Asp
Thr65Gln
Thr65Glu
Thr65Gly
Thr65Pro
Thr65Ser

TABLE 3

Loop 1 – Double Mutation Variants

Thr58Gln + Asn61Glu
Asn61Asp + Thr65Pro
Thr58Gln + Asp59Glu
Thr58Gln + Gly62Ser
Gly62Asn + Thr65Pro
Thr58Gln + Gly60Asp
Thr58Pro + Gly60Glu
Asn61Asp + Thr65Ser
Asp59Glu + Gly60Gln
Asp59Glu + Gly60Pro
Gly62Asp + Gly64Gln
Asn61Ser + Thr65Pro
Thr58Asp + Gly60Gln
Gly60Ser + Gly62Gln
Asp59Glu + Gly62Pro

TABLE 3-continued

Loop 1 - Double Mutation Variants

Gly62Asp + Thr65Gly
Asn61Gln + Thr65Pro
Asn61Gln + Gly64Asn
Gly60Gln + Gly62Gln
Thr58Gly + Asn61Asp
Thr58Gln + Gly62Gln
Gly64Asn + Gly62Gln
Gly60Asn + Gly62Asp
Thr58Glu + Gly62Pro
Gly64Asp + Thr65Pro
Asp59Glu + Thr65Ser
Gly60Gln + Thr65Gln
Asp59Glu + Gly62Ser
Asn61Glu + Gly64Gln
Asp59Glu + Gly60Ser
Gly60Ser + Gly62Ser
Thr58Gly + Gly64Glu
Thr58Asn + Asn61Ser
Asp59Glu + Thr65Asn
Gly60Asn + Asn61Ser
Gly60Glu + Gly62Gln
Thr58Pro + Gly62Asp
Thr58Ser + Asp59Glu
Thr58Asp + Gly62Pro
Asn61Asp + Gly62Pro
Thr58Ser + Gly62Ser
Gly60Asn + Gly62Ser
Gly64Pro + Thr65Asn
Gly64Asp + Thr65Gln
Gly64Glu + Thr65Pro
Gly64Asn + Thr65Pro
Asn61Ser + Gly64Asp

TABLE 4

Loop 1 - Triple Mutation Variants

Thr58Pro + Gly64Ser + Thr65Gly
Asn61Glu + Gly62Gln + Thr65Gln
Thr58Gln + Gly62Ser + Gly64Pro
Asp59Glu + Gly62Asn + Thr65Pro
Thr58Pro + Gly60Glu + Gly64Asn
Thr58Asn + Gly64Ser + Thr65Gly
Asp59Glu + Asn61Gln + Gly64Ser
Thr58Asn + Asn61Glu + Thr65Pro
Gly60Pro + Asn61Asp + Thr65Pro
Thr58Glu + Gly62Gln + Gly64Asn
Thr58Asn + Gly62Glu + Gly64Pro
Thr58Ser + Asp59Glu + Thr65Asn
Thr58Glu + Gly62Asn + Gly64Gln
Thr58Pro + Asp59Glu + Gly62Ser
Gly60Asn + Asn61Asp + Gly62Asn
Gly62Asp + Gly64Ser + Thr65Pro
Asp59Glu + Gly60Asn + Thr65Asn
Thr58Gly + Gly60Pro + Thr65Gly
Thr58Gln + Gly60Glu + Asn61Gln
Gly60Pro + Asn61Gln + Gly64Asp
Thr58Asn + Gly62Asn + Thr65Pro
Thr58Pro + Asp59Glu + Gly64Asn
Thr58Pro + Asn61Ser + Gly62Asp
Thr58Asp + Gly60Pro + Gly62Asn
Thr58Ser + Gly60Pro + Asn61Asp
Gly60Gln + Gly62Gln + Gly64Pro
Asp59Glu + Asn61Gln + Thr65Asn
Gly60Asp + Asn61Gln + Thr65Pro
Asn61Glu + Gly62Glu + Thr65Pro
Thr58Asp + Asp59Glu + Thr65Gln
Thr58Glu + Asp59Glu + Thr65Ser
Thr58Glu + Asp59Glu + Thr65Gly

TABLE 5

Loop 1 - Quadruple Mutation Variants

Asp59Glu + Gly60Pro + Gly62Asn + Gly64Gln
Thr58Pro + Gly60Pro + Gly62Glu + Thr65Gln
Thr58Ser + Gly60Pro + Gly64Gln + Thr65Pro
Thr58Pro + Asp59Glu + Asn61Ser + Gly62Asn
Thr58Glu + Gly60Asn + Gly64Ser + Thr65Pro
Thr58Glu + Gly60Ser + Asn61Gln + Thr65Gln
Thr58Pro + Asp59Glu + Gly60Asn + Asn61Gln
Thr58Gly + Gly60Pro + Gly62Glu + Thr65Ser
Gly60Asp + Gly62Ser + Gly64Gln + Thr65Gly
Thr58Asn + Gly60Pro + Gly62Ser + Gly64Asp
Thr58Pro + Asp59Glu + Gly60Asn + Gly62Asn
Asn61Asp + Gly62Gln + Gly64Pro + Thr65Asn
Thr58Glu + Gly60Pro + Gly62Asn + Gly64Ser
Thr58Asp + Gly60Gln + Gly62Pro + Thr65Asn
Thr58Asn + Asn61Asp + Gly62Glu + Thr65Gly
Thr58Ser + Gly60Ser + Asn61Asp + Gly62Glu
Thr58Glu + Asp59Glu + Asn61Gln + Thr65Ser
Thr58Asp + Asp59Glu + Gly62Pro + Thr65Gly
Gly60Asp + Asn61Asp + Gly62Ser + Thr65Gly
Gly60Glu + Asn61Glu + Gly62Gln + Gly64Pro
Thr58Pro + Gly60Asp + Asn61Asp + Gly64Asn
Asp59Glu + Gly60Asp + Gly64Gln + Thr65Ser
Asp59Glu + Gly60Asp + Gly64Gln + Thr65Pro
Thr58Pro + Asp59Glu + Gly60Asp + Gly64Asn
Thr58Ser + Asp59Glu + Gly60Asp + Gly62Asn
Asp59Glu + Gly60Glu + Asn61Glu + Gly62Ser
Thr58Glu + Asp59Glu + Gly60Asp + Thr65Pro
Asp59Glu + Gly60Asp + Gly62Glu + Thr65Pro
Thr58Ser + Asp59Glu + Asn61Asp + Gly62Asp

TABLE 6

Loop 2 - Single Mutation Variants

Val 94Ala
Val 94Asn
Val 94Asp
Val 94Cys
Val 94Gln
Val 94Glu
Val 94Gly
Val 94His
Val 94Met
Val 94Pro
Val 94Ser
Val 94Thr
Leu 95Ala
Leu 95Asn
Leu 95Asp
Leu 95Cys
Leu 95Gln
Leu 95Glu
Leu 95Gly
Leu 95His
Leu 95Ile
Leu 95Met
Leu 95Pro
Leu 95Ser
Leu 95Thr
Leu 95Val
Asn 96Asp
Asn 96Gln
Asn 96Glu
Asn 96Ser
Ser 97Asp
Ser 97Glu
Ser 98Asp
Ser 98Glu
Gly 99Asn
Gly 99Asp
Gly 99Gln
Gly 99Glu
Gly 99Pro
Gly 99Ser

TABLE 6-continued

| Loop 2 - Singie Mutation Variants |
| --- |
| Ser100Asp |
| Ser100Glu |
| Gly101Asn |
| Gly101Asp |
| Gly101Gln |
| Gly101Glu |
| Gly101Pro |
| Gly101Ser |
| Ser102Asp |
| Ser102Glu |
| Tyr103Ala |
| Tyr103Asn |
| Tyr103Asp |
| Tyr103Cys |
| Tyr103Gln |
| Tyr103Glu |
| Tyr103Gly |
| Tyr103His |
| Tyr103Ile |
| Tyr103Leu |
| Tyr103Met |
| Tyr103Pro |
| Tyr103Ser |
| Tyr103Thr |
| Tyr103Val |
| Ser104Asp |
| Ser104Glu |
| Gly105Asn |
| Gly105Asp |
| Gly105Gln |
| Gly105Glu |
| Gly105Pro |
| Gly105Ser |
| Ile106Ala |
| Ile106Asn |
| Ile106Asp |
| Ile106Cys |
| Ile106Gln |
| Ile106Glu |
| Ile106Gly |
| Ile106His |
| Ile106Leu |
| Ile106Met |
| Ile106Pro |
| Ile106Ser |
| Ile106Thr |
| Ile106Val |

TABLE 7

| Loop 2 - Double Mutation Variants |
| --- |
| Val 94Gln + Ser100Glu |
| Asn 96Ser + Gly 99Gln |
| Gly 99Glu + Ile106Met |
| Ser 97Asp + Gly105Gln |
| Ser102Glu + Tyr103Asn |
| Ser100Glu + Ile106Gly |
| Asn 96Asp + Ile106Ser |
| Gly 99Ser + Ser100Glu |
| Gly101Gln + Gly105Ser |
| Asn 96Asp + Gly 99Pro |
| Asn 96Gln + Ser104Asp |
| Leu 95Glu + Tyr103Pro |
| Asn 965er + Gly101Asp |
| Leu 95Val + Ser 97Glu |
| Leu 95Ala + Gly 99Pro |
| Val 94Thr + Gly 99Glu |
| Leu 95Gln + Ile106Ala |
| Leu 95Pro + Ile106Ala |
| Leu 95Val + Ser100Glu |
| Gly101Gln + Tyr103Gly |
| Asn 96Asp + Ile106Pro |
| Leu 95Ser + Ser100Asp |

TABLE 7-continued

| Loop 2 - Double Mutation Variants |
| --- |
| Gly 99Pro + Ser100Asp |
| Val 94Thr + Leu 95Asp |
| Ser100Glu + Ile106Gln |
| Ser100Asp + Gly101Pro |
| Leu 95Cys + Gly105Asp |
| Ser 98Glu + Gly101Ser |
| Gly101Asn + Tyr103Gln |
| Val 94Met + Ser102Glu |
| Gly 99Pro + Gly105Asp |
| Val 94Asn + SerlO2Asp |
| Val 94Cys + Ile106Thr |
| Val 94Gly + Ser104Asp |
| Val 94Pro + Gly101Pro |
| Val 94Ser + Gly105Glu |
| Val 94Met + Ser 98Asp |
| Val 94Gln + Ser104Asp |
| Asn 96Ser + Ser 98Asp |
| Ser104Glu + Ile106Gln |
| Val 94Asn + Tyr103Thr |
| Tyr103Ala + Ser104Asp |
| Gly 99Pro + Ser104Glu |
| Leu 95Cys + Tyr103Leu |
| Val 94Gly + Gly 99Ser |
| Gly101Gln + Tyr103Ser |
| Ser 97Asp + Gly105Pro |
| Ser 98Asp + Gly105Asn |
| Gly 99Gln + Ser100Glu |
| Gly 99Pro + Ser100Glu |
| Tyr103Ile + Gly105Ser |
| Ser100Glu + Gly105Pro |
| Asn 96Glu + Tyr103Gly |
| Val 94Met + Gly105Asn |
| Val 94His + Leu 95Glu |
| Ser100Asp + Tyr103Met |
| Leu 95Met + Gly101Gln |
| Gly 99Pro + Gly101Asp |
| Asn 96Asp + Gly101Asn |
| Val 94Ala + Gly 99Ser |

TABLE 8

| Loop 2 - Triple Mutation Variants |
| --- |
| Val 94Gln + Leu 95Thr + Ser100Glu |
| Ser100Glu + Tyr103Met + Ile106Thr |
| Ser 97Asp + Gly101Gln + Ile106Asn |
| Leu 95Gln + Gly105Ser + Ile106Gln |
| Leu 95His + Gly 99Gln + Ser100Glu |
| Val 94His + Leu 95Met + Asn 96Gln |
| Val 94Asn + Ser 97Glu + Tyr103Pro |
| Ser 97Asp + Cly101Ser + Tyr103Met |
| Ser 97Glu + Tyr103Met + Ile106Gln |
| Val 94Thr + Gly 99Pro + Gly105Asp |
| Leu 95Gly + Ser 98Glu + Tyr103Cys |
| Leu 95Pro + Gly101Asp + Tyr103Gly |
| Leu 95Val + Gly 99Pro + Ser104Asp |
| Leu 95Ile + Gly105Ser + Ile106Met |
| Ser 97Glu + Gly101Asn + Ile106Thr |
| Asn 96Ser + Gly101Asp + Tyr103Asn |
| Val 94Pro + Ser 98Glu + Ile106Asn |
| Gly 99Pro + Tyr103Glu + Ile106Ser |
| Asn 96Asp + Gly 99Asn + Tyr103Pro |
| Leu 95Gln + Ser 97Asp + Ile106Val |
| Val 94Pro + Ser 98Glu + Tyr103Val |
| Leu 95Asn + Gly101Pro + Ile106His |
| Val 94Ala + Leu 95His + Ser100Glu |
| Val 94Asn + Gly101Ser + Ser104Asp |
| Val 94Cys + Gly105Ser + Ile106Thr |
| Leu 95Gly + Gly101Asp + Ile106Cys |
| Ser102Glu + Tyr103Ile + Ile106Gly |
| Val 94Pro + Leu 95Asp + Ile106Pro |
| Val 94Pro + Leu 95Ile + Ile106Cys |
| Ser100Asp + Gly101Asp + Ile106Asn |
| Leu 95Glu + Asn 96Glu + Tyr103Pro |

TABLE 8-continued

| Loop 2 - Triple Mutation Variants |
|---|
| Gly101Glu + Ser102Asp + Tyr103Leu |
| Val 94Pro + Gly101Asp + Ser102Glu |
| Asn 96Asp + Ser 97Asp + Gly 99Pro |
| Ser 97Asp + Ser 98Asp + Gly 99Glu |
| Asn 96Glu + Ser 97Asp + Gly 99Asp |
| Gly 99Glu + Ser100Asp + Gly101Asp |
| Gly 99Glu + Ser100Glu + Gly101Glu |
| Leu 95Gln + Ser102Asp + Gly105Asp |
| Asn 96Ser + Ser102Glu + Ser104Glu |
| Ser102Asp + Ser104Glu + Gly105Pro |
| Ser102Asp + Tyr103Ser + Ser104Glu |
| Val 94Cys + Ser 97Glu + Gly 99Asp |
| Asn 96Asp + Ser 98Glu + Ile106Thr |
| Asn 96Asp + Ser 98Asp + Ile106Cys |
| Asn 96Glu + Ser 98Glu + Gly105Asn |
| Ser 98Glu + Ser100Glu + Ile106Ser |
| Ser 98Asp + Ser100Asp + Gly101Asn |
| Gly101Asp + Ser102Asp + Ser104Glu |
| Leu 95Glu + Ser 98Asp + Gly101Asp |
| Val 94Ser + Ser100Glu + Ser102Asp |
| Leu 95Val + Ser 97Glu + Ser100Glu |
| Asn 96Gln + Ser 97Asp + Ser100Asp |
| Asn 96Ser + Ser 97Asp + Ser100Asp |
| Val 94Asp + Gly 99Asn + Ser102Glu |
| Val 94Asp + Ser102Glu + Ile106His |
| Leu 95Asp + Gly 99Glu + Ser102Asp |
| Val 94Thr + Gly101Asp + Ser104Glu |
| Gly 99Pro + Gly101Asp + Ser104Asp |
| Ser 98Asp + Gly101Asp + Tyr103Pro |

TABLE 9

| Loop 2 - Quadruple Mutation Variants |
|---|
| Val 94Met + Leu 95Asn + Ser 98Asp + Gly105Ser |
| Asn 96Ser + Gly101Glu + Tyr103Ile + Gly105Asn |
| Leu 95Val + Ser 97Asp + Gly 99Asn + Tyr103Ile |
| Leu 95Ile + Asn 96Gln + Gly 99Asn + Tyr103Asp |
| Val 94His + Ser100Glu + Tyr103Ile + Ile106Met |
| Ser 97Glu + Tyr103Ile + Gly105Gln + Ile106Ala |
| Val 94Thr + Leu 95Ile + Ser 97Asp + Gly 995er |
| Val 94Thr + Leu 95Cys + Gly 99Asp + Ile106Val |
| Leu 95Cys + Ser 98Glu + Gly 99Asn + Ile106Met |
| Asn 96Gln + Ser 98Asp + Gly105Asn + Ile106Gly |
| Leu 95Thr + Ser100Glu + Tyr103Val + Ile106Pro |
| Val 94Thr + Leu 95Val + Asn 96Glu + Tyr103Asn |
| Val 94His + Leu 95Asn + Gly 99Gln + Gly105Gln |
| Val 94Ala + Leu 95Thr + Ser 98Asp + Tyr103Ile |
| Leu 95Val + Gly101Gln + Tyr103Cys + Ile106Glu |
| Gly 99Pro + Ser100Glu + Gly101Ser + Tyr103Thr |
| Leu 95Ala + Gly101Asp + Tyr103Ser + Gly105Asn |
| GLy 99Asn + Tyr103Asp + Gly105Asn + Ile106Thr |
| Asn 96Asp + Ser 97Asp + Gly101Ser + Tyr103Thr |
| Val 94Ala + Asn 96Glu + Ser 97Asp + Gly105Asn |
| Val 94Cys + Leu 95Gln + Asn 96Glu + Ser 97Glu |
| Val 94Gly + Asn 96Gln + Ser104Glu + Gly105Glu |
| Ser 97Asp + Ser 98Glu + Gly101Asn + Tyr103Val |
| Ser 97Glu + Ser 98Asp + Gly 99Gln + Gly101Gln |
| Leu 95Gly + Asn 96Ser + Ser 97Glu + Ser 98Glu |
| Asn 96Glu + Ser 97Glu + Ser 98Asp + Gly101Pro |
| Asn 96Asp + Ser 97Asp + Ser 98Asp + Tyr103Leu |
| Asn 96Asp + Ser 97Asp + Ser 98Glu + Tyr103Gly |
| Leu 95Glu + Asn 96Glu + Ser100Asp + Ile106Ala |
| Ser 97Asp + Gly 99Glu + Tyr103Cys + Gly105Asn |
| Val 94Gly + Asn 96Ser + Ser 97Glu + Gly 99Asp |
| Asn 96Ser + Tyr103Leu + Ser104Asp + Ile106Glu |
| Leu 95Ala + Asn 96Glu + Gly 99Ser + Ser100Asp |
| Asn 96Asp + Ser 97Glu + Ser100Glu + Ile106Val |
| Val 94Cys + Ser 97Asp + Ser 98Asp + Ser100Asp |
| Ser 97Asp + Ser 98Asp + Ser100Glu + Tyr103Thr |
| Asn 96Glu + Gly 99Glu + Gly101Asp + Tyr103Ala |
| Val 94Asp + Leu 95Ala + Gly101Glu + Ser102Glu |
| Ser 98Glu + Gly 99Pro + Ser100Asp + Gly101Glu |
| Val 94Glu + Asn 96Gln + Gly101Glu + Ile106Thr |

TABLE 9-continued

| Loop 2 - Quadruple Mutation Variants |
|---|
| Asn 96Ser + Ser102Asp + Tyr103Asn + Ile106Asp |
| Leu 95Cys + Ser 98Asp + Gly 99Asp + Gly101Asp |
| Ser100Glu + Gly101Pro + Ser102Glu + Ile106Ala |
| Val 94Cys + Ser100Glu + Gly101Pro + Ser102Glu |
| Val 94Gln + Ser100Asp + Ser102Giu + Tyr103Ile |
| Ser 97Asp + Ser100Glu + Gly101Glu + Tyr103Asn |
| Val 94Glu + Asn 96Glu + Gly 99Glu + Gly105Pro |
| Asn 96Gln + Ser100Glu + Gly101Asp + Ile106Glu |
| Val 94Pro + Leu 95Ala + Ser 97Asp + Ser100Asp |
| Leu 95Glu + Gly101Asn + Ser102Glu + Tyr103Ile |
| Val 94Asn + Asn 96Glu + Gly101Asp + Gly105Asp |
| Val 94Asp + Gly 99Asn + Ser100Asp + Ser102Asp |
| Val 94Asp + Leu 95Val + Ser102Asp + Tyr103Ala |
| Leu 95Glu + Gly 99Pro + Ser102Asp + Ser104Glu |
| Leu 95Ser + Asn 96Gln + Gly101Glu + Ser104Asp |
| Val 94Gln + Asn 96Gln + Gly101Glu + Ser104Glu |
| Gly101Asp + Tyr103Val + Ser104Glu + Ile106Val |
| Asn 96Asp + Ser102Asp + Tyr103Gly + Gly105Asp |
| Ser100Glu + Ser102Asp + Ser104Asp + Gly105Ser |
| Val 94Asp + Ser 97Asp + Ser100Asp + Gly105Gln |

TABLE 10

| Loop 3 - Single Mutation Variants |
|---|
| Leu125Ala |
| Leu125Asn |
| Leu125Asp |
| Leu125Cys |
| Leu125Gln |
| Leu125Glu |
| Leu125Gly |
| Leu125His |
| Leu125Ile |
| Leu125Met |
| Leu125Pro |
| Leu125Ser |
| Leu125Thr |
| Leu125Val |
| Gly126Asn |
| Gly126Asp |
| Gly126Gln |
| Gly126Glu |
| Gly126Pro |
| Gly126Ser |
| Gly127Asn |
| Gly127Asp |
| Gly127Gln |
| Gly127Glu |
| Gly127Pro |
| Gly127Ser |
| Ala128Asn |
| Ala128Asp |
| Ala128Gln |
| Ala128Glu |
| Ala128Gly |
| Ala128His |
| Ala128Pro |
| Ala128Ser |
| Ala128Thr |
| Ser129Asp |
| Ser129Glu |
| Gly130Asn |
| Gly130Asp |
| Gly130Gln |
| Gly130Glu |
| Gly130Pro |
| Gly130Ser |
| Ser131Asp |
| Ser131Glu |
| Thr132Asn |
| Thr132Asp |
| Thr132Gln |
| Thr132Glu |

TABLE 10-continued

| Loop 3 - Single Mutation Variants |
|---|
| Thr132Gly |
| Thr132Pro |
| Thr132Ser |

TABLE 11

| Loop 3 - Double Mutation Variants |
|---|
| Leu125Gln + Ser129Glu |
| Gly130Gln + Thr132Asn |
| Gly126Asp + Gly127Pro |
| Leu125Ile + Ser131Glu |
| Gly126Gln + Gly130Ser |
| Gly126Pro + Thr132Pro |
| Gly126Asp + Thr132Ser |
| Ala128Gly + Thr132Ser |
| Leu125Ala + Gly126Glu |
| Leu125Gln + Ser129Asp |
| Gly126Pro + Ser131Asp |
| Gly127Ser + Ser129Glu |
| Gly130Asn + Ser131Glu |
| Leu125Glu + Ala128Gln |
| Gly126Ser + Thr132Ser |
| Leu125Ala + Ser129Asp |
| Gly127Pro + Thr132Asp |
| Gly126Pro + Gly130Ser |
| Leu125Ala + Ala128Asp |
| Gly127Gln + Ser131Asp |
| Leu125Ala + Thr132Ser |
| Gly127Pro + Thr132Gly |
| Gly126Glu + Thr132Asn |
| Leu125Gly + Ser129Glu |
| Ala128Thr + Gly130Asp |
| Ala128Thr + Thr132Asp |
| Leu125Gly + Gly126Asn |
| Gly126Ser + Ser129Glu |
| Leu125Asn + Thr132Asn |
| Gly126Glu + Ala128Gly |
| Ser131Asp + Thr132Gln |
| Ser129Glu + Gly130Pro |
| Gly127Asn + Ser129Asp |
| Leu125Glu + Thr132Asn |
| Gly126Gln + Gly127Glu |
| Ala128Thr + Ser131Asp |
| Leu125Pro + Ser131Glu |
| Gly126Pro + Thr132Gly |
| Gly126Gln + Ser129Asp |
| Leu125Gly + Gly126Ser |
| Gly127Gln + Ser129Asp |
| Gly126Gln + Gly130Glu |
| Gly127Asp + Gly130Asn |
| Leu125Glu + Gly126Ser |
| Leu125Ile + Thr132Asp |
| Gly126Asn + Gly127Asp |
| Leu125cys + Gly126Gln |
| Leu125Glu + Ala128Asn |
| Gly126Gln + Ala128Asn |
| Gly126Asp + Gly130Asn |
| Leu125Ser + Gly130Ser |
| Gly126Asn + Ser129Asp |
| Leu125Ser + Ser131Asp |
| Ser129Asp + Thr132Asn |
| Gly127Glu + Ala128Thr |
| Leu125Thr + Gly130Pro |
| Ala128Pro + Thr132Asp |
| Gly127Ser + Ser131Glu |
| Gly126Asn + Thr132Glu |
| Gly130Asp + Thr132Asn |

TABLE 12

| Loop 3 - Triple Mutation Variants |
|---|
| Leu125Asn + Gly126Pro + Ser129Glu |
| Gly126Asn + Ser129Asp + Gly130Pro |
| Leu125Ala + Gly126Ser + Ser131Glu |
| Gly127Gln + Ala128Thr + Ser129Glu |
| Leu125Thr + Ser129Asp + Gly130Pro |
| Gly126Pro + Ala128Thr + Thr132Asp |
| Gly126Asn + Gly130Asn + Thr132Gln |
| Leu125Thr + Gly130Gln + Thr132Gln |
| Ala128Gly + Ser129Asp + Thr132Asn |
| Leu125Met + Ala128Gln + Ser129Asp |
| Leu125Gly + Ala128Asp + Gly130Pro |
| Leu125Ile + Gly127Ser + Thr132Asp |
| Leu125Val + Gly127Glu + Gly130Ser |
| Gly127Ser + Gly130Asn + Thr132Asn |
| Leu125Thr + Gly126Ser + Ala128Glu |
| Leu125Gln + Gly126Pro + Ser131Glu |
| Leu125Glu + Gly130Asn + Thr132Asn |
| Gly126Asn + Gly127Pro + Ser129Asp |
| Gly126Pro + Gly127Pro + Ala128His |
| Gly127Asn + Ala128His + Ser129Asp |
| Leu125Thr + Gly130Pro + Thr132Ser |
| Leu125Cys + Gly127Gln + Ser129Asp |
| Gly127Asn + Gly130Glu + Thr132Gly |
| Gly127Gln + Gly130Ser + Thr132Asp |
| Leu125Thr + Ser129Asp + Thr132Pro |
| Leu125Cys + Gly127Glu + Gly130Pro |
| Ala128Gly + Ser129Glu + Gly130Gln |
| Gly127Asp + Gly130Ser + Thr132Pro |
| Leu125Pro + Gly126Asn + Gly127Asn |
| Gly126Glu + Ala128Ser + Gly130Ser |
| Leu125Gly + Gly127Pro + Ser129Asp |
| Gly120Gln + Ala128Glu + Gly130Gln |
| Ala128Gly + Gly130Asn + Thr132Asp |
| Leu125Met + Gly126Pro + Gly127Gln |
| Leu125Gln + Ala128Asn + Ser129Asp |
| Gly127Ser + Ala128Asn + Thr132Gly |
| Gly126Gln + Gly127Asp + Gly130Ser |
| Gly127Asp + Ala128Pro + Thr132Pro |
| Leu125His + Ser129Asp + Thr132Pro |
| Leu125Ile + Gly126Gln + Thr132Gln |
| Gly126Asp + Gly130Ser + Thr132Asn |
| Gly127Asn + Ser129Glu + Gly130Pro |
| Leu125Pro + Gly127Asp + Gly130Asn |
| Leu125Ile + Ala128His + Ser131Asp |
| Gly126Pro + Ala128His + Thr132Pro |
| Leu125Val + Ala128Gln + Ser129Glu |
| Leu125Ser + Gly126Asp + Thr132Gly |
| Leu125Pro + Gly126Asp + Gly127Asp |
| Ala128Ser + Gly130Asp + Ser131Asp |
| Gly130Asp + Ser131Glu + Thr132Asn |
| Gly126Asn + Gly130Asp + Ser131Glu |
| Gly126Gln + Gly130Asp + Ser131Glu |
| Gly130Gln + Ser131Glu + Thr132Glu |
| Ala128Thr + Ser131Glu + Thr132Asp |
| Ala128Thr + Ser131Asp + Thr132Glu |
| Ala128Pro + Ser131Asp + Thr132Asp |
| Gly127Asp + Ala128Asp + Thr132Gln |
| Leu125Glu + Gly126Glu + Gly130Asn |
| Ala128Asp + Ser129Asp + Gly130Asn |
| Ser129Asp + Gly130Glu + Thr132Pro |

TABLE 13

| Loop 3 - Quadruple Mutation Variants |
|---|
| Leu125Asn + Ala128Asn + Ser131Glu + Thr132Pro |
| Leu125Ala + Gly126Gln + Gly127Pro + Gly130Ser |
| Leu125Pro + Gly126Asn + Gly127Gln + Ala128Pro |
| Leu125Gly + Gly126Asn + Ser129Glu + Gly130Asn |
| Ala128Gly + Gly130Asn + Ser131Asp + Thr132Ser |
| Leu125Ile + Gly126Pro + Ala128Gly + Thr132Glu |
| Leu125Thr + Gly130Pro + Ser131Asp + Thr132Gly |
| Leu125Asp + Gly126Pro + Gly127Ser + Thr132Gln |
| Leu125Gly + Gly126Pro + Gly127Asp + Thr132Pro |

TABLE 13-continued

Loop 3 - Quadruple Mutation Variants

Leu125Val + Gly127Glu + Gly130Asn + Thr132Asn
Leu125Cys + Ala128Pro + Gly130Ser + Ser131Glu
Gly126Gln + Gly127Ser + Ala128Thr + Gly130Glu
Leu125Gly + Gly127Ser + Gly130Ser + Thr132Gly
Leu125Pro + Gly126Ser + Ala128His + Thr132Asn
Leu125Val + Gly126Gln + Gly127Pro + Ser129Asp
Leu125Cys + Gly130Pro + Ser131Asp + Thr132Ser
Leu125Gly + Gly127Gln + Ser129Glu + Thr132Ser
Leu125Met + Ala128Ser + Gly130Pro + Thr132Gly
Leu125Ala + Gly126Asp + Ala128His + Thr132Ser
Gly127Gln + Gly130Glu + Ser131Asp + Thr132Asn
Gly126Ser + Gly127Gln + Gly130Glu + Ser131Glu
Gly127Pro + Gly130Glu + Ser131Glu + Thr132Pro
Ala128Gly + Gly130Pro + Ser131Asp + Thr132Glu
Gly126Asn + Ala128Pro + Ser131Asp + Thr132Asp
Gly126Gln + Ala128His + Ser131Asp + Thr132Asp
Leu125Thr + Gly127Glu + Ala128Asp + Gly130Gln
Gly126Asn + Ala128Gln + Ser129Glu + Gly130Asp
Ala128Gly + Ser129Glu + Gly130Glu + Thr132Gln
Gly126Gln + Ser129Asp + Gly130Glu + Thr132Asn
Gly126Asn + Ala128Thr + Ser129Glu + Gly130Glu
Gly126Ser + Gly127Asn + Ser129Glu + Gly130Glu
Leu125His + Gly127Glu + Ala128Glu + Ser129Asp
Leu125Thr + Gly127Glu + Ala128Asp + Ser129Glu
Gly126Pro + Gly127Glu + Ala128Asp + Ser129Glu
Ala128Gly + Ser129Glu + Gly130Asp + Ser131Asp
Gly126Gln + Ser129Asp + Gly130Asp + Ser131Asp
Gly127Ser + Ser129Glu + Gly130Glu + Ser131Glu
Ala128Gly + Ser129Asp + Gly130Asp + Ser131Glu
Gly126Asn + Ser129Asp + Gly130Asp + Ser131Glu
Ala128Asn + Ser129Asp + Gly130Asp + Ser131Asp
Gly127Pro + Ser129Glu + Gly130Asp + Ser131Glu
Gly126Ser + Gly130Asp + Ser131Asp + Thr132Glu
Leu125Met + Gly127Glu + Ser129Asp + Gly130Asp
Gly126Pro + Gly127Asp + Ser129Glu + Gly130Asp
Leu125Val + Gly127Glu + Ser129Asp + Gly130Asp
Gly127Asp + Ala128Asn + Ser129Asp + Gly130Glu
Gly127Glu + Ala128Thr + Ser129Glu + Gly130Ser
Gly127Asp + Ala128His + Ser129Glu + Gly130Ser
Gly126Ser + Gly127Glu + Ala128Thr + Ser129Glu
Gly126Pro + Gly127Asp + Ala128Asp + Gly130Glu
Leu125Gly + Gly126Asp + Gly127Glu + Ser129Glu
Gly126Asp + Gly127Glu + Ala128Ser + Ser129Asp
Gly127Ser + Ser129Asp + Gly130Gln + Ser131Asp
Ala128Gly + Ser129Glu + Gly130Asn + Ser131Glu
Leu125Val + Ser129Asp + Ser131Asp + Thr132Ser
Leu125Gly + Ala128Gly + Ser129Glu + Ser131Asp
Leu125Cys + Gly126Pro + Ser129Glu + Ser131Glu
Gly127Ser + Ala128Asn + Ser129Asp + Ser131Asp
Gly126Asn + Ser129Asp + Ser131Glu + Thr132Gln
Gly126Pro + Ala128Pro + Ser129Asp + Ser131Glu

TABLE 14

Loop 4 - Single Mutation Variants

Gly153Asn
Gly153Asp
Gly153Gln
Gly153Glu
Gly153Pro
Gly153Ser
Asn154Asp
Asn154Gln
Asn154Glu
Asn154Ser
Ser155Asp
Ser155Glu
Gly156Asn
Gly156Asp
Gly156Gln
Gly156Glu
Gly156Pro
Gly156Ser

TABLE 14-continued

Loop 4 - Single Mutation Variants

Asn157Asp
Asn157Gln
Asn157Glu
Asn157Ser
Ser158Asp
Ser158Glu
Gly159Asn
Gly159Asp
Gly159Gln
Gly159Glu
Gly159Pro
Gly159Ser
Ser160Asp
Ser160Glu
Thr161Asn
Thr161Asp
Thr161Gln
Thr161Glu
Thr161Gly
Thr161Pro
Thr161Ser
Asn162Asp
Asn162Gln
Asn162Glu
Asn162Ser
Thr163Asn
Thr163Asp
Thr163Gln
Thr163Glu
Thr163Gly
Thr163Pro
Thr163Ser
Ile164Ala
Ile164Asn
Ile164Asp
Ile164Cys
Ile164Gln
Ile164Glu
Ile164Gly
IIel64His
Ile164Leu
Ile164Met
Ile164Pro
Ile164Ser
Ile164Thr
Ile164Val
Gly165Asn
Gly165Asp
Gly165Gln
Gly165Glu
Gly165Pro
Gly165Ser
Tyr166Ala
Tyr166Asn
Tyr166Asp
Tyr166Cys
Tyr166Gln
Tyr166Glu
Tyr166Gly
Tyr166His
Tyr166Ile
Tyr166Leu
Tyr166Met
Tyr166Pro
Tyr166Ser
Tyr166Thr
Tyr166Val

TABLE 15

Loop 4 - Double Mutation Variants

Asn154Ser + Ser155Glu
Gly153Glu + Ile164Ala

TABLE 15-continued

Loop 4 - Double Mutation Variants

Gly159Glu + Gly165Pro
Asn154Glu + Gly156Ser
Gly156Pro + Gly159Asp
Gly153Ser + Ser160Asp
Ser155Asp + Gly165ser
Ile164Gly + Gly165Glu
Gly159Glu + Ile164Asn
Asn157Gln + Asn162Ser
Gly156Asp + Thr161Gln
Asn162Glu + Tyr166Gln
Asn157Glu + Gly165Gln
Asn162Glu + Gly165Gln
Gly153Pro + Ile164Cys
Thr163Glu + Gly165Asn
Gly153Asp + Ile164Asn
Gly153Ser + Thr161Asp
Gly156Asp + Tyr166Gln
Gly165Pro + Tyr166Ser
Gly153Ser + Asn162Glu
Gly159Glu + Tyr166Leu
Gly156Asp + Thr161Glu
Asn154Gln + Ser158Glu
Ser160Asp + Thr161Asn
Ser155Glu + Gly165Pro
Asn154Ser + Tyr166Ile
Gly153Asp + Thr161Asn
Ser158Asp + Thr161Pro
Asn162Glu + Thr163Ser
Gly159Gln + Tyr166Cys
Thr161Gly + Asn162Ser
Gly159Asp + Tyr166Asn
Ser160Glu + Ile164Thr
Ser158Asp + Ile164Leu
Asn154Ser + Asn157Asp
Asn154Asp + Thr161Gln
Gly156Ser + Ser160Glu
Gly156Gln + Tyr166Ile
Gly153Asn + Tyr166Ala
Asn154Asp + Ile164Ser
Ser155Asp + Thr163Asn
Gly156Glu + Gly159Gln
Gly156Ser + Asn161Asp
Gly153Ser + Asn157Glu
Ser160Glu + Gly165Pro
Gly153Pro + Asn157Asp
Gly153Gln + Ser160Asp
Asn154Gln + Thr163Asn
Gly156Ser + Gly159Asp
Gly159Asp + Thr162Gln
Gly159Ser + Tyr166Glu
Asn157Asp + Tyr166Leu
Thr161Asp + Asn162Gln
Asn162Gln + Gly165Glu
Gly156Asp + Asn162Gln
Asn154Gln + Ile164Gln
Asn157Asp + Asn162Ser
Asn154Asp + Ile164Asn
Gly159Asp + Gly165Pro

TABLE 16

Loop 4 - Triple Mutation Variants

Gly153Gln + Asn154Ser + Ser155Glu
Gly156Asp + Thr161Pro + Tyr166Ile
Asn157Glu + Gly159Gln + Asn162Gln
Asn154Glu + Asn162Gln + Ile164Leu
Gly153Pro + Gly159Gln + Ile164Asn
Asn154Ser + Ile164Met + Tyr166Cys
Gly159Gln + Ser160Asp + Ile164Thr
Gly156Asn + Thr161Ser + Ile164Cys
Gly156Asn + Ile164His + Tyr166Asp
Asn157Glu + Asn162Gln + Ile164Ala
Ser160Asp + Thr163Ser + Ile164Gly

TABLE 16-continued

Loop 4 - Triple Mutation Variants

Asn154Glu + Thr161Pro + Ile164Met
Thr163Asn + Ile164Asn + Gly165Pro
Asn157Glu + Asn162Gln + Ile164Thr
Asn162Gln + Ile164Thr + Gly165Glu
Asn154Gln + Gly159Asp + Tyr166Thr
Asn157Gln + Thr161Gly + Thr163Pro
Ser158Glu + Thr163Ser + Gly165Ser
Gly153Pro + Asn157Asp + Thr163Asn
Gly156Pro + Ser158Asp + Gly165Gln
Asn157Gln + Thr163Gly + Gly165Pro
Ser155Glu + Gly159Ser + Tyr166Thr
Gly153Gln + Asn154Gln + Gly165Glu
Gly153Gln + Asn154Ser + Gly159Pro
Thr161Gly + Asn162Asp + Gly165Asn
Ser158Glu + Gly159Ser + Gly165Gln
Ser155Asp + Gly159Asn + Ile164Ser
Asn157Gln + Thr163Gly + Gly165Glu
Gly153Ser + Gly159Ser + Asn162Asp
Gly153Ser + Ser158Glu + Ile164Thr
Gly153Asp + Thr161Ser + Gly165Asn
Thr161Ser + Ile164Ser + Tyr166Pro
Ser155Asp + Gly156Asn + Ile164Asn
Asn154Glu + Gly159Gln + Tyr166Ile
Gly153Gln + Gly156Gln + Thr161Asp
Gly159Asn + Thr163Asn + Tyr166Ser
Ser155Asp + Thr163Pro + Ile164Gly
Gly153Ser + Ser160Asp + Ile164Pro
Asn162Glu + Ile164Gln + Tyr166Gln
Gly156Glu + Asn157Glu + Thr161Gly
Gly159Asp + Ser160Glu + Ile164Gln
Ser155Asp + Gly156Glu + Thr163Asn
Ser155Glu + Gly156Asp + Gly165Ser
Ser155Glu + Gly156Asp + Ile164Met
Ser160Glu + Thr161Asp + Gly165Asn
Asn162Asp + Thr163Asp + Gly165Asn
Asn157Asp + Ser158Glu + Thr161Glu
Gly159Asp + Thr161Glu + Thr163Pro
Gly153Asp + Asn154Ser + Gly165Asp
Gly153Glu + Asn162Gln + Gly165Asp
Asn154Ser + Thr161Glu + Thr163Asp
Ser158Glu + Ser160Asp + Thr163Asn
Ser158Glu + Ser160Glu + Thr163Gly
Ser158Asp + Ser160Asp + Ile164Gly
Asn157Asp + Gly159Glu + Thr163Gln
Thr163Glu + Gly165Asp + Tyr166Pro
Ser160Asp + Asn162Glu + Gly165Asn
Asn154Glu + Gly156Asp + Asn157Glu
Gly159Asp + Ser160Asp + Asn162Glu
Asn154Glu + Ser155Glu + Asn157Asp

TABLE 17

Loop 4 - Quadruple Mutation Variants

Gly153Pro + Gly159Ser + Thr163Pro + Gly165Asn
Asn154Gln + Asn162Glu + Ile164Cys + Gly165Pro
Asn154Ser + Asn157Asp + Thr161Gly + Ile164Asn
G1Y159Glu + Thr161Gln + Thr163Asn + Gly165Gln
Gly159Ser + Ser160Glu + Thr163Gln + Tyr166Ile
Gly156Ser + Ser160Glu + Thr161Asn + Gly165Pro
Gly153Ser + Gly159Ser + Ser160Asp + Gly165Ser
Gly153Asn + Gly159Glu + Ile164Cys + Gly165Pro
Asn154Ser + Gly156Glu + Thr161Pro + Tyr166His
Gly153Ser + Ser160Glu + Gly165Asn + Tyr166Cys
Asn157Gln + Thr163Gly + Ile164His + Gly165Gln
Asn154Ser + Ser155Glu + Asn162Ser + Ile164His
Gly156Pro + Asn157Gln + Ser160Glu + Gly165Ser
Gly153Gln + Ser155Asp + Thr161Gln + Tyr166Gly
Asn157Asp + Thr161Gln + Thr163Asp + Ile164Thr
Gly153Ser + Ser160Asp + Asn162Gln + Tyr166Thr
Gly153Pro + Asn154Gln + Asn157Gln + Ser160Glu
Gly156Glu + Asn162Gln + Thr163Ser + Gly165Gln
Gly156Asn + Asn157Glu + Thr161Gly + Thr163Ser
Gly153Ser + Ser158Glu + Gly159Asp + Thr163Gly

TABLE 17-continued

| Loop 4 - Quadruple Mutation Variants |
|---|
| Asn154Gln + Ser158Asp + Gly159Asp + Thr163Asn |
| Ser158Asp + Gly159Asp + Thr163Asn + Tyr166Pro |
| Gly159Asp + Ser160Glu + Thr163Ser + Gly165Ser |
| Asn154Glu + Ser155Asp + Thr163Gln + Tyr166Met |
| Gly153Glu + Asn154Asp + Ser155Glu + Gly159Asn |
| Ser158Glu + Gly159Glu + Ser160Asp + Gly165Asn |
| Ser158Asp + Gly159Asp + Ser160Asp + Asn162Gln |
| Asn157Ser + Ser160Asp + Thr161Glu + Asn162Glu |
| Gly156Asn + Ser158Asp + Ser160Glu + Thr161Glu |
| Gly159Glu + Thr161Asp + Thr163Asn + Tyr166Val |
| Gly156Pro + Gly159Glu + Thr161Asp + Gly165Pro |
| Gly153Glu + Gly156Pro + Gly159Gln + Gly165Asp |
| Gly153Glu + Asn157Gln + Gly159Gln + Gly165Asp |
| Gly153Asn + Ser155Glu + Thr163Glu + Ile164Gly |
| Asn157Glu + Ser158Asp + Ser160Asp + Thr161Asn |
| Asn154Ser + Asn157Ser + Ser158Asp + Ser160Glu |
| Ser158Glu + Gly159Gln + Ser160Glu + Thr163Gln |
| Ser158Asp + Ser160Glu + Ile164Ala + Tyr166Gln |
| Gly153Pro + Asn157Gln + Ser158Glu + Ser160Asp |
| Gly153Gln + Gly156Pro + Ser158Glu + Ser160Asp |
| Gly156Ser + Asn157Glu + Gly159Glu + Ile164Leu |
| Thr163Asp + Ile164Cys + Gly165Asp + Tyr166Cys |
| Ser160Asp + Asn162Asp + Ile164Asn + Tyr166Thr |
| Asn157Ser + Ser160Glu + Asn162Asp + Ile164Met |
| Ser155Glu + Asn157Asp + Asn161Ser + Gly165Pro |
| Gly153Ser + Asn154Glu + Ser155Glu + Asn157Glu |
| Gly153Pro + Asn154Asp + Ser155Asp + Asn157Glu |
| Gly153Gln + Ser158Glu + Ser160Asp + Asn162Glu |
| Asn157Asp + Ser160Glu + Thr161Ser + Asn162Glu |
| Gly156Asp + Asn157Asp + Thr161Ser + Asn162Asp |
| Asn154Gln + Asn157Asp + Ser160Glu + Tyr166Ser |
| Gly153Gln + Gly156Glu + Ser158Glu + Asn162Glu |
| Gly156Glu + Gly159Pro + Thr163Asp + Gly165Asp |
| Ser155Glu + Thr161Ser + Thr163Ser + Gly165Asp |
| Asn154Asp + Thr163Gly + Gly165Glu + Tyr166Ser |
| Ser155Asp + Asn157Glu + Gly159Glu + Gly165Gln |
| Asn161Glu + Ile164Ala + Gly165Asp + Tyr166Thr |
| Gly156Gln + Asn162Asp + Gly165Asp + Tyr166Asn |
| Ser155Glu + Ser158Asp + Thr161Asn + Tyr166Met |
| Ser155Glu + Ser158Glu + Gly159Gln + Ile164Gly |

TABLE 18

| Loop 5 - Single Mutation Variants |
|---|
| Ala186Asn |
| Ala186Asp |
| Ala186Gln |
| Ala186Glu |
| Ala186Gly |
| Ala186His |
| Ala186Pro |
| Ala186Ser |
| Ala186Thr |
| Ser187Asp |
| Ser187Glu |
| Phe188Ala |
| Phe188Asn |
| Phe188Asp |
| Phe188Cys |
| Phe188Gln |
| Phe188Glu |
| Phe188Gly |
| Phe188His |
| Phe188Ile |
| Phe188Leu |
| Phe188Met |
| Phe188Pro |
| Phe188Ser |
| Phe188Thr |
| Phe188Tyr |
| Phe188Val |
| Ser189Asp |
| Ser189Glu |

TABLE 18-continued

| Loop 5 - Single Mutation Variants |
|---|
| Ser190Asp |
| Ser190Glu |

TABLE 19

| Loop 5 - Double Mutation Variants |
|---|
| Ala186Asp + Phe188Gln |
| Ala186Gly + Ser187Glu |
| Ala186Gln + Ser187Asp |
| Ala186His + Ser190Glu |
| Ser187Asp + Phe188Cys |
| Ser187Asp + Phe188Thr |
| Phe188Gly + Ser190Glu |
| Ala186Asn + Phe188Ser |
| Ala186Asp + Phe188Ile |
| Ala186Ser + Phe188Glu |
| Ala186Thr + Phe188Leu |
| Ser187Glu + Phe188Ser |
| Ser187Glu + Phe188Pro |
| Ser187Asp + Phe188Gln |
| Ala186Thr + Ser190Glu |
| Phe188His + Ser190Asp |
| Ala186Gln + Ser190Asp |
| Phe188Leu + Ser190Glu |
| Ala186His + Ser190Asp |
| Ala186Pro + Ser187Glu |
| Phe188Ile + Ser190Asp |
| Ala186Asp + Phe188Asn |
| Ala186Ser + Ser187Glu |
| Ser187Glu + Phe188Leu |
| Ala186Asn + Phe188Ile |
| Phe188Tyr + Ser190Glu |
| Ala186Pro + Ser190Glu |
| Ala186Thr + Phe188Asp |
| Ala186His + Ser187Asp |
| Ala186Gln + Phe188Thr |
| Phe188Cys + Ser190Glu |
| Ser187Glu + Phe188Thr |
| Ser187Asp + Phe188Met |
| Ala186Asn + Ser190Asp |
| Phe188Val + Ser190Asp |
| Ala186Pro + Phe188Ser |
| Ala186Asp + Phe188Ser |
| Ser187Glu + Phe188Asn |
| Ala186Thr + Ser187Asp |
| Ala186Thr + Phe188Asn |
| Ala186Gly + Phe188Leu |
| Phe188Asn + Ser190Glu |
| Ala186Thr + Ser187Glu |
| Ala186Thr + Ser190Asp |
| Ser187Asp + Phe188Ala |
| Ala186Asn + Ser187Glu |
| Ala186Gln + Phe188Tyr |
| Phe188Ile + Ser190Glu |
| Phe188Thr + Ser190Asp |
| Ala186Ser + Ser187Asp |
| Phe188Ala + Ser190Asp |
| Phe188Gln + Ser190Glu |
| Ala186Gly + Ser190Asp |
| Ala186Glu + Phe188Thr |
| Ala186Pro + Phe188Ala |
| Phe188Asn + Ser190Asp |
| Ala186Gly + Phe188Val |
| Phe188Leu + Ser190Asp |
| Ala186Asn + Phe188Met |
| Ala186Gln + Phe188Glu |

TABLE 20

Loop 5 - Triple Mutation Variants

Ala186Pro + Phe188Cys + Ser190Glu
Ala186Gln + Phe188Val + Ser190Glu
Ala186Thr + Phe188Asn + Ser190Glu
Ala186Gly + Phe188Gln + Ser190Glu
Ala186Pro + Phe188Gln + Ser190Glu
Ala186Gln + Phe188Asn + Ser190Asp
Ala186Asn + Ser187Asp + Phe188Leu
Ala186Gln + Ser187Asp + Phe188Pro
Ala186Gln + Ser187Glu + Phe188Met
Ala186Pro + Phe188Val + Ser190Glu
Ala186His + Phe188Met + Ser190Asp
Ala186Asn + Ser187Glu + Phe188Ile
Ala186Gln + Phe188Ala + Ser190Glu
Ala186Pro + Phe188Thr + Ser190Asp
Ala186Asn + Ser187Glu + Phe188Thr
Ala186Ser + Phe188Ala + Ser190Glu
Ala186His + Phe188Pro + Ser190Asp
Ala186His + Ser187Asp + Phe188Leu
Ala186Pro + Ser187Glu + Phe188Val
Ala186Asn + Ser187Asp + Phe188His
Ala186Gly + Ser187Glu + Phe188Leu
Ala186Pro + Ser187Asp + Phe188His
Ala186Gln + Phe188Ile + Ser190Asp
Ala186Pro + Phe188Ile + Ser190Asp
Ala186Gln + Phe188Thr + Ser190Asp
Ala186Gln + Phe188His + Ser190Glu
Ala186Gly + Phe188Ile + Ser190Asp
Ala186Thr + Ser187Glu + Phe188Tyr
Ala186His + Ser187Asp + Phe188Ser
Ala186His + Ser187Glu + Phe188Ser
Ala186His + Phe188Gly + Ser190Glu
Ala186Pro + Ser187Glu + Phe188Pro
Ala186Gln + Ser187Glu + Phe188Tyr
Ala186Asn + Phe188Cys + Ser190Asp
Ala186Gly + Phe188Gly + Ser190Asp
Ala186Gln + Ser187Asp + Phe188Val
Ala186Pro + Ser187Glu + Phe188Gly
Ala186Glu + Ser187Glu + Phe188Ile
Ala186Asp + Ser187Glu + Phe188Ala
Ala186Asp + Ser187Asp + Phe188Thr
Ala186Glu + Ser187Asp + Phe188Thr
Ala186Glu + Ser187Glu + Phe188Tyr
Ala186Asp + Ser187Asp + Phe188Ser
Ala186Asp + Ser187Glu + Phe188Ile
Ala186Pro + Ser187Asp + Phe188Asp
Ala186Gln + Ser187Glu + Phe188Glu
Ala186Gln + Ser187Glu + Phe188Asp
Ala186Glu + Ser187Glu + Phe188Asp
Ala186Glu + Ser187Asp + Phe188Glu
Ala186Thr + Phe188Asp + Ser190Glu
Ala186Ser + Phe188Asp + Ser190Asp
Ala186Gly + Phe188Asp + Ser190Glu
Ser187Asp + Phe188Glu + Ser190Asp
Ser187Glu + Phe188Glu + Ser190Asp
Ser187Asp + Phe188Glu + Ser190Glu
Ser187Glu + Phe188Glu + Ser190Glu
Ala186Glu + Phe188Glu + Ser190Glu
Ala186Glu + Phe188Asp + Ser190Asp
Ala186Asp + Ser187Asp + Ser190Glu
Ala186Asp + Ser187Glu + Ser190Asp

TABLE 21

Loop 5 - Quadruple Mutation Variants

Ala186Thr + Ser187Glu + Phe188Glu + Ser190Asp
Ala186Gln + Ser187Asp + Phe188Asp + Ser190Asp
Ala186Gly + Ser187Asp + Phe188Glu + Ser190Asp
Ala186Thr + Ser187Asp + Phe188Glu + Ser190Glu
Ala186His + Ser187Glu + Phe188Glu + Ser190Glu
Ala186Gln + Ser187Glu + Phe188Glu + Ser190Glu
Ala186Thr + Ser187Glu + Phe188Asp + Ser190Asp
Ala186Asn + Ser187Glu + Phe188Asp + Ser190Asp
Ala186Ser + Ser187Glu + Phe188Glu + Ser190Glu
Ala186Asn + Ser187Asp + Phe188Asp + Ser190Asp

TABLE 21-continued

Loop 5 - Quadruple Mutation Variants

Ala186Ser + Ser187Asp + Phe188Asp + Ser190Glu
Ala186Asn + Ser187Asp + Phe188Asp + Ser190Glu
Ala186His + Ser187Glu + Phe188Glu + Ser190Glu
Ala186Gln + Ser187Asp + Phe188Glu + Ser190Asp
Ala186Gly + Ser187Asp + Phe188Glu + Ser190Glu
Ala186Pro + Ser187Asp + Phe188Asp + Ser190Glu
Ala186Gly + Ser187Asp + Phe188Asp + Ser190Glu
Ala186Ser + Ser187Glu + Phe188Glu + Ser190Asp
Ala186Thr + Ser187Asp + Phe188Asp + Ser190Asp
Ala186Gly + Ser187Glu + Phe188Asp + Ser190Glu
Ala186Gly + Ser187Asp + Phe188Asp + Ser190Asp
Ala186Asp + Ser187Asp + Phe188Asn + Ser190Asp
Ala186Glu + Ser187Glu + Phe188Tyr + Ser190Glu
Ala186Asp + Ser187Asp + Phe188Ser + Ser190Glu
Ala186Asp + Ser187Glu + Phe188Gln + Ser190Glu
Ala186Glu + Ser187Glu + Phe188Ala + Ser190Glu
Ala186Glu + Ser187Glu + Phe188Gly + Ser190Glu
Ala186Asp + Ser187Asp + Phe188Ala + Ser190Asp
Ala186Glu + Ser187Glu + Phe188Cys + Ser190Glu
Ala186Glu + Ser187Glu + Phe188Ile + Ser190Asp
Ala186Glu + Ser187Glu + Phe188Ala + Ser190Asp
Ala186Glu + Ser187Glu + Phe188His + Ser190Asp
Ala186Asp + Ser187Asp + Phe188Leu + Ser190Glu
Ala186Asp + Ser187Asp + Phe188Gln + Ser190Glu
Ala186Asp + Ser187Glu + Phe188Asn + Ser190Asp
Ala186Asp + Ser187Asp + Phe188Cys + Ser190Glu
Ala186Asp + Ser187Asp + Phe188Thr + Ser190Asp
Ala186Glu + Ser187Glu + Phe188Leu + Ser190Asp
Ala186Glu + Ser187Glu + Phe188Leu + Ser190Glu
Ala186Asp + Ser187Asp + Phe188Pro + Ser190Glu
Ala186Asp + Ser187Glu + Phe188Val + Ser190Asp
Ala186Asp + Ser187Asp + Phe188His + Ser190Glu
Ala186Glu + Ser187Glu + Phe188Pro + Ser190Glu
Ala186Asp + Ser187Glu + Phe188Ser + Ser190Glu
Ala186Glu + Ser187Glu + Phe188Val + Ser190Glu
Ala186Asp + Ser187Glu + Phe188Gln + Ser190Asp
Ala186Asp + Ser187Glu + Phe188Asn + Ser190Asp
Ala186Asp + Ser187Glu + Phe188Gly + Ser190Glu
Ala186Asp + Ser187Asp + Phe188Cys + Ser190Asp
Ala186Asp + Ser187Glu + Phe188Tyr + Ser190Glu
Ala186Glu + Ser187Glu + Phe188Thr + Ser190Asp
Ala186Glu + Ser187Glu + Phe188Thr + Ser190Glu
Ala186Glu + Ser187Glu + Phe188Met + Ser190Glu
Ala186Asp + Ser187Asp + Phe188Gly + Ser190Glu
Ala186Asp + Ser187Glu + Phe188His + Ser190Glu
Ala186Asp + Ser187Glu + Phe188Met + Ser190Asp
Ala186Glu + Ser187Asp + Phe188Ser + Ser190Asp
Ala186Asn + Ser187Glu + Phe188Met + Ser190Asp
Ala186Gln + Ser187Asp + Phe188His + Ser190Asp
Ala186Asn + Ser187Glu + Phe188Ser + Ser190Glu

TABLE 22

Loop 6 - Single Mutation Variants

Ala199Asn
Ala199Asp
Ala199Gln
Ala199Glu
Ala199Gly
Ala199His
Ala199Pro
Ala199Ser
Ala199Thr
Pro200Asn
Pro200Asp
Pro200Gln
Pro200Glu
Pro200Gly
Pro200Ser
Gly201Asn
Gly201Asp
Gly201Gln
Gly201Glu
Gly201Pro

TABLE 22-continued

Loop 6 – Single Mutation Variants

Gly201Ser
Ala202Asn
Ala202Asp
Ala202Gln
Ala202Glu
Ala202Gly
Ala202His
Ala202Pro
Ala202Ser
Ala202Thr
Gly203Asn
Gly203Asp
Gly203Gln
Gly203Glu
Gly203Pro
Gly203Ser
Val204Ala
Val204Asn
Val204Asp
Val204Cys
Val204Gln
Val204Glu
Val204Gly
Val204His
Val204Met
Val204Pro
Val204Ser
Val204Thr
Tyr205Ala
Tyr205Asn
Tyr205Asp
Tyr205Cys
Tyr205Gln
Tyr205Glu
Tyr205Gly
Tyr205His
Tyr205Ile
Tyr205Leu
Tyr205Met
Tyr205Pro
Tyr205Ser
Tyr205Thr
Tyr205Val
Ser206Asp
Ser206Glu
Thr207Asn
Thr207Asp
Thr207Gln
Thr207Glu
Thr207Gly
Thr207Pro
Thr207Ser
Tyr208Ala
Tyr208Asn
Tyr208Asp
Tyr208Cys
Tyr208Gln
Tyr208Glu
Tyr208Gly
Tyr208His
Tyr208Ile
Tyr208Leu
Tyr208Met
Tyr208Pro
Tyr208Ser
Tyr208Thr
Tyr208Val
Pro209Asn
Pro209Asp
Pro209Gln
Pro209Glu
Pro209Gly
Pro209Ser
Thr210Asn
Thr210Asp
Thr210Gln
Thr210Glu
Thr210Gly
Thr210Pro
Thr210Ser
Asn211Asp
Asn211Gln
Asn211Glu
Asn211Ser
Thr212Asn
Thr212Asp
Thr212Gln
Thr212Glu
Thr212Gly
Thr212Pro
Thr212Ser
Tyr213Ala
Tyr213Asn
Tyr213Asp
Tyr213Cys
Tyr213Gln
Tyr213Glu
Tyr213Gly
Tyr213His
Tyr213Ile
Tyr213Leu
Tyr213Met
Tyr213Pro
Tyr213Ser
Tyr213Thr
Tyr213Val
Ala214Asn
Ala214Asp
Ala214Gln
Ala214Glu
Ala214Gly
Ala214His
Ala214Pro
Ala214Ser
Ala214Thr
Thr215Asn
Thr215Asp
Thr215Gln
Thr215Glu
Thr215Gly
Thr215Pro
Thr215Ser
Leu216Ala
Leu216Asn
Leu216Asp
Leu216Cys
Leu216Gln
Leu216Glu
Leu216Gly
Leu216His
Leu216Ile
Leu216Met
Leu216Pro
Leu216Ser
Leu216Thr
Leu216Val
Asn217Asp
Asn217Gln
Asn217Glu
Asn217Ser
Gly218Asn
Gly218Asp
Gly218Gln
Gly218Glu
Gly218Pro
Gly218Ser
Thr219Asn
Thr219Asp
Thr219Gln
Thr219Glu
Thr219Gly
Thr219Pro
Thr219Ser

TABLE 23

Loop 6 - Double Mutation Variants

Gly218Gln + Thr219Gln
Val204Ala + Thr207Gln
Tyr213Val + Gly218Pro
Pro209Gly + Tyr213Ile
Thr215Ser + Thr219Ser
Leu216Ala + Asn217Gln
Pro209Asp + Thr212Ser
Ala199Asn + Leu216Ile
Asn217Glu + Thr219Asn
Tyr208Ile + Thr215Asn
Ala202Gly + Pro209Glu
Gly201Ser + Thr219Gly
Thr215Pro + Gly218Ser
Tyr205Leu + Leu216His
Val204Asn + Ala214Asn
Asn217Ser + Gly218Pro
Ala202His + Tyr208Val
Gly201Gln + Tyr213Leu
Tyr213Cys + Thr219Gly
Pro200Asn + Thr210Pro
Ala202Asp + Thr219Asn
Gly201Pro + Val204Pro
Ala214Thr + Thr219Gln
Thr207Gln + Leu216Asp
Pro200Gln + Tyr213Met
Val204Ala + Thr215Glu
Thr212Gln + Thr215Asn
Leu216His + Asn217Glu
Ala202Thr + Ala214Asp
Val204Pro + Thr207Gln
Gly203Asp + Tyr205Leu
Tyr205His + Asn211Asp
Asn211Gln + Thr212Asn
Gly203Pro + Thr219Pro
Pro200Gly + Pro209Asp
Thr210Asp + Gly218Pro
Gly203Asp + Gly218Ser
Tyr205Glu + Gly218Pro
Thr212Gln + Thr219Pro
Ala214Ser + Asn217Glu
Ala202Asn + Leu216Ser
Val204Thr + Ala214Pro
Pro200Asn + Asn211Asp
Tyr205Gly + Thr219Pro
Ala199His + Asn217Ser
Gly201Ser + Asn211Asp
Gly203Ser + Tyr205Ala
Ala202Pro + Pro209Glu
Tyr213Pro + Gly218Glu
Pro200Gly + Ala202Glu
Thr210Gly + Asn211Asp
Val204Asn + Thr215Asn
Pro200Asn + Tyr208Leu
Ala202Pro + Ala214Thr
Tyr205Cys + Leu216His
Leu216Ser + Gly218Gln
Thr215Glu + Thr219Gln
Tyr205Leu + Pro209Glu
Ala214Glu + Thr215Pro
Gly203Glu + Gly218Gln
Tyr205Cys + Thr212Pro
Leu216Asn + Thr219Asn
Ala199Ser + Thr219Asn
Gly201Gln + Tyr213Val
Gly203Asn + Thr215Gln
Pro209Glu + Asn211Gln
Ala199Gly + Asn211Asp
Ala214Glu + Leu216Met
Val204Pro + Asn211Asp
Ala202Glu + Gly218Gln
Tyr208Ile + Gly218Glu
Tyr205Ser + Leu216Thr
Asn211Glu + Tyr213Gly
Thr212Asn + Thr219Asn
Asn217Asp + Thr219Gln
Thr207Asn + Asn217Asp
Gly201Ser + Tyr208Gln

TABLE 23-continued

Loop 6 - Double Mutation Variants

Thr210Pro + Thr212Gly
Val204Asn + Thr210Gly
Ala199His + Tyr208Val
Tyr208Gly + Tyr213Val
Gly201Pro + Ala214Asp
Gly201Gln + Leu216Gly
Gly201Gln + Thr207Asn
Gly203Asn + Gly218Glu
Tyr208Asn + Thr219Ser
Thr207Gly + Leu216Glu
Gly218Glu + Thr219Asn
Ala199Gln + Thr212Glu
Thr212Asp + Ala214Gly
Gly203Asn + Ala214Ser
Asn211Ser + Thr212Gln
Pro209Asp + Tyr213Thr
Gly201Gln + Ala202Thr
Val204Thr + Tyr208Cys
Gly201Asn + Ala202Asn
Ala199His + Thr210Asp
Val204Ser + Thr212Asp
Tyr208Ser + Thr219Gln
Tyr205Pro + Thr215Asp
Asn211Gln + Gly218Gln
Asn217Asp + Gly218Pro
Ala202Gln + Thr210Pro
Tyr205Asn + Gly218Gln
Gly201Gln + Thr219Ser
Ala202Asp + Thr207Asn
Thr212Gly + Asn217Gln
Thr215Asn + Thr219Ser
Ala214Glu + Thr215Gly
Thr210Asn + Tyr213Gln
Ala199Gln + Tyr205Glu
Tyr205His + Thr210Asp
Gly201Asn + Gly203Asp
Gly203Ser + Pro209Asp
Gly201Gln + Thr210Glu
Pro209Asn + Thr215Ser
Thr215Gln + Thr219Gly
Gly201Gln + Thr215Asp
Tyr208Gly + Tyr213Pro
Gly201Asn + Tyr213Asn
Ala202Pro + Pro209Asn
Ala199Thr + Tyr208Met
Thr210Gln + Gly218Asn
Thr210Pro + Asn211Asp
Asn211Asp + Gly218Pro
Gly201Asn + Tyr205Gly
Ala202Gln + Tyr213Glu
Ala199His + Ala202Asp
Tyr205Ser + Tyr213Glu
Gly201Gln + Pro209Asp
Ala202Ser + Thr219Gln
Leu216Met + Thr219Asn
Val204Ser + Tyr205Ser
Val204Thr + Tyr208Ser
Gly203Asn + Ala214Thr
Thr210Gly + Thr219Asn
Pro200Gly + Thr210Pro
Ala214Glu + Gly218Pro
Pro200Gly + Thr219Gln
Ala202Ser + Asn211Asp
Ala199Thr + Val204Gln
Ala199Gln + Pro200Ser
Pro209Ser + Leu216Thr
Tyr205Pro + Leu216Ala
Gly201Pro + Pro209Gly
Thr207Asn + Thr215Glu
Pro200Ser + Tyr205Ala
Thr210Gln + Asn217Gln
Ala199Asn + Gly203Gln
Gly201Asn + Thr207Pro
Gly203Asp + Tyr208Asn
Thr207Asn + Asn211Asp
Tyr205Leu + Gly218Asp
Gly203Ser + Thr210Pro

TABLE 23-continued

| Loop 6 - Double Mutation Variants |
|---|
| Tyr205Cys + Asn211Ser |
| Ala214Glu + Asn217Ser |
| Ala199Pro + Gly201Gln |
| Gly201Asn + Tyr213Met |
| Tyr205His + Tyr208Gly |
| Gly203Glu + Thr210Ser |
| Thr207Asn + Ala214Ser |
| Tyr205Val + Thr219Ser |
| Val204Asn + Thr207Pro |
| Thr207Ser + Asn211Asp |
| Tyr205Leu + Gly218Glu |
| Asn211Ser + Thr219Pro |
| Tyr205Gln + Asn211Ser |
| Pro200Gly + Val204Asn |
| Ala202Glu + Tyr213His |
| Gly201Pro + Gly218Gln |
| Ala204Asn + Asn217Gln |
| Gly201Asn + Asn211Asp |
| Pro209Ser + Thr212Gln |
| Gly203Gln + Val204Gln |
| Gly201Gln + Thr215Pro |
| Gly201Asn + Ala202Ser |
| Thr207Gln + Thr212Asp |
| Val204Gly + Thr212Asp |
| Gly201Asn + Thr210Asp |
| Thr210Asp + Tyr213Cys |

TABLE 24

| Loop 6 - Triple Mutation Variants |
|---|
| Pro200Gly + Thr212Ser + Tyr213Met |
| Gly201Pro + Pro209Glu + Thr212Gly |
| Gly203Asp + Val204Met + Asn217Gln |
| Pro200Gly + Thr212Ser + Ala214Asp |
| Ala199Gly + Tyr213Asp + Gly218Ser |
| Gly201Asn + Thr207Ser + Thr215Glu |
| Pro200Ser + Ala214Gly + Asn217Glu |
| Ala199Pro + Thr207Ser + Thr210Pro |
| Gly201Asn + Thr210Ser + Asn211Glu |
| Gly203Asn + Thr207Asn + Asn217Glu |
| Gly201Asn + Tyr205Pro + Thr207Ser |
| Pro200Asn + Gly201Gln + Gly203Ser |
| Pro200Gln + Asn211Glu + Tyr213Ala |
| Ala202His + Thr212Asp + Tyr213His |
| Ala199Thr + Gly201Asn + Asn211Ser |
| Pro200Ser + Gly201Gln + Pro209Asn |
| Ala202Gly + Tyr205Pro + Asn211Ser |
| Gly203Gln + Tyr205Val + Thr210Pro |
| Gly203Glu + Asn211Gln + Asn217Ser |
| Pro200Asn + Pro209Glu + Asn211Ser |
| Gly201Pro + Thr210Ser + Tyr213Thr |
| Tyr205Ile + Leu216Asp + Thr219Gly |
| Pro200Ser + Val204Met + Pro209Asp |
| Tyr205Asp + Thr207Gly + Tyr208Gln |
| Pro200Ser + Thr210Asp + Thr212Pro |
| Gly201Gln + Asn211Asp + Tyr213Gly |
| Tyr208Val + Thr210Gly + Leu216Val |
| Pro209Gly + Thr215Pro + Leu216Ala |
| Val204His + Thr215Glu + Leu216Cys |
| Ala199Pro + Gly203Ser + Thr210Ser |
| Gly201Asn + Tyr205Met + Thr210Asp |
| Pro200Gly + Tyr205Cys + Thr212Asn |
| Ala199Pro + Pro200Ser + Leu216Glu |
| Gly201Asn + Tyr205Asp + Tyr213Ile |
| Pro200Ser + Ala202Gly + Thr210Asp |
| Ala202Asn + Val204Ser + Gly218Glu |
| Gly203Gln + Val204Cys + Thr207Ser |
| Val204Cys + Thr207Asn + Thr212Asp |
| Gly201Pro + Gly203Ser + Tyr208Gly |
| Gly203Asn + Tyr208Cys + Leu216Met |
| Thr210Gln + Thr215Asp + Thr219Ser |
| Pro209Asp + Tyr213Leu + Ala214Thr |
| Ala202Asp + Tyr213Pro + Thr215Gln |

TABLE 24-continued

| Loop 6 - Triple Mutation Variants |
|---|
| Thr215Glu + Gly218Ser + Thr219Gln |
| Pro200Gly + Val204His + Thr207Ser |
| Gly203Ser + Pro209Asp + Thr219Ser |
| Ala202Asn + Thr207Gln + Ala214His |
| Thr207Ser + Ala214Glu + Leu216Ser |
| Pro200Asn + Pro209Asn + Thr210Pro |
| Pro209Gln + Tyr213His + Ala214Thr |
| Thr210Asn + Thr215Pro + Leu216Gln |
| Gly203Gln + Val204Ser + Thr210Glu |
| Pro200Asn + Asn211Gln + Gly218Ser |
| Pro200Gln + Thr207Gln + Leu216Glu |
| Tyr213Pro + Gly218Glu + Thr219Asn |
| Tyr208Cys + Thr210Asp + Thr219Ser |
| Pro200Gln + Tyr205His + Thr219Ser |
| Pro209Asp + Thr212Gln + Thr219Gln |
| Gly201Asn + Val204Asn + Thr210Asp |
| Pro200Gly + Tyr208Leu + Thr210Asn |
| Pro200Gln + Thr207Gln + Thr219Gln |
| Tyr205Val + Pro209Ser + Thr210Asp |
| Gly203Pro + Val204His + Tyr213Glu |
| Gly203Asn + Pro209Asn + Tyr213His |
| Ala199Asn + Gly201Asn + Leu216Asp |
| Pro209Asp + Tyr213His + Gly218Ser |
| Gly201Ser + Gly203Asp + Asn211Ser |
| Gly203Asn + Val204Cys + Thr212Gly |
| Gly201Pro + Tyr208Met + Leu216Glu |
| Gly201Ser + Val204Gln + Leu216His |
| Ala199Gly + Ala202Pro + Leu216Ser |
| Gly203Gln + Tyr205Pro + Thr219Gly |
| Tyr205Gly + Tyr213Val + Asn217Asp |
| Gly201Asn + Ala214His + Thr215Gln |
| Pro200Gly + Ala202Gln + Tyr213Cys |
| Gly203Pro + Tyr208Met + Thr219Pro |
| Pro200Asn + Tyr205Leu + Gly218Glu |
| Pro209Gly + Thr212Glu + Tyr213Thr |
| Pro200Gln + Thr210Pro + Thr219Asn |
| Gly201Ser + Gly218Pro + Thr219Asn |
| Pro200Ser + Gly201Pro + Thr219Gly |
| Thr207Pro + Tyr213Ala + Leu216Glu |
| Ala199Ser + Thr207Asn + Thr212Asp |
| Thr207Gln + Tyr208Ile + Thr210Asp |
| Tyr213Ser + Thr215Gln + Thr219Pro |
| Pro200Gly + Tyr208Ile + Ala214Ser |
| Gly201Asn + Pro209Ser + Thr215Asp |
| Pro200Ser + Pro209Asp + Tyr213Met |
| Tyr208Gly + Thr210Glu + Thr215Ser |
| Ala202Ser + Ala214Asp + Thr219Ser |
| Val204Pro + Pro209Asn + Thr219Asn |
| Thr207Asn + Pro209Asn + Gly218Ser |
| Pro200Gly + Leu216Cys + Gly218Ser |
| Pro209Gly + Leu216Val + Gly218Glu |
| Asn211Gln + Tyr213Thr + Thr215Ser |
| Tyr213Val + Thr215Glu + Gly218Ser |
| Tyr213Pro + Gly218Gln + Thr219Ser |
| Gly201Pro + Ala202Thr + Val204Cys |
| Ala202Ser + Tyr208Leu + Pro209Asp |
| Tyr208Thr + Thr210Asn + Ala214Thr |
| Tyr205Pro + Pro209Ser + Thr215Gln |
| Tyr205Cys + Tyr208Gly + Leu216Glu |
| Ala199Gly + Gly203Asp + Pro209Asn |
| Val204Gln + Thr207Gly + Gly218Gln |
| Ala202His + Gly218Asp + Thr219Gln |
| Gly203Asp + Asn211Ser + Leu216Met |
| Pro200Ser + Val204Cys + Thr215Glu |
| Thr207Asn + Leu216Pro + Asn217Glu |
| Ala199His + Tyr205His + Thr212Pro |
| Ala199Gln + Gly203Asp + Thr219Gly |
| Ala199His + Pro200Gln + Asn217Asp |
| Val204Ser + Tyr213Leu + Thr219Gln |
| Val204Ser + Pro209Ser + Leu216Glu |
| Ala202Gly + Pro209Asn + Thr219Asn |
| Thr215Gln + Gly218Asn + Thr219Gln |
| Ala199Pro + Ala214Ser + Leu216Val |
| Gly203Asn + Thr215Asn + Gly218Glu |
| Thr207Pro + Tyr208Ala + Thr219Asn |
| Ala199Ser + Thr210Ser + Gly218Gln |
| Pro209Asn + Thr210Ser + Asn211Ser |

TABLE 24-continued

| Loop 6 - Triple Mutation Variants |
|---|
| Gly201Asn + Val204Cys + Tyr213Val |
| Gly201Ser + Val204Ser + Pro209Asn |
| Gly201Pro + Thr210Ser + Asn211Ser |
| Tyr205Gln + Tyr208His + Thr210Asp |
| Tyr208Ile + Thr215Ser + Gly218Glu |
| Thr212Glu + Ala214His + Thr215Gln |
| Gly201Asn + Val204Gly + Tyr205Gln |
| Ala199Thr + Pro209Glu + Thr210Ser |
| Pro209Gly + Thr210Asn + Gly218Glu |
| Gly203Pro + Pro209Asn + Thr210Asn |
| Gly203Glu + Tyr213Pro + Leu216Thr |
| Ala199Pro + Thr212Glu + Ala214Thr |
| Thr207Gln + Pro209Asn + Thr219Ser |
| Ala199Thr + Tyr205Gln + Thr219Pro |
| Val204Met + Ala214Gly + Asn217Glu |
| Gly201Gln + Val204Pro + Thr210Glu |
| Tyr208Leu + Thr212Asp + Gly218Asn |
| Gly201Gln + Tyr205His + Thr210Glu |
| Gly201Pro + Ala214Gly + Thr219Ser |
| Gly203Asp + Tyr205Ala + Tyr208Ser |
| Thr212Pro + Asn217Ser + Gly218Asp |
| Tyr205Asp + Thr207Gly + Tyr208Leu |
| Gly201Pro + Ala202Glu + Leu216Ser |
| Ala202His + Tyr208Pro + Thr215Asp |
| Tyr208Thr + Thr212Glu + Thr219Ser |
| Val204Met + Pro209Gln + Leu216Asp |
| Thr207Pro + Thr210Asn + Tyr213Glu |
| Gly201Ser + Val204Gln + Asn211Asp |
| Gly203Gln + Tyr205Asn + Tyr213Ser |
| Ala199Thr + Thr210Asn + Tyr213Glu |
| Tyr208Ile + Pro209Ser + Thr212Pro |
| Tyr205Leu + Tyr208Thr + Ala214Glu |
| Pro200Gln + Val204Gln + Ala214Glu |
| Gly203Pro + Asn211Asp + Asn217Gln |
| Gly201Asn + Gly218Gln + Thr219Pro |
| Ala199Gln + Gly203Gln + Ala214Asp |
| Ala202Thr + Tyr205Cys + Tyr213Ile |
| Gly201Gln + Val204Cys + Asn211Glu |
| Tyr208Thr + Pro209Gly + Thr215Asp |
| Thr210Glu + Asn211Gln + Tyr213Leu |
| Val204Cys + Tyr208Pro + Thr219Pro |
| Ala202Asp + Gly203Asn + Gly218Asn |
| Ala199Asn + Val204Gly + Tyr205Pro |
| Gly203Pro + Val204Met + Tyr208His |
| Pro200Gly + Tyr213Pro + Leu216Cys |
| Val204Ala + Ala214His + Asn217Glu |
| Ala202Gln + Thr207Asn + Ala214Gly |
| Gly203Ser + Val204Gly + Tyr213Thr |
| Asn211Asp + Leu216Cys + Thr219Asn |
| Pro200Asn + Thr212Gly + Gly218Asn |
| Tyr205His + Tyr208Leu + Thr21%Gln |
| Gly203Ser + Tyr205His + Thr219Ser |
| Val204Asn + Thr212Pro + Thr215Asp |
| Thr212Ser + Thr215Ser + Leu216Ala |
| Tyr208Leu + Thr212Glu + Leu216Met |
| Thr207Asn + Tyr208Leu + Leu216Asp |
| Thr210Gly + Thr212Pro + Asn217Asp |
| Asn211Ser + Ala214Asn + Leu216Glu |
| Thr207Ser + Tyr208Thr + Ala214His |
| Ala202Asp + Val204Ser + Tyr208Thr |

TABLE 25

| Loop 6 - Quadruple Mutation Variants |
|---|
| Pro200Ser + Thr207Ser + Tyr213Cys + Gly218Gln |
| Ala202Gln + Tyr208Cys + Thr210Pro + Tyr213Asn |
| Gly203Asp + Tyr205Ile + Thr215Pro + Thr219Ser |
| Gly201Gln + Gly203Gln + Val204Asn + Thr207Asn |
| Pro200Ser + Gly201Ser + Ala202Ser + Pro209Glu |
| Gly201Ser + Thr207Pro + Thr215Asp + Thr219Pro |
| Ala202Gln + Asn211Gln + Tyr213Ser + Thr219Asn |
| Gly201Pro + Tyr213Ala + Ala214Pro + Thr215Ser |
| Ala199Gly + Pro200Gly + Ala202Glu + Gly218Pro |

TABLE 25-continued

| Loop 6 - Quadruple Mutation Variants |
|---|
| Tyr205Thr + Tyr208Met + Thr210Ser + Asn217Gln |
| Gly201Ser + Ala214Ser + Leu216Gly + Gly218Asn |
| Pro200Gln + Gly203Gln + Asn211Glu + Thr215Pro |
| Pro200Ser + Tyr208Leu + Asn211Ser + Gly218Asp |
| Ala199Asn + Pro209Asn + Thr210Ser + Tyr213Met |
| Ala199H15 + Gly203Ser + Pro209Asp + Thr212Gln |
| Tyr205Gly + Thr212Gly + Thr215Asn + Asn217Gln |
| Ala199Gln + Tyr208Thr + Thr210Asn + Tyr213Gln |
| Gly203Ser + Pro209Asp + Asn211Ser + Ala214Thr |
| Pro209Asn + Thr215Ser + Gly218Asp + Thr219Gly |
| Ala199Pro + Thr207Gln + Thr210Glu + Thr215Pro |
| Ala202Asn + Val204Gly + Thr207Gly + Thr212Asp |
| Val204Thr + Tyr208Leu + Asn211Ser + Asn217Asp |
| Pro200Gly + Tyr205Val + Leu216Asp + Thr219Gly |
| Pro200Gly + Tyr208Ser + Ala214Ser + Thr219Ser |
| Ala199Thr + Gly203Glu + Thr207Asn + Tyr213Cys |
| Pro200Gly + Tyr213Thr + Asn217Gln + Thr219Pro |
| Gly203Asn + Val204Thr + Thr207Asn + Thr210Ser |
| Ala202Gly + Thr207Gln + Pro209Gln + Thr210Asp |
| Ala199His + Gly201Gln + Tyr205Asp + Thr219Gln |
| Thr207Ser + Asn211Asp + Tyr213Thr + Leu216Ser |
| Ala199Ser + Thr210Glu + Asn211Gln + Leu216Ile |
| Gly201Ser + Gly203Ser + Thr212Pro + Ala214Glu |
| Pro200Gly + Gly201Gln + Gly203Gln + Leu216His |
| Ala199Pro + Gly201Gln + Gly203Pro + Thr212Glu |
| Ala199His + Gly201Asn + Val204Thr + Tyr208Ser |
| Val204Thr + Tyr208Ile + Ala214Glu + Thr219Pro |
| Ala199Ser + Tyr205Pro + Thr212Ser + Thr219Gln |
| Val204Met + Leu216Cys + Asn217Ser + Thr219Gly |
| Gly201Ser + Tyr205His + Pro209Gln + Thr219Ser |
| Pro200Gln + Pro209Asn + Asn211Asp + Thr219Gly |
| Val204Met + Thr210Gly + Thr212Asp + Ala214Ser |
| Pro200Gly + Thr207Asn + Asn211Glu + Leu216His |
| Tyr208Ala + Thr210Asp + Thr215Gln + Thr219Gly |
| Gly203Asn + Thr207Gln + Pro209Asp + Thr215Gly |
| Ala199Ser + Pro209Glu + Leu216His + Thr219Pro |
| Gly203Asp + Tyr205His + Tyr213Val + Ala214Thr |
| Pro200Asn + Thr212Asn + Leu216His + Gly218Pro |
| Ala199Ser + Pro209Gln + Thr215Gln + Asn217Glu |
| Gly203Asp + Thr207Pro + Thr212Gly + Ala214Gln |
| Gly201Pro + Gly203Gln + Thr207Pro + Ala214Asp |
| Val204Gln + Ala214Asp + Leu216Thr + Gly218Ser |
| Thr207Asn + Tyr208Pro + Pro209Asp + Tyr213Asn |
| Pro209Asp + Asn211Gln + Thr215Gln + Gly218Pro |
| Val204Gln + Asn211Ser + Asn217Gln + Gly218Pro |
| Gly201Gln + Ala202His + Asn217Asp + Gly218Gln |
| Val204Thr + Tyr208Leu + Ala214Pro + Gly218Asp |
| Gly201Ser + Thr207Pro + Thr212Ser + Thr215Pro |
| Ala202Gly + Val204Gly + Asn211Glu + Leu216Gly |
| Ala199Ser + Gly201Gln + Ala214Ser + Asn217Ser |
| Ala202Gln + Thr207Pro + Pro209Glu + Tyr213Pro |
| Ala199Thr + Ala202Ser + Val204Ala + Thr207Gln |
| Ala199His + Thr207Ser + Pro209Gln + Ala214Glu |
| Ala202His + Gly203Asp + Val204Pro + Gly218Pro |
| Ala202Asn + Gly203Glu + Val204Gln + Thr210Gln |
| Pro200Asn + Val204Gly + Tyr205Gln + Thr207Ser |
| Ala202Glu + Gly203Pro + Thr207Gly + Thr219Gly |
| Gly201Asn + Tyr208Val + Gly218Glu + Thr219Asn |
| Pro200Ser + Gly201Gln + Tyr205Asp + Thr219Gly |
| Pro200Ser + Thr207Gly + Ala214Pro + Thr215Asp |
| Val204Ala + Thr207Gln + Asn211Asp + Thr215Pro |
| Ala202Thr + Val204Asn + Thr207Ser + Pro209Asn |
| Ala202Asn + Val204Thr + Thr207Gly + Pro209Ser |
| Ala199Pro + Thr210Gln + Tyr213Cys + Ala214Thr |
| Ala199Pro + Pro200Gln + Ala214Glu + Thr215Asn |
| Pro200Ser + Val204Gln + Thr207Ser + Leu216Thr |
| Ala199Ser + Thr207Asn + Leu216Gln + Gly218Gln |
| Gly201Ser + Tyr208Ala + Ala214Ser + Leu216Gln |
| Val204Thr + Thr207Ser + Thr215Asp + Asn217Ser |
| Gly201Asn + Thr207Pro + Tyr213Met + Asn217Asp |
| Val204Ala + Asn211Gln + Thr215Glu + Gly218Ser |
| Pro200Gly + Pro209Ser + Thr212Gly + Asn217Glu |
| Ala199Pro + Tyr205Ile + Thr210Gly + Thr219Gly |
| Pro200Gly + Tyr205Ala + Thr212Pro + Tyr213Glu |
| Gly203Ser + Thr212Ser + Leu216Ala + Asn217Asp |
| Gly201Pro + Gly203Gln + Pro209Asp + Thr215Gly |
| Ala202His + Gly203Ser + Tyr208Cys + Gly218Asn |

TABLE 25-continued

| Loop 6 - Quadruple Mutation Variants |
|---|
| Ala199Pro + Ala202Gln + Val204Gly + Thr212Gly |
| Ala199Asn + Pro200Gly + Gly201Gln + Val204Gln |
| Gly201Asn + Gly203Pro + Pro209Ser + Thr215Asp |
| Gly201Asn + Thr210Ser + Tyr213Asp + Leu216Gln |
| Gly203Gln + Val204His + Gly218Gln + Thr219Gly |
| Gly201Asn + Tyr213Val + Ala214Glu + Thr219Gly |
| Ala202Glu + Thr207Ser + Thr215Ser + Thr219Ser |
| Gly203Glu + Thr212Asn + Asn217Gln + Thr219Ser |
| Gly203Ser + Thr210Asn + Thr212Glu + Leu216Met |
| Val204Ala + Asn211Asp + Tyr213Met + Leu216Ile |
| Thr207Pro + Tyr208Asn + Tyr213Pro + Leu216Gln |
| Gly201Gln + Gly203Glu + Tyr213Met + Ala214Thr |
| Pro200Gln + Thr212Ser + Tyr213Pro + Thr215Asn |
| Pro200Asn + Val204Asn + Asn211Glu + Tyr213Gln |
| Pro209Ser + Asn211Gln + Asn217Asp + Thr219Asn |
| Pro200Gly + Gly203Asn + Tyr205Val + Tyr208His |
| Ala202Glu + Gly203Pro + Thr212Ser + Gly218Asn |
| Ala202Gln + Val204Gly + Pro209Asp + Thr215Asn |
| Tyr208Ala + Asn211Glu + Thr215Gln + Thr219Ser |
| Tyr208Gln + Tyr213Ala + Leu216Thr + Asn217Asp |
| Ala199Thr + Pro200Gln + Gly201Asn + Asn211Asp |
| Ala199Thr + Pro200Ser + Gly201Asn + Tyr208Gly |
| Val204Ser + Thr207Gly + Thr212Asp + Gly218Gln |
| Pro200Asn + Ala214His + Thr215Gly + Thr219Asn |
| Thr207Ser + Tyr208Ser + Leu216Asn + Gly218Asp |
| Pro200Gly + Gly203Glu + Thr212Gly + Gly218Asn |
| Pro200Ser + Gly201Ser + Tyr208Gln + Thr219Asn |
| Pro200Asn + Gly201Pro + Asn211Glu + Asn217Gln |
| Val204Met + Thr207Asn + Asn217Gln + Thr219Gly |
| Pro200Gly + Gly201Pro + Thr210Glu + Leu216Thr |
| Pro200Asn + Gly203Pro + Val204Gln + Thr219Gln |
| Ala202Asp + Pro209Asn + Tyr213Cys + Leu216Ala |
| Pro200Gln + Gly201Ser + Ala202Glu + Tyr205Gly |
| Thr207Pro + Tyr208Asn + Asn211Ser + Tyr213Ser |
| Ala202Ser + Val204Gly + Thr207Asn + Tyr213Gln |
| Gly201Ser + Gly203Gln + Thr212Ser + Leu216Asp |
| Ala199Thr + Tyr205Met + Tyr208Val + Ala214Thr |
| Gly201Gln + Ala202Thr + Val204Cys + Tyr205Leu |
| Pro200Gln + Tyr205Cys + Thr210Glu + Thr212Asn |
| Pro200Gln + Tyr213Pro + Asn217Glu + Gly218Asn |
| Tyr208Pro + Tyr213His + Ala214Glu + Asn217Ser |
| Pro200Ser + Ala202Gly + Tyr208Val + Thr212Gln |
| Pro200Asn + Tyr205Gly + Pro209Gln + Asn211Ser |
| Tyr205Gly + Asn211Gln + Thr215Gly + Thr219Gly |
| Gly201Asn + Gly203Asn + Thr212Asp + Ala214Gly |
| Val204Pro + Pro209Gly + Thr210Glu + Leu216Pro |
| Tyr205Pro + Tyr213Ala + Gly218Asn + Thr219Pro |
| Ala199Gln + Val204His + Asn211Asp + Thr215Gly |
| Pro209Gln + Thr215Gln + Asn217Asp + Thr219Asn |
| Gly201Asn + Asn211Glu + Tyr213Ile + Asn217Gln |
| Gly201Ser + Thr207Asn + Tyr213Glu + Ala214Gly |
| Ala199Ser + Thr210Asn + Thr215Gln + Gly218Pro |
| Val204Asn + Tyr205Thr + Tyr208Met + Thr215Pro |
| Val204Gly + Tyr205Val + Thr210Asp + Thr215Gln |

TABLE 25-continued

| Loop 6 - Quadruple Mutation Variants |
|---|
| Ala202Ser + Val204Ala + Leu216Ser + Asn217Asp |
| Asn211Asp + Thr212Ser + Ala214Asn + Thr215Gly |
| Ala199His + Tyr208Leu + Asn217Gln + Thr219Asn |
| Ala202Pro + Tyr208Cys + Leu216Ala + Thr219Asn |
| Ala199Gly + Pro200Gly + Gly201Asn + Ala202Asp |
| Pro200Ser + Ala202Gln + Thr210Gln + Leu216Asp |
| Gly201Gln + Gly203Glu + Val204Gly + Leu216Asn |
| Val204Pro + Tyr208Thr + Pro209Ser + Asn211Glu |
| Tyr208Thr + Thr215Ser + Leu216Glu + Gly218Gln |
| Gly201Asn + Tyr205Ser + Tyr213Asp + Gly218Pro |
| Ala202Gln + Gly203Gln + Tyr205Ile + Asn217Glu |
| Thr212Ser + Tyr213Glu + Thr215Ser + Leu216Cys |
| Gly203Glu + Thr212Pro + Tyr213Leu + Ala214Ser |
| Pro200Ser + Gly201Gln + Ala202Asp + Thr210Asn |
| Val204Gln + Thr210Asp + Tyr213Ser + Ala214Thr |
| Ala199Pro + Gly201Ser + Val204Gly + Asn217Gln |
| Pro200Asn + Ala202Ser + Thr207Gln + Tyr208Met |
| Pro200Gln + Gly203Pro + Ala214Glu + Gly218Pro |
| Pro200Ser + Thr207Gly + Gly218Asn + Thr219Gly |
| Gly203Ser + Thr207Gln + Thr210Gln + Asn217Ser |
| Gly201Ser + Thr210Glu + Asn211Glu + Thr219Asn |
| Thr207Gly + Thr210Asp + Asn211Asp + Gly218Pro |
| Pro200Asn + Thr210Glu + Asn211Glu + Thr219Pro |
| Val204Ser + Thr210Asp + Asn211Glu + Thr219Asn |
| Ala199Ser + Tyr205Thr + Ala214Asp + Thr215Asp |
| Pro200Asn + Thr215Asp + Leu216Asp + Thr219Ser |
| Tyr208Asn + Tyr213His + Thr215Asp + Leu216Asp |
| Gly201Ser + Asn211Glu + Thr212Asp + Ala214His |
| Val200Thr + Asn211Glu + Thr212Asp + Ala214Pro |
| Pro200Gly + Thr212Gly + Asn217Glu + Gly218Asp |
| Thr207Gln + Ala214Gly + Asn217Glu + Gly218Glu |
| Thr207Asn + Pro209Gly + Asn217Asp + Gly218Glu |
| Tyr213Thr + Leu216Val + Asn217Glu + Gly218Glu |
| Ala199Thr + Ala202Asp + Gly203Glu + Gly218Pro |
| Val204His + Tyr205Asp + Thr212Gly + Thr215Glu |
| Pro200Ser + Tyr205Glu + Thr215Glu + Leu216Cys |
| Ala202Glu + Gly203Asp + Asn217Glu + Thr219Pro |
| Pro209Glu + Asn211Asp + Leu216His + Thr219Pro |
| Thr207Pro + Tyr208Ser + Pro209Glu + Asn211Asp |
| Val201Thr + Pro209Asp + Asn211Asp + Thr212Pro |

TABLE 26

| Loop 6 - Quintuple Substitution Variants |
|---|
| Pro200Asn + Ala202Asn + Val204Gly + Asn211Asp + Thr219Gly |
| Pro200Gly + Gly201Pro + Pro209Glu + Asn211Ser + Thr212Gly |
| Pro200Ser + Asn211Gln + Ala214Gly + Asn217Glu + Thr219Asn |
| Gly201Asn + Gly203Ser + Thr207Ser + Tyr213Pro + Thr215Gly |
| Pro200Ser + Tyr205Pro + Tyr208Leu + Asn211Ser + Gly218Asp |
| Pro200Gly + Pro209Gly + Thr212Asp + Thr215Asn + Leu216Thr |
| Gly201Gln + Ala202Pro + Thr212Asn + Ala214Gln + Thr215Glu |
| Tyr205Pro + Tyr208Ser + Thr215Asp + Asn217Ser + Thr219Gln |
| Pro200Gly + Thr207Gly + Thr212Gln + Ala214Asn + Thr215Asn |
| Tyr205Ile + Thr207Pro + Tyr208Ala + Ala214Gln + Leu216Asn |
| Gly203Pro + Val204His + Thr207Gln + Tyr213Glu + Thr219Ser |
| Tyr205Met + Thr207Gly + Pro209Glu + Thr215Ser + Thr219Asn |
| Pro200Gly + Thr207Gln + Asn211Asp + Thr215Pro + Gly2183er |
| Ala202His + Gly203Pro + Asn211Glu + Tyr213Gly + Thr219Gln |
| Ala199Gly + Tyr208Val + Thr210Glu + Tyr213Leu + Thr219Gln |

TABLE 26-continued

| Loop 6 - Quintuple Substitution Variants |
|---|
| Ala199His + Pro200Gln + Val204Cys + Thr21SAsn + Asn217Asp |
| Ala199Gly + Pro200Gln + Tyr205Ile + Thr210Gly + Thr215Asp |
| Tyr208Met + Pro209Asn + Thr210Ser + Asn211Ser + Ala214Glu |
| Pro200Asn + Gly201Gln + Pro209Asn + Leu216Ala + Gly218Glu |
| Gly203Gln + Pro209Gly + Thr210Asn + Asn211Ser + Tyr213Val |
| Gly201Pro + Thr207Asn + Thr210Gln + Tyr213His + Ala214Thr |
| Pro200Gln + Gly201Ser + Val204Cys + Thr210Asn + Asn217Glu |
| Ala199Pro + Gly203Gln + Tyr205Val + Asn211Asp + Thr215Asn |
| Ala202Asn + Val204Ser + Asn211Ser + Tyr213Asn + Leu216Asp |
| Thr210Glu + Thr212Ser + Ala214Gly + Thr215Gln + Leu216Ile |
| Ala199Asn + Ala202Asn + Val204Gly + Tyr205Met + Thr215Asn |
| Thr210Gln + Thr212Pro + Tyr213Thr + Leu216Gln + Asn217Gln |
| Ala199Gln + Pro200Gly + Ala202Pro + Thr212Gln + Thr215Ser |
| Ala202Gln + Thr207Asn + Thr210Gln + Asn211Glu + Ala214Gly |
| Gly203Gln + Thr207Asn + Pro209Gly + Tyr213Asn + Gly218Asp |
| Val204Cys + Tyr205Thr + Thr207Asn + Leu216Thr + Thr219Gln |
| Gly201Gln + Val204His + Tyr2083er + Thr212Ser + Thr215Gly |
| Pro200Gln + Ala202Asp + Tyr208Gly + Thr212Ser + Leu216Thr |
| Ala199Ser + Gly201Ser + Asn211Asp + Ala214Thr + Thr219Gly |
| Ala202Gln + Val204Ser + Tyr208Leu + Pro209Asp + Tyr213Gln |
| Ala199Ser + Tyr205Ala + Thr210Glu + Thr212Gly + Leu216Ala |
| Ala199His + Ala202Glu + Thr210Gly + Asn211Gln + Tyr213Pro |
| Ala199Ser + Gly203Glu + Tyr213Met + Leu216Ala + Gly218Ser |
| Gly201Gln + Gly203Ser + Thr207Asn + Gly218Pro + Thr219Pro |
| Ala199Gly + Pro209Asp + Thr212Ser + Leu216Met + Gly218Ser |
| Pro200Ser + Tyr205Ala + Asn211Ser + Thr212Glu + Thr215Pro |
| Pro209Glu + Thr212Gly + Ala214Thr + Leu216Asn + Thr219Pro |
| Gly203Asn + Tyr205Gln + Pro209Asn + Gly218Asn + Thr219Ser |
| Gly201Asn + Ala202Gln + Gly203Pro + Thr210Gly + Asn217Ser |
| Pro200Ser + Gly201Pro + Tyr208Val + Thr210Gly + Thr212Asn |
| Ala199His + Gly201Gln + Tyr205Glu + Leu216Met + Gly218Asn |
| Tyr205Ser + Asn211Gln + Thr212Asp + Thr21SSer + Thr219Gly |
| Ala199Thr + Gly201Gln + Ala202Thr + Gly203Glu + Tyr213Pro |
| Ala199Gln + Val204Asn + Thr207Asn + Tyr208Gly + Gly218ser |
| Ala199His + Gly203Pro + Thr207Gln + Asn211Asp + Ala214Asn |
| Ala202Ser + Gly203Pro + Tyr205Ser + Thr210Glu + Leu216Asn |
| Thr207Gly + Tyr208Gly + Thr212Asp + Leu216Pro + Thr219Asn |
| Ala202Asp + Val204Thr + Tyr208Ile + Thr212Asn + Gly218Ser |
| Gly203Gln + Val204Ala + Tyr205Pro + Asn211Gln + Thr215Gln |
| Pro200Ser + Gly203Pro + Thr212Pro + Leu216Met + Gly218Glu |
| Ala199Gly + Gly201Gln + Thr207Ser + Leu216Cys + Asn217Glu |
| Ala199Thr + Tyr205Met + Tyr208Val + Ala214Thr + Leu216Ile |
| Ala202Asp + Tyr205Pro + Thr207Ser + Tyr208Thr + Thr210Pro |
| Ala199Gln + Pro200Gln + Thr207Asn + Leu216Val + Gly218Ser |
| Gly201Ser + Tyr208Met + Asn211Asp + Thr212Ser + Thr219Gly |
| Gly203Ser + Thr207Pro + Asn211Ser + Asn217Asp + Gly218Gln |
| Gly201Pro + Gly203Asp + Tyr208Asn + Thr212Ser + Thr215Asn |
| Ala199Pro + Pro200Ser + Tyr205Asp + Thr212Pro + Leu216Val |
| Tyr208Ala + Tyr213Ile + Ala214Gly + Thr215Pro + Asn217GIn |
| Ala199Ser + Pro200Gly + Gly203Asp + Leu216His + Asn217Ser |
| Gly201Pro + Gly203Ser + Val204Asn + Leu216Ala + Asn217Asp |
| Val204Gln + Tyr208His + Asn211Asp + Tyr213His + Leu216Thr |
| Pro200Gly + Gly201Asn + Val204Gln + TYr208Cys + Thr210Pro |
| Ala202Asn + Tyr205Gln + Pro209Glu + Thr210Gly + Gly218Asn |
| Pro200Gly + Thr207Pro + Tyr208Met + Leu216Val + Asn217Glu |
| Gly201Asn + Tyr205Gln + Thr212Asp + Thr215Pro + Asn217Gln |
| Gly203Glu + Tyr208Ile + Asn211Gln + Thr215Ser + Thr219Gly |
| Gly201Asn + Ala202Ser + Gly203Gln + Asn211Gln + Ala214Asn |
| Pro200Gly + Val204Asn + Pro209Gln + Thr210Pro + Thr219Ser |
| Tyr208Leu + Pro209Asn + Thr210Gln + Thr215Asn + Gly218Asn |
| Ala202Ser + Val204Cys + Thr210Asn + Ala214Glu + Thr215Gly |
| Pro200Asn + Gly203Gln + Tyr208ser + Pro209Gln + Gly218Pro |
| Ala202Thr + Gly203Asp + Tyr205Leu + Thr212Gly + Tyr213Gln |
| Gly203Gln + Val204Pro + Thr210Asp + Gly218Gln + Thr219Gly |
| Tyr208His + Thr210Ser + Asn211Asp + Leu216Asn + Asn217Gln |
| Gly201Gln + Tyr205His + Thr210Glu + Tyr213Ile + Leu216Ala |
| Pro200Asn + Gly201Ser + Ala202Glu + Gly203Gln + Thr219Ser |
| Ala199Gln + Gly201Asn + Ala202Asp + Thr212Asn + Tyr213Thr |
| Ala199Pro + Val204Ser + Tyr213His + Asn217Asp + Gly218Gln |
| Pro200Asn + Gly201Ser + Ala202Pro + Thr207Ser + Ala214Thr |
| Ala199Asn + Gly201Pro + Gly203Asp + Tyr213Cys + Gly218Gln |
| Gly201Gln + Gly203Asn + Val204Thr + Thr210Ser + Thr212Gln |
| Gly201Asn + Ala202Pro + Thr210Gln + Asn211Gln + Thr215Gln |
| Pro200Asn + Gly203Glu + Tyr205Val + Thr207Pro + Tyr208Ser |
| Ala199Gln + Gly201Ser + Ala202Pro + Thr207Pro + Asn217Glu |
| Pro200Gln + Tyr205Met + Thr212Pro + Leu216Glu + Thr219Ser |
| Ala199Pro + Pro200Gln + Ala202Gly + Thr207Gln + Asn217Glu |

TABLE 26-continued

| Loop 6 - Quintuple Substitution Variants |
| --- |
| Tyr208Thr + Asn211Ser + Tyr213Gln + Leu216Gly + Thr219Pro |
| Gly203Ser + Val204Thr + Tyr208Ala + Tyr213Pro + Thr219Asn |
| Gly201Asn + Gly203Pro + Val204Ala + Asn211Ser + Thr219Gly |
| Gly203Glu + Thr207Ser + Tyr208Ser + Thr215Asn + Leu216Cys |
| Gly201Asn + Tyr208Leu + Asn211Glu + Leu216Gly + Asn217Ser |
| Gly201Pro + Tyr208Val + Thr210Pro + Leu216Gln + Gly218Asn |
| Pro200Asn + Ala202Thr + Thr207Ser + Thr212ser + Ala214Asp |
| Gly203Glu + Val204Asn + Thr210Pro + Ala214His + Gly218Asn |
| Gly201Ser + Val204Met + Ala214Gly + Leu216Ser + Thr219Ser |
| Pro200Gly + Tyr208Val + Tyr213His + Leu216Ala + Asn217Glu |
| Thr212Glu + Tyr213Asn + Ala214Thr + Leu216Gln + Gly218Pro |
| Gly203Pro + Val204Asn + Tyr208Cys + Asn217Glu + Thr219Ser |
| Pro200Asn + Gly201Pro + Val204Thr + Leu216Asp + Asn217Gln |
| Tyr205Met + Tyr208Asn + Pro209Asn + Tyr213Ile + Ala214His |
| Gly201Gln + Gly203Pro + Tyr205Cys + Thr210Gln + Asn217Asp |
| Ala202Asn + Gly203Asp + Thr207Gly + Asn211Ser + Thr219Pro |
| Pro200Gly + Gly201Ser + Val204Cys + Thr207Gly + Gly218Asp |
| Pro200Ser + Gly203Pro + Tyr208Pro + Thr210Asn + Asn211Glu |
| Pro200Gly + Gly201Gln + Tyr205Leu + Pro209Asn + Ala214His |
| Tyr205Ser + Thr207Gln + Tyr208Ser + Thr212Ser + Thr219Asn |
| Ala202Gly + Asn211Asp + Thr212Gln + Ala214Thr + Leu216His |
| Ala202Pro + Val204Ala + Pro209Gln + Asn211Ser + Thr212Glu |
| Ala202Gly + Thr207Pro + Pro209Gly + Asn217Ser + Gly218Asp |
| Gly201Gln + Pro209Asn + Thr215Ser + Leu216Thr + Thr219Gly |
| Val204Thr + Tyr208Val + Thr215Asn + Asn217Glu + Gly218Asn |
| Tyr205Gln + Tyr213Pro + Thr215Ser + Leu216Gly + Gly218Gln |
| Gly203Asn + Thr207Ser + Thr210Asn + Asn211Asp + Leu216Met |
| Tyr208His + Pro209Ser + Leu216Gly + Asn217Glu + Gly218Gln |
| Thr207Ser + Pro209Gly + Asn211Glu + Thr215Ser + Leu216Ile |
| Ala199Gly + Ala202Glu + Thr207Pro + Tyr213Val + Ala214Gly |
| Ala199His + Pro200Gly + Gly201Ser + Gly218Asp + Thr219Pro |
| Ala202Glu + Tyr208Ala + Thr212Ser + Tyr213His + Thr219Asn |
| Ala199Thr + Val204Thr + Thr207Asn + Thr210Asn + Tyr213Glu |
| Tyr208Gln + Pro209Gly + Ala214Asn + Thr215Glu + Gly218Asn |
| Tyr208Thr + Tyr213Val + Thr21SAsp + Leu216Val + Gly218Gln |
| Thr207Pro + Pro209Ser + Thr210Glu + Asn217Ser + Thr219Pro |
| Pro200Ser + Gly201Gln + Tyr205Ile + Pro209Gly + Thr219Gln |
| Val204Met + Thr207Pro + Tyr208Gln + Pro209Asn + Thr215Asp |
| Val204Ala + Pro209Asn + Thr210Gly + Tyr213Asp + Ala214Pro |
| Pro200Ser + Tyr208His + Tyr213Glu + Leu216Cys + Thr219Ser |
| Gly201Gln + Ala202Asp + Tyr205Ala + Leu216Thr + Asn217Gln |
| Ala199Gly + Gly201Asn + Val204Gly + Ala214Asn + Thr219Pro |
| Pro200Asn + Ala202Asn + Gly203Gln + Tyr208Asn + Asn217Asp |
| Val204Gly + Tyr205Asp + Asn211Gln + Tyr213Met + Ala214Gly |
| Gly201Asn + Thr207Gln + Pro209Gln + Ala214Asp + Gly218Pro |
| Pro200Gly + Tyr208Ser + Asn211Asp + Tyr213Ser + Thr219Gly |
| Ala202Thr + Val204Pro + Thr210Ser + Asn211Asp + Leu216Thr |
| Gly203Glu + Val204Met + Tyr205His + Asn211Gln + Thr219Gln |
| Gly201Gln + Ala202Gly + Val204Ser + Thr207Gln + Asn211Glu |
| Gly203Asn + Tyr208Ala + Pro209Asp + Thr212Asn + Thr215Gln |
| Ala199Gln + Pro200Asn + Tyr205Met + Asn211Asp + Thr219Gln |
| Val204Gln + Tyr208Val + Thr210Pro + Asn211Gln + Leu216Asp |
| Pro200Asn + Val204Pro + Tyr205Gly + Thr210Pro + Ala214Gly |
| Gly201Asn + Tyr205Met + Tyr213Cys + Leu216Ile + Thr219Asn |
| Ala199Gly + Gly201Asn + Gly203Gln + Val204Thr + Pro209Glu |
| Ala199His + Ala202Gly + Pro209Asp + Thr210Asp + Gly218Ser |
| Gly201Gln + Tyr208Ser + Pro209Asp + Thr210Glu + Gly218Ser |
| Ala199Asn + Pro200Ser + Thr212Asn + Ala214Asp + Thr215Glu |
| Ala199His + Pro200Ser + Thr215Gly + Asn217Asp + Gly218Glu |
| Tyr205Thr + Thr207Ser + Asn217Glu + Gly218Asp + Thr219Gly |
| Ala202Thr + Tyr205Glu + Tyr208Thr + Thr215Glu + Leu216Gln |
| Tyr205Asp + Thr212Gly + Thr215Glu + Asn217Ser + Gly218Ser |
| Pro200Gly + Ala202Glu + Val204Ala + Tyr208Leu + Asn217Asp |
| Pro200Gln + Ala202Asp + Tyr205Gly + Tyr213Ile + Asn217Asp |
| Pro209Asp + Asn211Asp + Tyr213Thr + Leu216Cys + Thr219Asn |
| Ala202Asn + Val204His + Pro209Glu + Asn211Glu + Thr219Asn |
| Pro200Ser + Ala202Asp + Val204Gln + Leu216Glu + Asn217Glu |
| Ala199Gly + Pro200Gln + Ala202Gln + Thr210Glu + Thr212Asp |
| Gly203Asp + Pro209Gly + Tyr213His + Asn217Asp + Gly218Ser |
| Gly203Asp + Val204Thr + Tyr208Ala + Tyr213Gln + Thr215Asp |
| Tyr205Pro + Thr207Gly + Pro209Glu + Thr212Asp + Gly218Ser |
| Ala199His + Ala202Glu + Gly203Gln + Asn211Gln + Gly218Asp |
| Ala199Asn + Ala202Glu + Thr207Gln + Thr212Gln + Gly218Asp |
| Ala202Asp + Gly203Asn + Tyr213Val + Leu216Ile + Gly218Glu |
| Pro200Gly + Ala202Thr + Tyr208Met + Ala214Glu + Leu216Asp |
| Gly203Glu + Thr207Gln + Thr212Ser + Ala214Glu + Thr215Glu |
| Val204His + Tyr205Asp + Tyr208Met + Tyr213Glu + Asn217Gln |

TABLE 26-continued

| Loop 6 - Quintuple Substitution Variants |
|---|
| Tyr205Gly + Tyr213Ile + Leu216Glu + Gly218Glu + Thr219Gly |
| Val204Ser + Asn211Gln + Tyr213Thr + Thr215Glu + Asn217Glu |
| Tyr208Leu + Thr210Gly + Thr212Gln + Tyr213Glu + Thr215Glu |
| Ala202Glu + Tyr205Glu + Thr210Gly + Asn211Gln + Leu216Asp |
| Pro200Asn + Thr210Ser + Thr212Asp + Tyr213Glu + Thr215Asp |
| Ala199Thr + Thr207Ser + Thr210Asp + Thr212Asn + Tyr213Asp |
| Ala202Glu + Val204Pro + Tyr205Thr + Tyr208His + Thr215Glu |
| Gly203Glu + Tyr208Ile + Thr210Gln + Tyr213Gly + Gly218Asp |
| Tyr208Gln + Pro209Glu + Tyr213Thr + Ala214Glu + Thr219Gln |
| Tyr205Asp + Thr210Ser + Thr215Gln + Asn217Asp + Gly218Glu |
| Gly201Asn + Tyr205Glu + Tyr208Leu + Asn217Asp + Gly218Glu |

TABLE 27

| Loop 6 Sextuple Substitution Variants |
|---|
| Pro200Gly + Gly203Asp + Thr210Gln + Thr212Asn + Ala214His + Leu216Asn |
| Pro200Gly + Thr207Asn + Thr210Gln + Thr212Pro + Thr215Asp + Gly218Pro |
| Pro200Gln + Gly203Ser + Thr207Asn + Tyr208Ile + Pro209Ser + Thr210Glu |
| Gly203Pro + Tyr205Gly + Tyr208Gly + Asn211Glu + Tyr213Pro + Gly218Gln |
| Ala199His + Gly201Gln + Gly203Gln + Thr212Pro + Leu216Ile + Gly218Asp |
| Val204Met + Tyr205Thr + Thr207Ser + Tyr213His + Ala214Glu + Thr219Asn |
| Ala199Thr + Gly201Ser + Gly203Asp + Thr207Pro + Thr210Gly + Thr212Pro |
| Pro200Gly + Tyr208Ile + Asn211Glu + Tyr213Ser + Ala214Ser + Thr215Gln |
| Ala199Thr + Gly201Gln + Pro209Gln + Thr212Asn + Tyr213His + Thr219Gly |
| Ala199Gly + Pro200Gly + Gly201Pro + Val204Cys + Thr207Gly + Thr215Gln |
| Ala199Gly + Pro200Ser + Thr207Pro + Leu216Ala + Asn217Glu + Gly218Asn |
| Pro200Gln + Val204Met + Asn211Gln + Ala214Gln + Thr215Gln + Leu216Asp |
| Ala199Ser + Gly203Asn + Thr207Gln + Pro209Asp + Thr215Gly + Leu216His |
| Gly201Pro + Tyr208Ile + Thr210Glu + Ala214Gly + Leu216Val + Thr219Ser |
| Ala199Gln + Ala202Asn + Pro209Asn + Tyr213Asn + Thr215Gln + Gly218Ser |
| Pro200Gln + Gly203Pro + Val204Gly + Thr212Pro + Ala214Pro + Thr215Glu |
| Val204Met + Tyr208Asn + Tyr213Asp + Ala214His + Thr215Gln + Leu216Thr |
| Ala199Gly + Pro200Asn + Ala202Thr + Val204Ser + Gly218Glu + Thr219Pro |
| Ala199Ser + Gly201Pro + Gly203Asn + Thr207Ser + Thr212Gly + Thr219Gln |
| Ala199His + Tyr205Asn + Tyr208Ala + Asn211Gln + Tyr213Asn + Asn217Asp |
| Tyr205Asp + Thr207Gly + Pro209Asn + Thr210Pro + Tyr213Ser + Leu216Ser |
| Gly201Gln + Ala202His + Thr207Gly + Pro209Glu + Thr210Ser + Ala214Gly |
| Pro200Asn + Val204Gln + Tyr205Cys + Thr207Gln + Thr212Gln + Thr219Ser |
| Pro200Ser + Tyr205Asp + Thr210Ser + Thr215Gln + Leu216Asn + Asn217Gln |
| Ala202His + Tyr205Thr + Tyr208His + Thr212Asp + Tyr213Ile + Gly218Gln |
| Gly201Asn + Pro209Glu + Asn211Gln + Thr212Ser + Tyr213Gln + Thr219Gln |
| Ala199Pro + Pro200Asn + Tyr205Val + Thr210Glu + Leu216Gly + Gly218Asn |
| Ala199Gln + Pro200Gln + Val204Thr + Tyr208Thr + Leu216Met + Asn217Asp |
| Val204Met + Thr210Ser + Thr212Asn + Tyr213Cys + Thr215Asn + Thr219Pro |
| Ala199Gln + Gly201Pro + Ala202His + Thr207Asn + Leu216Val + Gly218Ser |
| Ala199Thr + Gly203Ser + Tyr208Val + Tyr208Val + Thr210Pro + Ala214Glu |
| Ala199Asn + Pro200Gln + Tyr205Met + Tyr208Cys + Thr212Glu + Ala214Gln |
| Ala202Ser + Thr207Gln + Thr210Glu + Asn211Gln + Tyr213Ile + Leu216Ala |
| Ala199Gly + Pro200Gly + Thr207Pro + Tyr213Ser + Leu216Asn + Asn217Ser |
| Gly201Ser + Ala202Gly + Tyr205Asn + Pro209Gly + Thr210Asn + Asn211Gln |
| Gly201Ser + Ala202Gly + Gly203Asp + Thr207Asn + Asn211Gln + Thr215Gly |
| Val204Gln + Tyr205His + Thr207Gln + Tyr208His + Asn211Asp + Leu216Thr |
| Ala202Glu + Val204Ser + Tyr205His + Tyr208Ile + Ala214Gln + Leu216Gln |
| Ala199Gly + Gly203Glu + Tyr205Val + Tyr213His + Ala214Asn + Asn217Ser |
| Pro200Ser + Gly201Ser + Tyr205Asn + Thr210Ser + Thr212Glu + Gly218Asn |
| Ala199Thr + Gly201Gln + Pro209Ser + Thr210Asp + Thr215Gly + Leu216Ser |
| Gly201Pro + Tyr205Thr + Thr207Ser + Tyr213His + Gly218Asp + Thr219Gly |
| Gly203Glu + Tyr208Ile + Asn211Gln + Ala214Gln + Thr215Ser + Thr219Gly |
| Ala199Gly + Gly203Gln + Thr207Gln + Asn211Asp + Thr215Pro + Thr219Gln |
| Ala199Pro + Thr207Gly + Pro209Glu + Thr210Ser + Thr212Gly + Leu216Val |
| Val204Asn + Thr207Pro + Asn211Gln + Ala214His + Asn217Glu + Gly218Gln |
| Ala202Glu + Gly203Ser + Val204Cys + Thr210Gly + Asn211Gln + Ala214Pro |
| Ala199Asn + Ala202Gln + Gly203Asn + Thr207Pro + Thr212Pro + Thr215Pro |
| Ala199Thr + Gly203Gln + Thr207Asn + Tyr208Asn + Tyr213Glu + Thr215Gly |
| Pro200Ser + Ala202Asn + Val204Ser + Tyr205Ile + Thr207Gln + Asn211Asp |
| Pro200Gln + Val204Pro + Tyr208Pro + Pro209Asn + Leu216Glu + Thr219Ser |
| Pro200Gly + Ala202Gln + Tyr205Thr + Thr210Gln + Asn211Gln + Ala214Asp |
| Gly203Asn + Pro209Ser + Thr210Glu + Ala214Pro + Gly218Asn + Thr219Asn |
| Pro200Ser + Gly201Pro + Ala202Thr + Ala214Gly + Leu216Asp + Thr219Ser |
| Ala202Ser + Tyr205His + Thr212Gln + Thr215Glu + Asn217Gln + Thr219Ser |
| Ala202Gly + Thr207Asn + Pro209Gly + Thr210Pro + Tyr213Met + Thr215Gly |
| Pro200Gln + Val204Ser + Thr207Ser + Tyr208Cys + Thr212Asn + Gly218Gln |
| Ala199Pro + Pro200Gly + Ala202Thr + Thr207Gly + Thr212Glu + Thr219Ser |

TABLE 27-continued

| Loop 6 Sextuple Substitution Variants |
| --- |
| Ala199His + Gly203Gln + Tyr205Gly + Thr207Ser + Thr210Asn + Thr212Ser |
| Gly203Glu + Val204Asn + Tyr205Pro + Thr210Pro + Ala214His + Cly218Asn |
| Pro200Gln + Val204Ala + Tyr208Cys + Ala214Gln + Leu216Val + Asn217Glu |
| Gly201Gln + Ala202Asp + Tyr205Gly + Thr210Gly + Leu216Val + Gly218Ser |
| Pro200Asn + Gly201Ser + Thr207Gln + Thr212Asp + Tyr213Gly + Thr215Pro |
| Ala202Asn + Gly203Asp + Val204Cys + Thr207Gly + Asn211Ser + Thr219Pro |
| Ala199Ser + Gly201Ser + Tyr205Ser + Thr207Asn + Tyr213Val + Leu216Ala |
| Pro200Gln + Tyr205Ser + Thr207Gln + Tyr208Ser + Thr212Ser + Thr219Asn |
| Pro200Asn + Ala202Gly + Asn211Asp + Thr212Gln + Ala214Thr + Leu216His |
| Gly201Pro + Gly203Glu + Val204Met + Pro209Gly + Asn217Ser + Thr219Ser |
| Pro200Gly + Gly201Pro + Tyr208Asn + Thr212Ser + Tyr213Leu + Ala214Asn |
| Ala199Ser + Gly201Pro + Gly203Asn + Asn211Asp + Leu216Cys + Thr219Asn |
| Gly203Pro + Val204Gly + Thr207Gln + Leu216Gly + Asn217Ser + Gly218Asn |
| Val204Gln + Thr207Gln + Thr210Gly + Asn211Glu + Ala214Gly + Thr219Pro |
| Ala202His + Tyr208Asn + Thr210Asn + Leu216Asn + Gly218Pro + Thr219Gly |
| Gly201Pro + Gly203Asp + Tyr205Met + Thr207Ser + Tyr213Gln + Asn217Gln |
| Gly201Ser + Ala202Ser + Thr207Asn + Tyr208Gly + Asn211Ser + Leu216Pro |
| Ala202Gln + Gly203Asn + Val204Met + Tyr208Ser + Thr212Gln + Leu216A3p |
| Ala199Asn + Ala202Thr + Pro209Glu + Thr210Pro + Asn217Ser + Thr219Gly |
| Gly203Asn + Tyr208Ser + Asn211Glu + Ala214His + Leu216Met + Gly218Pro |
| Ala199Ser + Pro200Gln + Val204A3n + Tyr208Asn + Thr215Asp + Thr219Gln |
| Gly201Asn + Thr207Asn + Tyr208Gln + Pro209Asn + Asn211Asp + Leu216Cys |
| Pro206Ser + Gly203Asn + Thr207Gln + Thr212Gln + Asn217Asp + Gly218Asn |
| Val204His + Tyr205Ala + Thr210Asn + Thr215Pro + Leu216Val + A3n217Glu |
| Ala199Pro + Gly201Asn + Ala202Asp + Val204Thr + Thr210Gly + Thr219Ser |
| Pro200Asn + Ala202Gly + Gly203Glu + Thr207Gln + Tyr208His + Asn211Gln |
| Pro200Gly + Ala202Asn + Gly203Asn + Thr212Asp + Ala214Ser + Leu216Pro |
| Ala199Gly + Gly201Pro + Thr207Gly + Pro209Asp + Thr215Asn + Gly218Ser |
| Gly203Asn + Tyr205Thr + Asn211Asp + Ala214Gly + Gly218Asn + Thr219Gly |
| Gly201Pro + Val204His + Tyr208Cys + Thr215Glu + Leu216Asn + Gly218Pro |
| Val204Ala + Pro209Asn + Thr210Asp + Tyr213Leu + Leu216Ser + Thr219Gly |
| Ala202Asp + Tyr205Val + Thr207Asn + Thr210Asn + Tyr213Pro + Ala214Asn |
| Gly201Ser + Thr207Gly + Thr212Pro + Thr215Ser + Leu216Asn + Thr219Gly |
| Ala199His + Gly2G3Gln + Tyr205Gln + Tyr208His + Ala214Gln + Thr215Asn |
| Val204Asn + Tyr205Ile + Pro209Glu + Thr210Ser + Tyr213Val + Leu216Ser |
| Ala199Ser + Pro200Ser + Gly201Asn + Val204Thr + Thr207Pro + Gly218Glu |
| Ala199Gly + Pro200Gly + Pro209Gln + Thr215Asp + Leu216Cys + Thr219Gly |
| Gly201Ser + Gly203Ser + Tyr205Cys + Thr207Gln + Thr212Gly + Ala214Thr |
| Pro200Asn + Ala202Gln + Pro209Gly + Thr210Asp + Thr215Pro + Gly218Asn |
| Tyr205Pro + Thr207Gln + Thr210Glu + Tyr213Cys + Leu216Pro + Thr219Ser |
| Gly201Gln + Tyr205Val + Tyr208Val + Thr210Gln + Thr215Glu + Gly218Asn |
| Ala199Ser + Tyr208Asn + Asn211Gln + Leu216Ile + Asn217Glu + Gly218Pro |
| Pro200Asn + Gly201Pro + Val204Thr + Tyr205His + Thr215Glu + Leu216Thr |
| Gly203Pro + Val204His + Pro209Gly + Thr210Glu + Thr215Pro + Gly218Asn |
| Tyr205Leu + Asn211Gln + Ala214Gln + Leu216Gly + Asn217Asp + Gly218Asn |
| Ala199Ser + Gly201Gln + Gly203Pro + Tyr208Thr + Thr215Gly + Thr219Asn |
| Pro209Glu + Thr210Ser + Thr212Ser + Tyr213Pro + Ala214Thr + Thr21SPro |
| Pro200Ser + Ala202Pro + Gly203Asn + Thr207Pro + Thr210Asp + Tyr213Val |
| Gly201Asn + Thr207Gly + Pro209Ser + Tyr213Met + Leu216Ile + Gly218Asp |
| Gly201Pro + Val204His + Thr212Gly + Leu216Asn + Asn217Ser + Thr219Gly |
| Thr212Gln + Ala214Glu + Thr215Ser + Asn217Ser + Gly218Ser + Thr219Asn |
| Gly203Ser + Tyr205Met + Tyr208Thr + Thr210Asn + Ala214Glu + Leu216Ile |
| Gly201Gln + Tyr208Gln + Thr210Gly + Thr212Gln + Asn217Ser + Thr219Asn |
| Gly201Gln + Tyr205Cys + Thr212Pro + Tyr213Met + Leu216Asn + Gly218Gln |
| Ala202Gln + Tyr205Val + Pro209Gln + Thr210Asp + Asn211Ser + Thr215Gln |
| Gly201Pro + Val204Pro + Thr207Asn + Asn211Gln + Asn217Glu + Thr219Asn |
| Ala199Ser + Tyr213Ser + Ala214Thr + Leu216Ser + Asn217Ser + Gly218Glu |
| Pro200Gln + Gly201Ser + Val204Ala + Thr207Gln + Thr210Asn + Ala214Glu |
| Tyr205Gln + Tyr208Cys + Thr212Gln + Leu216Ser + Gly218Gln + Thr219Ser |
| Pro200Gly + Gly201Pro + Gly203Pro + Thr207Gln + Thr210Gly + Thr219Pro |
| Ala199Gln + Pro200Gly + Val204Ser + Thr215Glu + Asn217Ser + Thr219Pro |
| Ala199Ser + Pro200Gln + Gly201Pro + Val204Pro + Thr210Pro + Thr219Gln |
| Ala202Gln + Thr207Gln + Thr210Glu + Ala214Ser + Thr215Pro + Gly218Gln |
| Pro200Gln + Ala202Glu + Thr207Pro + Pro209Asn + Thr212Gln + Leu216Val |
| Gly201Asn + Asn211Glu + Tyr213Cys + Ala214Thr + Thr215Ser + Leu216His |
| Ala199His + Ala202Gly + Tyr205Ala + Thr207Gly + Asn211Asp + Ala214Gln |
| Gly203Ser + Thr207Asn + Pro209Glu + Thr210A3p + Asn217Gln + Thr219Gly |
| Gly201Gln + Val204Met + Thr210Asp + Asn211Asp + Leu216Gln + Gly218Ser |
| Gly203Pro + Tyr205Ile + Tyr208Gln + Asn211Asp + Thr212Glu + Gly218Gln |
| Gly203Ser + Tyr205Val + Thr207Asn + Leu216Glu + Asn217Asp + Thr219Ser |
| Val204Ala + Tyr205Pro + Pro209Ser + Leu216A1a + Asn217Asp + Gly218Glu |
| Pro200Asn + Gly201Ser + Tyr208Thr + Thr215Gln + Asn217Asp + Gly218Asp |
| Ala202Asn + Tyr208Met + Thr210Gln + Asn211Gln + Asn217Asp + Gly218Asp |
| Ala199Gln + Ala202Asp + Gly203Glu + Thr207Gln + Tyr208Asn + Asn211Gln |
| Ala202Asp + Gly203Asp + Thr207Ser + Tyr208Cys + Thr210Asn + Thr215Pro |
| Ala202Glu + Gly203Asp + Thr207Gly + Tyr208Leu + Leu216Val + Thr219Gln |
| Pro200Ser + Gly201Asn + Pro209Asp + Thr210Asp + Asn211Asp + Leu216Ser |

TABLE 27-continued

| Loop 6 Sextuple Substitution Variants |
|---|
| Ala199Gln + Val204Gln + Tyr205Asp + Tyr208Leu + Thr210Gln + Thr215Glu |
| Pro200Gln + Gly203Gln + Tyr205Glu + Thr212Gly + Thr215Glu + Thr219Pro |
| Pro200Asn + Thr207Ser + Thr210Asp + Asn211Asp + Thr212Glu + Leu216Met |
| Ala202Asp + Gly203Asp + Val204Ser + Thr210Ser + Asn217Asp + Gly218Pro |
| Val204Ser + Thr207Pro + Tyr213His + Thr215Glu + Leu216Asp + Asn217Glu |
| Val204Gly + Asn211Ser + Ala214Gln + Thr215Glu + Leu216Glu + Asn217Glu |
| Tyr208Ile + Tyr213Ser + Ala214His + Leu216Glu + Asn217Asp + Gly218Asp |
| Gly203Asp + Thr207Ser + Ala214His + Thr215Asp + Leu216Asp + Thr219Ser |
| Ala199Ser + Gly201Asn + Thr207Ser + Pro209Glu + Asn211Asp + Thr219Ser |
| Gly203Glu + Tyr205Glu + Thr210Gly + Tyr213Asn + Ala214Gln + Thr215Asp |
| Ala199His + Gly203Asp + Val204His + Thr212Ser + Asn217Asp + Gly218Pro |
| Tyr205Glu + Thr210Gly + Asn211Ser + Ala214Asp + Thr215Ser + Asn217Gln |
| Gly201Asn + Tyr205Asp + Asn211Gln + Thr212Ser + Ala214Glu + Gly218Ser |
| Ala199Asn + Gly201Asn + Gly203Asp + Tyr208Thr + Thr215Asp + Leu216Thr |
| Pro200Gly + Tyr208Pro + Pro209Glu + Thr212Asp + Gly218Ser + Thr219Ser |
| Pro200Asn + Val204Gly + Thr207Asn + Pro209Asp + Thr212Glu + Tyr213Ala |
| Ala199Pro + Gly203Asp + Tyr205Glu + Pro209Ser + Ala214His + Thr215Asn |
| Pro200Gly + Gly203Glu + Thr207Ser + Thr215Gln + Asn217Asp + Gly218Asp |
| Ala202Glu + Gly203Glu + Tyr208Gln + Tyr213Thr + Ala214Ser + Gly218Asp |
| Pro200Gln + Gly203Asp + Tyr213Asn + Ala214Asp + Thr215Asp + Leu216Ile |
| Ala202Ser + Gly203Ser + Tyr205Glu + Pro209Gly + Thr215Asp + Asn217Glu |
| Ala202Gln + Thr207Pro + Thr212Asp + Tyr213Pro + Ala214Glu + Thr219Gly |
| Pro200Ser + Val204Pro + Thr212Asp + Tyr213Ala + Ala214Asp + Thr219Asn |
| Ala199Ser + Ala202Asp + Val204Pro + Pro209Ser + Thr215Asn + Leu216Asp |
| Ala199Gly + Ala202Asn + Val204Asn + Tyr213Asp + Ala214Glu + Leu216Glu |
| Ala199Thr + Gly203Gln + Thr210Gln + Thr212Gln + Tyr213Glu + Thr215Glu |
| Pro200Gln + Gly201Pro + Pro209Asp + Tyr213Glu + Thr215Pro + Gly218Asn |
| Val204Asn + Tyr205Val + Pro209Asp + Thr212Pro + Tyr213Asp + Ala214Gly |
| Tyr205Leu + Asn211Glu + Thr212Glu + Tyr213Leu + Ala214Glu + Thr215Gly |
| Ala199Ser + Ala202Glu + Tyr213Pro + Ala214Gly + Thr215Asp + Gly218Pro |
| Pro200Gly + Gly203Asp + Val204His + Thr210Asn + Asn211Gln + Gly218Asp |
| Gly201Ser + Ala202Gly + Gly203Asp + Ala214Asn + Gly218Glu + Thr219Gly |
| Ala199Gln + Pro200Ser + Ala202Ser + Thr210Asp + Asn211Glu + Ala214Glu |
| Ala202Glu + Thr207Ser + Asn211Gln + Ala214Asp + Leu216Glu + Gly218Ser |
| Ala199Gln + Pro200Ser + Tyr205Asp + Pro209Ser + Thr215Gly + Asn217Glu |
| Ala199Ser + Tyr205Asp + Tyr213Met + Ala214Thr + Asn217Asp + Thr219Asn |
| Pro200Gln + Ala202Asn + Gly203Gln + Tyr213Glu + Leu216Glu + Thr219Asn |
| Ala199Pro + Ala202Gln + Gly203Asn + Thr212Glu + Thr215Asp + Leu216Asp |
| Ala199Gln + Gly201Gln + Val204Thr + Asn211Asp + Ala214Asp + Thr215Asp |
| Gly203Gln + Val204Met + Asn211Glu + Thr212Ser + Ala214Asp + Thr219Gly |
| Thr207Gly + Tyr208Val + Thr210Gly + Thr215Glu + Leu216Asn + Gly218Asp |
| Pro200Gly + Val204Asn + Thr207Gly + Thr210Glu + Tyr213Val + Ala214Asp |
| Gly203Glu + Thr207Asn + Thr210Gly + Thr212Asp + Thr215Asp + Leu216Gln |
| Gly203Gln + Val204Cys + Pro209Asn + Thr210Ser + Thr212Asp + Thr215Asp |
| Gly203Asn + Val204Gly + Tyr205Asp + Ala214Glu + Thr215Pro + Gly218Asp |

TABLE 28

| Loop 6 - Heptuple Substitution Mutation Variants |
|---|
| Pro200Asn + Ala202Gln + Tyr208Cys + Thr210Pro + Tyr213Asn + Ala214Asn + Thr219Ser |
| Gly203Pro + Val204Gln + Tyr205Gly + Tyr208Gly + Asn211Glu + Tyr213Pro + Gly218Gln |
| Gly201Asn + Gly203Gln + Val204Cys + Thr207Ser + Thr212Asp + Thr215Pro + Thr219Gly |
| Gly203Gln + Val204Gln + Tyr205Pro + Thr212Gly + Tyr213Val + Asn217Asp + Thr219Gly |
| Gly201Gln + Ala202Gln + Val204Pro + Asn211Asp + Tyr213Ile + Leu216Gly + Gly218Pro |
| Pro200Gly + Ala202Gln + Val204Pro + Pro209Asn + Tyr213Ala + Asn217Asp + Thr219Pro |
| Ala199Thr + Gly201Ser + Val204Ser + Thr210Gly + Asn211Asp + Gly218Ser + Thr219Ser |
| Gly201Gln + Tyr208Val + Pro209Gln + Asn211Ser + Thr215Pro + Asn217Gln + Thr219Gln |
| Ala199His + Pro200Gly + Pro209Asn + Thr212Gln + Tyr213Ile + Leu216Gln + Thr219Gly |
| Pro200Gln + Thr210Pro + Asn211Ser + Thr212Gln + Leu216Gln + Asn217Asp + Thr219Pro |
| Pro200Ser + Val204His + Tyr205Ala + Tyr208Ser + Asn211Gln + Ala214His + Thr215Asn |
| Ala199Ser + Pro200Ser + Gly201Pro + Tyr205Met + |

TABLE 28-continued

| Loop 6 - Heptuple Substitution Mutation Variants |
|---|
| Thr207Pro + Thr210Asp + Thr212Ser |
| Gly201Gln + Val204Ser + Tyr205Asn + Tyr213Ala + Ala214Glu + Thr215Gln + Leu216Thr |
| Ala199Gln + Val204Thr + Thr2075er + Tyr208Asn + Pro209Asn + Thr212Gln + Gly218Pro |
| Pro200Asn + Gly203Pro + Thr207Pro + Thr210Gln + Tyr213His + Leu216Ile + Gly218Asp |
| Ala202Gly + Gly203Gln + Val204Gly + Tyr205Ser + Thr212Gln + Asn217Ser + Thr219Gly |
| Pro209Gly + Thr210Gln + Asn211Asp + Tyr213Gln + Ala214Ser + Leu216Asn + Asn217Ser |
| Ala199His + Val204Pro + Tyr205Glu + Pro209Asn + Tyr213Ala + Leu216Thr + Gly218Asn |
| Ala199Gln + Pro200Asn + Ala202Thr + Gly203Pro + Val204Gln + Thr212Ser + Tyr213Gln |
| Gly201Asn + Ala202Asn + Gly203Asp + Tyr208Thr + Thr212Gln + Tyr213Thr + Gly218Asn |
| Ala199Thr + Gly203Asp + Val204Thr + Thr207Asn + Thr210Asn + Asn211Ser + Tyr213Val |
| Pro200Gly + Thr207Pro + Tyr208Met + Pro209Glu + Tyr213His + Thr215Pro + Leu216Gln |
| Pro200Ser + Gly201Asn + Ala202Asp + Tyr205Cys + Tyr208Ala + Tyr213His + Thr219Asn |

TABLE 28-continued

| Loop 6 - Heptuple Substitution Mutation Variants |
|---|
| Ala199Pro + Val204Met + Thr207Gln + Tyr208Val + Asn211Glu + Ala214Ser + Thr219Ser |
| Gly201Asn + Tyr205Leu + Tyr208Pro + Thr210Pro + Thr212Asn + Tyr213Leu + Ala214Asn |
| Pro200Ser + Gly201Pro + Gly203Pro + Val204Asn + Thr207Asn + Ala214Asp + Leu216His |
| Pro200Gly + Gly201Gln + Val204Gln + Thr207Gln + Tyr213His + Ala214Ser + Gly218Pro |
| Pro200Gln + Val204His + Pro209Ser + Asn211Ser + Thr212Glu + Tyr213Gly + Ala214Pro |
| Ala199His + Gly201Gln + Ala202Asn + Thr210Asn + Asn211Ser + Ala214Asn + Thr219Gln |
| Pro200Gly + Gly201Asn + Val204Gln + Thr212Gly + Thr215Pro + Asn217Ser + Thr219Pro |
| Ala199Thr + Val204Thr + Tyr205Gly + Tyr208Met + Thr210Asn + Tyr213His + Leu216Cys |
| Pro200Asn + Ala202Asp + Val204Pro + Tyr205Gly + Thr207Asn + Tyr208Cys + Thr210Gln |
| Thr207Ser + Thr210Ser + Thr212Gly + Ala214Thr + Thr215Asn + Asn217Asp + Thr219Gln |
| Ala199Ser + Pro200Ser + Gly203Gln + Thr207Ser + Tyr208Ile + Asn211Glu + Leu216Met |
| Ala199Gly + Pro200Asn + Gly201Asn + Gly203Ser + Ala214His + Thr215Asp + Leu216Pro |
| Pro200Gln + Gly201Ser + Ala202Asp + Thr207Asn + Tyr208Pro + Thr215Gln + Leu216Cys |
| Val204Thr + Tyr205Pro + Tyr208Thr + Asn211Gln + Thr212Asp + Tyr213Cys + Thr219Asn |
| Pro200Gln + Ala202Gly + Gly203Asn + Tyr205Met + Tyr208Val + Tyr213Val + Thr219Asn |
| Ala199Gly + Pro200Asn + Ala202Pro + Tyr205Asp + Thr207Gln + Thr212Gln + Leu216Cys |
| Gly201Pro + Ala202Gly + Val204Thr + Tyr205Pro + Asn211Glu + Ala214Pro + Thr215Gly |
| Ala199Gln + Ala202Pro + Val204Met + Tyr205Ile + Tyr208Ile + Asn217Asp + Thr219Pro |
| Ala199Thr + Gly203Asn + Tyr208Leu + Pro209Gly + Tyr213Ile + Ala214Glu + Leu216Gly |
| Gly201Gln + Val204Ala + Tyr208Gly + Thr210Gln + Thr215Gln + Asn217Gln + Gly218Asn |
| Pro200Gln + Gly201Asn + Val204Ser + Tyr205Glu + Tyr213Ser + Ala214Gln + Asn217Gln |
| Pro200Ser + Gly203Asn + Thr207Gly + Thr210Pro + Tyr213His + Ala214Thr + Thr215Pro |
| Ala199Asn + Tyr208Ile + Pro209Asp + Thr212Gln + Tyr213Ser + Ala214His + Asn217Gln |
| Ala199Asn + Pro200Gln + Ala202Pro + Val204Cys + Tyr208His + Thr215Gln + Thr219Asn |
| Ala199Ser + Ala202His + Val204Pro + Thr210Asn + Thr212Pro + Gly218Asp + Thr219Asn |
| Gly201Pro + Tyr205Glu + Thr210Gly + Asn211Ser + Tyr213Gln + Ala214Thr + Gly218Gln |
| Ala199Pro + Gly203Gln + Thr207Asn + Asn211Asp + Ala214Gln + Thr215Gly + Thr219Gly |
| Ala199Gln + Pro200Asn + Thr212Ser + Tyr213Ser + Leu216Ile + Asn217Asp + Thr219Pro |
| Pro209Asn + Thr212Gln + Ala214Ser + Leu216Gly + Asn217Asp + Gly218Asn + Thr219Asn |
| Gly201Ser + Gly203Pro + Thr207Ser + Thr212Ser + Ala214His + Asn217Asp + Gly218Gln |
| Ala199Ser + Pro200Gln + Gly201Asn + Tyr205Asn + Ala214Ser + Asn217Asp + Gly218Pro |
| Ala199His + Ala202Gly + Gly203Glu + Tyr208Gln + Pro209Gln + Leu216Asn + Thr219Ser |
| Ala199Pro + Thr207Ser + Tyr208Cys + Asn211Gln + Tyr213Gly + Leu216Thr + Thr219Gly |
| Pro200Gly + Ala202Thr + Tyr205Cys + Thr212Glu + Leu216Thr + Asn217Ser + Gly218Pro |
| Ala199Thr + Gly203Asn + Tyr208Ser + Pro209Gly + Asn211Ser + Tyr213Pro + Gly218Pro |
| Ala199Gly + Tyr205Gln + Pro209Asn + Asn211Glu + Ala214His + Thr215Gln + Thr219Asn |
| Ala199Asn + Pro200Asn + Gly203Pro + Tyr208Ile + Pro209Gly + Tyr213Asp + Ala214His |
| Gly203Asn + Val204Thr + Asn211Gln + Thr212Pro + Thr215Asp + Leu216His + Thr219Gln |
| Ala199Gln + Gly201Ser + Val204Pro + Tyr205Asn + Pro209Asp + Thr210Gln + Thr219Asn |
| Pro200Asn + Gly201Ser + Val204Ser + Tyr205Asp + Thr210Asn + Thr212Pro + Asn217Ser |
| Pro200Asn + Gly201Asn + Tyr205Asp + Tyr208Pro + Thr215Pro + Asn217Gln + Thr219Gly |
| Ala199Gln + Gly201Pro + Tyr205Ile + Tyr208Asn + Thr215Gly + Gly218Asp + Thr219Pro |
| Ala199Pro + Gly201Gln + Tyr205Asn + Thr207Ser + Thr210Gly + Tyr213Met + Ala214Ser |
| Pro200Asn + Ala202Glu + Val204Thr + Thr207Asn + Tyr208His + Tyr213Gln + Asn217Gln |
| Gly201Ser + Ala202Asp + Val204Pro + Thr207Gly + Pro209Gln + Tyr213Pro + Gly218Ser |
| Gly201Asn + Ala202Asn + Tyr205Cys + Thr210Gly + Tyr213Gln + Ala214Pro + Thr219Gly |
| Pro200Asn + Gly203Ser + Thr207Gly + Thr210Pro + Thr215Asp + Leu216Ser + Gly218Ser |
| Gly201Gln + Ala202Glu + Tyr208Gly + Thr212Pro + Ala214His + Leu216Thr + Thr219Gln |
| Ala199Asn + Pro200Gln + Ala202Asn + Tyr205Pro + Thr207Pro + Tyr208Pro + Pro209Asp |
| Gly201Pro + Ala202Glu + Pro209Ser + Thr212Ser + Thr215Pro + Leu216Cys + Gly218Asn |
| Ala202Thr + Gly203Asp + Thr207Gln + Tyr208Cys + Ala214Pro + Leu216Gln + Asn217Ser |
| Gly201Ser + Ala202Asn + Gly203Pro + Tyr205Met + Asn211Ser + Leu216Glu + Gly218Gln |
| Ala199Gly + Tyr205Gly + Asn211Ser + Thr212Ser + Ala214Gln + Asn217Glu + Thr219Asn |
| GIy203Gln + Tyr205Gln + Tyr208Met + Pro209Glu + Thr210Glu + Thr215Pro + Thr219Gln |
| Pro200Gly + Tyr205Ile + Thr207Gln + Tyr208Pro + Pro209Asp + Thr210Glu + Leu216Pro |
| Ala199Pro + Pro200Gly + Gly203Gln + Tyr208Asn + Thr210Asp + Asn211Glu + Leu216Pro |
| Thr207Asn + Tyr208Gln + Pro209Gly + Ala214Asn + Thr215Glu + Leu216Asp + Gly218Asn |
| Ala199Thr + Pro200Gln + Thr210Ser + Ala214Gly + Thr215Asp + Leu216Glu + Gly218Gln |
| Ala202Gln + Gly203ser + Val204Cys + Tyr213Ile + Ala214Pro + Leu216Asp + Asn217Asp |
| Pro200Gly + Gly203Pro + Tyr205Asp + Tyr208Asn + Thr212Gly + Thr215Asp + Gly218Pro |
| Ala202Glu + Gly203Glu + Val204Cys + Tyr205Pro + Asn217Glu + Gly218Gln + Thr219Pro |
| Pro200Gly + Ala202Glu + Val204Cys + Thr207Asn + Leu216Ile + Asn217Glu + Gly218Glu |
| Ala199Pro + Gly201Pro + Thr207Gln + Tyr208Leu + Thr212Glu + Tyr213Asp + Ala214Asp |
| Ala199Gly + Gly201Pro + Ala202Pro + Tyr208Ala + Pro209Glu + Asn211Asp + Thr212Gly |
| Thr207Pro + Pro209Glu + Asn211Glu + Tyr213Met + Ala214Ser + Thr215Gln + Leu216Cys |
| Gly201Gln + Gly203Glu + Thr207Gln + Tyr208Met + Thr215Asn + Asn217Asp + Thr219Pro |
| Gly201Asn + Ala202His + Gly203Pro + Tyr205Asp + Thr212Gln + Ala214Glu + Thr219Ser |
| Val204Ser + Thr207Pro + Pro209Glu + Thr212Asp + Tyr213Ser + Leu216Gln + Thr219Pro |
| Ala199Thr + Thr207Pro + Pro209Glu + Thr212Glu + Tyr213Thr + Leu216Ser + Asn217Ser |
| Pro200Asn + Tyr205His + Pro209Asp + Thr212Asp + Tyr213Ala + Ala214Pro + Thr219Gly |
| Ala199Pro + Pro200Gly + Gly201Ser + Val204His + Pro209Glu + Thr212Asp + Thr219Gln |
| Ala199Pro + Ala202Gln + Gly203Asp + Thr207Gly + Tyr208Gln + Leu216Glu + Gly218Pro |
| Gly203Glu + Val204Ser + Tyr208Val + Tyr213Pro + Ala214Asp + Thr215Glu + Leu216Asp |
| Gly201Gln + Gly203Glu + Val204Gln + Thr207Ser + Thr215Asp + Leu216Ala + Asn217Glu |
| Ala202Asn + Val204Gly + Asn211Ser + Ala214Asp + Thr215Glu + Leu216Glu + Asn217Glu |
| Ala199His + Pro200Ser + Gly201Gln + Ala202Glu + Leu216Ile + Gly218Asp + Thr219Gly |
| Ala202Gly + Gly203Glu + Val204Gln + Thr207Gly + Thr215Gln + Asn217Glu + Gly218Asp |

TABLE 28-continued

| Loop 6 - Heptuple Substitution Mutation Variants |
| --- |
| Ala199Asn + Gly203Glu + Thr210Gly + Ala214Asn + Thr215Pro + Asn217Glu + Gly218Asp |
| Ala202Pro + Gly203Asn + Tyr205Glu + Asn211Gln + Thr215Gln + Leu216Glu + Thr219Asn |
| Pro200Gly + Val204Thr + Thr207Ser + Tyr208Cys + Thr210Asp + Asn211Glu + Tyr213Glu |
| Ala202Glu + Gly203Pro + Val204Thr + Thr212Ser + Tyr213Val + Thr215Glu + Asn217Asp |
| Pro200Gln + Val204Met + Pro209Gly + Thr210Asp + Thr212Asp + Tyr213Asp + Ala214Asp |
| Ala199His + Pro200Gln + Ala202Gly + Val204Cys + Thr215Glu + Leu216Cys + Asn217Asp |
| Val204Gly + Tyr20BLeu + Pro209Glu + Thr210Asn + Tyr213Glu + Ala214Asp + Thr215Ser |
| Pro200Gly + Gly201Gln + Ala202Ser + Pro209Gly + Thr212Glu + Ala214Asp + Leu216Ala |
| Gly201Asn + Tyr205His + Tyr2o8Ser + Tyr213Asp + Ala214Asp + Thr215Ser + Leu216Asp |
| Gly203Asn + Tyr208Gln + Asn211Gln + Tyr213Asp + Thr21SAsp + Asn217Gln + Thr219Gln |
| Ala202Ser + Thr207Pro + Tyr208Cys + Tyr213Asp + Ala214Ser + Thr215Asp + Leu216Cys |
| Ala199Thr + Gly201Pro + Tyr20SSer + Thr207Asn + Tyr208Ile + Asn211Glu + Tyr213Glu |
| Ala199Pro + Ala202Ser + Gly203Pro + Tyr208Gly + Asn211Asp + Tyr213Glu + Thr215Gln |
| Ala199Gln + Pro200Asn + Gly203Asp + Tyr205Glu + Tyr208Asn + Tyr213Met + Ala214Asp |
| Gly201Asn + Thr207Pro + Thr210Asp + Asn211Glu + Thr212Glu + Ala214Glu + Leu216Pro |
| Pro200Gln + Gly201Asn + Gly203Asn + Thr207Asn + Asn211Asp + Thr212Glu + Ala214Glu |
| Thr210Gly + Asn211Asp + Tyr213Asp + Ala214Asp + Asn217Ser + Gly218Pro + Thr219Asn |
| Ala199Asn + Gly201Ser + Tyr208Ala + Thr210Glu + Tyr213Glu + Ala214Pro + Leu216His |
| Ala202Asn + Gly203Asp + Tyr205Gln + Thr212Ser + Thr215Glu + Gly218Asp + Thr219Pro |
| Pro200Gly + Gly203Glu + Thr207Gln + Ala214Gln + Tbr215Asp + Leu216Asn + Gly218Glu |
| Ala199Ser + Gly201Ser + Ala202Glu + Gly203Gln + Thr207Ser + Thr215Asp + Thr219Ser |
| Ala202Asp + Tyr205Thr + Thr207Asn + Tyr208Ala + Thr215Glu + Leu216Cin + Gly218Asn |
| Pro200Asn + Gly203Asp + Val204Pro + Tyr208Cys + Leu216Cys + Asn217Ser + Gly218Glu |
| Ala199Asn + Pro200Ser + Gly201Asn + Gly203Glu + Val204Gly + Asn211Gln + Gly218Glu |
| Ala199Thr + Gly201Gln + Ala202Pro + Thr210Asp + Asn211Glu + Ala214Asp + Thr219Asn |
| Ala199Gly + Pro200Ser + Tyr205Glu + Thr210Pro + Asn211Asp + Tyr213Asp + Thr215Glu |
| Pro200Ser + Ala202Glu + Thr207Gln + Asn211Ser + Ala214Glu + Asn217Glu + Gly218Asn |
| Ala202Ser + Val204His + Thr207Ser + Thr212Asp + Tyr213Asp + Thr215Asn + Leu216Asp |
| Gly203Pro + Tyr205Pro + Pro209Asp + Asn211Asp + Ala214Glu + Thr215Asp + Thr219Gly |
| Thr207Ser + Pro209Ser + Thr212Glu + Tyr213Glu + Thr215Glu + Leu216Gln + Asn217Asp |
| Ala199Ser + Pro200Gly + Gly201Ser + Thr212Gly + Ala214Glu + Asn217Glu + Gly218Pro |
| Gly201Gln + Tyr208Thr + Ala214Asp + Thr215Pro + Leu216Asn + Asn217G1u + Gly218Pro |
| Ala199Ser + Tyr205Glu + Thr207Ser + Thr210Asn + Tyr213Glu + Ala214Gln + Asn217Asp |
| Gly203Glu + Pro209Asp + Thr210Asp + Asn211Glu + Ala214Thr + Thr215Gln + Thr219Asn |
| Ala202Pro + Gly203Asp + Tyr205Cys + Thr212Asp + Thr21SPro + Leu216Glu + Asn217Asp |
| Ala199Asn + Gly201Pro + Ala202Glu + Gly203Glu + Tyr205Glu + Thr207Gly + Thr212Asp |
| Ala202Asn + Thr207Pro + Asn211Glu + Thr212Asp + Ala214Ser + Thr215Asp + Leu216Val |
| Gly201Gln + Ala202Glu + Val204Ser + Tyr205Asp + Tyr213Glu + Thr215Asn + Leu216Thr |
| Pro200Gly + Gly203Asn + Tyr205Glu + Thr212Glu + Tyr213Val + Ala214Asn + Leu216Glu |
| Ala202His + Thr207Gln + Pro209Gln + Thr210Gln + Thr215Glu + Asn217Gln + Gly218Glu |
| Ala199Gly + Gly201Gln + Pro209Gly + Thr212Gly + Thr215Glu + Asn217Ser + Gly218Glu |
| Gly203Asp + Val204Met + Thr212Asp + Tyr213Val + Ala214Asp + Asn217Glu + Thr219pro |
| Ala202Asp + Gly203Asn + Tyr208Met + Thr212Asp + Asn217Glu + Gly218Glu + Thr219Gly |
| Pro200Gln + Val204Asn + Thr207Gly + Thr210Glu + Asn211Gln + Tyr213Val + Ala214Asp |
| Gly203Gln + Tyr205Ile + Tyr208His + Thr210Asp + Ala214Asp + Thr215Pro + Leu216Val |
| Gly203Gln + Tyr208Ala + Pro209Gln + Thr210Glu + Asn211Gln + Ala214Asp + Leu216cys |
| Gly201Gln + Gly203Glu + Val204Ser + Pro209Asn + Asn211Glu + Tyr213Asp + Thr215Glu |
| Tyr205Asp + Thr207Pro + Pro209Ser + Thr210Glu + Ala214Glu + Asn217Ser + Thr219Pro |
| Ala199Asn + Gly201Ser + Ala202Thr + Gly203Asp + Thr210Pro + Ala214Asp + Gly218Glu |
| Gly203Glu + Thr207Ser + Tyr208Thr + Pro209Gln + Thr212Glu + Ala214Ser + Thr215Glu |
| Ala199Pro + Gly201Ser + Val204Gln + Tyr205Asp + Thr212Asp + Leu216Ala + Thr219Pro |
| Pro200Gln + Tyr208Ile + Pro209Glu + Ala214Glu + Leu216Asp + Asn217Ser + Gly218Glu |
| Ala199Thr + Ala202Glu + Gly203Glu + Thr210Asp + Ala214Ser + Gly218Glu + Thr219Gln |
| Ala199Thr + Pro200Ser + Ala202Asp + Gly203Asp + Thr210Gly + Thr212Glu + Gly218Glu |
| Ala199Pro + Ala202Glu + Tyr208Leu + Thr210Asp + Ala214Ser + Leu216Glu + Gly218Asp |
| Gly201Asn + Tyr205Ala + Thr207Pro + Thr210Asp + Asn211Asp + Ala214Asp + Asn217Glu |
| Ala199Ser + Gly203Gln + Tyr205Gln + Pro209Glu + Thr212Glu + Tyr213Asn + Leu216Asp |
| Ala199Gln + Pro200Asn + Tyr205Glu + Tyr208Leu + Pro209Glu + Thr210Asp + Tyr213Gly |
| Pro200Gly + Gly203Glu + Pro209Glu + Thr212Ser + Tyr213Pro + Thr215Asp + Asn217Gln |
| Gly201Pro + Tyr205Val + Thr207Ser + Pro209Asp + Ala214Glu + Asn217Glu + Thr219Gln |
| Pro200Asn + Ala202Thr + Pro209Gly + Asn211Glu + Thr212Glu + Ala214Asn + Leu216Asp |
| Gly201Ser + Thr207Ser + Thr212Asp + Ala214Pro + Leu216Asp + Asn217Asp + Gly218Pro |
| Tyr205Asp + Thr207Asn + Pro209Asp + Asn211Glu + Thr212Pro + Gly218Ser + Thr219Pro |
| Pro200Gly + Ala202Asn + Gly203Asn + Thr210Ser + Thr212Glu + Tyr213Asp + Asn217Glu |
| Gly203Pro + Pro209Ser + Thr212Asn + Tyr213Glu + Asn217Glu + Gly218Asp + Thr219Gln |
| Ala202Ser + Tyr205Ala + Pro209Glu + Thr210Asp + Leu216Ser + Asn217Asp + Gly218Gln |
| Val204Met + Pro209Asp + Thr210Glu + Ala214Gln + Leu216Gln + Gly218Asp + Thr219Pro |
| Ala202Glu + Val204Met + Thr207Ser + Pro209Glu + Thr210Glu + Thr212Ser + Gly218Pro |
| Pro200Ser + Ala202His + Thr210Asp + Asn211Glu + Leu216Gly + Gly218Asp + Thr219Gly |
| Pro200Gly + Gly201Asn + Ala202Ser + Thr210Asp + Asn211Glu + Ala214His + Thr215Asp |
| Pro200Gln + Pro209Gly + Thr210Glu + Asn211Asp + Thr212Gln + Tyr213Met + Leu216Asp |
| Pro200Gly + Gly203Glu + Tyr208Thr + Thr210Asp + ASn211Asp + Ala214Thr + Leu216Asn |
| Gly203Ser + Val204Cys + Thr207Asn + Pro209Ser + Thr210Glu + Thr215Glu + Leu216Glu |
| Ala199Asn + Pro200Asn + Gly201Pro + Gly203Asn + Asn211Asp + Thr215Asp + Leu216Asp |
| Ala202Thr + Tyr208Met + Pro209Asn + Asn211Glu + Thr212Glu + Ala214Gly + Gly218Glu |
| Gly203Gln + Val204Cys + Tyr205Gly + Tyr208Pro + Asn211Glu + Thr212Asp + Gly218Glu |
| Pro200Gln + Ala202Asp + Tyr205Met + Thr212Asp + Tyr213Glu + Gly218Gln + Thr219Gln |

TABLE 28-continued

| Loop 6 - Heptuple Substitution Mutation Variants |
|---|
| Ala199Gln + Gly203Pro + Pro209Asn + Thr210Gln + Thr212Asp + Asn217Asp + Gly218Asp |
| Gly201Asn + Tyr208Asn + Pro209Ser + Thr212Glu + Tyr213Pro + Asn217Asp + Gly218Asp |
| Ala199Gln + Gly201Pro + Tyr205Ser + Asn211Glu + Ala214Asn + Asn217Glu + Gly218Glu |

TABLE 29

| Multi-loop Double Mutation Variants |
|---|
| Leu 95Gly + Gly203Pro |
| Thr 58Gln + Asn211Glu |
| Asp 59Glu + Leu216Gln |
| Tyr103Cys + Thr212Gly |
| Gly156Glu + Ala202Gln |
| Gly126Gln + Thr215Pro |
| Ser187Glu + Ala214Gly |
| Asn 96Gln + Ile106Ala |
| Gly101Asp + Tyr205Pro |
| Asn 61Ser + Gly165Gln |
| Gly 64Gln + Thr132Gly |
| Asp 59Glu + Tyr205Asn |
| Ser100Glu + Tyr205His |
| Ala128Ser + Thr161Gln |
| Ser158Asp + Gly203Ser |
| Asn 61Asp + Asn162Ser |
| Thr161Glu + Pro209Gln |
| Gly E2Asp + Pro209Asn |
| Ile106Leu + Asn211Asp |
| Tyr103Glu + Gly203Pro |
| Tyr166Pro + Thr215Glu |
| Ile106Leu + Pro209Glu |
| Thr163Pro + Ala202Pro |
| Thr132Gly + Leu216Ser |
| Ser104Glu + Phe188Val |
| Tyr166Asp + Ala186Thr |
| Ser160Glu + Thr215Ser |
| Gly 62Gln + Gly165Asp |
| Leu 95Gln + Ala128Glu |
| Ser 97Glu + Asn211Ser |
| Leu 95Asn + Phe188Leu |
| Asn157Gln + Thr212Ser |
| Leu12SGln + Gly159Asp |
| Asn211Asp + Tyr213Ala |
| Ser158Asp + Tyr20SCys |
| Ser160Glu + Asn162Gln |
| Ser187Asp + Tyr213Pro |
| Ser158Asp + Leu216Gln |
| Met198Ser + Ala202Asp |
| Gly 99Asn + Ala214Glu |
| Thr 58Asp + Gly130Gln |
| Gly116Glu + Tyr208Pro |
| Gly10SPro + Leu216Ile |
| Ser187Asp + Tyr205Gln |
| Thr215Ser + Gly218Asp |
| Gly 60Asn + Ala128Glu |
| Thr 65Gln + Leu12SAsn |
| Gly10 Gln + Gly218Asp |
| Asn211Ser + Thr212Asp |
| Thr212Gln + Thr215Gly |
| Gly203Glu + Tyr205Gly |
| Thr132Pro + Thr215Ser |
| Tyr103Asp + Gly165Gln |
| Thr 65Pro + Gly203Glu |
| Thr 58Glu + Gly 60Pro |
| Gly153Pro + Leu216Val |
| Asn 96Gln + Pro209Glu |
| Gly 99Asn + Gly153Asn |
| Ala128Asn + Ala202His |
| Gly105Glu + Gly130Ser |
| Thr212Gly + Gly218Glu |
| Phe188Val + Tyr205Ser |
| Asn217Glu + Thr219Gly |

TABLE 29-continued

| Multi-loop Double Mutation Variants |
|---|
| Leu 95Gln + Thr215Asp |
| Val 94Gln + Thr212Glu |
| Asn 61Ser + Gly203Asp |
| Ser129Glu + Asn154Gln |
| Gly 62Glu + Thr219Asn |
| Ser129Glu + Asn157Gln |
| Tyr103Ile + Thr215Pro |
| Ile164Thr + Thr215Ser |
| Gly101Gln + Tyr208Gln |
| Asn 61Gln + Thr212Asp |
| Thr212Asp + Leu216Ile |
| Asn211Glu + Leu216His |
| Gly153Glu + Thr163Gln |
| Gly203Asp + Thr215Asn |
| Asn 61Ser + Thr132Asn |
| Ser158Glu + Gly203Pro |
| Leu 95Asn + Thr215Asn |
| Thr 58Ser + Ser100Asp |
| Ile164Met + Tyr205Ala |
| Ser158Glu + Tyr205Met |
| Phe188Leu + Thr212Glu |
| Gly130Pro + Ser19OGlu |
| Gly101Asp + Gly126Ser |
| Asn 61Ser + Ala186Ser |
| Asn162Gln + Phe188Ser |
| Thr 58Gly + Thr 65Asp |
| Ser129Asp + Thr210Pro |
| Ser129Glu + Gly153Asn |
| Asp 59Glu + Tyr213Thr |
| Asn154Glu + Leu216Gln |
| Ser 97Asp + Ala199Pro |
| Gly203Asn + Gly218Asp |
| Thr 65Ser + Gly126Gln |
| Thr215Gln + Leu216Ala |
| Asn 96Glu + Tyr205His |
| Thr 65Ser + Gly156Asp |
| Ala128Ser + Thr163Gln |
| Thr215Asp + Leu216Val |
| Ser129Glu + Leu216Ala |
| Asn211Asp + Tyr213Leu |
| Val 94Ser + Phe188Val |
| Ser158Glu + Thr212Gln |
| Gly 99Pro + Asn154Gln |
| Gly203Asn + Thr215Gln |
| Ala202Ser + Tyr205Glu |
| Tyr205Val + Asn217Glu |
| Val 94Gly + Thr215Asp |
| Ser104Glu + Thr215Gln |
| Gly201Pro + Tyr20SGlu |
| Asn 96Ser + Gly127Glu |
| Tyr205Thr + Ala214Thr |
| Gly 62Ser + Thr215Gly |
| Thr 65Ser + Asn211Glu |
| Gly153Pro + Gly203Ser |
| Ala128Thr + Leu216Glu |
| Asn 96Glu + Leu216Gln |
| Thr215Asn + Leu216Ala |
| Asp 59Glu + Ala202Pro |
| Val 94Thr + Leu216Met |
| Ser 97Glu + Thr212Gln |
| Gly101Asp + Ala202Asn |
| Ser129Asp + Ala202Gly |
| Tyr103Ala + Thr132Ser |
| Leu 95Met + Leu216Asp |
| Ser100Asp + Gly101Pro |
| Ser100Asp + Thr219Pro |
| Val 94Asn + Thr215Pro |
| Tyr103Asn + Ala128Asp |
| Gly201Asn + Tyr205Asp |
| Thr 58Glu + Ile106Cys |
| Thr 65Glu + Tyr103Pro |
| Val 94Met + Ser 98Glu |
| Gly203Glu + Thr210Pro |
| Pro209Glu + Gly218Ser |
| Thr161Pro + Gly203Ser |
| Ser 97Glu + Leu125Pro |
| Ala128Asp + Ala199His |

TABLE 29-continued

Multi-loop Double Mutation Variants

Ile106Gly + Ala214Pro
Asp 59Glu + Tyr205Ile
Asn154Asp + Tyr208His
Thr210Asp + Leu21GVal
Thr215Asp + Thr219Gln
Gly 60Glu + Leu125Ser
Ser 97Asp + Gly153Asn
Tyr166Pro + Tyr205Gly
Ser129Glu + Gly203Gln
Gly153Gln + Pro209Gln
Gly203Gln + Thr215Gln
Asn 61Glu + Thr212Ser
Thr163Asp + Tyr205His
Asn154Glu + Tyr166Thr
Asn 96Ser + Gly105Asp
Phe188Gly + Asn211Ser
Gly153Glu + Gly218Asn
Ser100Asp + Thr212Pro
Gly126Pro + Gly156Asp
Leu125Ser + Thr215Glu
Asp 59Glu + Thr 65Gly
Gly156Pro + Gly159Asp
Thr 58Asp + Ala202Ser
Leu 95Met + Gly 99Ser
Asn 61Gln + Tyr205Glu
Gly126Asn + Gly159Pro
Leu 95Thr + Gly218Asn
Thr 65Gln + Leu216Ala
Gly130Pro + Gly203Glu
Gly 64Gln + Ser 98Glu
Gly126Asn + Gly127Gln
Thr132Asn + Gly153Asn
Thr 58Pro + Gly105Glu
Gly130Asp + Ala214His
Gly126Glu + Tyr205Pro
Tyr103His + Ser129Asp
Ser 98Asp + Pro209Ser
Asp 59Glu + Tyr205Ser
Gly 60Gln + Thr215Asn
Pro209Asn + Asn211Asp
Thr132Asp + Ala202Asn
Gly218Ser + Thr219Gly
Thr 58Asp + Gly203Gln
Ile106Asp + Ala202Thr
Thr161Asn + Ser190Asp
Ser129Glu + Thr215Gln
Thr212Asn + Leu216Asp
Asn 96Gln + Ser158Glu
Gly203Pro + Thr215Asp
Val 94Asp + Tyr205Asn
Ala128Pro + Thr215Asp
Gly201Gln + Leu216Pro
Thr161Pro + Leu216Cys
Gly126Asp + Tyr205Met
Ser 97Asp + Thr212Pro
Thr210Asn + Leu216His
Ala186Asn + Tyr205Pro
Ser131Asp + Phe188Thr
Thr132Ser + Leu216Asn
Asn 61Asp + Gly130Pro
Leu 95Asn + Thr132Gly
Ser100Asp + Thr215Asn
Tyr166Thr + Asn211Gln
Thr207Pro + Leu216Thr
Ile106Ala + Gly165Asp
Tyr20SAsn + Thr215Asn
Asn 96Gln + Gly218Asn
Ser160Asp + Phe188Gly
Thr210Gly + Thr212Ser
Gly 64Ser + Asn 96Gln
Gly101Asp + Asn154Gln
Gly 64Asn + Asn157Glu
Asn157Glu + Gly203Gln
Tyr213Asn + Thr215Ser
Gly101Asn + Ala186Asn
Ser160Glu + Leu216Ile
Tyr103His + Ser187Glu

TABLE 29-continued

Multi-loop Double Mutation Variants

Asn 96Ser + Ala214Asn
Gly 62Asn + Ser 98Asp
Ile106Ser + Asn157Glu
Thr 65Glu + Thr212Gly
Gly 62Asn + Thr215Pro
Gly127Ser + Thr210Asp
Gly156Ser + Asn217Glu
Ser 98Asp + Tyr103Thr
Gly127Asn + Gly165Pro
Gly153Glu + Leu21 Met
Ser129Asp + Gly165Pro
Asn 61Asp + Thr163Gln
Gly126Asn + Tyr20SMet
Asn157Gln + Thr212Gln
Ser190Glu + Thr215Gly
Ser129Glu + Gly165Gln
Thr 65Glu + Gly101Pro
Val 94Gln + Gly165Glu
Tyr103Ile + Ser190Glu
Asn217Gln + Gly218Ser
Ser 98Glu + Gly 99Asn
Ser102Asp + Thr212Ser
Thr212Ser + Thr215Asp
Gly130Glu + Pro209Asn
Ala128Pro + Gly165Pro
Asn217Gln + Gly218Asn
Leu125His + Thr163ger
Thr212Asp + Tyr213Ala
Thr 65Pro + Thr210Ser
Gly105Pro + Ala202Gln
Val 94Thr + Ser158Glu
Thr132Gly + Tyr205Cys
Gly105Gln + Ala214His
Gly127Gln + Tyr205Cys
Gly127Glu + Gly130Ser
Phe188Tyr + Asn211Ser
Gly 64Asn + Phe188Asp
Thr212Ser + Leu216Asp
Met198His + Gly203Pro
Tyr208Val + Thr210Asp
Gly165Glu + Tyr205Met
Asn 96Gln + Thr132Glu
Ser 98Glu + Gly101Pro
Leu12SCys + Thr215Asp
Leu125Cys + Gly126Ser
Ser190Asp + Thr215Asn
Gly 99Gln + Gly153Asp
GIy 60Asp + Thr218Ser
Ser160Asp + Phe188Leu
Va1204Gln + Thr215Glu
Asn157Glu + Gly203ger
Tyr213Glu + Leu216Cys
Asn 61Gln + Leu216Asp
Leu12SGly + Ser155Asp
Ala186Pro + Val204Gln
Ile106Met + Ser160A5p
Leu125Ile + Leu216Ser
Gly 60Gln + Gly203Asn
Gly203Asn + Pro209Glu
Gly 60Ser + Gly 62Asp
Asn154Glu + Tyr213Gln
Asn154Gln + Gly203Asp
Asn154Glu + Thr219Gln
Thr212Ser + Leu216His
Tyr205His + Thr215Asp
Gly 60Asp + Gly126Pro
Gly203Glu + Leu216Ala
Gly156Ser + Gly203Ser
Ser155Asp + Gly165Gln
Ala202Gly + Thr212Asp
Asn157Gln + Tyr213Ser
Gly 99Ser + Gly130Ser
Gly203Ser + Thr219Asp
Gly130Ser + Ala214Asn
Thr210Gln + Thr212Asp
Asn211Gln + Thr212Glu
Gly153Asn + Thr212Asp

TABLE 29-continued

Multi-loop Double Mutation Variants

Gly153Asp + Tyr205Ser
Ser100Glu + Tyr205Thr
Gly126Asn + Asn154Glu
Ser190Asp + Tyr205Val
Ser102Glu + Gly166Thr
Asn157Ser + Pro209Gly
Asp 59Glu + Tyr205Leu
Ser131Glu + Thr132Asn
Gly127Asp + Leu216Thr
Thr210Asn + Asn217Gln
Gly203Ser + Gly218Asp
Ile106Gln + Gly203Asp
Thr161Asp + Tyr205Pro
Gly105Pro + Thr212Asp
Tyr205Thr + Leu216Cys
Asn 96Ser + Ser158Glu
Asn 61Glu + Tyr205Ala
Tyr205Ser + Thr212Glu
Thr163Gln + Phe188Glu
Tyr103Ala + Thr212Asp
Gly101Asp + Ala202His
Ser155Glu + Gly218Asn
Val 94Thr + Thr163Ser
Ser102Glu + Asn217Gln
Gly159Ser + Ala202Glu
Asn151Ser + Tyr166Ala
Asp 59Glu + Phe188Gly
Thr163Gln + Gly218Ser
Gly153Asn + Tyr205Val
Ser129Glu + Leu216Pro
Gly126Ser + Thr212Glu
Gly203Asp + Leu216Asn
Gly126Glu + Thr212Pro
Val 94Pro + Ala186Glu
Gly165Gln + Thr215Glu
Ser129Asp + Gly153Asn
Ser 98Glu + Thr215Ser
Gly203Ser + Leu216Pro
Gly105Asp + Leu216His
Ile106Met + Thr210Asp
Leu216Asn + Asn217Glu
Gly127Gln + Thr219Glu
Val 94Glu + Ala202Gly
Thr132Asn + Leu216His
Asp 59Glu + Ala202Asn
Leu 95Ile + Tyr205Pro
Thr 65Glu + Thr215Pro
Ser104Glu + Thr215Asn
Ser160Glu + Gly203Pro
Gly203Asp + Leu216Pro
Ala128Glu + Tyr213Met
Ser 98Asp + Leu216Cys
Ser158Asp + Thr215Gln
Val 94Asp + Thr215Asn
Gly127Asp + Asn154Ser
Gly126Ser + Gly156Gln
Leu125Gly + Thr212Asp
Thr110Glu + Leu216Asn
Asn154Ser + Ala202Asn
Asn 96Gln + Gly126Asn
Gly 64Ser + Gly127Ser
Asn211Ser + Thr212Gly
Ser160Asp + Gly218Gln
Tyr205Ala + Thr210Glu
Thr212Asp + Leu216Ser
Ser158Asp + Thr215Ser

TABLE 33

Multi-loop Triple Mutation Variants

Leu 95Gly + Gly203Pro + Asn211Glu
Thr 58Gln + Asp 59Glu + Leu216Gln
Tyr103Cys + Ala202Gln + Thr212Gly

TABLE 33-continued

Multi-loop Triple Mutation Variants

Gly126Gln + Gly156Glu + Thr215Pro
Asn 96Gln + Ile106Ala + Tyr205Pro
Asn 61Ser + Gly101Asp + Gly165Gln
Gly 64Gln + Thr132Gly + Gly153Glu
Ala128Ser + Ser158Asp + Gly203Ser
Tyr103Glu + Ile106Leu + Gly203Pro
Thr163Pro + Ala202Pro + Leu216Ser
Thr 58Asp + Gly130Gln + Tyr208Pro
Gly105Pro + Gly156Glu + Leu216Ile
Gly 60Asn + Thr215Ser + Gly218Asp
Thr 65Gln + Leu125Asn + Ala128Glu
Asn211Ser + Thr212Asp + Gly218Gln
Gly203Glu + Thr212Gln + Thr215Gly
Thr132Pro + Tyr205Gly + Thr215Ser
Gly 60Pro + Thr 65Pro + Gly203Glu
A5n 96Gln + Gly203Asp + Thr215Gly
Gly 99Asn + Gly153Asn + Pro209Gly
Gly105Glu + Ala128Asn + Ala202His
Tyr205Ser + Thr212Gly + Gly218Glu
Gly 99Gln + Asn217Glu + Thr219Gly
Leu 95Gln + Ala202Thr + Thr215Asp
Ser129Glu + Asn157Gln + Thr219Asn
Asp 59Glu + Tyr103Ile + Thr215Pro
Gly 99Asp + Ile164Thr + Thr215Ser
Asn 61Gln + Tyr208Gln + Thr212Asp
Gly153Glu + Thr163Pro + Thr215Ser
Asn 61Ser + Thr132Asn + Gly203Pro
Leu 95Asn + Ser158Glu + Thr215Asn
Thr 58Ser + Ser100Asp + Tyr205Ala
Ser158Glu + Phe188Leu + Tyr205Met
Asn 61Ser + Ala186Ser + Phe188Ser
Asn154Glu + Tyr213Thr + Leu216Gln
Ser 97Asp + Ala199Pro + Gly203Asn
Thr 65Ser + Gly126Glu + Gly218Asp
Tyr205His + Thr215Gln + Leu216Ala
Ala128Ser + Thr163Gln + Thr215Asp
Val 94Ser + Ser100Asp + Phe188Val
Gly 99Pro + Asn154Gln + Gly203Asn
Asn 96Ser + Thr163Asp + Ala214Thr
Tyr166Asp + Tyr205Thr + Ala214Thr
Gly 62Ser + Thr 65Ser + Thr215Gly
Gly153Pro + Gly203Ser + Thr219Glu
Asp 59Glu + Ala202Pro + Leu216Ala
Val 94Thr + Thr212Gln + Leu216Met
Ser129Asp + Thr132Ser + Ala202Gly
Leu 95Met + Tyr103Ala + Leu216Asp
Ser104Asp + Gly203Asn + Thr215Asn
Thr 65Glu + Tyr103Pro + Ile106cys
Val 94Met + Ser 98Glu + Thr210Pro
Ser 97Glu + Thr161Pro + Gly203Ser
Leu125Pro + Ala128Asp + Ala199Pro
Asp 59Glu + Tyr20SIle + Ala214Pro
Ser129Glu + Tyr166Pro + Gly203Gln
Gly203Gln + Pro209Gln + Thr215Gln
Asn 96Ser + Asn154Glu + Tyr16GThr
Gly105Asp + Phe188Gly + Asn211Ser
Thr 58Asp + Gly156Pro + Ala202Ser
Leu 95Met + Gly 99Ser + Ser131Glu
Gly126Asn + Gly159Pro + Tyr205Glu
Leu 95Thr + Leu216Ala + Gly218Asn
Gly105Glu + Gly130Pro + Leu216Thr
Thr S8Pro + Thr132Asn + Gly153Asn
Gly 60Gln + Pro209Asn + Thr215Asn
Thr132Asp + Ala202Asn + Thr219Gly
Thr 58Asp + Gly203Gln + Gly218Ser
Ser129Glu + Thr212Asn + Thr215Gln
Gly203Pro + Tyr205Asn + Thr215Asp
Ala128Pro + Thr215Asp + Leu216Pro
Thr161Pro + Gly201Gln + Leu216Cys
Gly126Asp + Tyr205Met + Thr212Pro
Ser 97Asp + Thr210Asn + Leu216His
Ala186Asn + Phe188Thr + Tyr205Pro
Asn 61Asp + Thr132Ser + Leu216Asn
Leu 95Asn + Thr132Gly + Thr215Asp
Ile106Asp + Tyr166Thr + Asn211Gln
Ile106Ala + Thr207Pro + Leu216Thr
Tyr205Asn + Thr215Asn + Gly218Asn TABLE 33-continued

| Multi-loop Triple Mutation Variants |
|---|
| Asn 96Gln + Ser160Asp + Phe188Gly |
| Gly 64Ser + Gly101Asp + Asn154Gln |
| Thr 58Asn + Gly 64Asn + Asn157Glu |
| Gly101Asn + Ala186Asn + Thr215Ser |
| Gly 62Asn + Asn 96Ser + Ala214Asn |
| Gly130Asp + Phe188Asn + Gly218Pro |
| Gly 99Ser + Ala128Glu + Leu216Gly |
| Val 94A1a + Pro209Ser + Thr215Asp |
| Leu 95Thr + Gly126Gln + Leu216Gly |
| Asp 59Glu + Gly159Ser + Tyr205Pro |
| Ala199Gly + Ala202Gln + Gly203Gln |
| Ser158Glu + Thr161Gly + Tyr205Asn |
| Thr 58Ser + Ser190Glu + Tyr205Pro |
| Leu 95Asn + Tyr205Ala + Pro209Glu |
| Thr 58Asn + Gly153Pro + Thr210Pro |
| Ala128Gly + Gly203Asn + Tyr205Pro |
| Val 94Cys + Asn157Gln + Tyr205Gln |
| Ser129Glu + Tyr205Asn + Thr215Asn |
| Thr 65Gly + Gly127Asn + Thr212Gln |
| Gly 60Asn + Tyr205Thr + Asn217Gln |
| Gly126Pro + Ala214Pro + Thr215Gly |
| Thr163Gly + Ala202Pro + Thr212Pro |
| Thr 58Pro + Gly130Ser + Ser160Asp |
| Gly153Ser + Asn154Glu + Thr212Gly |
| Leu125Gly + Tyr205Thr + Thr210Glu |
| Tyr103Val + Thr132Gly + Pro200Gln |
| Ser100Glu + Gly127Asn + Leu216Ala |
| Ser160Glu + Ala186Ser + Tyr205Ser |
| Gly159Ser + Thr163Glu + Ile164His |
| Gly101Asp + Tyr166Cys + Gly203Pro |
| Thr 58Asn + Asn 61Glu + Ala214Ser |
| Gly127Glu + Phe188Net + Ala202Gly |
| Asn162Glu + Gly203Ser + Gly218Asn |
| Tyr166Asn + Thr210Glu + Ala214His |
| Ile106Asp + Thr212Ser + Thr215Gln |
| Asn162Glu + Ala202Ser + Thr215Asn |
| Tyr103Pro + Ser187Glu + Tyr205Pro |
| Val204Thr + Thr212Ser + Thr215Gln |
| Ser100Asp + Gly101Asn + Leu2I6His |
| Leu 95Cys + Gly203Ser + Leu216Thr |
| Asn 96Ser + Gly153Glu + Tyr205Pro |
| Ile106Pro + Ala202Ser + Thr212Pro |
| Ser102Asp + Gly203Ser + Thr215Ser |
| Leu 95Cys + Ser104Glu + Phe188Cys |
| Asp 59Glu + Ala214Gly + Thr215Gly |
| Leu125Cys + Thr212Gly + Thr215Ser |
| Leu125Val + Ala202His + Thr215Pro |
| Gly10lAsp + Gly127Asn + Gly203Gln |
| Thr 58Pro + Gly105Asn + Gly203Glu |
| Tyr166Cys + Gly203Ser + Tyr205Asp |
| Gly126Gln + Ile164Val + Leu216His |
| Gly153Ser + Thr215Pro + Leu216Glu |
| Ser160Asp + Gly218Gln + Thr219Asn |
| Asn 61Glu + Asn157Ser + Ala214Ser |
| Gly 62Ser + Ala128Ser + Asn154Asp |
| Ile106Gly + Tyr205Val + Thr215Ser |
| Ser160Glu + Asn211Gln + Thr215Pro |
| Thr 65Gly + Ser100Glu + Thr215Pro |
| Thr 65Ser + Ser104Glu + Gly203Pro |
| Asn 61Ser + Ile106Ser + Thr219Pro |
| Ser102Asp + Gly153Pro + Leu216His |
| Thr 65Glu + Gly126Gln + Gly203Ser |
| Ser187Glu + Phe188Ile + Leu216Thr |
| Thr132Gln + Gly165Asp + Thr212Ser |
| Ser129Asp + Asn211Ser + Leu216Thr |
| Leu125Ile + Asn154Ser + Leu216Met |
| Thr 65Pro + Gly101Pro + Thr212Asp |
| Thr 65Gln + Leu125Asn + Leu216Met |
| Pro209Gly + Ala214Glu + Thr215Pro |
| Leu125Val + Tyr205Ser + Leu216His |
| Leu 95Asn + Gly156Asp + Thr212Gln |
| Leu125Pro + Thr210Asp + Thr215Ser |
| Gly105Asn + Thr161Asn + Tyr205Val |
| Gly126Ser + Ser160Glu + Gly218Asn |
| Val 94Thr + Thr207Gly + Thr212Glu |
| Tyr208Gln + Thr212Gln + Gly218Asp |
| Ile106Asn + Gly159Asn + Phe188Asp |

TABLE 33-continued

| Multi-loop Triple Mutation Variants |
|---|
| Tyr205Met + Thr212Gln + Tyr213Thr |
| Ser13lAsp + Thr132Pro + Tyr213Asn |
| Gly105Ser + Ala128Thr + Thr215Pro |
| Leu 95His + Asn 96Asp + Thr215Gly |
| Gly 60Ser + Gly156Asp + Pro209Asn |
| Asn162Asp + Thr163Asn + Ala199Gly |
| Tyr103Glu + Leu125His + Thr215Ser |
| Gly127Glu + Asn157Gln + Tyr205Leu |
| Asp 59Glu + Gly105Pro + Ala186Asn |
| Ala128Asp + Tyr213His + Leu216His |
| Thr 65Pro + Ile106His + Ser13lGlu |
| Gly126Gln + Thr161Asp + Ala202Ser |
| Gly 99Gln + Gly126Asp + Thr212Gly |
| Thr 58Asp + Gly159Ser + Thr212Ser |
| Asp 59Glu + Ala186Gly + Gly203Gln |
| Gly 62Glu + Tyr205Ala + Leu216Gln |
| Asn154Gln + Tyr205Ser + Tyr213Met |
| Leu 95Ser + Ser158Glu + Thr212Gly |
| Tyr166Asn + Tyr205Glu + Leu216Asn |
| Asp 59Glu + Ala128Asn + Gly153Pro |
| Gly 99Asp + Gly159Asn + Asn211Ser |
| Gly165Pro + Thr215Gln + Leu216Thr |
| Gly165Asn + Thr215Asn + Leu216Asp |
| Gly 60Asp + Gly159Asn + Thr212Gln |
| Thr 58Glu + Thr163Gly + Thr210Gln |
| Gly159Ser + Ala186Gly + Ala199Thr |
| Gly203Glu + Asn211Gln + Tyr213Gln |
| Gly 99Ser + Asn162Asp + Thr215Gln |
| Thr 65Gly + Ser190Glu + Thr219Ser |
| Val 94Met + Asn162Ser + Ser190Glu |
| Asn 61Gln + Leu 95Ser + Tyr205Asp |
| Gly126Glu + Gly201Pro + Gly203Ser |
| Thr 58Gly + Thr212Pro + Gly218Glu |
| Ser104Asp + Gly105Ser + Gly159Pro |
| Thr 58Gln + Thr163Gly + Tyr205Pro |
| Gly 60Ser + Thr 65Pro + Thr163Gly |
| Leu125Met + Ser13lGlu + Thr210Gly |
| Phe188Gln + Gly201Ser + Ala202Gly |
| Gly203Pro + Leu216Glu + Asn217Gln |
| Gly 62Asn + Gly126Pro + Thr210Asn |
| Gly 60Asn + Ser104Asp + Gly127Gln |
| Ser155Glu + Thr163Pro + Gly203Pro |
| Leu 95Met + Thr132Asp + Asn211Ser |
| Tyr103Ile + Gly159Asp + Ala202Gly |
| Gly101Gln + Tyr166Pro + Asn211Gln |
| Asn157Ser + Ala202Ser + Thr215Gly |
| Thr132Pro + Ser155Glu + Ala214His |
| Thr132Ser + Thr212Asp + Leu216Gly |
| Gly126Asn + Thr212Asp + Gly218Gln |
| Tyr205cys + Thr212Pro + Leu216Met |
| Asn 96Gln + Thr163Gln + Leu216Glu |
| Ala202Ser + Tyr205Asn + Gly218Asp |
| Leu 95Asp + Gly126Asn + Ala202Ser |
| Ser100Glu + Ile106Gln + Ala202Gln |
| Thr 58Ser + Ser100Glu + Ile164Leu |
| Gly101Ser + Phe188Asp + Tyr213Gly |
| Ser104Glu + Gly156Gln + Thr212Gly |
| Leu125Val + Gly203Asn + Tyr205Thr |
| Thr163Gln + Thr215Asn + Asn217Glu |
| Gly 99Pro + Gly165Glu + Ala214Gln |
| Met198Ser + Gly203Glu + Tyr213Val |
| Asn 96Ser + Ser 97Asp + Thr212Ser |
| Ala202Glu + Gly203Ser + Tyr205Gln |
| Gly 64Asn + Asn154Gln + Asn157Glu |
| Thr 65Ser + Gly130Pro + Tyr205Asp |
| Gly126Gln + Thr161Gln + Pro209Ser |
| Asp 59Glu + Phe188Leu + Leu216Ala |
| Ser13lAsp + Thr212Pro + Thr215Gln |
| Va1204Pro + Gly218Asn + Thr219Glu |
| Thr 58Ser + Gly203Glu + Thr212Pro |
| Gly 62Gln + Tyr205Gly + Thr212Glu |
| Thr 65Gly + Ser129Asp + Met198Gly |
| Leu 95Cys + Asn162Ser + Ala202Thr |
| Leu125Asp + Tyr205Thr + Leu216Thr |
| Asn157Asp + Tyr205Ser + Leu216Pro |
| Gly156Asn + Gly165Asn + Thr215Glu |
| Ala128Ser + Thr163Glu + Ala199Ser |

TABLE 33-continued

Multi-loop Triple Mutation Variants

Val 94Ser + Ser187Glu + Thr215Gln
Val 94Pro + Thr215Gly + Asn217Glu
Val 94Asn + Gly130Glu + Gly203Ser
Gly127Gln + Ile164Cys + Thr210Gln
Ser187Glu + Thr212Gln + Thr215Asn
Asn 96Gln + Gly126Gln + Gly203Asp
Gly165Asp + Thr210Ser + Tyr213Ile
Thr 58Gln + Gly153Ser + Asn217Gln
Gly203Asp + Tyr205Met + Thr210Ser
Ala128Pro + Thr132Glu + Thr215Pro
Ser104Glu + Phe188Ser + Thr212Gly
Ser104Glu + Asn157Ser + Ala214Ser
Ile106Cys + Tyr205Glu + Thr215Asn
Gly156Gln + Tyr205Pro + Thr219Asp
Asn157Glu + Tyr213Thr + Leu216Ile
Thr 58Ser + Asn162Ser + Ser190Asp
Gly 62Ser + Thr 65Asp + Tyr205Ile
Leu125Pro + Gly203Asp + Thr212Ser
Thr 58Gln + Ser 98Asp + Thr212Pro
Ser 97Asp + Leu125Val + Tyr213Ile
Ile106Leu + Phe188Glu + Thr212Asn
Thr 58Pro + Gly153Pro + Asn162Gln
Ser190Asp + Thr210Gln + Leu216Ala
Ser100Glu + Thr215Gly + Leu216Net
Gly127Glu + Ala128Gln + Thr212Pro
Val 94Pro + Gly127Ser + Thr215Glu
Thr161Asp + Ala199Asn + Tyr213Gln
Thr132Pro + Tyr166Leu + Thr212Pro
Gly203Gln + Thr215Asn + Leu216Met
Gly127Pro + Gly203Asp + Tyr205Ile
Thr163Ser + Tyr205Ala + Pro209Gln
Val 94Cys + Thr215Asn + Gly218Pro
Gly126Glu + Gly165Pro + Ala202Thr
Thr 58Glu + Tyr103Asp + Pro200Gln
Phe 88Thr + Ala202Asn + Asn217Ser
Gly 60Asp + Leu 95Thr + Tyr205Ile
Ser102Glu + Ala202Ser + Leu216Gln
Gly 99Asn + Ser102Asp + Gly218Gln
Ile106Ala + Thr132Pro + Asn157Asp
Gly203Ser + Tyr205Gln + Thr212Glu
Ser 97Asp + Ile106His + Asn211Gln
Ser100Glu + Gly201Asn + Tyr205His
Thr212Gln + Ala214Glu + Thr215Glu
Asn 61Glu + Gly 62Glu + Gly203Pro
Asn211Glu + Thr212Asp + Leu216Ile
Gly 99Glu + Ser100Asp + Gly156Pro
Ala202Asp + Gly203Glu + Tyr205Pro
Ser 97Asp + Ser 98Glu + Thr163Gln
Ala128Thr + Tyr205Asp + Thr215Asp
Ser102Asp + Gly105Asp + Leu216Gly
Gly127Glu + Gly165Asp + Tyr205Thr
Gly203Asp + Tyr205Ala + Asn217Glu
Asp 59Glu + Asn 61Glu + Gly130Ser
Gly 60Glu + Ser 97Glu + Gly 99Asn
Tyr166Ala + Gly203Gln + Leu216Asp
Ser158Asp + Ser160Glu + Tyr205Cys
Ser129Asp + Tyr166Glu + Thr215Gln
Ser160Asp + Asn162Glu + Thr210Gly
Ser129Asp + Ser131Asp + Gly218Asn
Asn 61Gln + Leu 95Asp + Ser 97Asp
Gly 62Ser + Leu216Asp + Gly218Glu
Asp 59Glu + Gly165Asn + Pro209Glu
Leu 95Gly + Gly105Glu + Gly203Ser
Asn157Glu + Asn162Asp + Thr215Gln
Tyr103His + Asn162Glu + Ser190Asp
Ser158Asp + Asn162Glu + Thr163Pro
Gly 62Glu + Ser 97Glu + Gly153Glu
Gly 99Gln + Asn154Asp + Ser187Glu
Ser155Asp + Gly156Asp + Thr219Asp
Gly153Ser + Asn154Asp + Gly165Asp
Asp 59Glu + Asn 96Glu + Tyr205Ser
Asp 59Glu + Asn 96Asp + Leu216Ile
Ser104Asp + Ser131Asp + Thr210Gly
Ser 97Glu + Gly101Asp + Ala202Asn
Asn 96Asp + Ser102Glu + Ile106Gly
Asn 61Asp + Leu 95Glu + Val224Gln
Gly156Asp + Thr161Asp + Gly203Ser

TABLE 33-continued

Multi-loop Triple Mutation Variants

Ser100Asp + Tyr103Asp + Gly126Asn
Thr 65Asp + Tyr205Asp + Thr215Asp
Thr 58Asp + Ser 97Asp + Thr132Gly
Thr215Pro + Leu216Asp + Thr219Glu
Ser100Glu + Gly105Glu + Asn162Gln
Ala186Glu + Ala202Glu + Thr215Asp
Asn 61Asp + Ser100Glu + Asn162Ser
Ser104Asp + Thr132Glu + Tyr205Met
Gly 99Asn + Thr210Asp + Ala214Glu
Asn157Asp + Ala186Glu + Thr212Ser
Gly 62Asp + Pro209Asn + Asn211Asp
Gly105Pro + Gly153Glu + Asn162Asp
Ala186Ser + Thr212Asp + Thr215Asp
Gly 99Glu + Ser102Asp + Leu125Gly
Gly 62Ser + Gly 99Glu + Ser102Asp
Gly126Glu + Ser155Glu + Tyr205Pro
Ser158Glu + Phe188Asp + Ala202Ser
Gly 60Glu + Leu 95Glu + Ile106Leu
Ala128Asp + Asn154Asp + Thr215Gln
Ala128Asp + Asn162Glu + Asn217Ser
Asn157Gln + Ser187Glu + Asn217Asp
Gly 62Asp + Ser 98Asp + Thr212Glu
Gly159Glu + Ser160Asp + Phe188Asp
Gly126Asp + Thr210Glu + Asn211Glu
Ser104Asp + Gly105Asp + Ala128Glu
Asp 59Glu + Tyr205Glu + Thr215Glu
Gly 60Asp + Tyr205Glu + Thr215Asp
Asn 61Glu + Pro209Asp + Thr215Glu
Asn 61Asp + Ser 97Glu + Tyr205Asp
Ser102Asp + Gly105Glu + Pro209Asp
Ser158Asp + Gly203Asp + Thr215Glu
Asn157Asp + Gly203Asp + Thr215Asp
Gly127Glu + Ser129Glu + Thr215Glu
Asn 96Glu + ser100Asp + Thr212Glu
Ser190Glu + Gly203Glu + Tyr205Glu
Ser129Asp + Phe188Glu + Ser190Asp
Ser100Asp + Ser104Glu + Thr212Pro
Ser129Glu + Gly153Glu + Asn157Gln
Ser 97Glu + Thr212Glu + Ala214Glu
Ser100Asp + Ser102Glu + Ser150Asp
Asp 59Glu + Ser 97Glu + Asn157Asp
Ser 97Glu + Asn157Glu + Ser160Glu
Gly101Asn + Leu125Glu + Ser129Glu
Gly101Glu + Gly130Glu + Thr161Ser
Asn154Glu + Ser158Glu + Gly203Gln
Val 94Asp + Ser187Asp + Ser190Glu

TABLE 34

Multi-loop Quadruple Mutation Variants

Thr 58Gln + Leu 95Gly + Gly203Pro + Asn211Glu
Asp 59Glu + Tyr103Cys + Thr212Gly + Leu216Gln
Gly126Gln + Gly156Glu + Ala202Gln + Thr215Pro
Asn 61Ser + Gly101Asp + Gly165Gln + Tyr205Pro
Ser104Glu + Thr132Gly + Phe188Val + Leu216Ser
Gly127Glu + Thr212Asn + Thr215Ser + Leu216Gln
Leu125Thr + Thr210Gln + Thr212Asp + Thr215Ser
Thr132Pro + Gly203Glu + Tyr205Gly + Thr215Gly
Asn 96Gln + Gly153Pro + Pro209Gln + Leu216Val
Gly 99Asn + Ala128Asn + Gly153Asn + Ala202His
Phe188Val + Tyr205Ser + Thr212Gly + Gly218Glu
Tyr103Ile + Ser129Glu + Asn157Gln + Thr215Pro
Leu 95Asn + Ser158Asp + Gly203Pro + Thr215Asn
Thr 58Ser + ser100Asp + Ile164Met + Tyr205Ala
Thr 65Ser + Gly126Gln + Gly203Asn + Gly218Asp
Asn 96Glu + Tyr205His + Thr215Gln + Leu216Ala
Thr 65Ser + Ala128Ser + Gly156Asp + Thr163Gln
Asn154Gln + Asn157Glu + Gly203Asn + Thr215Gln
Gly 62Ser + Tyr205Thr + Ala214Thr + Thr215Gly
Asp 59Glu + Asn 61Gln + Ala202Pro + Leu216Ala
Leu 95Met + Tyr103Ala + Thr132Ser + Tyr205Asp
Ser 97Glu + Leu125Pro + Thr161Pro + Gly203Ser
Asp 59Glu + Ile106Gly + Tyr205Ile + Ala214Pro TABLE 34-continued Multi-loop Quadruple Mutation Variants Ser129Glu + Tyr166Pro + Gly203Gln + Tyr205Gly
Asn 61Glu + Gly203Gln + Thr212Ser + Thr215Gln
Gly153Glu + Phe188Gly + Asn211Ser + Gly218Asn
Tyr103Val + Gly126Asn + Pro209Asn + Leu216Asp
Ala128Ser + Ser190Asp + Tyr213Ala + Leu216Val
Gly127Ser + Asn154Ser + Tyr205Leu + Thr212Gln
Ala128Glu + Asn154Gln + Asn157Gln + Leu216His
Ser155Asp + Gly156Ser + Gly203Ser + Leu216Ala
Gly 99Ser + Gly130Ser + Asn157Gln + Tyr213Ser
Gly130Ser + Gly203Ser + Ala214Asn + Thr219Asp
Asp 59Glu + Asn157Ser + Tyr166Thr + Pro209Gly
Gly203Ser + Thr210Asn + Leu216Thr + Asn217Gln
Tyr103Ala + Thr163Gln + Ala202His + Thr212Asp
Gly 62Glu + Asn154Ser + Tyr166Ala + Phe188Gly
Asp 59Glu + Thr163Gln + Tyr205Val + Gly218Ser
Val 94Pro + Gly153Asn + Gly165Gln + Thr215Glu
Ser 98Asp + Asn154Ser + Gly203Ser + Leu216Pro
Ile106Glu + Thr132Asn + Ala202Gly + Leu216His
Asp 59Glu + Leu 95Ile + Ala202Asn + Tyr205Pro
Thr 65Gln + Asn 96Gln + Ser104Glu + Thr215Pro
Leu125Gly + Gly126Ser + Asn154Ser + Gly156Gln
Asn 96Gln + Gly126Asn + Gly127Ser + Ala202Asn
Gly 64Ser + Ser160Asp + Asn211Ser + Thr212Gly
Gly101Pro + Ser158Asp + Thr215Ser + Leu216Ser
Val 94Glu + Ala202Ser + Tyr205Ser + Thr212Gly
Gly153Ser + Asn154Gln + Thr161Asn + Thr212Gly
Tyr103Val + Leu125Gly + Thr132Gly + Pro200Gln
Gly127Pro + Phe188Met + Ala202Gly + Thr215Glu
Asn162Glu + Gly203Ser + Ala214His + Gly218Asn
Asn 96Gln + Gly 99Pro + Thr132Asn + Thr212Pro
Gly101Asn + Tyr205Gly + Tyr213Met + Thr215Asp
Leu125Pro + Gly126Asn + Ala202Gly + Gly203Asp
Gly 99Pro + Gly127Glu + Tyr205His + Thr212Gln
Tyr103Pro + Tyr166Ile + Gly203Ser + Thr207Gly
Thr 58Gly + Gly 62Ser + Gly105Glu + Ala128Ser
Ile106Gly + Tyr205Val + Thr215Ser + Leu216Asp
Asn 61Ser + Ile106Ser + Ser190Asp + Thr219Pro
Thr 65Glu + Gly126Asn + Gly203Ser + Leu216His
Ser187Glu + Phe188Ile + Thr212Ser + Leu216Thr
Leu125Ile + Asn154Ser + Asn211Ser + Leu216Met
Thr 65Gln + Leu125Asn + Pro209Gly + Ala214Glu
Leu125Val + Tyr205Ser + Thr215Pro + Leu216His
Leu 95Asn + Leu125Pro + Gly156Asp + Thr212Gln
Gly126Ser + Ser160Glu + Thr161Asn + Gly218Asn
Leu 9SGln + Phe188Ile + Ala202His + Thr212Asn
Ser104Glu + Thr212Gln + Tyr213Thr + Thr215Pro
Ala128Thr + Ser131Asp + Thr132Pro + Tyr213Asn
Leu 95His + Ser129Glu + Thr215Gly + Leu216Asn
Gly105Pro + Ala128Asp + Tyr213His + Leu216His
Gly159Ser + Tyr205Ala + Thr212Gly + Leu216Ala
Gly 62Glu + Asn154Gln + Tyr205Ser + Leu216Gln
Leu 95Ser + Ser158Glu + Val204Gln + Thr212Gly
Ser 98Asp + Leu216Ile + Asn217Ser + Gly218Asn
Leu125Gly + Ala128Gln + Gly203Glu + Pro209Gln
Gly166Val + Tyr166Val + Ala202Asp + Thr215Pro
Ser 97Asp + Ala202Gln + Pro209Gln + Thr215Gly
Leu 95Thr + Tyr205Ile + Leu216Val + Thr219Ser
Gly 99Asn + Ser102Asp + Tyr205Ser + Gly218Gln
Thr 65Pro + Gly165Asn + Thr210Ser + Gly201Ser
Asn154Asp + Gly203Gln + Tyr205Asn + Thr212Asn
Ile106His + Ala186Gly + Thr212Asn + Leu216Asp
Gly126Glu + Gly127Gln + Ala128Asn + Ala202Asn
Leu 95er + Ala128Gly + Thr161Gln + Asn217Glu
Asp 59Glu + Gly101Pro + Ala199Gly + Gly203Ser
Asn 61Asp + Val204Thr + Tyr205Cys + Thr215Ser
Gly101Asn + Asn162Asp + Phe188Ala + Tyr205His
Ala186Thr + Gly203Asp + Thr215Pro + Asn217Asp
Tyr103Gln + Phe188Met + Thr210Glu + Thr219Pro
Gly 62Asp + Gly126Ser + Leu216Pro + Thr219Asn
Gly 60Gln + Tyr205Pro + Thr212Ser + Thr215Asp
Ile106Val + Ser187Glu + Thr212Pro + Thr215Ser
Gly159Asp + Asn211Ser + Ala214Gln + Thr219Pro
Asn 96Ser + Ser160Asp + Ala214Gln + Leu216Gly
Ser104Asp + Gly203Ser + Tyr205Ser + Thr215Pro
Gly153Gln + Phe188Tyr + Thr215Glu + Leu216Ile
Ser129Asp + Thr132Pro + Thr212Ser + Leu216Thr
Ala128Gln + Ala186Asn + Thr215Asp + Gly218Asn TABLE 34-continued Multi-loop Quadruple Mutation Variants Asn 96Asp + Ala202Pro + Tyr205Gln + Pro209Ser
Thr132Asp + Gly165Pro + Thr210Pro + Leu216Cys
Gly105Pro + Gly130Ser + Thr161Glu + Thr215Pro
Ile106Cys + Asn157Gln + Tyr205His + Thr212Gln
Leu 95Gly + Ser100Glu + Gly101Pro + Gly126Ser
Gly 60Ser + Gly105Asp + Thr132Pro + Tyr205Thr
Thr132Ser + Ile164Val + Gly203Glu + Gly218Asn
Gly203Gln + Thr212Pro + Thr215Asn + Leu216Pro
Asn 61Ser + Val 94Gln + Thr132Asp + Val204Gly
Gly201Ser + Thr212Gly + Thr215Pro + Leu216Pro
Gly153Pro + Ser160Glu + Gly165Gln + Gly218Ser
Tyr166Ile + Tyr213Ser + Ala214Glu + Gly218Asn
Thr132Ser + Thr163Asp + Tyr166Val + Ala199His
Thr132Gln + Asn157Ser + Tyr208Gly + Thr215Asp
Gly203Glu + Tyr205Ile + Tyr208Pro + Thr215Ser
Gly127Ser + Gly165Ser + Tyr213Ile + Leu216His
Gly156Glu + Pro209Asn + Asn211Ser + Thr212Ser
Gly165Gln + Phe18BLeu + Ala202His + Thr212Glu
Ser102Asp + Gly130Asn + Asn162Ser + Leu216Thr
Val 94Cys + Gly156Ser + Tyr205Ala + Leu216Ala
Gly 99Pro + Tyr103Glu + Phe188His + Leu216Cys
Tyr103Gln + Gly126Asn + Gly156Pro + Tyr166Ala
Leu125Pro + Gly153Glu + Asn162Ser + Thr215Ser
Gly 64Ser + Gly 99Asn + Gly203Asp + Thr210Gln
Gly 99Asn + Ala202Pro + Thr212Asn + Gly218Ser
Ala128Ser + Gly203Asn + Pro209Glu + Gly218Ser
Thr 58Ser + Tyr103Gly + Leu125Gly + Tyr205Gly
Asn154Glu + Thr161Ser + Asn162Gln + Gly203Gln
Gly101Pro + Asn154Ser + Leu216His + Asn217Glu
Thr163Asp + Ala186Ser + Tyr205His + Leu216Pro
Gly159Glu + Gly203Ser + Thr210Gly + Leu216His
Leu125Ser + Thr163Glu + Ala202Pro + Thr210Gln
Gly153Pro + Ser155Glu + Thr210Asn + Leu216Cys
Gly101Asp + Gly126Asn + Tyr166Ile + Gly203Pro
Ser158Asp + Gly201Asn + Val204Asn + Pro209Ser
Tyr166Pro + Tyr205Pro + Thr215Asp + Leu216Ala
Gly 64Asn + Ser160Asp + Tyr205Leu + Thr215Gly
Gly101Ser + Thr132Gln + Gly159Pro + Thr161Ser
Tyr103Val + Asn154Gln + Gly159Ser + Asn211Asp
Gly127Glu + Asn157Ser + Thr161Asn + Thr212Gly
Asn 61Asp + Ile164Asn + Pro209Asn + Leu216Val
Ser158Asp + Asn162Ser + Tyr205Asn + Thr212Gly
Leu125Val + Ala202Thr + Pro209Asn + Thr219Pro
Gly 60Asp + Asn154Gln + Gly203Pro + Tyr205Leu
Leu125Gln + Asn162Ser + Gly203Asp + Thr215Gly
Ser102Asp + Tyr103Ile + Tyr205Met + Thr212Gln
Gly 99Gln + Ala214Gln + Leu216Ala + Gly218Glu
Gly105Asn + Gly156Gln + Gly203Pro + Gly218Asp
Ile106Ser + Thr212Asn + Leu216Glu + Gly218Gln
Asn 96Asp + Tyr166Thr + Gly203Ser + Gly218Pro
Ser155Asp + Gly203Asn + Tyr213Thr + Thr215Gly
Gly101Ser + Thr212Gly + Thr215Asn + Leu216His
Thr 65Ser + Leu 95Asn + Thr132Ser + Asn162Asp
Leu 95Met + Thr132Asn + Gly203Asp + Thr215Gly
Asn154Ser + Gly203Glu + Thr212Gly + Leu216Ala
Gly 60Ser + Ser131Glu + Thr210Ser + Asn217Gln
Gly 62Asn + Asn162Gln + Gly203Asp + Thr215Ser
Gly 99Ser + Tyr103Ala + Thr210Gln + Thr219Ser
Asn162Gln + Gly203Gln + Thr215Gln + Thr219Gly
Asn162Gln + Gly165Asn + Leu216Ile + Gly218Ser
Thr 65Asn + Gly 99Gln + Thr212Ser + Leu216Asp
Phe188Val + Ala214Asp + Thr215Asp + Leu216Gln
Gly 99Glu + Ser100Asp + Gly156Pro + Tyr205Glu
Val 94Asn + Tyr103Asp + Ser104Asp + Thr215Pro
Gly 64Gln + Asn154Asp + Ser155Glu + Leu216Ser
Asn154Glu + Ser155Glu + Gly156Gln + Thr215Pro
Gly153Pro + Asn157Ser + Tyr205Asp + Thr215Asp
Tyr103Leu + Phe188Met + Tyr205Glu + Thr215Glu
Tyr205Ala + Thr210Glu + Thr212Asp + Gly218Gln
Ala202His + Tyr205Val + Thr210Glu + Thr212Asp
Gly203Asp + Tyr205His + Thr212Ser + Thr215Asp
Gly127Glu + Ser129Asp + Gly153Asn + Thr210Pro
Ala128Asn + Tyr166Ala + Gly203Asp + Leu216Asp
Ser 98Glu + Ser100Glu + Gly203Ser + Asn217Gln
Asn 61Asp + Gly 62Pro + Asn 96Asp + Ser 97Glu
Gly159ser + Thr161Glu + Thr163Glu + Ile164His
Ser160Glu + Asn162Glu + Asn211Gln + Thr215Pro TABLE 34-continued Multi-loop Quadruple Mutation Variants Asn 61Asp + Gly 99Asp + Thr161Gly + Thr212Pro
Ile106Val + Ala186Asp + Ala202Glu + Thr215Gln
Asp 59Glu + Gly 64Asn + Thr 65Glu + Tyr213Ser
Val 94Pro + Thr215Asp + Leu216His + Asn217Asp
Asp 59Glu + Gly127Asn + Ala186Pro + Pro209Asp
Tyr103Glu + Ser131Glu + Tyr213His + Thr215Ser
Ser129Asp + Thr132Gln + Gly165Asp + Leu216Thr
Tyr205Ile + Thr212Glu + Ala214Glu + Thr219Gln
Thr 58Gly + Thr212Glu + Tyr213Asp + Thr215Asp
Asp 59Glu + Gly 62Gln + Ser 97Glu + Tyr205Gly
Phe188Asp + Tyr208Gln + Thr212Gln + Gly218Asp
Ala186Asp + Ala202Asp + Gly203Glu + Tyr205Pro
Asn154Ser + Ser155Asp + Gly165Ser + Ser187Asp
Ser 97Asp + Ser100Glu + Gly201Asn + Tyr205His
Ser 97Asp + Ser100Asp + Gly165Ser + Tyr205Thr
Gly105Ser + Asn157Glu + Ser160Glu + Thr215Pro
Gly156Asp + Thr161Asp + Ser190Asp + Gly203Ser
Thr 65Gly + Ser100Asp + Leu125Glu + Thr215Pro
Gly 62Glu + Ser 97Glu + Gly153Gln + Pro209Gln
Gly 62Glu + Asn157Gln + Gly203Gln + Thr210Glu
Asn154Asp + Gly165Glu + Thr212Gly + Gly218Pro
Asn162Asp + Gly165Asp + Thr212Gln + Leu216Cys
Ser100Glu + Gly126Glu + Ala186Gln + Tyr205Ala
Asn154Ser + Ser158Asp + Ser190Glu + Thr215Gln
Ser129Asp + Thr132Asp + Gly203Gln + Thr215Gln
Asn 96Ser + Thr163Asp + Tyr166Asp + Ala214Thr
Gly 60Glu + Ser 97Glu + Tyr166Asn + Thr210Glu
Ile106Gln + Asn154Glu + Gly203Asp + Gly218Asp
Ser100Glu + Gly105Glu + Asn162Gln + Phe188Ser
Ala186Asp + Ala202Glu + Thr215Asp + Asn217Gln
Asp 59Glu + Gly 99Asp + Ile164Thr + Thr215Ser
Ser129Glu + Asn154Glu + Asn162Ser + Gly165Asp
Ser104Glu + Thr132Glu + Tyr205Met + Thr215Pro
Gly 62Asp + Ile106Leu + Pro209Asn + Asn211Asp
Asp S9Glu + Ser 98Glu + Gly156Asn + Gly218Asn
Asn 96Asp + Ser100Asp + Ser104Glu + Thr132Asn
Ala128Asp + Asn154Asp + Tyr213Met + Thr215Gln
Ser131Glu + Gly153Asp + Gly165Asp + Tyr205Gly
Gly101Asp + Gly105Asp + Gly126Asn + Ser131Glu
Ser129Asp + Asn157Glu + Thr163Glu + Thr212Pro
Gly 99Asn + Ala128Asp + Asn162Glu + Asn217Ser
Ser 98Asp + Ser100Asp + Ser104Glu + Thr212Pro
Asn 96Gln + Ile106Ala + Gly156Glu + Ser160Asp
Gly203Asp + Pro209Glu + Thr215Asp + Leu216Pro
Asn 96Asp + Ser 97Glu + Ser164Asp + Ala214Ser
Gly159Asn + Gly165Glu + Leu216Cys + Thr219Asp
Gly153Asp + Ser187Asp + Gly203Asn + Leu216Ser
Thr 65Glu + Tyr103Pro + Thr215Asp + Asn217Asp
Gly 62Asp + Ala202Glu + Thr215Asp + Leu216Ser
Thr 65Asp + Gly101Gln + Gly130Ser + Tyr205Asp
Asn 61Ser + Thr 65Asp + Thr132Asn + Tyr205Asp
Gly 99Pro + Ser187Glu + Gly203Glu + Thr215Asp
Thr 65Ser + Gly126Asp + Thr210Glu + Asn211Glu
Asn 96Asp + Thr161Asp + Asn162Glu + Ala202Asn
Gly101Glu + Ile106Met + Ala214Asp + Thr215Glu
Asn 61Asp + Ala186Asp + Ser187Glu + Leu216Pro
Ser104Asp + Tyr205Val + Thr215Asp + Leu216Asp
Leu 95Asp + Ala202His + Thr215Glu + Leu216Glu
Ser129Asp + Gly130Asp + Thr210Glu + Thr215Asp
Ile106Glu + Asn162Ser + Asn211Asp + Thr212Glu
Thr 58Asp + Asp 59Glu + Ile106Glu + Phe188Ser
Ser104Asp + Gly105Asp + Ala128Glu + Thr215Gly
Gly 99Asp + Ser100Asp + Thr161Asp + Pro209Gln
Gly 99Asp + Ser100Glu + Ser190Asp + Tyr205His
Asp 59Glu + Ala202Asp + Gly203Glu + Leu216Cys
Asp 59Glu + Gly 60Glu + Ala128His + Thr215Asp
Gly126Asn + Asn154Glu + Ser155Asp + Gly203Asp
Ser 97Asp + Ser 98Asp + Ser131Asp + Asn162Ser
Ser 97Asp + Ser 98Glu + Ser104Asp + Asn217Gln
Gly156Ser + Ser158Glu + Tyr205Asp + Thr215Asp
Asn 61Glu + Ser 97Glu + Ala128His + Tyr205Asp
Gly 64Asn + Thr 65Glu + Phe188Tyr + Thr215Glu
Tyr103Glu + Ile106Glu + Gly203Pro + Gly218Glu
Gly 99Glu + Ser102Asp + Leu125Gly + Ser131Glu
Ser102Glu + Asn154Glu + Ser190Asp + Tyr205Val
Gly127Glu + Gly165Glu + Tyr205Thr + Thr215Glu
Val 94Glu + Gly105Asp + Gly165Pro + Thr212Glu TABLE 34-continued Multi-loop Quadruple Mutation Variants Asn 96Glu + Ser 98Asp + Tyr103Leu + Ser155Asp
Asp 59Glu + Asn 61Glu + Gly105Glu + Gly130Ser
Asp 59Glu + Asn 61Asp + Thr 65Gly + Tyr205Glu
Leu 95Gln + Tyr103Asp + Gly203Asp + Thr215Asp
Asn157Asp + Gly203Asp + Thr215Asp + Thr219Glu
Ser 98Glu + Gly203Glu + Thr215Glu + Gly218Ser
Ser131Asp + Asn154Gln + Gly203Asp + Thr215Glu
Gly101Asn + Ile106Glu + Gly159Asp + Thr161Asp
Gly127Glu + Ser129Asp + Gly130Ser + Thr215Glu
Gly153Gln + Ser155Asp + Pro209Glu + Thr212Asp
Gly203Glu + Thr210Asp + Leu216Asp + Gly218Pro
Val 94Ser + Ser 98Glu + Ser100Asp + Phe188Asp
Asn 96Asp + Ser100Asp + Gly153Ser + Asn162Glu
Gly 62Glu + Leu 95Glu + Ile106Leu + Thr212Glu
Ser160Asp + Asn162Asp + Ala202Asp + Thr215Gln
Asn 61Glu + Ser 98Asp + Gly126Glu + Leu216Asn
Ser100Asp + Ser104Asp + Gly105Asn + Tyr205Cys
Asn 61Asp + Gly 99Glu + Tyr103Thr + Ser131Asp
Val 94Glu + Asn157Asp + Thr163Glu + Tyr205Ala
Gly127Asp + Ser131Glu + Thr132Asn + Ser190Asp
Gly 60Glu + Gly156Ser + Asn211Asp + Thr212Gln
Gly126Asp + Gly156Glu + Ser158Glu + Tyr205Met
Asn157Asp + Tyr205Val + Thr215Asp + Asn217Glu
Asp 59Glu + Gly203Glu + Tyr205Asn + Pro209Asp
Gly105Glu + Ser131Asp + Gly156Asn + Leu216Pro
Asp 59Glu + Ser 97Glu + Asn157Asp + Phe188Asp
Ser 97Asp + Ser100Asp + Ala202Pro + Thr212Glu
Val 94Gly + Ser104Glu + Asn157Asp + Ser160Asp
Asn 61Glu + Asn162Glu + Ser190Asp + Thr215Gly
Asn 61Asp + Asn 96Glu + Gly127Ser + Gly130Asp
Thr 65Glu + Gly165Glu + Phe188Val + Ser190Glu
Tyr103Pro + Asn154Glu + Ser158Glu + Tyr205Pro
Ser131Glu + Gly156Glu + Tyr166Asp + Ala186Thr
Asn 61Glu + Thr 65Asp + Tyr103Pro + Ser131Asp
Gly130Glu + Asn154Asp + Ser187Asp + Tyr208His
Ser131Glu + Thr163Pro + Gly203Asp + Gly218Glu
Asp 59Glu + Asn162Asp + Thr163Gln + Thr210Glu
Leu125Asp + Gly165Asp + Cly203Asp + Tyr213Glu
Gly101Asp + Asn162Asp + Gly165Glu + Leu216Asn
Ser155Glu + Ser158Asp + Tyr205Glu + Leu216Pro
Gly 60Asp + Tyr205Pro + Thr212Asp + Thr215Glu
Ser160Asp + Thr163Asp + Tyr205His + Thr215Asp
Thr 58Pro + Asn 61Glu + Asn154Glu + Asn157Asp
Asp 59Glu + Gly 99Ser + Gly153Asn + Thr212Asp
Ser 97Glu + Gly101Asp + Thr132Glu + Ala202Asn
Thr 58Glu + Asn 61Asp + Ala186Gly + Ser187Asp
Thr 58Glu + Asn 61Glu + Ile106cys + Thr132Asn
Ser158Glu + Gly203Glu + Asn211Gln + Ala214Asp
Ser129Asp + Gly203Glu + Ala214Glu + Thr215Ser
Ser104Asp + Ser155Glu + Asn157Gln + Asn162Glu
Thr 65Glu + Ser160Glu + Tyr205Cys + Thr210Asp
Asn 61Asp + Leu 95Glu + Tyr205Asp + Leu216Asn
Ser100Glu + Gly127Glu + Thr215Asp + Leu216Pro
Ser102Glu + Gly127Glu + Ala128Pro + Asn162Glu
Asn 96Asp + Gly105Glu + Asn162Asp + Thr212Glu
Ser 98Glu + Gly127Asp + Ser131Glu + Ala202Ser
Asp 59Glu + Leu 95Asp + Gly159Asp + Tyr205Val
Thr 65Glu + Ser187Glu + Thr215Gln + Gly218Glu
Gly156Glu + Gly159Glu + Tyr205Met + Thr215Glu
Gly 64Gln + Gly130Glu + Thr132Gly + Gly153Glu
Asp 59Glu + Gly 99Glu + Ser129Glu + Tyr205Asn
Gly126Glu + Ala186Glu + Gly203Asp + Thr212Pro
Thr 58Asp + Tyr103Val + Ser104Glu + Thr132Asp
Ser104Glu + Thr132Asp + Ala202Glu + Asn217Gln
Ser 98Glu + Thr132Gly + Ser187Asp + Thr219Glu
Gly 62Asp + Ser100Asp + Gly105Asn + Tyr205Val
Ser 97Asp + Ala186Asn + Thr212Glu + Thr215Asp
Ser187Asp + Ala202Gly + Thr212Glu + Thr215Asp
Asp 59Glu + Ser 98Glu + Gly153Ser + Asn154Glu
Gly126Glu + Thr132Asp + Ser155Asp + Ala202Gly
Asp 59Glu + Gly 62Pro + Ser158Glu + Phe188Glu
Ser104Asp + Gly130Asp + Tyr205Pro + Thr212Glu
Thr 65Pro + Ser102Asp + Gly126Asp + Ala202Asp
Gly 62Asp + Ser129Glu + Thr215Asp + Leu216Val
Ala128Asp + Asn162Asp + Ala202Ser + Tyr205Glu
Ser 97Glu + Thr132Gly + Gly153Asp + Ser187Asp
Ser102Asp + Leu125Asp + Gly156Asp + Gly218Asn

TABLE 34-continued

Multi-loop Quadruple Mutation Variants

Asn 6 Gln + Ser160Glu + Ser190Asp + Gly203Glu
Asn 96Asp + Tyr166Asp + Ser190Glu + Leu216Cys
Thr 65Asp + Asn162Glu + Tyr205Asp + Thr215Pro
Thr 65Asp + Ser 97Glu + Gly105Glu + Leu216Met
Val 94Asp + Ser 98Asp + Ser158Asp + Thr215Gln
Thr 65Glu + Gly101Asp + Thr215Glu + Gly218Asn
Thr 58Asp + Gly156Ser + Asn211Asp + Thr215Glu
Gly 99Gln + Gly126Gln + Asn154Asp + Thr161Asp
Gly156Asn + Ala186Asp + Thr212Glu + Leu216Asp
Ser 97Asp + Ile106Gln + Leu125Asp + Thr215Ser
Ser100Glu + Ser104Glu + Tyr166Ala + Ser187Asp
Ser 98Asp + Ser102Glu + Thr215Glu + Leu216Gln
Ser129Asp + Thr132Gln + Ser155Glu + Ser160Asp
Ser 97Glu + Thr163Asp + Ser187Glu + Thr219Ser
Leu125Cys + Ser129Glu + Ser155Glu + Thr215Gly
Asn 61Asp + Gly126Glu + Ala214Asp + Thr219Gln
Thr 58Asn + Gly 64Pro + Thr 65Glu + Val 94Asp
Tyr205Leu + Tyr213Asp + Thr215Gly + Asn217Asp
Asp 59Glu + Ala202Gln + Thr212Asp + Asn217Asp
Asp 59Glu + Ser187Asp + Pro209Asn + Thr212Asp
Thr 58Asn + Leu 95Glu + Phe188Asp + Gly203Asp
Ser187Glu + Tyr205Ile + Thr212Glu + Leu216Glu
Ser129Glu + Gly156Gln + Thr212Asp + Leu216Asp
Gly101Glu + Ser129Glu + Asn157Glu + Tyr205Thr
Gly 60Glu + Leu125Ser + Gly153Glu + Ala202Asp
Asn 61Glu + Phe188Glu + Tyr205Ala + Thr212Glu
Asn 61Glu + Gly153Asn + Gly159Asp + Thr212Asp
Thr 65Gly + Tyr205Glu + Asn211Glu + Leu216Cys
Thr 65Glu + Asn 96Glu + Gly156Asp + Leu216Cys

TABLE 35

Multi-loop Quintuple Mutation Variants

Tyr103Cys + Gly156Glu + Ala202Gln + Thr212Gly + Leu216Gln
Asn 61Ser + Gly101Asp + Thr132Gly + Gly165Gln + Tyr205Pro
Gly 60Asn + Asn162Gln + Thr212Pro + Tyr213Gln + Asn217Asp
Gly 60Ser + Leu 95His + Ser100Glu + Gly156Pro + Thr215Gly
Leu 95Ile + Thr163Gln + Tyr205Glu + Tyr213Ala + Thr219Asn
Gly159Glu + Phe188Tyr + Gly203Pro + Tyr205Gly + Ala214Thr
Gly126Pro + Gly127Gln + Tyr208Asn + Thr212Gly + Leu216Ala
Leu 95Gly + Asn162Ser + Gly165Glu + Pro209Gly + Thr210Gly
Thr 58Ser + Leu 95Asn + Ser100Asp + Tyr205Ala + Thr215Asn
Asn 61Ser + Ser100Glu + Asn162Gln + Phe188Ser + Gly203Ser
Tyr103Ser + Thr161Pro + Phe188Gln + Gly201Gln + Leu216Pro
Ser 97Asp + Gly 99Pro + Tyr205Pro + Thr210Asn + Leu216His
Leu 95Met + Ser187Asp + Tyr205Val + Thr212Gly + Leu216Asn
Ile106Asp + Tyr166Thr + Thr207Pro + Asn211Gln + Leu216Thr
Asn 96Gln + Ser160Asp + Phe188Gly + Thr215Asn + Gly218Asn
Thr 58Pro + Ser 98Asp + Gly130Pro + Tyr205Val + Tyr208Pro
Val 94Ala + Gly 99Ser + Ala128Glu + Phe188Asn + Leu216Gly
Leu 95Thr + Gly126Gln + Pro209Ser + Thr215Asp + Leu216Gly
Ser 98Glu + Asn154Gln + Gly203Ser + Thr215Ser + Leu216Pro
Thr 58Asp + Leu125Pro + Ala202Thr + Gly203Pro + Tyr205Val
Ala128Asp + Gly153Gln + Ala186His + Ala199Gln + Gly203Asn
Asp 59Glu + Gly159Gln + Ala186His + Leu216Ser + Gly218Ser
Ala186His + Phe188Gln + Ser190Glu + Pro200Ser + Tyr205Val
Val 94Gly + Ser 98Asp + Tyr166Pro + Ala202Gly + Tyr205His
Asn 61Gln + Tyr103Met + Asn157Asp + Thr161Ser + Gly203Asn
Thr 65Gln + Gly203Gln + Pro209Ser + Thr215Gln + Asn217Asp
Gly126Ser + Ser160Asp + Thr163Gln + Gly203Ser + Tyr205Gly
Tyr103Gln + Gly156Pro + Tyr166Asn + Phe288Tyr + Thr215Glu
Val 94Met + Gly 99Asn + Thr212Asn + Tyr213Gly + Thr215Glu
Ala128Ser + Ala202Pro + Gly203Gln + Pro209Glu + Gly218Ser
Thr 58Ser + Tyr103Gly + Leu125Gly + Tyr205Gly + Gly218Ser
Leu125Pro + Asn154Glu + Thr161Ser + Asn162Gln + Gly203Gln
Gly 60Asp + Gly 62Pro + Asn 96Ser + Ala186Gly + Thr210Gln
Asn 61Gln + Thr 65Ser + Leu 95Met + Tyr103Gly + Ser104Asp
Asn 61Ser + Gly153Gln + Gly156Gln + Ala202Gly + Asn211Gln
Ser102Asp + Gly126Gln + Ala202Asn + Tyr205Leu + Thr212Gly
Gly 60Asn + Ser104Asp + Gly105Asn + Thr163Ser + Tyr205Ala
Val 94Asn + Gly101Asn + Leu125Asn + Gly130Asp + Leu216Cys
Gly159Pro + Gly165Pro + Ala186Thr + Gly201Pro + Leu216Ser
Leu 95Cys + Gly130Gln + Thr212Ser + Ala214Asn + Leu216Val
Gly 60Glu + Thr161Gly + Gly203Gln + Tyr205Ile + Thr212Gly
Gly153Ser + Gly159Asn + Ala186Pro + Gly203Ser + Thr219Asn
Asp 59Glu + Gly 62Gln + Leu125Ala + Thr215Asn + Asn217Gln
Val 94Gly + Leu125Ser + Gly203Glu + Thr215Gln + Leu216Asn
Ala186Gln + Ser187Glu + Gly201Gln + Ala202Pro + Gly203Ser
Asn157Asp + Gly203Gln + Thr212Pro + Ala214Gln + Leu216Ala
Thr 65Ser + Ser 98Asp + Thr161Ser + Gly203Ser + Tyr20SCys
Gly 99Asp + Gly165Ser + Met198Cys + Pro209Gly + Thr215Gly
Gly153Pro + Tyr208Ile + Thr212Ser + Ala214His + Gly218Glu
Ser 98Asp + Ile106Ala + Tyr166Leu + Ala202Gln + Ala214Thr
Gly 99Gln + Ser129Glu + Thr161Asn + Phe188Cys + Tyr205Thr

TABLE 35-continued

Multi-loop Quintuple Mutation Variants

Gly 60Asn + Gly159Gln + Ser160Glu + Thr163Pro + Ala186Gly
Asn 96Asp + Gly 99Pro + Val204Ala + Tyr205Val + Asn217Gln
Gly 60Ser + Phe188Ile + Thr212Asn + Thr215Ser + Leu216Asp
Ala128Gly + Thr132Gln + Gly165Gln + Met198Thr + Gly203Glu
Asn 96Asp + Asn157Ser + Gly201Asn + Thr212Gly + Thr215Gly
Gly 99Asp + Phe188Val + Gly203Asn + Thr207Asn + Leu216Pro
Ala128Pro + Thr132Pro + Thr163Pro + Phe188Thr + Thr212Glu
Val 94His + Gly105Glu + Ala186Pro + Thr210Gln + Thr212Gly
Gly101Pro + Thr132Asp + Asn162Ser + Thr212Gln + Leu216Pro
Gly 60Asn + Tyr103Asn + Gly105Gln + Ile106Ala + Leu216Gln
Gly126Pro + Gly203Pro + Tyr205Val + Thr215Asn + Leu216Ser
Thr 58Glu + Thr161Gly + Tyr205Asn + Tyr208Leu + Leu216Thr
Gly101Asn + Gly159Pro + Asn162Ser + Ala202Gly + Tyr205Gln
Tyr103Ile + Gly105Pro + Ala202Gln + Thr210Gln + Leu216Pro
Gly 60Asp + Gly153Ser + Thr163Gly + Thr212Pro + Leu216Met
Gly101Pro + Ser104Glu + Gly105Pro + Gly153Ser + Tyr205Thr
Asn162Asp + Phe188His + Ala199Gly + Thr212Pro + Leu216Pro
Ala186Gly + Ala202Pro + Tyr205Met + Thr210Gln + Leu216Val
Gly 62Ser + Tyr103Met + Asn154Glu + Thr212Gly + Leu216Met
Thr 65Ser + Gly101Pro + Tyr103Leu + Thr161Asp + Thr219Ser
Gly105Ser + Ile106His + Ala186Thr + Met198Pro + Thr212Pro
Thr163Gly + Gly203Asp + Thr212Asn + Leu216His + Asn217Gln
Gly126Ser + Thr161Gln + Gly203Pro + Thr210Pro + Leu216Val
Thr 65Gln + Ser131Asp + Ala186Gly + Thr215Ser + Leu216His
Thr132Gln + Asn162Ser + Gly165Asp + Tyr205Gly + Tyr208Cys
Gly127Gln + Gly153Glu + Gly203Pro + Thr215Gly + Thr219Gly
Ile106Met + Leu125Cys + Gly126Ser + Ser131Glu + Gly156Asn
Ser 97Glu + Thr132Gly + Pro200Gly + Tyr205Ala + Asn211Ser
Thr 65Asp + Tyr166Gln + Gly203Asn + Thr210Ser + Thr212Gln
Gly 99Ser + Tyr166Ser + Ser187Glu + Tyr205Gln + Leu216Ser
Gly126Ser + Gly130Asn + Thr161Asp + Phe188Val + Thr207Gln
Leu 95Pro + Pro200Ser + Tyr205Leu + Thr210Glu + Leu216Cys
Tyr103Glu + Gly127Gln + Tyr166Thr + Ala202His + Thr210Ser
Thr 58Gly + Ala202Pro + Pro209Gln + Thr212Ser + Ala214Glu
Gly 62Gln + Tyr103Thr + Thr163Gly + Ser187Asp + Gly203Gln
Gly101Gln + Leu125Glu + Thr132Ser + Gly203Ser + Thr212Gln
Asn 96Ser + Ala128His + Ala186Gln + Tyr205His + Thr215Ser
Gly101Ser + Gly165Asp + Thr210Gly + Thr212Gly + Thr215Gly
Gly156Gln + Ala202Gly + Ala214His + Thr215Pro + Leu216Thr
Val 94Cys + Gly 99Gln + Gly126Asn + Gly159Pro + Thr219Pro
Leu 95Pro + Gly105Pro + Thr161Asp + Gly203Pro + Leu216Asn
Gly 60Glu + Asn 61Gln + Thr 65Gln + Thr210Gly + Leu216Gln
Leu125Gly + Ser187Asp + Phe188Gln + Ala202Asn + Thr212Asn
Phe188Ile + Gly203Glu + Thr210Gly + Thr212Gln + Leu216Pro
Asp 59Glu + Leu 95Ile + Ile106Leu + Gly203Gln + Tyr213Ile
Gly 99Gln + Ala186Pro + Tyr205Gly + Thr215Glu + Gly218Gln
Ser 98Glu + Thr161Pro + Ala202Gln + Tyr205Leu + Thr207Gln
Ser100Glu + Gly153Asn + Thr163Gln + Thr212Pro + Leu216Gln
Leu 95Ser + Ile106Asp + Tyr205Val + Leu216Pro + Thr219Asn
Tyr166Val + Ser190Asp + Thr207Gly + Thr212Ser + Leu216Asn
Asp 59Glu + Gly105Gln + Thr132Gln + Ala186Ser + Tyr205Ile
Gly 60Pro + Tyr205Ile + Asn211Gln + Leu216Ile + Asn217Gln
Gly 99Asn + Leu125Thr + Asn157Gln + Asn162Glu + Thr212Gln
Ile106Ala + Asn162Glu + Tyr16EHis + Asn211Ser + Thr215Gln
Asn154Asp + Phe188Gly + Gly203Pro + Tyr205Ala + Pro209Ser
Leu 95Asn + Gly105Glu + Tyr166Ala + Tyr205Leu + Thr212Ser
Val 94Ala + Ser131Glu + Thr132Glu + Phe188His + Thr212Gly
Gly 64Gln + Gly159Asp + Ser160Glu + Thr215Pro + Leu216Ala
Thr 58Glu + Asp 59Glu + Pro209Gln + Thr212Asn + Thr215Gln
Asn 96Asp + Ser 97Glu + Tyr205Thr + Ala214Thr + Leu216Ser
Asp 59Glu + Gly 60Glu + Gly159Asn + Thr210Pro + Gly218Asn
Asp 59Glu + Gly 60Asp + Leu 95Ser + Gly203Pro + Tyr205Ser
Tyr103Ile + Asn154Ser + Tyr205Glu + Ala214His + Thr215Asp
Gly105Asn + Gly127Gln + Ala202Glu + Gly203Ser + Asn217Glu
Asn 61Asp + Thr 65Gln + Ser 97Asp + Tyr205Ala + Leu216Ser
Asn 61Glu + Ser 97Glu + Gly105Gln + Asn162Ser + Thr212Ser
Asn 61Asp + Leu 95Ser + Ser 97Glu + Val204Gln + Thr212Gly
Tyr103His + Asn154Glu + Phe188Ile + Ser190Glu + Thr212Ser
Val 94Pro + Asn 96Asp + Ser 98Glu + Tyr103Pro + Thr212Ser
Val 94Met + Ser158Asp + Thr161Glu + Gly203Ser + Gly218Ser
Gly203Asp + Tyr213Pro + Thr215Asn + Asn217Asp + Gly218Asp
Ser160Glu + Asn162Glu + Tyr205Val + Asn211Gln + Thr215Pro
Asn 61Asp + Ser 98Glu + Tyr103Cys + Gly203Ser + Tyr213Ala
Gly101Asn + Tyr103Pro + Ile106Asn + Asn157Glu + Thr161Asp
Gly130Asn + Ala186Glu + Ala202Glu + Thr215Pro + Thr219Asn
Gly126Asp + Ala128Glu + Thr132Ser + Met198Cys + Gly218Ser
Val 94Pro + Leu125Gly + Thr215Asp + Leu216His + Asn217Asp

TABLE 35-continued

Multi-loop Quintuple Mutation Variants

Gly 62Ser + Ile106Ala + Ala128Thr + Thr215Asp + Asn217Glu
Gly105Pro + Ser129Glu + Thr132Asn + Gly165Glu + Asn211Gln
Asp 59Glu + Asn 96Asp + Ser 97Glu + Phe188His + Thr210Pro
Asn 61Gln + Gly153Glu + Thr163Asp + Gly203Gln + Leu216Ser
Asp 59Glu + Thr 65Gly + Leu 95Gly + Ser 97Asp + Tyr166Gly
Asn157Asp + Ser160Asp + Asn162Glu + Thr210Gly + Thr212Ser
Ser 97Glu + Ser100Asp + Gly101Ser + Thr207Gln + Thr212Asn
Gly 64Ser + Gly203Ser + Thr212Asp + Ala214Asp + Thr215Asp
Gly 60Asn + Thr132Asn + Ser155Glu + Gly156Glu + Asn162Asp
Gly 99Ser + Tyr103Ile + Gly130Gln + Phe188Glu + Thr219Glu
Gly156Asp + Thr161Asp + Ser190Asp + Gly203Ser + Ala214Gln
Gly101Asp + Ser104Asp + Gly127Ser + Thr210Gln + Thr212Gln
Gly130Gln + Ser155Asp + Tyr213Met + Gly218Asp + Thr219Glu
Gly 99Ser + Asn154Ser + Gly203Asp + Leu216Asn + Gly218Asp
Ser102Glu + Gly130Asp + Ser131Asp + Ala202His + Thr210Asn
Gly153Pro + Gly159Asp + Asn162Asp + Ala186Gln + Ala202Gln
Asn 96Asp + Ser100Glu + Gly105Asp + Val204Thr + Thr215Pro
Asn162Asp + Gly165Asp + Thr212Gln + Thr215Ser + Leu216Cys
Ser155Asp + Gly165Ser + Ser187Glu + Tyr205His + Thr212Gly
Ser100Glu + Gly126Glu + Ala186Pro + Tyr205Asn + Tyr213Gln
Gly 62Pro + Ser104Glu + Ser131Asp + Thr212Gln + Tyr213Thr
Gly203Asp + Tyr205Asn + Asn211Gln + Thr212Gly + Ala214Asp
Ile106Cys + Asn154Glu + Ala186Glu + Gly203Ser + Leu216Ala
Thr 58Pro + Asn 61Asp + Val 94Glu + Asn 96Asp + Gly165Pro
Leu 95Glu + Ser 97Glu + Ser102Glu + Thr161Ser + Tyr205Leu
Thr 58Gly + Ala128Pro + Gly156Asp + Thr161Asp + Gly203Asp
Gly 60Ser + Gly126Pro + Thr161Glu + Ser190Glu + Thr212Gly
Gly 60Ser + Ser102Glu + Gly105Asp + Ser131Glu + Gly203Asn
Asn154Gln + Ala186Ser + Tyr213Glu + Leu216Glu + Thr219Pro
Gly101Asp + Ile106Cys + Gly126Asp + Met198Gln + Thr219Pro
Leu 95Gln + Asn154Asp + Ser190Asp + Thr212Gly + Asn217Glu
Thr 58Gln + Asn 61Glu + Ser100Asp + Tyr205Ala + Thr215Gly
Asn 61Glu + Gly 99Gln + Ser100Glu + Tyr103Met + Leu125Ser
Asp 59Glu + Gly 99Asp + Tyr103Ile + Ile164Thr + Thr215Ser
Ala128Ser + Gly130Ser + Gly159Asp + Thr163Glu + Tyr205Cys
Leu 95Ile + Ser102Asp + Ser131Asp + Ile164Val + Leu216Ile
Asn 96Gln + Thr212Pro + Ala214Asp + Leu216Glu + Thr219Glu
Ile106Glu + Ser131Asp + Ala202Gly + Tyr205Asn + Thr215Ser
Thr 65Gln + Asn154Asp + Thr215Glu + Leu216His + Asn217Glu
Ile106Glu + Gly130Ser + Ser131Asp + Phe188Ala + Tyr205Pro
Asn 61Gln + Gly 99Gln + Asn154Glu + Ser158Asp + Ser187Glu
Gly101Ser + Gly126Asn + Thr212Glu + Thr215Asp + Leu216Gln
Asp 59Glu + Thr 65Pro + Ser 98Asp + Tyr103Pro + Leu125Ile
Gly153Ser + Ser155Asp + Gly165Asp + Ser187Asp + Asn217Ser
Ser100Asp + Ser102Glu + Gly130Glu + Gly156Pro + Tyr205Ile
Thr 58Asp + Asn 96Glu + Ala186Gly + Gly203Pro + Thr219Gly
Gly105Ser + Gly153Glu + Thr215Asn + Leu216Asp + Asn217Glu
Asn154Asp + Ser160ASp + Gly165Ser + Ser190Asp + Ala202Ser
Asp 59Glu + Ser 98Glu + Tyr103Asn + Thr132Ser + Pro209Glu
Ala128Asp + Asn154Asp + Tyr166Ala + Pro200Gly + Tyr205Met
Gly101Gln + Asn157Gln + Gly203Asp + Thr215Gly + Thr219Asp
Asn 61Gln + Gly126Asp + Asn162Glu + Ser190Asp + Thr215Gly
Thr 58Gln + Asp 59Glu + Leu 95Gly + Gly203Pro + Asn211Glu
Ile106Asn + Leu125Val + Ser129Glu + Thr163Asp + Ala214Gly
Gly126Gln + Gly127Asp + Ala128Ser + Ser155Asp + Ser158Glu
Ser190Glu + Ala202Glu + Thr212Asn + Thr215Gly + Asn217Asp
Ser155Glu + Gly156Glu + Ala202Asp + Thr215Gly + Thr219Gln
Ser160Glu + Ser190Asp + Gly203Gln + Tyr205Asn + Thr212Asn
Gly156Asn + Tyr166Ala + Gly203Glu + Thr212Glu + Leu216Asp
Gly 99Gln + Ser102Glu + Gly126Asp + Asn154Glu + Tyr205Asn
Thr 65Pro + Gly127Glu + Ser131Glu + Ser155Asp + Tyr205Cys
Asn 96Gln + Thr 61Gly + Ser190Glu + Thr210Glu + Asn211Asp
Gly130Asn + Ser187Glu + Pro209Gln + Ala214Asp + Thr215Glu
Gly101Glu + Ile106Met + Thr2105er + Ala214Asp + Thr215Glu
Ser104Asp + Thr210Gly + Thr212Gln + Ala214Glu + Thr215Glu
Asn 96Gln + Ser158Asp + Gly159Asp + Thr163Asn + Leu216Glu
Asn 96Gln + Ser158Glu + Gly203Pro + Thr215Asp + Leu216Asp
Gly127Asn + Gly130Gln + Ser160Glu + Thr215Asp + Leu216Asp
Gly 60Asn + Asn 61Glu + Gly 62Glu + Asn157Asp + Tyr205Ser
Gly105Asn + Ala128Glu + Ser129Glu + Gly153Pro + Ala202Asp
Thr 58Asp + Tyr103Met + Gly153Ser + Asn157Glu + Ser158Glu
Gly 64Ser + Gly 99Asn + Ser129Asp + Gly130Asp + Asn157Asp
Asn154Gln + Ala202Asp + Asn211Glu + Thr212Asp + Leu216Ile
Gly101Asp + Ser102Glu + Gly159Glu + Ile164Cys + Asn217Gln
Gly 62Pro + Gly101Asp + Ser102Glu + Ser190Glu + Thr215Asn
Thr 58Glu + Asp 59Glu + Gly130Glu + Ala214Gln + Leu216Val
Asn 61Ser + Ser102Glu + Ser160Glu + Thr161Asp + Leu216Val

TABLE 35-continued

Multi-loop Quintuple Mutation Variants

Ser102Asp + Ser160Glu + Thr161Asp + Tyr205Ser + Asn211Gln
Gly 62Pro + Ser104Glu + Gly105Asp + Leu125Met + Ala214Asp
Val 94Cys + Gly105Asp + Asn162Glu + Thr163Glu + Leu216Ile
Ser 97Asp + Ser 98Asp + Ala202Asp + Tyr205His + Leu216Thr
Gly 62Glu + Asn 96Glu + Gly105Asp + Tyr166ser + Pro209Gly
Val 94Asp + Ala128Asp + Thr132Asn + Gly165Asp + Thr212Ser
Ser102Glu + Gly105Glu + Asn154Asp + Gly156Asn + Leu216Gly
Tyr103Glu + Gly130Gln + Ile164Leu + Thr210Glu + Thr212Asp
Asp 59Glu + Asn157Ser + Tyr164Met + Gly203Asp + Asn217Asp
Gly 60Gln + Gly130Asn + Ser155Glu + Thr215Glu + Asn217Asp
Val 94Thr + Gly 99Asp + Gly153Pro + Tyr205Glu + Ala214Glu
Gly101Asn + Ser131Asp + Asn154Gln + Gly203Asp + Thr215Glu
Gly101Pro + Gly127Pro + Asn157Glu + Gly203Asp + Thr215Asp
Thr 65Gln + Gly153Glu + Gly165Glu + Gly203Asp + Leu216Cys
Ser 98Asp + Ser100Glu + Ala128Gly + Gly159Asp + Gly165Pro
Ser 98Asp + Ser100Asp + Ser187Asp + Gly203Asn + Thr212Ser
Ser 98Glu + Ser100Glu + Ser155Asp + Asn162Ser + Thr210Asn
Asn 96Asp + Ser100Asp + Gly127Asn + Tyr205Cys + Thr219Asp
Asn 96Asp + Ser100Glu + Gly159Asp + Tyr205Gln + Ala214Pro
Leu 95Gln + Gly101Pro + Ser102Asp + Gly153Asp + Tyr166Glu
Asn 96Ser + Gly159Asp + Ser190Asp + Tyr205Ile + Ala214Gly
Thr 65Glu + Ser 97Glu + Gly101Glu + Ala186Pro + Pro200Gly
Gly 99Asn + Gly126Asp + Ser158Glu + Ser160Glu + Tyr205Gln
Gly 62Glu + Leu 95Glu + Ile106Leu + Thr212Glu + Ala214Ser
Asn 61Ser + Gly 99Pro + Ser104Asp + Gly203Asp + Tyr205Asp
Gly101Ser + Tyr103Ala + Gly203Gln + Tyr205Asp + Gly218Asp
Ser160Asp + Asn162Asp + Phe188Pro + Thr212Glu + Leu216Ser
Thr 65Pro + Ser155Asp + Asn157Asp + Ala186Thr + Leu216Asp
Ile106Ser + Ser160Glu + Asn162Glu + Gly203Asp + Leu216Val
Val 94Asp + Gly126Asp + Gly130Pro + Thr212Ser + Leu216Asn
Ser100Glu + Gly105Pro + Ala128Gly + Asn157Asp + Thr163Glu
Gly126Glu + Ala186Asp + Ala202Asp + Gly203Gln + Leu216Asn
Thr132Gly + Ser160Asp + Ala186Glu + Ala202Asp + Tyr205Gln
Tyr103Pro + Ser129Glu + Ala186Glu + Ala202Glu + Thr215Asn
Leu125Pro + Ser129Asp + Gly153Glu + Asn162Ser + Leu216Ile
Asp 59Glu + Thr 65Glu + Gly105Ser + Ser131Asp + Tyr213Ser
Gly126Asp + Gly156Glu + Ser158Glu + Ile164Met + Tyr205Met
Asn 96Glu + Tyr103Gly + Leu125Glu + Asn154Glu + Thr163Gln
Gly 99Asp + Leu125Thr + Gly156Glu + ser158Asp + Gly203Pro
Thr 58Glu + Ala128Ser + Gly156Asp + Thr163Asp + Thr210Gln
Gly101Glu + Gly156Asp + Ser158Asp + Ala202Gln + Pro209Asn
Ser131Glu + Gly156Asp + Ser158Glu + Phe188Leu + Gly203Asn
Gly 62Ser + Ser129Glu + Agn157Gln + Gly165Asp + Thr215Glu
Ser 97Asp + Ser129Glu + Gly165Asp + Thr215Asn + Asn217Ser
Ala186Asp + Tyr205Cys + Thr212Asp + Ala214Asp + Thr215Ser
Val 94His + Ser158Glu + Thr212Asp + Ala214Glu + Thr215Gln
Leu125Glu + Gly159Pro + Ala186His + Thr212Asp + Ala214Glu
Asn 61Asp + Tyr103Gln + Gly105Gln + Leu125Asp + Pro209Asp
Gly 99Gln + Gly159Ser + Pro209Asp + Thr215Glu + Leu216Ala
Ser100Asp + Ser102Asp + Gly105Asn + Gly203Asp + Asn211Gln
Ser 97Glu + Ser100Glu + Gly165Glu + Phe188Val + Leu216Asn
Asn 96Ser + Leu125Asp + Ser129Glu + Tyr205Gln + Thr215Pro
Asn 96Glu + Asn157Asp + Gly165Gln + Ser187Asp + Tyr205Val
Gly 62Glu + Thr 65Gln + Asn157Asp + Asn162Asp + Thr215Gln
Leu 95Asp + Ser102Asp + Gly203Glu + Val204Ser + Leu216Ser
Ser131Glu + Gly165Asp + Leu216Cys + Asn217Gln + Thr219Asp
Val 94Asp + Ser157Asp + Ser190Glu + Tyr205Asn + Thr215Pro
Asp 59Glu + Asn 96Gln + Ser187Glu + Ser190Asp + Thr215Asn
Ser158Asp + Asn162Asp + Gly203Ser + Leu216Glu + Asn217Ser
Gly126Pro + Ser158Asp + Asn162Asp + Thr212Asp + Leu216Thr
Ser102Asp + Ser158Asp + Thr163Asp + Met198Gly + Thr207Pro
Gly 60Glu + Leu125Val + Ser155Glu + Gly165Glu + Val204Asn
Ser131Glu + Asn154Glu + Ser187Glu + Tyr213Val + Asn217Asp
Gly 62Asp + Ala128His + Asn154Glu + Ser187Glu + Gly2033er
Asn 61Gln + Gly 62Pro + Gly105Asp + Gly203Glu + Gly218Asp
Ser102Asp + Gly203Glu + Ala214Gly + Thr215Pro + Gly218Asp
Asp 59Glu + Asn157Asp + Thr163Pro + Pro209Gly + Thr210Asp
Leu125Glu + Asn162Ser + Gly165Glu + Thr212Asp + Thr215Asp
Ile106Asn + Ser155Glu + Tyr166Val + Ser187Asp + Thr212Asp
Gly105Pro + Ser155Glu + Ser187Asp + Tyr205Pro + Thr215Asp
Asn 96Glu + Ser155Glu + Ser158Asp + Thr161Pro + Thr215Pro
Thr 58Asp + Thr 65Asp + Tyr103Val + Thr132Asp + Phe188Gly
Asp 59Glu + Asn 96Glu + Ser190Glu + Gly203Ser + Ala214Ser
Ser155Glu + Ile164Ser + Ala202Asp + Tyr205Asp + Leu216Pro
Tyr103Ala + Ser104Asp + Ser131Asp + Ser1EOAsp + Tyr213Leu
Thr 58Glu + Asn 61Asp + Ala186Gly + Ser187Asp + Tyr205Ala
Asn 96Glu + Ser102Glu + Gly153Asp + Gly203Pro + Asn217Gln

TABLE 35-continued

Multi-loop Quintuple Mutation Variants

Asn 96Glu + Ser102Asp + Gly105Pro + Asn162Glu + Tyr213Val
Ser129Asp + Gly153Asn + Gly203Glu + Ala214Glu + Thr215Gln
Ser100Glu + Gly127Glu + Gly203Glu + Tyr205Ala + Tyr213Thr
Ser158Asp + Ser190Asp + Gly203Asp + Thr212Pro + Thr215Gly
Leu 95Ile + Thr132Gly + Ser187Asp + Tyr213Asp + Leu216Asp
Gly 60Glu + Gly 62Pro + Ala128Glu + Ser155Glu + Ala202Ser
Thr 58Asp + Ser 97Asp + Gly153Ser + Gly159Glu + Ala214Thr
Asn 61Asp + Ser100Glu + Gly126Asn + Ser129Asp + Thr219Ser
Asp 59Glu + Leu 95Asp + Phe188Glu + Pro209Ser + Gly218Ser
Tyr103Glu + Ser187Glu + Thr212Ser + Thr215Gln + Gly218Asp
Ser104Glu + Ser190Asp + Tyr205Asn + Tyr208Val + Gly218Asp
Ala128Asp + Ser131Glu + Thr161Gln + Tyr205Glu + Leu216Met
Ser102Asp + Ala128Glu + Ile164Gly + Gly203Asn + Thr212Ser
Gly 62Asp + Gly105Glu + Tyr208Ala + Thr210Ser + Thr212Asp
Ser 97Glu + Ser102Glu + Ile106Ser + Asn157Ser + Leu216Gly
Gly 62Asn + Leu 95Met + Ser 97Asp + Ser102Asp + Asn217Ser
Ser102Glu + Leu125Cys + Ser131Asp + Ala202Ser + Asn217Glu
Ser102Asp + Ser131Glu + Thr163Asp + Thr207Gly + Thr215Asn
Thr 58Asp + Gly127Asp + Ala128Thr + Ser155Asp + Gly203Ser
Ser 97Asp + Ile106Thr + Ala186Asp + Gly203Asp + Thr215Gly
Val 94Gly + Gly127Asp + Ser155Asp + Gly156Gln + Tyr205Glu
Ile106Glu + Gly126Asp + Gly127Asn + Gly156Glu + Ala202Asn
Ser 97Asp + Gly203Pro + Asn211Ser + Thr215Asp + Gly218Glu
Gly 99Asp + Ser104Asp + Ile106Val + Thr132Asp + Thr215Asn
Gly 62Glu + Ser100Glu + Gly127Pro + Tyr205Ile + Thr212Gln
Gly 99Glu + Gly126Asp + Ala186Glu + Gly203Ser + Asn217Ser
Thr132Asp + Tyr205Glu + Pro209Gln + Thr212Glu + Asn217Ser
Ser 97Asp + Gly127Gln + Ala186Asn + Thr212Glu + Thr215Asp
ser102Asp + Asn154Gln + Thr212Asp + Thr215Asp + Leu216Gly
Leu125Gln + Ser129Asp + Asn162Gln + Thr212Asp + Thr215Asp
Asp 59Glu + Ser 98Glu + Leu125Gly + Ala128Asn + Ser129Asp
Asp 59Glu + Ser 98Asp + Gly156Asn + Ala202Asp + Gly218Asn
Asn 61Ser + Asn157Glu + Gly203Asp + Tyr205His + Thr219Asp
Ile106Asp + Gly130Asp + Tyr166Ile + Ala186Ser + Thr212Asp
Asp 59Glu + Gly156Asp + Thr161Asn + Leu216Ala + Gly218Asp
Thr 58Asp + Asn 96Glu + Ser131Asp + Phe188Val + Thr215Gly
Leu 95Val + Ser155Glu + Tyr166Ala + Ala186Glu + Thr210Asp
Ser 98Asp + Leu125Cys + Ala128Asp + Thr161Gly + Asn162Glu
Asn 96Gln + Ile106Ala + Gly156Glu + Ser160Asp + Thr210Glu
Asp 59Glu + Tyr166Glu + Tyr205Asn + Thr210Gly + Asn211Glu
Asp 59Glu + Gly153Glu + Pro209Ser + Asn211Asp + Thr212Pro
Asp 59Glu + Tyr103Gly + Gly153Glu + Ser187Glu + Asn211Gln
Asp 59Glu + Thr163Ser + Ser187Glu + Val204Thr + Asn217Glu
Ser104Glu + Ile106Ala + Gly156Asp + Gly165Asp + Tyr205Asn
Gly126Glu + Ser131Asp + Asn154Ser + Tyr205ser + Thr215Asp
Asp 59Glu + Gly101Gln + Thr212Glu + Ala214Pro + Leu216Asp
Thr 65Glu + Ile106Asp + Gly127Asn + Thr215Asp + Leu216His
Asn154Ser + Ile164Cys + Thr212Asn + Ala214Asp + Gly218Glu
Gly 60Gln + Gly 99Asp + Gly127Glu + Tyr205Glu + Thr215Asn
Thr 58Gln + Gly 60Glu + Ile106Val + Tyr205Glu + Asn211Glu
Gly130Pro + Gly159Glu + Phe188Leu + Ser190Glu + Thr212Glu
Asn 61Glu + Gly127Asp + Ser190Glu + Tyr205Ala + Leu216Ser
Ser187Glu + Pro209Asp + Thr212Asn + Ala214Ser + Thr215Asp
Ser155Glu + Tyr166Glu + Gly203Glu + Val204Pro + Thr215Ser
Ser 98Asp + Ser102Glu + Ala202Ser + Thr205Glu + Leu216Gln
Val 94Asn + Gly101Asn + Leu125Glu + Ser129Glu + Thr212Asp
Ser129Asp + Ser155Asp + Ala202His + Gly203Asn + Asn211Ser
Asn 96Asp + Tyr103His + Gly105Asn + Ala202Glu + Ala214Glu
Leu 95His + Gly 99Gln + Ser190Glu + Ala202Asp + Thr210Asn
Gly101Asp + Ala128Glu + Thr132Glu + Gly156Asn + Tyr166Ile
Gly105Asp + Leu125Asp + Ala202Pro + Gly203Glu + Leu216Gln
Gly105Asp + Leu125Glu + Gly203Glu + Thr212Gly + Leu216Cys
Gly 62Glu + Val 94Ala + Ser129Asp + Tyr205Asp + Thr212Ser
Asn 61Asp + Gly101Glu + Tyr205Glu + Thr215Pro + Leu216His
Ser104Asp + Leu125Glu + Ser190Glu + Asn211Gln + Leu216Asn
Gly105Asn + Gly127Asp + Ala128Gly + Ser158Asp + Thr219Glu
Ser 97Asp + Ser155Glu + Ser160Asp + Asn211Gln + Thr215Ser
Asp 59Glu + Gly 64Gln + Gly130Glu + Gly153Glu + Tyr205Asn
Asn157Asp + Tyr205Leu + Thr212Glu + Thr215Gly + Leu216Glu
Thr 58Glu + Gly101Glu + Gly105Pro + Gly130Ser + Tyr166Asp
Ser 97Glu + Gly159Asp + Tyr166Ala + Ser187Glu + Leu216Val
Gly101Asp + Ser131Glu + Thr212Gln + Thr215Asp + Leu216Ile
Gly153Asn + Asn157Asp + Tyr213Leu + Asn217Ser + Thr219Asp
Gly153Asp + Ser158Glu + Tyr205Gly + Leu216Val + Gly218ser
Gly 99Ser + Ser187Asp + Gly203Glu + Pro209Asp + Asn211Gln

TABLE 35-continued

Multi-loop Quintuple Mutation Variants

Leu 95Ala + Ser102Asp + Ser187Glu + Gly203Asp + Thr219Gln
Gly 62Asp + Ala128Thr + Ser187Glu + Gly203Glu + Asn211Ser
Gly101Asp + Ala128Thr + Asn154Gln + Phe188Asp + Leu216Glu

TABLE 36

Multi-loop Sextuple Mutation Variants

```
Tyr103Cys + Gly126Gln + Gly156Glu + Ala202Gln + Thr212Gly + Thr215Pro
Asn 61Gln + Gly101Asp + Ile106Ala + Asn162Ser + Gly1G5Gln + Tyr205Pro
Gly126Pro + Ala128His + Ser187Glu + Gly203Ser + Tyr208Asn + Leu216Ala
Thr 6SSer + Gly126Gln + Gly203A5n + Thr215Gln + Leu216Ala + Gly218Asp
Ile106Ala + Gly165Asp + Tyr166Thr + Thr207Pro + Asn211Gln + Leu216Thr
Ser158Glu + Thr161Gly + Ala199Gly + Ala202Gln + Gly203Gln + Tyr205Asn
Thr 58Asn + Leu 95Asn + Gly153Pro + Tyr205Asn + Pro209Glu + Thr210Pro
Gly126Glu + Ala128Gly + Asn157Gln + Gly16SAsn + Gly203Asn + Tyr205Pro
Gly 64Ser + Asn 96Gln + Gly126Asn + Gly127Ser + Asn211Ser + Thr212Gly
Gly126Asn + Ser158Asp + Gly203Pro + Tyr205Met + Thr215Gly + Thr219Gln
Leu105Val + Gly156Asp + Tyr205Ser + Thr212Gly + Thr215Pro + Leu216His
Gly105Asn + Gly126Ser + Ser160Glu + Thr161Asn + Tyr205Val + Gly218Asn
Gly105Ser + Ala128Thr + Thr132Pro + Ser160Glu + Tyr213Asn + Thr215Pro
Asp 59Glu + Gly105Pro + Asn157Gln + Ala186Asn + Tyr213His + Leu21GHis
Gly 99Gln + Gly126Gln + Asn154Asp + Gly159Pro + Tyr205Ala + Thr212Gly
Thr 58Gln + Ser104Asp + Gly105Ser + Gly159Pro + Thr163Gly + Tyr205Pro
Leu125Met + Ser131Glu + Phe188Gln + Gly201Ser + Ala202Gly + Thr210Gly
Gly 60Asn + Gly 62Asn + Ser104Asp + Gly126Pro + Gly127Gln + Thr210Asn
Gly101Gln + Asn157Ser + Tyr166Pro + Ala202Ser + Asn211Ser + Thr215Gly
Ser 97Asp + Gly130Pro + Thr163Pro + Val204Thr + Tyr205Cys + Ala214Pro
Tyr103Ala + Ala128His + Gly153Gln + Asn154Ser + Ser187Glu + Gly203Ser
Ala128His + Tyr166Pro + Thr207Ser + Thr212Pro + Thr215Pro + Gly218Glu
Asn157Gln + Ser187Asp + Phe188Ala + Gly203Pro + Tyr205Ser + Thr212Ser
Val 94Pro + Tyr103Gly + Gly105Gln + Gly126Ser + Ala214Asp + Thr215Gly
Leu 95Asn + Gly203Pro + Tyr205Met + Thr212Asn + Thr215Gln + Leu216His
Leu 95His + Tyr166Cys + Ala202Gly + Thr207Gln + Pro209Gly + Leu216His
Gly 62Ser + Asn 96Gln + Thr132Gln + Gly159Ser + Gly165Pro + Thr219Glu
Thr132Gln + Asn157Ser + Tyr166Val + Ala199His + Tyr20BGly + Thr215Asp
Gly127Ser + Gly165Ser + Gly203Glu + Tyr205Ile + Tyr208Pro + Thr215Ser
Gly156Glu + Pro209Asn + Asn211Ser + Thr212Ser + Tyr213Ile + Leu216His
Tyr103Gln + Gly126Gln + Ala128Gln + Gly156Pro + Tyr166Asn + Ala202Thr
Thr 58Ser + Tyr103Gly + Leu125Gly + Thr161Ser + Asn162Gly + Tyr205Gly
Gly 60Ser + Gly101Gln + Gly127Asp + Gly203Pro + Pro209Gly + Thr215Gln
Gly105Gln + Leu125Asn + Ser187Glu + Pro200Gly + Ala214Ser + Leu216Thr
Asn 61Glu + Leu 95Ile + Asn 96Ser + Tyr166Asn + Thr2105er + Gly218Ser
Gly 60Asn + Ser104Asp + Gly105Asn + Thr161Ser + Thr163Ser + Tyr205Ala
Val 94Gly + Asn162Asp + Gly165Asn + Asn211Gln + Leu216Ile + Gly218Ser
Ser 97Glu + Tyr103Met + Gly153Pro + Pro200Ser + Gly203Ser + Leu216Met
Thr 97Gln + Tyr103Leu + Ala128Asp + Ile164His + Tyr205Thr + Leu216Ser
Gly127Glu + Phe188Gln + Gly203Gln + Pro209Asn + Leu210Met + Gly218Pro
Gly 62Glu + Gly156Asn + Asn162Gln + Gly201Ser + Thr210Pro + Thr212Asn
Gly 60Pro + Tyr103Asn + Gly127Asn + Thr161Gly + Thr215Asp + Gly218Gln
Gly 60Asn + Gly159Gln + Ser160Glu + Thr163Pro + Ala215Gly + Pro209Gln
Ala202Thr + Gly203Ser + Tyr205Ala + Pro209Glu + Thr210Gln + Thr215Gln
Val 94Asn + Ile106Asp + Gly126Pro + Tyr205Cys + Thr215Ser + Leu216Cys
Val 94Gln + Gly105Pro + Gly159Asp + Ala202Ser + Thr2105er + Thr215Ser
Asn 61Ser + Asn154Asp + AlalB6Thr + Pro209Ser + Tyr213Ile + Ala214Gln
Thr S8Pro + Gly127Ser + Gly159Ser + Ala186Glu + Thr215Pro + Thr219Asn
Ala128Gly + Ser129Glu + Thr132Gly + Gly165Gly + Met198Thr + Thr219Gln
Val 94Gln + Asn157Asp + Tyr166Cys + Tyr205Ser + Thr207Pro + Thr215Asn
Asn 96Gln + Thr132Glu + Ile164Ser + Thr210Pro + Thr212Gln + Leu216Met
Gly101Asn + Tyr103Ile + Gly159Pro + Asn162Ser + Ala202Gly + Thr210Gln
Gly 60Asn + Val 94Gln + Ser 97Glu + Gly203Gln + Tyr205Pro + Leu216Met
Tyr103Gln + Gly130Pro + Ser155Glu + Gly159Asn + Tyr205Pro + Thr212Ser
Asn157Gln + Gly203Asp + Pro209Ser + Thr215Ser + Leu216Cys + Thr219Ser
Gly101Pro + Ile106Val + Gly126Glu + Ala128His + Asn157Ser + Thr219Pro
Gly 64Pro + Gly203Ser + Tyr205Pro + Pro209Asp + Thr210Asp + Ala214Ala
Thr 65Gln + Gly203Pro + Pro209Gln + Thr212Pro + Gly218Glu + Thr219Asp
Asn 61Ser + Ser104Asp + Gly105Asp + Asn162Gln + Ala186Ser + Phe188Ser
Tyr103Asp + Ser104Asp + Gly153Ser + Asn162Ser + Ala202Gly + Tyr208Gln
Asn154Asp + Ser155Glu + Asn162Ser + Gly203Asn + Pro209Gly + Leu216Asn
Ser 97Glu + Ser 98Glu + Asn157Gln + Ala202Asn + Tyr205Asn + Leu21Met
Thr 6SGln + Gly 99Ser + Thr132Ser + Asn154Asp + Ser15SAsp + Ser190Asp
Ash 96Asp + Gly 99Asp + Gly165Pro + Gly203Asn + Thr215Gln + Leu216Thr
ASp S9Glu + Asn 61Asp + Val 94Asn + Gly101Ser + Asn217Gln + Thr219Ser
Gly101Asn + Ile106Gln + Gly130Gln + Gly159Asp + Thr161Asp + Phe188Ser
```

Ser 98Glu + Gly 99Ser + Ser100Glu + Tyr103Ala + Gly203Ser + Asn217Gln
Thr 65Gly + Val 94Met + Asn157Asp + Ser190Glu + Leu216Ser + Thr219Ser
Gly130ASn + Ser160Glu + ASn162Glu + Ala186Asn + Gly203Pro + Tyr205Gln
Asn 61Glu + Leu 95Pro + Ser 98Glu + Leu12SCys + Phe188Cys + Gly203Pro
Ser129Asp + Ser131Asp + Gly203Pro + Tyr205Asn + Thr212Ser + Thr215Gln
Gly101Asp + Tyr103Asp + Leu125Thr + Thr161Asn + Thr212Gly + Leu216Asn
Gly105Pro + Ser129Glu + Thr132Asn + Gly165Glu + Ala202Asn + Asn211Gln
Ala186Pro + Phe188Met + Ala202Glu + Gly203Ser + Tyr213Val + Leu216Glu
Ile106His + Ser131Asp + Tyr205Ser + Thr210Gly + Asn211Asp + Tyr213Asp
Thr 65Asn + Gly203Gln + Pro209Gln + Thr212Asp + Tyr213Glu + Thr215Asp
Gly 62Asn + Asn 96Ser + Tyr103His + Asn162Glu + Ser190Asp + Ala214Asn
Ile106Asn + Gly156Glu + Gly159Asn + Phe188Asp + Tyr208Gln + Gly218Asp
Gly 6GPro + Gly 62Gln + Ala202Asp + Thr215Gly + Leu216Thr + Thr219Glu
Gly153Asp + Gly156Pro + Ser187Glu + Phe188Asp + Gly203Gln + Ala214Mis
Ala186Glu + Ala202Glu + Tyr205Ala + Tyr213Val + Thr215Asp + Asn217Glu
Asp 59Glu + Asn157Gln + Ala186Thr + Gly203Gln + Pro209Glu + Thr212Asp
Asp 59Glu + Asn 96Glu + Gly 99Glu + Gly101Glu + Tyr103His + Tyr205Ser
Gly1S9Ser + Ser160Glu + Thr163Glu + Ile164His + Ala186Ser + Tyr205Ser
Asn154Ser + Ser158Asp + Ser190Glu + Thr212Gly + Thr215Gln + Gly218Pro
Thr 58Asp + Asn 96Ser + Ser 97Asp + Ile106Pro + Thr132Gly + Thr212Pro
Ser155Asp + Ser160Asp + Asn162Glu + Phe188Gly + Thr210Gly + Thr212Ser
Asp 59Glu + Gly 99Asp + Ser100Asp + Tyr103Ile + Ile164Thr + Thr215Ser
Gly127Gln + Ser187Glu + Gly203Gln + Thr212Gln + Thr215Asn + Gly218Glu
Gly 60Glu + Ser 97Glu + Gly 99Asn + Tyr166Asn + Thr210Glu + Ala214His
Leu 95Ser + Tyr103Met + Leu125Glu + Gly165Glu + Ser190Glu + Gly218Pro
Asn 96Asp + Ser 97Glu + Ser100Asp + Ser104Glu + Thr132Asn + Leu216His
Leu 95Ile + Ser104Glu + Ala128Glu + Ser129Glu + Ser131Asp + Asn157Gln
Asp 59Glu + Asn 61Asp + Ser100Glu + Gly203Asn + Tyr205Ile + Thr212Gln
Thr 58Asn + Thr132Ser + Asn157Ser + Thr163Glu + Phe188Glu + Tyr205Pro
Ser129Glu + Asn154Glu + Gly156Asn + Asn162Ser + Gly165Asp + Leu216Cys
Gly 60Glu + Gly153Asn + Gly159Ser + Tyr205Asp + Ala214Asp + Thr215Glu
Val 94Glu + Ser102Asp + Gly105Asp + Ala128Asp + Thr215Gly + Leu216Gly
Gly126Asp + Gly156Glu + Ile164Met + Phe188Leu + Ser190Glu + Tyr205Ala
Gly 62Gln + Ser155Asp + Ser190Asp + Leu216Glu + Asn217Ser + Thr219Glu
Val 94Cys + Gly203Asp + Val204Asn + Tyr205Ile + Thr212Glu + Thr215Asp
Asn 61Ser + Val 94Gln + Leu 95Gln + Gly203Asp + Thr212Glu + Thr215Asp
Asn 61Gln + Gly 99Gln + Gly153Gln + Asn154Glu + Ser158Asp + Ser187Glu
Gly 99Glu + Gly101Gln + Gly126Asp + Phe188Met + Tyr205Ser + Thr212Pro
Gly101Asn + Tyr205Gly + Thr212Asp + Tyr213Met + Thr215Asp + Leu216Ile
Gly130Pro + Asn154Glu + Ser160Glu + Ser187Asp + Ser190Glu + Tyr205Leu
Leu125Pro + Asn154Glu + Thr161Ser + Ala202Glu + Gly203Gln + Leu216Glu
Gly101Asp + Ile106Ala + Gly153Asp + Ser190Asp + Leu216Asn + Thr219Asp
Gly 60Gln + Tyr103Gly + Tyr205Leu + Thr212Glu + Thr215Glu + Asn217Asp
Gly 62Gln + Asn154Asp + Ser155Asp + Ser160Asp + Gly165Glu + Tyr205Met
Gly 62Glu + Asn154Gln + Tyr205Ala + Tyr213Met + Thr215Asp + Leu216Gln
Asn154Ser + Asn157Asp + Ala202Asp + Gly203Glu + Tyr205Asp + Thr219Gly
Leu 95Gln + Gly126Glu + Asn154Ser + Gly159Asn + Ser190Asp + Gly218Asp
Asn 61Ser + Thr 65Asp + Thr132Asn + Gly203Asp + Tyr205Asp + Thr215Asn
Asn 61Glu + Leu 95Asp + Ser 97Glu + Thr132Asp + Thr161Pro + Thr163Ser
Gly126Ser + Ser131Glu + Gly203Glu + Tyr205Ala + Leu216Asp + Gly218Glu
Gly 60Glu + Ser100Asp + Gly101Asp + Ile106His + Gly130Gln + Ala214His
Gly 62Pro + Gly101Asp + Ser102Glu + Gly126Glu + Ser190Glu + Thr215Asn
Asn 61Asp + Gly 99Asp + Ser100Glu + Thr161Glu + Pro209Gln + Ala214Asn
Thr 58Gln + Asp 59Glu + Leu 95Gly + Gly203Pro + Asn211Glu + Leu216Gln
Asn 96Gln + Gly156Asp + Gly165Glu + Tyr205Asn + Thr215Asn + Gly218Asn
Gly 60Pro + Ser102Glu + Tyr103Glu + Thr163Glu + Tyr166Asp + Gly203Ser
Gly127Gln + Gly153Gln + Asn157Glu + Ser160Glu + Thr163Glu + Asn217Glu
Asn 61Gln + Ser102Asp + Gly126Asp + Ser155Glu + Ser190Asp + Ala202Ser
Leu125Pro + Gly156Asp + Phe188Glu + Tyr205Cys + Thr212Gly + Leu216Asp
Thr 58Gly + Asn 61Glu + Gly126Ser + Thr212Pro + Leu216Asp + Gly218Glu
Val 94Ser + Gly156Asp + Thr161Ser + Thr212Gly + Thr215Asp + Leu216Glu
Val 94Gly + Gly101Glu + Gly159Asp + Ser160Asp + Ala186Pro + Leu216Pro
Asn 61Asp + Gly 62Glu + Leu12SGln + Asn154Asp + Gly159Asn + Thr212Gln
Asn 96Gln + Gly101Asp + Ser102Glu + Gly159Glu + Ile164Cys + Asn217Gln
Thr 58Asp + Asp 59Glu + Ser190Glu + Gly203Gln + Tyr205Cys + Pro209Ser
Gly 62Pro + Gly105Glu + Ile106Glu + Asn154Asp + Leu216Gln + Thr219Asn
Val 91Ser + Ala128Asn + Ala202Glu + Gly203Asp + Tyr205Cys + Thr212Asp
Asn 61Glu + Tyr103Glu + Ser104Glu + Gly203Asn + Thr212Asn + Thr215Pro
Thr 6SSer + Ser 97Asp + Ser 98Glu + Ser104Glu + Thr163Gln + Gly203Pro
Gly12EAsp + Ala128Pro + Gly156Asp + Ser160Glu + Thr161Asp + Gly203Asn
Thr 6SGly + Ser100Glu + Gly101Asn + Leu125Glu + Ser129Glu + Thr215Pro
Asn 61Glu + Gly159Ser + Ala186Gly + Pro209Asp + Asn211Gln + Thr215Glu
Val 94Ser + Ser100Glu + Gly101Gln + Gly126Asp + Ser131Asp + Gly203Ser
Asn 61Asp + Thr 65Gln + Ser 97Asp + Gly203Glu + Tyr205Ala + Leu216Val
Gly156Ser + Ser158Glu + Ala186Ser + Tyr205Asp + Thr212Asp + Thr215Asp
Asp 59Glu + Gly 60Glu + Tyr205Ala + Tyr213Glu + Thr215Glu + Leu216Cys
Thr132Ser + Thr163Asp + Ser190Glu + Tyr205Gly + Pro209Asp + Thr215Asn
Gly 62Glu + Asn 96Glu + Ser 98Glu + Ser15SAsp + Tyr166Ala + Leu216Val
Ser160Asp + Tyr205Ala + Thr210Glu + Thr212Asp + Leu216Ser + Gly218Gln
Thr 65Pro + Leu 95Glu + Gly 99Glu + Ile106His + Leu125Gly + Ser131Glu
Gly 60Glu + Thr 65Gly + Gly 99Ser + Gly203Glu + Tyr213Gln + Thr215Glu
Gly 62Asp + Asn 96Gln + Gly101Glu + Leu125Cys + Gly127Ser + Pro209Asp

Ser 98Asp + Ser100Asp + Ala202Gln + Thr210Glu + Thr212Gly + Thr215Asn
Ser 98Glu + Ser100Asp + Ala128Gln + Gly130Gln + Thr210Gln + Asn217Asp
Leu 95Pro + Gly130Asn + Ser 55Glu + Phe188Glu + Tyr205Asn + Thr215Glu
Asp 59Glu + Val 94Glu + Ser 98Asp + Ser104Glu + Gly126Ser + Tyr213Gly
Ser 00Asp + Ser102Asp + Gly127Asn + Tyr205Asp + Thr215Asn + Leu216His
Gly127Asp + Ala186Gly + Ser190Glu + Tyr205Val + Thr212Gln + Leu216Thr
Leu 95Glu + Ser 97Glu + Ser102Glu + Gly159Asp + Tyr205Leu + Leu216Ala
Gly 60Glu + Asn 61Glu + Leu125Asp + Gly165Glu + Phe18BHis + Gly203Asn
Ser10ZGlu + Ser104Asp + Ala202Thr + Gly203Ser + Thr212Glu + Ala214Glu
Gly 62Glu + Leu 95Glu + Ile106Leu + Tyr166Ile + Gly203Ser + Thr212Glu
Asn154Ser + Ala202Asn + Gly203Asp + Tyr205Glu + Thr210Glu + Leu216Asn
Asn 61Glu + Ser 98Asp + Gly 99Ser + Gly101Glu + Asn154Asp + Gly203Gln
Ser160Asp + Asn162Asp + Ala202Glu + Tyr208Thr + Asn211Ser + Thr215Gln
Gly101Asp + Ser160Asp + Asn162Glu + Thr163Ser + Tyr205Asn + Thr2 2Gln
Val 94Asn + Ser160Glu + Asn162Glu + Asn211Gln + Thr212Asp + Thr215Pro
Thr 58Asn + Ser 97Glu + Ser155Asp + Asn157Asp + Thr212Ser + Leu216Cys
Ser104Glu + Leu125Thr + Ala186Thr + Tyr205Glu + Pro209Asn + Leu216Asp
Asp 59Glu + Gly 64Gln + Ser 97Asp + Ser100Asp + Ser160Asp + Tyr213Val
Gly101Pro + Gly130Asp + Asn154Ser + Thr215Glu + Leu216His + Asn217Glu
Ala186Asp + Gly203Asn + Tyr205Cys + Thr212Asp + Ala214Asp + Thr215Ser
Gly 99Asp + Ile106Gly + Ala128Asn + Asn154Gln + Thr212Asp + Ala214Glu
Thr 65Gln + Asn 96Ser + Ser100Asp + Gly126Pro + Ala202Asp + Leu216Asp
Thr 65Ser + Ser129Asp + Gly153Asn + Tyr205Leu + Tyr213Asp + Thr215Asp
Asn 61Ser + Ser104Asp + Ile106Glu + Ala128Asp + Thr163Asp + Thr212Gln
Gly105Glu + Ser131Asp + Gly156Asn + Tyr205Ala + Thr215Pro + Leu216pro
Gly 62Asp + Ser100Asp + Ala128Asn + Tyr166Ala + Gly203Asp + Leu216Asp
Gly 60Asn + Asn 61Glu + Gly 62Asp + Ser187Glu + Ala202Glu + Tyr205Ser
Ser 97Glu + Ser100Asp + Leu12SAsp + Gly203Pro + Thr207Gln + Thr215Asp
Asn 96Ser + Ser 98Asp + Ser102Glu + Tyr205Gln + Thr212Gln + Thr215Gly
Gly 64Ser + Ser 9BGlu + Ser100Glu + Ser155Asp + Ser187Asp + Ala199Gln
Ser104Asp + Leu125His + Ser129Asp + Ser131Asp + Ala202Glu + Gly218Asn
Ser155Glu + Thr163Glu + Ala202Glu + Tyr205Glu + Thr207Gly + Gly218ser
Asn 61Ser + Thr132Gln + Ser155Glu + Gly159Asp + Thr212Pro + Thr215Gln
Ser100Glu + GlY127Glu + Gly130Asn + Gly203Asp + Thr215Asp + Leu216Thr
Asn162Asp + Phe188His + Ser190Asp + Pro209Glu + Thr212Pro + Leu216Pro
Ser129Glu + Gly130Asp + Gly153Asn + Asn162Ser + Asn211Glu + Ala214Glu
Gly 60Asp + Thr 65Asn + Ser 98Asp + Gly159Asn + Leu216Asp + Gly218Glu
Gly 62Pro + Ser131Glu + Gly165Glu + Tyr2osser + Leu216Thr + Thr219Asp
Gly 62Glu + Asn 96Asp + Ser100Asp + Thr132Glu + Thr215Pro + Gly218Pro
Thr 58Asn + Gly105Gln + Ser187Asp + Ser190Glu + Thr212Glu + Leu216Pro
GlY127Glu + Ser129Glu + Gly153Ser + Asn154Glu + Thr212Gly + Thr215Glu
Thr 65Pro + Ser102Asp + Ser104Glu + Gly126Asp + Asn162Ser + Ala202Asp
Thr 58Asn + Gly 64Pro + Thr 65Glu + Val 94Asp + Tyr205Asp + Thr212Asp
Ser102Glu + Ser104Asp + Gly203Pro + Thr207pro + Thr212Asp + Thr215Asp
Gly 62Asp + Ser104Glu + Gly159Gln + Thr210Asp + Thr212Pro + Leu216Pro
Gly105Gln + Gly1S3Ser + Gly156Asp + Ala186Glu + Ala214Glu + Thr215Pro
Thr 5BGln + Leu 95Pro + Ser15SGlu + Gly165Glu + Gly203Pro + Leu216Glu
Gly 99Glu + Tyr103Pro + Asn154Glu + Ser158Glu + Ser187Glu + Tyr205Pro
Asn 96Asp + Ser 97Asp + Leu125Val + Tyr166Asp + Ser190Glu + Leu216Cys
Leu 95Thr + Asn154Asp + Ser187Asp + Phe188Asn + Thr212Asp + Thr215Gly
Ser131Glu + Asn154Glu + Ser187Glu + Tyr205Gln + Tyr213Val + Asn217Gln
Gly 62Asp + Ser129Glu + Gly203Asp + Tyr213Leu + Thr215Asp + Leu216Val
Gly101Asp + Ala128Asp + Ser15SAsp + Ser187Asp + Thr207Gly + Thr212Gln
Ser131Asp + Asn162Ser + Gly203Asp + Thr212Ser + Thr215Asn + Gly218Glu
Gly101Gln + Gly130Pro + Gly159Glu + Ser190Glu + Asn211Glu + Thr212Glu
Tyr103Asn + Ile106Asp + Tyr166Ala + Ala186Glu + Leu216Pro + Thr219Glu
Asn 96Glu + Ile106Glu + Ala128Ser + Ser158Asp + Ser160Asp + Ala214Asn
Thr 58Asp + Val 94His + Ser155Glu + Ser158Asp + Gly159Asn + Tyr213Pro
Asp 59Glu + Val 94Pro + Asn 96Asp + Tyr103Pro + Gly159Glu + Leu216Val
Ser 97Asp + Asn154Glu + Asn157Ser + Thr163Glu + Ala202Ser + Asn217Glu
Leu 95Gly + Gly127Asp + Ser131Glu + Asn154Ser + Thr161Asn + Asn162Asp
Gly 60Asp + Leu125Gly + Gly126Ser + Gly156Gln + Thr212Asp + Thr215Glu
Ser100Glu + Ala128Glu + Gly165Pro + Phe188Tyr + Gly203Ser + Tyr205Gly
Leu 95Gly + Asn157Asp + Asn162Ser + Gly165Glu + Pro209Gly + Thr210Gly
Ser104Glu + Ser131Glu + Thr132Gly + Gly156Glu + Phe188Val + Leu216Ser
Gly 99Glu + Ser100Asp + Ala128Glu + Pro209Gly + Thr212Asn + Ala214Glu
Thr 58Asn + Asn 96Glu + Ser102Asp + Tyr103Met + Ser155Asp + Gly156Gln
Leu 95His + Gly126Glu + Gly165Gln + Ser190Glu + Tyr213Asp + Thr215Asp
Gly105Glu + Leu12SCys + Ser129Glu + Gly165Glu + Thr212Ser + Thr219Glu
Ser 98Asp + Ser102Asp + Gly105Asp + Phe188Leu + Tyr205Glu + Thr212Pro
Leu 95Val + Gly 99Asp + Tyr103Val + Gly105Asp + Tyr205Asp + Thr215Asp
Gly159Glu + Gly165Asp + Thr215Ser + Leu216Cys + Asn217Glu + Thr219Asp
Tyr103Ile + Ser129Asp + Gly159Asp + Phe188Glu + Ser190Asp + Ala202Gly
Asp 59Glu + Asn 96Asp + Gly105Glu + Asn162Asp + Thr163Gln + Thr212Gln
Gly 99Pro + Gly101Glu + Ser104Glu + Gly153Glu + Asn162Asp + Thr215Gln
Asn 61Glu + Gly126Asp + Gly159Gln + Asn162Glu + Ser190Asp + Thr215Gly
Gly 99Asp + Ser158Asp + Asn162Asp + Thr163Asn + Ser187Glu + Ala199Gly
Asn154Glu + Ser155Glu + Gly156Gln + Thr210Asp + Leu216Asp + Gly218Pro
Gly126Asn + Ser129Asp + Asn162Glu + Ala186Ser + Ala202Glu + Asn217Asp
Ser100Asp + Gly101Asp + Ala128Thr + Asn154Gln + Phe18BAsp + Leu216Glu
Asn 61Ser + Ile106Ser + Ser158Glu + Ser190Asp + Tyr205Asp + Thr219Pro
Thr 58Ser + Val 94Ala + Ser 98Glu + Ser158Glu + Ser190Glu + Tyr205Pro Ser100Glu + Gly127Glu + Asn154Glu + Gly203Glu + Tyr205Ala + Tyr213Thr
Gly101Glu + Leu125Gly + Ser155Asp + Tyr205Val + Leu216Pro + Thr219Asp
Ser 97Asp + Asn157Gln + Gly165Ser + Tyr205Ser + Leu216Asp + Thr219Asp
Ser 97Glu + Ser 98Asp + Gly105Glu + Gly165Gln + Ser190Glu + Thr215Ser
Gly 60Gln + Thr 6SGln + Val 94Asp + Leu125Glu + Ser131Asp + Ala202Gly
Tyr166Glu + Ser187Asp + Ser190Glu + Gly203Pro + Tyr205Gly + Leu216Asp
Thr 58Pro + Val 94Glu + Ser 97Asp + Gly165Glu + Tyr205Ser + Tyr213His
Gly 62Asp + Val 94Ala + Ser129Glu + Gly203Gln + Tyr205Val + Thr212Glu
Tyr103Asn + GlY130G1U + Ser131Asp + Ser155Glu + Phe188Met + Thr212Asp
Ser155Asp + Gly203Asn + Pro209Asp + Thr212Asp + Thr215Ser + Asn217Glu
Asn 96Glu + Ser160Glu + Asn162Ser + Asn211Gln + Ala214Glu + Thr215Asp
Asn 96Glu + Ser158Asp + Gly1S9Asp + Thr163Asn + Thr210Pro + Leu216Glu
Thr 58Asn + Ser129Asp + Gly130Glu + Gly156Glu + Thr161Ser + Tyr205Asp
G1Y153Gln + Ser158Asp + Ala202Asp + Asn211Glu + Thr212Asp + Leu216Mis
Ser104Glu + Leu125Cys + Gly156Pro + Ala202Glu + Gly203Asp + Pro209Glu
Thr 65Asp + Ser100Glu + Gly105Asp + Gly127Ser + Gly203ser + Tyr20BMet
Ser 97Asp + Ser 98Asp + Ser158Asp + Thr212Gln + Thr215Pro + Leu216Glu
Gly 62Gln + Ser 97Glu + Ser 98Asp + Gly126Glu + Gly130Pro + Thr212Glu
Gly 60Asp + Asn157Glu + Tyr205Glu + Tyr213Thr + Thr215Asp + Leu216Ile
Gly 62Glu + Ser102Asp + Gly127Glu + ser155Asp + Tyr213Pro + Ala214Gln
Thr 58Pro + Asn 96Asp + Gly127Glu + Ser155Glu + Asn162Ser + Thr212Ser
Gly 62Gln + Ser100Glu + Gly130Glu + Asn154Gln + Gly203Glu + Asn217Glu
Asp 59Glu + Gly 62Pro + Phe188Glu + Ala202Ser + Tyr205Glu + Pro209Asp
Asn 61Glu + Ser 97Glu + Ala128His + Asn162Gln + Tyr166Glu + Tyr205Asp
Ile106Pro + Gly126Pro + Gly153Glu + Ser158Glu + Gly203Glu + Thr215Glu
Ser102Glu + Tyr103Pro + Gly105Ser + Gly130Glu + Ser158Glu + Ala199Pro
Asp 59Glu + Asn 61Ser + Ser158Asp + Thr161Asn + Ser190Glu + Asn211Asp
Asn 61Gln + Ser104Asp + Gly127Glu + Asn157Glu + Asn162Glu + Tyr205Ala
Val 94Asp + Gly105Glu + Gly165Asp + Ala186Pro + Ala202Asp + Gly203Gln
Asn 61Glu + Val 94Gln + Ser102Asp + Leu125Asp + Gly159Gln + Gly165Ser
Ile106Asp + Ser131Glu + Asn162Glu + Ala202Ser + Thr212Ser + Thr215Asn
Ile106Asp + Ser131Asp + Gly159Asp + Gly203Pro + Leu216Ala + Thr219Gln
Asn154Gln + Gly159Asp + Ser190Asp + Ala214Glu + Leu216Pro + Gly218Asp
Asn 61Asp + Ser158Asp + Gly203Asp + Thr212Gln + Ala214Gly + Thr215Glu
Gly 62Asp + Thr 6SGlu + Leu 95Met + Ser104Asp + Thr132Gln + Asn162Asp
Asn 96Asp + Ser 98Asp + Gly127Asn + Ser129Asp + Tyr205Asn + Thr215Asp
Ser 97Asp + Gly126Pro + Thr161Ser + Ala186Glu + Phe188Glu + Thr212Glu
Gly 60Asn + Ser 98Glu + Gly159Asn + Gly203Glu + Thr212Asp + Asn217Glu
Ser131Asp + Ser190Asp + Gly203Asp + Tyr205His + Thr215Asp + Leu216Gln
Asn 61Glu + Gly105Gln + Ser131Asp + Met198Gly + Pro209Gly + Thr210Glu
Thr132Pro + Gly153Asp + Asn162Glu + Gly203Asn + Pro209Gln + Leu216Glu
Ser100Glu + Gly105Pro + Asn157Asp + Gly203Glu + Asn211Ser + Leu216Glu
Thr 58Asn + Ser 98Glu + Gly156Glu + Gly203Asp + Ala214Gln + Leu216Asp
Asp 59Glu + Gly 99Gln + Ser100Asp + Gly101Pro + Ser102Glu + Gly203Glu
Ser 98Asp + Gly126Gln + Thr161Asn + Ala202Asn + Thr212Glu + Thr215Glu
Ser160Asp + Thr161Asn + Thr212Glu + Thr215Glu + Leu216Val + Thr219Ser
Ser 98Glu + Ser100Asp + Ser160Asp + Phe188Asp + Val204Pro + Asn211Gln
Leu 95Gly + Ser 98Glu + Ser100Glu + Gly101Asn + Gly203Asp + Thr210Glu
Asn 96Glu + Ser100Asp + Asn157Asp + Thr163Pro + Ala202Pro + Thr212Glu
Asp S9Glu + Gly 99Asp + Ser104Glu + Gly127G1U + Gly203Asn + Tyr205Gly
Gly 62Glu + Thr132Gln + Gly156Glu + Thr163Asp + Ala186Pro + Ala202Asp
Ser 98Asp + Ser158Glu + Ser160Asp + Phe188Ile + Pro209Asn + Gly218Glu
Thr 58Asn + Gly 62Glu + Gly 64Asn + Asn157Glu + Ser190Glu + Gly203Glu
Asn 61Asp + Gly 99Pro + Ser104Asp + Gly203Asp + Tyr205Asp + Thr212Pro
Gly 60Asp + Ile106Pro + Gly127Glu + Ala202Asp + Leu216Ile + Gly218Asp
Asn 61Asp + Ser129Glu + Ser131Asp + Thr161Asn + Ala214Gln + Thr215Glu
Asn 61Asp + Ser 98Asp + Ile106Ser + Ser131Asp + Ser160Glu + Ile164His
Ser100Glu + Ser160Glu + Tyr205Asp + Thr210Pro + Thr212Ser + Leu216Glu
Leu 95Pro + Gly105Asp + Thr161Glu + Tyr205Glu + Leu216Asp + Thr219Gly
Ser 98Asp + Ser102Glu + Leu 25Glu + Ala128Pro + Tyr213Gly + Leu216Asp
Leu 95Val + Ser155Glu + Tyr166Ala + Ala186Glu + Thr210Asp + Leu216Met
Thr 58Asn + Gly 99Glu + Gly105Glu + Gly127Glu + Ser190Asp + Tyr205Leu
Asp 59Glu + Gly 99Glu + Leu12SSer + Thr212Glu + Leu216Asp + Gly218Ser
Thr 58Gln + Gly130Glu + Thr132Glu + Gly203Asn + Thr212Glu + Asn217Asp
Ser 97Glu + Gly127Gln + Ser129Asp + Gly156Asp + Ser158Glu + Asn211Ser
Ser102Glu + Gly126Glu + Gly153Ser + Ser190Glu + Ala202Thr + Asn211Asp
Tyr103Glu + Leu125His + Ser131Glu + Gly203Asp + Asn211Asp + Thr215Ser
Ser129Asp + Gly130Gln + Gly165Asp + Gly203Asp + Thr212Glu + Leu216Val
Gly127Asn + Ser131Asp + Gly1S9Glu + Tyr205Gln + Thr212Asp + Ala214Glu
Ser 97Glu + Ile106Glu + Tyr166Gly + Ala202Asp + Thr215Ser + Leu216Asp
Leu 95Glu + Leu125His + Gly126Asp + Tyr205Gln + Thr215Asp + Thr219Asn
Asp 59Glu + Ser 97Glu + Ala128Asn + Thr132Glu + Asn157Asp + Tyr205Gly
Ser 98Asp + Ser102Asp + Ala128His + Ser187Glu + Thr215Pro + Gly218Asp
Thr 58Pro + Gly130Ser + Gly156Asp + Ser160Asp + Thr212Ser + Thr215Glu
Thr 58Ser + Gly 60Glu + Thr 65Asp + Ser100Glu + Gly159Glu + Leu216His
Ser 97Glu + Ser100Glu + Asn154Glu + Gly203Pro + Thr212Asn + Thr215Glu
Ser 97Asp + Ser100Asp + Ile106Val + Ser155Asp + Gly203Pro + Thr215Asp
Ser 97Glu + Asn157Glu + Ser160Asp + Thr210Gln + Thr212Asn + Asn217Asp
Asp 59Glu + Leu 95Cys + Ala128Asn + Thr132Gly + Gly153Asp + Ser187Asp
Thr 65Asp + Leu125Asp + Ser190Glu + Gly203Asn + Asn211Asp + Thr219Ser
Asp 59Glu + Asn 96Asp + Leu125Cys + Thr215Asp + Leu216Ile + Thr219Asp
Ser 98Glu + Gly105Asp + Leu125His + Asn162Asp + Ser190Glu + Ala202Ser

```
Gly 60Ser  + Thr  65Glu + Ser158Glu + Thr163Gly + Thr215Pro + Leu216Asp
Val 94Glu  + Asn  96Ser + Gly101Pro + Ser102Asp + Ser155Glu + Thr212Asp
Ser100Glu  + Gly127Asn + Ser129Asp + Thr132Glu + Asn162Glu + Leu216Ala
Ser  98Glu + Ser102Asp + Ala202His + Thr212Pro + Thr215Asp + Gly218Asp
Asn  61Asp + Asn  96Asp + Gly16SGlu + Tyr166Ser + Gly203Asp + Asn211Gln
Asn  61Asp + Asn  96Glu + Gly127Ser + Gly130Asp + Gly203Glu + Thr212Pro
Ser  97Glu + Gly101Asp + Ser129Glu + Ser158Glu + Thr161Ser + Ala214Gln
Gly  62Glu + Ser  97Asp + Ser129Asp + Ala199Pro + Leu216Gln + Gly218Asp
Ser129Glu + Asn157Gln + Ser187Asp + Ser190Glu + Gly203Asn + Tyr205Asp
Gly156Asn + Asn162Gln + Ser187Glu + Gly203Glu + Thr215Gln + Thr219Gly
Ala128Ser + Ser187Glu + Gly203Glu + Tyr205Leu + Thr2105er + Leu216Thr
Thr  58Gly + Thr  6SAsp + Ser100Glu + Gly105Glu + Ala128Asp + Leu216Thr
Asp  S9Glu + Thr  65Gly + Gly156Asp + Tyr205Glu + Leu216Cys + Asn217Asp
Thr  58Pro + Asn  96Asp + Ser160Asp + Ser190Asp + Ala202Asn + Thr212Asn
Ser160Glu + ser190Asp + Tyr205Asp + Thr207Pro + Thr212Gln + Leu21GMet
Asn  61Asp + Leu  95Glu + Tyr166Asn + Tyr205Glu + Asn211Glu + Leu216Asn
Ser  98Glu + Ser158Glu + Thr163Glu + Tyr166Leu + Gly203Glu + Tyr205Thr
Asp  59Glu + Ser104Glu + Ser158Asp + Thr163Glu + Phe188His + Thr212Pro
Ser158Asp + Thr  63Glu + Ala202Asp + Tyr205Cys + Thr212Asn + Leu216Pro
Tyr166Glu + Ser190Glu + Met198Ser + Gly203Asn + Asn211Asp + Tyr213Pro
Asn  61Ser + Gly  64Ser + Thr  65Asp + Ser129Glu + Tyr205Glu + Tyr213Gly
Ala128Pro + Thr132Glu + Gly153Ser + Asn154Asp + Gly16SAsp + Gly203Glu
Asp  59Glu + Thr132Glu + Thr163Pro + Tyr166Ile + Thr210Asp + Leu216Asp
Thr  58Asp + Asn  96Gln + Ser104Asp + Gly126Gln + Gly203Asp + Pro209Glu
Gly  64Asn + Thr  6SGlu + Gly126Glu + Tyr166Ala + Phe188Tyr + Thr215Glu
Asp  59Glu + Asn  96Asp + Gly105Asn + Gly127Asp + Ser158Glu + Thr215Ser
Ser104Asp + Ser131Asp + Gly159Glu + Phe188Asp + Thr210Gly + Thr212Gln
Val  94Met + Ser104Asp + Gly126Ser + Ser131Glu + Thr210Glu + Thr215Asp
Thr  58Asp + Ser  97Asp + Gly105Asp + Ser187Glu + Met198Thr + Tyr205Val
Val  94Asp + Gly  99Asp + Gly126Asn + Thr163Glu + Gly203Glu + Leu216Cys
Thr  58Glu + Gly  62Glu + Gly105Glu + Gly156Glu + Phe188Thr + Thr212Gly
Thr  58Gln + Gly159Asp + Ser190Glu + Gly203Asp + Tyr205Ile + Gly218Ser
Thr  58Pro + Ser131Glu + Tyr166Thr + Tyr205Asp + Thr215Ser + Gly218Asp
Gly  60Asp + Thr161Asp + Gly165Glu + Pro209Gln + Thr215Gly + Thr219Gly
Asp  59Glu + Ser102Asp + Thr161Asp + Asn162Gln + Ser190Glu + Ala202Ser
Leu  95Cys + Ser100Glu + Ser104Glu + Phe188Cys + Tyr205Met + Leu216Asp
Ser100Asp + Ser104Asp + Gly105Asn + Tyr205Cys + Tyr208Asn + Pro209Glu
Gly  64Ser + Thr  65Gln + Ser100Glu + Ser104Glu + Ser160Asp + Thr207Asn
Thr  65Gly + Gly  99Asp + Ala128Glu + Ser155Glu + Gly203Gln + Thr215Asp
Gly  99Asp + Ala128Asp + Ser155Asp + Ala202Glu + Thr210Asn + Leu216Val
Thr  58Asp + Ser  97Asp + Thr132Asp + Thr215Gln + Leu216Asn + Gly218Glu
Thr  58Asp + Ser  97Glu + Gly127Asp + Tyr166Ala + Ala186Ser + Asn217Glu
Thr  65Asp + Thr132Glu + Asn154Asp + Thr212Glu + Leu216Gly + Asn217Ser
Gly  99Gln + Ser131Glu + Thr161Asn + Tyr205Thr + Pro209Asp + Thr215Glu
Tyr103His + Ser131Glu + Gly156Asp + Gly159Glu + Thr212Glu + Leu216Met
Thr  58Gln + Ser  98Asp + Ser102Glu + Ala202His + Thr212Pro + Thr215Asp
Gly127Glu + Asn162Glu + Phe188Met + Ala202Gly + Gly203Ser + Gly218Asn
```

II. Cleaning Compositions

In another embodiment of the present invention, an effective amount of one or more of the enzyme variants are included in compositions useful for cleaning a variety of surfaces in need of proteinaceous stain removal. Such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form); oral cleaning compositions, unlimited in form (e.g., dentifrice, toothpaste and mouthwash formulations); denture cleaning compositions, unlimited in form (e.g., liquid, tablet); and contact lens cleaning compositions, unlimited in form (e.g., liquid, tablet).

The cleaning compositions also comprise, in addition to the subtilisin Carlsberg variants described hereinbefore, one or more cleaning composition materials compatible with the protease enzyme. the term "cleaning composition material", as used herein, means any liquid, solid or gaseous material selected for the particular type of cleaning composition desired and the form of the product (e.g., liquid, granule, bar, spray, stick, paste, gel), which materials are also compatible with the subtilisin Carlsberg variant used in the composition. the specific selection of cleaning composition materials are readily made by considering the surface material to be cleaned, the desired form of the composition for the cleaning condition during use (e.g., through the wash detergent use). The term "compatible", as used herein, means the cleaning composition materials do not reduce the proteolytic activity of the subtilisin Carlsberg variant to such an extent that the protease is not effective as desired during normal use situations. Specific cleaning composition materials are exemplified in detail hereinafter.

As used herein, "effective amount of enzyme variant" refers to the quantity of enzyme variant necessary to achieve the enzymatic activity necessary in the specific cleaning composition. Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like. Preferably the cleaning compositions comprise from about 0.0001% to about 10% of one or more enzyme variants of the present invention, more preferably from about 0.001% to about 1%, more preferably still from about 0.01% to about 0.1%. Several examples of various cleaning compositions wherein the enzyme variants may be employed are discussed in further detail below. All parts, percentages and ratios used herein are by weight unless otherwise specified.

As used herein, "non-fabric cleaning compositions" include hard surface cleaning compositions, dishwashing compositions, oral cleaning compositions, denture cleaning compositions and contact lens cleaning compositions.

A. Cleaning Compositions for Hard Surfaces, Dishes and Fabrics

The enzyme variants of the present invention can be used in a variety of detergent compositions where high sudsing and good insoluble substrate removal are desired. Thus the enzyme variants can be used with various conventional ingredients to provide fully-formulated hard-surface cleaners, dishwashing compositions, fabric laundering compositions and the like. Such compositions can be in the form of liquids, granules, bars and the like. Such compositions can be formulated as modern "concentrated" detergents which contain as much as 30%–60% by weight of surfactants.

The cleaning compositions herein can optionally, and preferably, contain various anionic, nonionic, zwitterionic, etc., surfactants. Such surfactants are typically present at levels of from about 5% to about 35% of the compositions.

Nonlimiting examples of surfactants useful herein include the conventional $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)x(CHOSO_3)^-M^+)CH_3$ and $CH_3(CH_2)y(CHOSO_3^-M^+) CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxylpropoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. (Use of such surfactants in combination with the aforesaid amine oxide and/or betaine or sultaine surfactants is also preferred, depending on the desires of the formulator.) Other conventional useful surfactants are listed in standard texts. Particularly useful surfactants include the $C_{10}$–$C_{18}$ N-ethyl glucamides disclosed in U.S. Pat. No. 5,194,639, Connor et al., issued Mar. 16, 1993, incorporated herein by reference.

A wide variety of other ingredients useful in detergent cleaning compositions can be included in the compositions herein, including other active ingredients, carriers, hydrotropes, processing aids, dyes or pigments, solvents for liquid formulations, etc. If an additional increment of sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additionally sudsing.

The liquid detergent compositions herein can contain water and other solvents as carriers. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g., 1,3propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11.0. Finished products thus are typically formulated at this range. Techniques for controlling pH at recommended usage levels include the use of buffers, alkalis, acids, etc., and are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases and proteases in such compositions, typically at levels of from about 0.001% to about 1% by weight. Various detersive and fabric care enzymes are wellknown in the laundry detergent art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various suds suppressors, especially silicones and secondary alcohols, various fabric softeners, especially smectite clays, and the like can all be used in such compositions at levels ranging from about 1% to about 35% by weight. Standard formularies and published patents contain multiple, detailed descriptions of such conventional materials.

Enzyme stabilizers may also be used in the cleaning compositions. Such enzyme stabilizers include propylene glycol (preferably from about 1% to about 10%), sodium formate (preferably from about 0.1% to about 1%) and calcium formate (preferably from about 0.1% to about 1%).

1. Hard surface cleaning compositions

As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more enzyme variants of the present invention, preferably from about 0.001% to about 10%, more preferably from about 0.01% to about 5%, more preferably still from about 0.05% to about 1% by weight of active enzyme of the composition. In addition to comprising one or more of the enzyme variants, such hard surface cleaning compositions typically comprise a surfactant and a water-soluble sequestering builder. In certain specialized products such as spray window cleaners, however, the surfactants are sometimes not used since they may produce a filmy/streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%.

Preferably the pH should be in the range of about 8 to 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3-pentanediol and 2-ethyl-1,3-hexanediol. When used, such solvents are typically present at levels of from about 0.5% to about 15%, preferably from about 3% to about 11%.

Additionally, highly volatile solvents such as isopropanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

The hard surface cleaning composition embodiment of the present invention is illustrated by the following examples.

Liquid Hard Surface Cleaning Compositions

| Component | Example No. | | | | | |
|---|---|---|---|---|---|---|
| | 7 | 8 | 9 | 10 | 11 | 12 |
| Thr58Asn | 0.05 | 0.50 | 0.02 | 0.03 | 0.10 | 0.03 |
| Thr58Gln + Asn61Glu | — | — | — | — | 0.20 | 0.02 |
| Na$_2$DIDA* EDTA** | — | — | 2.90 | 2.90 | — | — |
| Na Citrate | — | — | — | — | 2.90 | 2.90 |
| NaC$_{12}$Alkyl-benzene sulfonate | 1.95 | — | 1.95 | — | 1.95 | — |
| NaC$_{12}$ Alkylsulfate | — | 2.20 | — | 2.20 | — | 2.20 |
| NaC$_{12}$(ethoxy)*** sulfate | — | 2.20 | — | 2.20 | — | 2.20 |
| C$_{12}$ Dimethylamine oxide | — | 0.50 | — | 0.50 | — | 0.50 |
| Na Cumene sulfonate | 1.30 | — | 1.30 | — | 1.30 | — |
| Hexyl Carbitol*** | 6.30 | 6.30 | 6.30 | 6.30 | 6.30 | 6.30 |
| Water**** | balance to 100% | | | | | |

*Disodium N-diethyleneglycol-N,N-iminodiacetate
**Na$_4$ ethylenediamine diacetic acid
***Diethyleneglycol monohexyl ether
****All formulas adjusted to pH 7

In Examples 7–10, the subtilisin Carlsberg variants recited in Tables 3–36, among others, are substituted for Thr58Asn, with substantially similar results.

In Examples 11–12, any combination of the subtilisin Carlsberg variants recited in Tables 3–36, among others, are substituted for Thr58Asn and Thr58Gln+Asn61Glu, with substantially similar results.

Spray Compositions for Cleaning Hard Surfaces
and Removing Household Mildew

| Component | Example No. | | | | | |
|---|---|---|---|---|---|---|
| | 13 | 14 | 15 | 16 | 17 | 18 |
| Val94Ala | 0.50 | 0.05 | 0.60 | 0.30 | 0.20 | 0.30 |
| Leu125Asn + Gly126Pro + Ser129Glu | — | — | — | — | 0.30 | 0.10 |
| Sodium octyl sulfate | 2.00 | 2.00 | 2.00 | 2.00 | 2.00 | 2.00 |
| Sodium dodecyl sulfate | 4.00 | 4.00 | 4.00 | 4.00 | 4.00 | 4.00 |
| Sodium hydroxide | 0.80 | 0.80 | 0.80 | 0.80 | 0.80 | 0.80 |
| Silicate (Na) | 0.04 | 0.04 | 0.04 | 0.04 | 0.04 | 0.04 |
| Perfume | 0.35 | 0.35 | 0.35 | 0.35 | 0.35 | 0.35 |
| Water | balance to 100% | | | | | |

Product pH is adjusted to 7.

In Examples 13–16, the subtilisin Carlsberg variants recited in Tables 3–36, among others, are substituted for Val94Ala, with substantially similar results.

In Examples 17–18, any combination of the subtilisin Carlsberg variants recited in Tables 3–36, among others, are substituted for Val94Ala and Leu125Asn+Gly126Pro+Ser129Glu, with substantially similar results.

2. Dishwashing Compositions

In another embodiment of the present invention, dishwashing compositions comprise one or more enzyme variants of the present invention. As used herein, "dishwashing composition" refers to all forms for compositions for cleaning dishes, including but not limited to, granular and liquid forms. The dishwashing composition embodiment of the present invention is illustrated by the following examples.

Dishwashing Composition

| Component | Example No. | | | | | |
|---|---|---|---|---|---|---|
| | 19 | 20 | 21 | 22 | 23 | 24 |
| Gly153Asn | 0.05 | 0.50 | 0.02 | 0.40 | 0.10 | 0.03 |
| Ala186Asp + Phe188Gln | — | — | — | — | 0.40 | 0.02 |
| C$_{12}$–C$_{14}$ N-methyl-glucamide | 0.90 | 0.90 | 0.90 | 0.90 | 0.90 | 0.90 |
| C$_{12}$ ethoxy (1) sulfate | 12.00 | 12.00 | 12.00 | 12.00 | 12.00 | 12.00 |
| 2-methyl undecanoic acid | 4.50 | 4.50 | 4.50 | 4.50 | 4.50 | 4.50 |
| C$_{12}$ ethoxy (2) carboxylate | 4.50 | 4.50 | 4.50 | 4.50 | 4.50 | 4.50 |
| C$_{12}$ alcohol ethoxylate (4) | 3.00 | 3.00 | 3.00 | 3.00 | 3.00 | 3.00 |
| C$_{12}$ amine oxide | 3.00 | 3.00 | 3.00 | 3.00 | 3.00 | 3.00 |
| Sodium cumene sulfonate | 2.00 | 2.00 | 2.00 | 2.00 | 2.00 | 2.00 |
| Ethanol | 4.00 | 4.00 | 4.00 | 4.00 | 4.00 | 4.00 |
| Mg$^{++}$(as MgCl$_2$) | 0.20 | 0.20 | 0.20 | 0.20 | 0.20 | 0.20 |
| Ca$^{++}$(as CaCl$_2$) | 0.40 | 0.40 | 0.40 | 0.40 | 0.40 | 0.40 |
| Water | balance to 100% | | | | | |

Product pH is adjusted to 7.

In Examples 19–22, the subtilisin Carlsberg variants recited in Tables 3–36, among others, are substituted for Gly153Asn, with substantially similar results.

In Examples 23–24, any combination of the subtilisin Carlsberg variants recited in Tables 3–36, among others, are substituted for Gly153Asn and Ala186Asp+Phe188Gln, with substantially similar results.

3. Fabric cleaning compositions

In another embodiment of the present invention, fabric cleaning compositions comprise one or more enzyme variants of the present invention. As used herein, "fabric cleaning composition" refers to all forms for detergent compositions for cleaning fabrics, including but not limited to, granular, liquid and bar forms. Preferred fabric cleaning compositions are those in the liquid form.

a. Granular fabric cleaning compositions

The granular fabric cleaning compositions of the present invention contain an effective amount of one or more enzyme variants of the present invention, preferably from about 0.001% to about 10%, more preferably from about 0.005% to about 5%, more preferably from about 0.01% to about 1% by weight of active enzyme of the composition. In addition to one or more enzyme variants, the granular fabric cleaning compositions typically comprise at least one surfactant, one or more builders, and, in some cases, a bleaching agent.

The granular fabric cleaning composition embodiment of the present invention is illustrated by the following examples.

EXAMPLES 25–28

Granular Fabric Cleaning Composition

| | Example No. | | | |
|---|---|---|---|---|
| Component | 25 | 26 | 27 | 28 |
| Pro200Asn | 0.10 | 0.20 | 0.03 | 0.05 |
| Gly203Asp + Tyr205Ala + Tyr208Ser | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 25–26, the subtilisin Carlsberg variants recited in Tables 3–36, among others, are substituted for Pro200Asn, with substantially similar results.

In Examples 27–28, any combination of the subtilisin Carlsberg variants recited in Tables 3–36, among others, are substituted for Pro200Asn and Gly203Asp+Tyr205Ala+Tyr208Ser, with substantially similar results.

EXAMPLES 29–32

Granular Fabric Cleaning Composition

| | Example No. | | | |
|---|---|---|---|---|
| Component | 29 | 30 | 31 | 32 |
| Pro200Asn + Ala202Asn + Val204Gly + Asn211Asp + Thr219Gly | 0.10 | 0.20 | 0.03 | 0.05 |
| Leu 95Gly + Gly203Pro | — | — | 0.02 | 0.05 |
| $C_{12}$ allkyl benzene sulfonate | 12.00 | 12.00 | 12.00 | 12.00 |
| Zeolite A (1–10 micrometer) | 28.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 29–30, the subtilisin Carlsberg variants recited in Tables 3–36, among others, are substituted for Pro200Asn+Ala202Asn+Val204Gly+Asn211Asp+Thr219Gly, with substantially similar results.

In Examples 31–32, any combination of the subtilisin Carlsberg variants recited in Tables 3–36, among others, are substituted for Pro200Asn+Ala202Asn+Val204Gly+Asn211 Asp+Thr219Gly and Leu 95Gly+Gly203Pro, with substantially similar results.

EXAMPLES 33–36

Granular Fabric Cleaning Composition

| | Example No. | | | |
|---|---|---|---|---|
| Component | 33 | 34 | 35 | 36 |
| Thr 58Gln + Asp 59Glu + Leu216Gln | 0.10 | 0.20 | 0.03 | 0.05 |
| Pro200Asn + Ala202Gln + Tyr208Cys + Thr210Pro + Tyr213Asn + Ala214Asn + Thr219Ser | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 33–34, the subtilisin Carlsberg variants recited in Tables 3–36, among others, are substituted for Thr 58Gln+Asp 59Glu+Leu216Gln, with substantially similar results.

In Examples 35–36, any combination of the subtilisin Carlsberg variants recited in Tables 3–36, among others, are substituted for Thr 58Gln+Asp 59Glu+Leu216Gln and Pro200Asn+Ala202Gln+Tyr208Cys+Thr210Pro+Tyr213Asn+Ala214Asn+Thr219Ser, with substantially similar results.

EXAMPLES 37–40

Granular Fabric Cleaning Composition

| | Example No. | | | |
|---|---|---|---|---|
| Component | 37 | 38 | 39 | 40 |
| Asp59Glu + Gly60Pro + Gly62Asn + Gly64Gl | 0.10 | 0.20 | 0.03 | 0.05 |
| Leu125Ala | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 37–38, the subtilisin Carlsberg variants recited in Tables 3–36, among others, are substituted for Asp59Glu+Gly60Pro+Gly62Asn+Gly64Gl, with substantially similar results.

In Examples 39–40, any combination of the subtilisin Carlsberg variants recited in Tables 3–36, among others, are substituted for Asp59Glu+Gly60Pro+Gly62Asn+Gly64Gl and Leu125Ala, with substantially similar results.

EXAMPLES 41–42

Granular Fabric Cleaning Composition

| Component | Example No. 41 | Example No. 42 |
|---|---|---|
| Linear alkyl benzene sulphonate | 11.4 | 10.70 |
| Tallow alkyl sulphate | 1.80 | 2.40 |
| $C_{14-15}$ alkyl sulphate | 3.00 | 3.10 |
| $C_{14-15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| Diethylene triamine penta methylene phosphonic acid | 1.00 | 0.20 |
| Gly127Glu + Asn162Glu + Phe188Met + Ala202Gly + Gly203Ser + Gly218Asn | 0.30 | 0.30 |
| Lipase | 0.36 | 0.40 |
| Amylase | 0.30 | 0.30 |
| Sodium silicate | 2.00 | 2.50 |
| Sodium sulphate | 3.50 | 5.20 |
| Polyvinyl pyrrolidone | 0.30 | 0.50 |
| Perborate | 0.5 | 1 |
| Phenol sulphonate | 0.1 | 0.2 |
| Peroxidase | 0.1 | 0.1 |
| Minors | Up to 100 | Up to 100 |

EXAMPLES 43–44

Granular Fabric Cleaning Composition

| Component | Example No. 43 | Example No. 44 |
|---|---|---|
| Sodium linear $C_{12}$ alkyl benzene-sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Polyvinyl pyrrolidone | 0.5 | 0.7 |
| Tetraacetylethylene diamine | 3.0 | 3.0 |
| Boric acid | 4.0 | — |
| Perborate | 0.5 | 1 |
| Phenol sulphonate | 0.1 | 0.2 |
| Gly218Gln + Thr219Gln | 0.4 | 0.4 |
| Fillers (e.g., silicates; carbonates; perfumes; water) | Up to 100 | Up to 100 |

EXAMPLE 45

Compact Granular Fabric Cleaning Composition

| Component | Weight % |
|---|---|
| Alkyl Sulphate | 8.0 |
| Alkyl Ethoxy Sulphate | 2.0 |
| Mixture of $C_{25}$ and $C_{45}$ alcohol 3 and 7 times ethoxylated | 6.0 |
| Polyhydroxy fatty acid amide | 2.5 |
| Zeolite | 17.0 |
| Layered silicate/citrate | 16.0 |
| Carbonate | 7.0 |
| Maleic acid acryiic acid copolymer | 5.0 |
| Soil release polymer | 0.4 |
| Carboxymethyl cellulose | 0.4 |

Compact Granular Fabric Cleaning Composition -continued

| Component | Weight % |
|---|---|
| Poly (4-vinylpyridine)-N-oxide | 0.1 |
| Copolymer of vinylimidazole and vinylpyrrolidone | 0.1 |
| PEG2000 | 0.2 |
| Pro209Gln | 0.5 |
| Lipase | 0.2 |
| Cellulase | 0.2 |
| Tetracetylethylene diamine | 6.0 |
| Percarbonate | 22.0 |
| Ethylene diamine disuccinic acid | 0.3 |
| Suds suppressor | 3.5 |
| Disodium-4,4'-bis (2-morpholino-4-anilino-s-triazin-6-ylamino) stilbene-2,2'-disulphonate | 0.25 |
| Disodium-4,4'-bis (2-sulfostyril) biphenyl | 0.05 |
| Water, Perfume and Minors | Up to 100 |

EXAMPLE 46

Granular Fabric Cleaning Composition

| Component | Weight % |
|---|---|
| Linear alkyl benzene sulphonate | 7.6 |
| $C_{16}$–$C_{18}$ alkyl sulfate | 1.3 |
| $C_{14-15}$ alcohol 7 times ethoxylated | 4.0 |
| Coco-alkyl-dimethyl hydroxyethyl ammonium chloride | 1.4 |
| Dispersant | 0.07 |
| Silicone fluid | 0.8 |
| Trisodium citrate | 5.0 |
| Zeolite 4A | 15.0 |
| Maleic acid acrylic acid copolymer | 4.0 |
| Diethylene triamine penta methylene phosphonic acid | 0.4 |
| Perborate | 15.0 |
| Tetraacetylethylene diamine | 5.0 |
| Smectite clay | 10.0 |
| Poly (oxyethylene) (MW 300,000) | 0.3 |
| Thr58Pro + Gly64Ser + Thr65Gly | 0.4 |
| Lipase | 0.2 |
| Amylase | 0.3 |
| Cellulase | 0.2 |
| Sodium silicate | 3.0 |
| Sodium carbonate | 10.0 |
| Carboxymethyl cellulose | 0.2 |
| Brighteners | 0.2 |
| Water, perfume and minors | Up to 100 |

EXAMPLE 47

Granular Fabric Cleaning Composition

| Component | Weight % |
|---|---|
| Linear alkyl benzene sulfonate | 6.92 |
| Tallow alkyl sulfate | 2.05 |
| $C_{14-15}$ alcohol 7 times ethoxylated | 4.4 |
| $C_{12-15}$ alkyl ethoxy sulfate - 3 times ethoxylated | 0.16 |
| Zeolite | 20.2 |
| Citrate | 5.5 |
| Carbonate | 15.4 |
| Silicate | 3.0 |
| Maleic acid acrylic acid copolymer | 4.0 |
| Carboxymethyl cellulase | 0.31 |
| Soil release polymer | 0.30 |
| Val 94Gln + Ser100Glu | 0.2 |
| Lipase | 0.38 |
| Cellulase | 0.13 |

-continued

| Granular Fabric Cleaning Composition | |
|---|---|
| Component | Weight % |
| Perborate tetrahydrate | 11.64 |
| Perborate monohydrate | 8.7 |
| Tetraacetylethylene diamine | 5.0 |
| Diethylene tramine penta methyl phosphonic acid | 0.38 |
| Magnesium sulfate | 0.40 |
| Brightener | 0.19 |
| Perfume, silicone, suds suppressors | 0.85 |
| Minors | Up to 100 | b. Liquid fabric cleaning compositions

Liquid fabric cleaning compositions of the present invention comprise an effective amount of one or more enzyme variants of the present invention, preferably from about 0.005% to about 5%, more preferably from about 0.01% to about 1%, by weight of active enzyme of the composition. Such liquid fabric cleaning compositions typically additionally comprise an anionic surfactant, a fatty acid, a water-soluble detergency builder and water.

The liquid fabric cleaning composition embodiment of the present invention is illustrated by the following examples.

EXAMPLES 48–52

| Liquid Fabric Cleaning Compositions | | | | | |
|---|---|---|---|---|---|
| | Example No. | | | | |
| Component | 48 | 49 | 50 | 51 | 52 |
| Leu125Ala + Gly12GGlu | 0.05 | 0.03 | 0.30 | 0.03 | 0.10 |
| Gly153Glu + Ile164Ala | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In Examples 48–50 the subtilisin Carlsberg variants recited in Tables 3–36, among others, are substituted for Leu125Ala+Gly126Glu, with substantially similar results.

In Examples 51–52, any combination of the subtilisin Carlsberg variants recited in Tables 3–36, among others, are substituted for Leu125Ala+Gly126Glu and Gly153Glu+Ile164Ala, with substantially similar results.

EXAMPLES 53–57

| Liquid Fabric Cleaning Compositions | | | | | |
|---|---|---|---|---|---|
| | Example No. | | | | |
| Component | 53 | 54 | 55 | 56 | 57 |
| Phe188Ser | 0.05 | 0.03 | 0.30 | 0.03 | 0.10 |
| Ala186Gln + Ser187Glu + Phe188Asp | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |

-continued

| Liquid Fabric Cleaning Compositions | | | | | |
|---|---|---|---|---|---|
| | Example No. | | | | |
| Component | 53 | 54 | 55 | 56 | 57 |
| Monethanolamine | 2.50 | 2.50 | 2.50 | 2.50 | 2.50 |
| Water/propylene glycol/ethanol (100:1:1) | balance to 100% | | | | |

In Examples 53–55 the subtilisin Carlsberg variants recited in Tables 3–36, among others, are substituted for Phe188Ser, with substantially similar results.

In Examples 56–57, any combination of the subtilisin Carlsberg variants recited in Tables 212, among others, are substituted for Phe188Ser and Ala186Gln+Ser187Glu+Phe188Asp, with substantially similar results.

EXAMPLES 58–59

| Granular Fabric Cleaning Composition | | |
|---|---|---|
| | Example No. | |
| Component | 58 | 59 |
| $C_{12–14}$ alkenyl succinic acid | 3.0 | 8.0 |
| Citric acid monohydrate | 10.0 | 15.0 |
| Sodium $C_{12–15}$ alkyl sulphate | 8.0 | 8.0 |
| Sodium sulfate of $C_{12–15}$ alcohol 2 times ethoxylated | — | 3.0 |
| $C_{12–15}$ alcohol 7 times ethoxylated | — | 8.0 |
| $C_{12–15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Thr 58Ser + Ser100Asp + Ile164Met + Tyr205Ala | 0.2 | 0.2 |
| Polyvinyl pyrrolidone | 1.0 | 2.0 |
| Suds suppressor | 0.15 | 0.15 |
| NaOH | up to pH 7.5 | |
| Perborate | 0.5 | 1 |
| Phenol sulphonate | 0.1 | 0.2 |
| Peroxidase | 0.4 | 0.1 |
| Waters and minors | up to 100 parts | |

In each of Examples 58 and 59 herein, the subtilisin Carlsberg variants recited in Tables 3–36, among others, are substituted for Thr 58Ser+Ser100Asp+Ile164Met+Tyr205Ala, with substantially similar results.

EXAMPLES 60–62

| Liquid Fabric Cleaning Composition | | | |
|---|---|---|---|
| | Example No. | | |
| Component | 60 | 61 | 62 |
| Citric Acid | 7.10 | 3.00 | 3.00 |
| Fatty Acid | 2.00 | — | 2.00 |
| Ethanol | 1.93 | 3.20 | 3.20 |
| Boric Acid | 2.22 | 3.50 | 3.50 |
| Monoethanolamine | 0.71 | 1.09 | 1.09 |
| 1,2 Propanediol | 7.89 | 8.00 | 8.00 |
| NaCumene Sulfonate | 1.80 | 3.00 | 3.00 |
| NaFormate | 0.08 | 0.08 | 0.08 |
| NaOH | 6.70 | 3.80 | 3.80 |

-continued

Liquid Fabric Cleaning Composition

| Component | Example No. | | |
|---|---|---|---|
| | 60 | 61 | 62 |
| Silicon anti-foam agent | 1.16 | 1.18 | 1.18 |
| Asn61Glu | 0.0145 | — | — |
| Tyr103Cys + Gly156Glu + Ala202Gln + Thr212Gly + Leu216Gln | — | 0.0145 | — |
| Gly105Asn + Gly126Ser + Ser160Glu + Thr161Asn + Tyr205Val + Gly218Asn | — | — | 0.0145 |
| Lipase | 0.200 | 0.200 | 0.200 |
| Cellulase | — | 7.50 | 7.50 |
| Soil release polymer | 0.29 | 0.15 | 0.15 |
| Anti-foaming agents | 0.06 | 0.085 | 0.085 |
| Brightener 36 | 0.095 | — | — |
| Brightener 3 | — | 0.05 | 0.05 |
| $C_{12}$ alkyl benzenesulfonic acid | 9.86 | — | — |
| $C_{12-15}$ alkyl polyethoxylate (2.5) sulfate | 13.80 | 18.00 | 18.00 |
| $C_{12}$ glucose amide | — | 5.00 | 5.00 |
| $C_{12-13}$ alkyl polyethoxylate (9) | 2.00 | 2.00 | 2.00 |
| Water, perfume and minors | balance to 100% | | | c. Bar fabric cleaning compositions

Bar fabric cleaning compositions of the present invention suitable for hand-washing soiled fabrics contain an effective amount of one or more enzyme variants of the present invention, preferably from about 0.001% to about 10%, more preferably from about 0.01% to about 1% by weight of the composition.

The bar fabric cleaning composition embodiment of the present invention is illustrated by the following examples.

EXAMPLES 63–66

Bar Fabric Cleaning Compositions

| Component | Example No. | | | |
|---|---|---|---|---|
| | 63 | 64 | 65 | 66 |
| Thr207Glu | 0.3 | — | 0.1 | 0.02 |
| Leu125Ile + Ser131Glu | — | — | 0.4 | 0.03 |
| $C_{12}$–$C_{16}$ alkyl sulfate, Na | 20.0 | 20.0 | 20.0 | 20.00 |
| $C_{12}$–$C_{14}$ N-methyl glucamide | 5.0 | 5.0 | 5.0 | 5.00 |
| $C_{11}$–$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10μ) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

In Examples 63–64 the subtilisin Carlsberg variants recited in Tables 3–36, among others, are substituted for Thr207Glu, with substantially similar results.

In Examples 65–66, any combination of the subtilisin Carlsberg variants recited in Tables 3–36, among others, are substituted for Thr207Glu and Leu125Ile+Ser131Glu, with substantially similar results.

EXAMPLES 67–70

Bar Fabric Cleaning Compositions

| Component | Example No. | | | |
|---|---|---|---|---|
| | 67 | 68 | 69 | 70 |
| Pro200Ser + Ala214Gly + Asn217Glu | 0.3 | — | 0.1 | 0.02 |
| Gly101Asp + Ala128Asp + Ser155Asp + Ser187Asp + Thr20Gly + Thr212Gln | — | 0.3 | 0.4 | 0.03 |
| $C_{12}$–$C_{16}$ alkyl sulfate, Na | 20.0 | 20.0 | 20.0 | 20.00 |
| $C_{12}$–$C_{14}$ N-methyl glucamide | 5.0 | 5.0 | 5.0 | 5.00 |
| $C_{11}$–$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10μ) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

In Example 67, the subtilisin Carlsberg variants recited in Tables 3–36, among others, are substituted for Pro200Ser+Ala214Gly+Asn217Glu, with substantially similar results.

In Example 68, the subtilisin Carlsberg variants recited in Tables 3–36, among others, are substituted for Pro200Ser+Ala214Gly+Asn217Glu and Gly101Asp+Ala128Asp+Ser155Asp+Ser187Asp+Thr207Gly+Thr212Gln, with substantially similar results.

In Examples 69–70, any combination of the subtilisin Carlsberg variants recited in Tables 3–36, among others, are substituted for Val203Glu and Gly100Glu+Ile107Ser, with substantially similar results.

B. Additional Cleaning Compositions

In addition to the hard surface cleaning, dishwashing and fabric cleaning compositions discussed above, one or more enzyme variants of the present invention may be incorporated into a variety of other cleaning compositions where hydrolysis of an insoluble substrate is desired. Such additional cleaning compositions include but are not limited to, oral cleaning compositions, denture cleaning compositions, and contact lens cleaning compositions.

1. Oral cleaning compositions

In another embodiment of the present invention, a pharmaceutically-acceptable amount of one or more enzyme variants of the present invention are included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral cleaning compositions comprise from about 0.0001% to about 20% of one or more enzyme variants of the present invention, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in U.S. Pat. No. 5,096,700, Seibel, issued Mar. 17, 1992; U.S. Pat. No. 5,028,414, Sampathkumar, issued Jul. 2, 1991; and U.S. Pat. No. 5,028,415, Benedict, Bush and Sunberg, issued Jul. 2, 1991; all of which are incorporated herein by reference.

The oral cleaning composition embodiment of the present invention is illustrated by the following examples.

EXAMPLES 71–74

Dentifrice Composition

| Component | Example No. | | | |
|---|---|---|---|---|
| | 71 | 72 | 73 | 74 |
| Thr212Gln | 2.000 | 3.500 | 1.500 | 2.000 |
| Sorbitol (70% aqueous solution) | 35.000 | 35.000 | 35.000 | 35.000 |
| PEG-6* | 1.000 | 1.000 | 1.000 | 1.000 |
| Silica dental abrasive** | 20.000 | 20.000 | 20.000 | 20.000 |
| Sodium fluoride | 0.243 | 0.243 | 0.243 | 0.243 |
| Titanium dioxide | 0.500 | 0.500 | 0.500 | 0.500 |
| Sodium saccharin | 0.286 | 0.286 | 0.286 | 0.286 |
| Sodium alkyl sulfate (27.9% aqueous solution) | 4.000 | 4.000 | 4.000 | 4.000 |
| Flavor | 1.040 | 1.040 | 1.040 | 1.040 |
| Carboxyvinyl Polymer*** | 0.300 | 0.300 | 0.300 | 0.300 |
| Carrageenan**** | 0.800 | 0.800 | 0.800 | 0.800 |
| Water | balance to 100% | | | |

*PEG-6 = Polyethylene glycol having a molecular weight of 600.
**Precipitated silica identified as Zeodent 119 offered by J.M. Huber.
***Carbopol offered by B.F. Goodrich Chemical Company.
****Iota Carrageenan offered by Hercules Chemical Company.

In Examples 71–74 the subtilisin Carlsberg variants recited in Tables 3–36, among others, are substituted for Thr212Gln, with substantially similar results.

EXAMPLES 75–78

Mouthwash Composition

| Component | Example No. | | | |
|---|---|---|---|---|
| | 75 | 76 | 77 | 78 |
| Val204Asn + Thr215Asn | 3.00 | 7.50 | 1.00 | 5.00 |
| SDA 40 Alcohol | 8.00 | 8.00 | 8.00 | 8.00 |
| Flavor | 0.08 | 0.08 | 0.08 | 0.08 |
| Emulsifier | 0.08 | 0.08 | 0.08 | 0.08 |
| Sodium Fluoride | 0.05 | 0.05 | 0.05 | 0.05 |
| Glycerin | 10.00 | 10.00 | 10.00 | 10.00 |
| Sweetener | 0.02 | 0.02 | 0.02 | 0.02 |
| Benzoic acid | 0.05 | 0.05 | 0.05 | 0.05 |
| Sodium hydroxide | 0.20 | 0.20 | 0.20 | 0.20 |

-continued

Mouthwash Composition

| Component | Example No. | | | |
|---|---|---|---|---|
| | 75 | 76 | 77 | 78 |
| Dye | 0.04 | 0.04 | 0.04 | 0.04 |
| Water | balance to 100% | | | |

In Examples 75–78, the subtilisin Carlsberg variants recited in Tables 3–36, among others, are substituted for Val204Asn+Thr215Asn, with substantially similar results.

EXAMPLES 79–82

Lozenge Composition

| Component | Example No. | | | |
|---|---|---|---|---|
| | 79 | 80 | 81 | 82 |
| Thr 65Asp + Thr132Glu + Asn154Asp + Thr212Glu + Leu218Gly + Asn217Ser | 0.01 | 0.03 | 0.10 | 0.02 |
| Sorbitol | 17.50 | 17.50 | 17.50 | 17.50 |
| Mannitol | 17.50 | 17.50 | 17.50 | 17.50 |
| Starch | 13.60 | 13.60 | 13.60 | 13.60 |
| Sweetener | 1.20 | 1.20 | 1.20 | 1.20 |
| Flavor | 11.70 | 11.70 | 11.70 | 11.70 |
| Color | 0.10 | 0.10 | 0.10 | 0.10 |
| Corn Syrup | balance to 100% | | | |

In Examples 79–82, the subtilisin Carlsberg variants recited in Tables 3–36, among others, are substituted for Thr 65Asp+Thr132Glu+Asn154Asp+Thr212Glu+Leu216Gly+Asn217Ser, with substantially similar results.

EXAMPLES 83–86

Chewing Gum Composition

| Component | Example No. | | | |
|---|---|---|---|---|
| | 83 | 84 | 85 | 86 |
| Tyr103Ala | 0.03 | 0.02 | 0.10 | 0.05 |
| Sorbitol crystals | 35.44 | 38.40 | 38.40 | 38.40 |
| Paloja-T gum base* | 20.00 | 20.00 | 20.00 | 20.00 |
| Sorbitol (70% aqueous solution) | 22.00 | 22.00 | 22.00 | 22.00 |
| Mannitol | 10.00 | 10.00 | 10.00 | 10.00 |
| Glycerine | 7.56 | 7.56 | 7.56 | 7.56 |
| Flavor | 1.00 | 1.00 | 1.00 | 1.00 |

*Supplied by L.A. Dreyfus Company.

In Examples 83–86, the subtilisin Carlsberg variants recited in Tables 3–36, among others, are substituted for Tyr103Ala, with substantially similar results.

2. Denture cleaning compositions

In another embodiment of the present invention, denture cleaning compositions for cleaning dentures outside of the oral cavity comprise one or more enzyme variants of the present invention. Such denture cleaning compositions comprise an effective amount of one or more of the enzyme variants, preferably from about 0.0001% to about 50% of one or more of the enzyme variants, more preferably from about 0.001% to about 35%, more preferably still from about 0.01% to about 20%, by weight of the composition, and a denture cleansing carrier. Various denture cleansing composition formats such as effervescent tablets and the like are well known in the art (see for example U.S. Pat. No. 5,055,305, Young, incorporated herein by reference), and are generally appropriate for incorporation of one or more of the enzyme variants for removing proteinaceous stains from dentures.

The denture cleaning composition embodiment of the present invention is illustrated by the following examples.

EXAMPLES 87–90

Two-layer Effervescent Denture Cleansing Tablet

| | Example No. | | | |
|---|---|---|---|---|
| Component | 87 | 88 | 89 | 90 |
| Acidic Layer | | | | |
| Leu216Pro | 1.0 | 1.5 | 0.01 | 0.05 |
| Tartaric acid | 24.0 | 24.0 | 24.00 | 24.00 |
| Sodium carbonate | 4.0 | 4.0 | 4.00 | 4.00 |
| Sulphamic acid | 10.0 | 10.0 | 10.00 | 10.00 |
| PEG 20,000 | 4.0 | 4.0 | 4.00 | 4.00 |
| Sodium bicarbonate | 24.5 | 24.5 | 24.50 | 24.50 |
| Potassium persulfate | 15.0 | 15.0 | 15.00 | 15.00 |
| Sodium acid pyrophosphate | 7.0 | 7.0 | 7.00 | 7.00 |
| Pyrogenic silica | 2.0 | 2.0 | 2.00 | 2.00 |
| TAED* | 7.0 | 7.0 | 7.00 | 7.00 |
| Ricinoleylsulfosuccinate | 0.5 | 0.5 | 0.50 | 0.50 |
| Flavor | 1.0 | 1.0 | 1.00 | 1.00 |
| Alkaline Layer | | | | |
| Sodium perborate monohydrate | 32.0 | 32.0 | 32.00 | 32.00 |
| Sodium bicarbonate | 19.0 | 19.0 | 19.00 | 19.00 |
| EDTA | 3.0 | 3.0 | 3.00 | 3.00 |
| Sodium tripolyphosphate | 12.0 | 12.0 | 12.00 | 12.00 |
| PEG 20,000 | 2.0 | 2.0 | 2.00 | 2.00 |
| Potassium persulfate | 28.0 | 26.0 | 26.00 | 26.00 |
| Sodium carbonate | 2.0 | 2.0 | 2.00 | 2.00 |
| Pyrogenic silica | 2.0 | 2.0 | 2.00 | 2.00 |
| Dye/flavor | 2.0 | 2.0 | 2.00 | 2.00 |

*Tetraacetylethylene diamine

In Examples 87–90, the subtilisin Carlsberg variants recited in Tables 3–36, among others, are substituted for Leu216Pro, with substantially similar results.

3. Contact Lens Cleaning Compositions

In another embodiment of the present invention, contact lens cleaning compositions comprise one or more enzyme variants of the present invention. Such contact lens cleaning compositions comprise an effective amount of one or more of the enzyme variants, preferably from about 0.01% to about 50% of one or more of the enzyme variants, more preferably from about 0.01% to about 20%, more preferably still from about 1% to about 5%, by weight of the composition, and a contact lens cleaning carrier. Various contact lens cleaning composition formats such as tablets, liquids and the like are well known in the art (see for example U.S. Pat. No. 4,863,627, Davies, Meaken and Rees, issued Sep. 5, 1989; U.S. Pat. Re. No. 32,672, Huth, Lam and Kirai, reissued May 24, 1988; U.S. Pat. No. 4,609,493, Schäfer, issued Sep. 2, 1986; U.S. Pat. No. , 4,690,793, Ogunbiyi and Smith, issued Sep. 1, 1987; U.S. Pat. No. 4,614,549, Ogunbiyi, Riedhammer and Smith, issued Sep. 30, 1986; and U.S. Pat. No. 4,285,738, Ogata, issued Aug. 25, 1981; each of which are incorporated herein by reference), and are generally appropriate for incorporation of one or more enzyme variants of the present invention for removing proteinaceous stains from contact lens.

The contact lens cleaning composition embodiment of the present invention is illustrated by the following examples.

EXAMPLES 91–94

Enzymatic Contact Lens Cleaning Solution

| | Example No. | | | |
|---|---|---|---|---|
| Component | 91 | 92 | 93 | 94 |
| Ala199Thr + Val204Gln | 0.01 | 0.5 | 0.1 | 2.0 |
| Glucose | 50.00 | 50.0 | 50.0 | 50.0 |
| Nonionic surfactant (polyoxyethlene-polyoxypropylene copolymer) | 2.00 | 2.0 | 2.0 | 2.0 |
| Mionic surfactant (polyoxyethylene alkylphenylether sodium sulfricester) | 1.00 | 1.0 | 1.0 | 1.0 |
| Sodium chloride | 1.00 | 1.0 | 1.0 | 1.0 |
| Borax | 0.30 | 0.3 | 0.3 | 0.3 |
| Water | balance to 100% | | | |

In Examples 91–94, the subtilisin Carlsberg variants recited in Tables 3–36, among others, are substituted for Ala199Thr+Val204Gln, with substantially similar results.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. An isolated subtilisin Carlsberg variant having a modified amino acid sequence of the Subtilisin Carlsberg wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at one or more position in one of the loop regions; wherein A. when the substitution occurs in the first loop region, the substitution occurs at one of positions 58, 60, 61, 62, 64 or 65; wherein
  a. when a substitution occurs at position 58, the substituting amino acid is Asn, Gln, Pro or Ser;
  b. when a substitution occurs at position 60, the substituting amino acid is Asn, Gln, Pro or Ser;
  c. when a substitution occurs at position 61, the substituting amino acid is Gln or Ser;
  d. when a substitution occurs at position 62, the substituting amino acid is Asn, Gln, Glu, Pro or Ser;
  e. when a substitution occurs at position 64, the substituting amino acid is Asn, Asp, Gln, Glu, Pro or Ser; and
  f. when a substitution occurs at position 65, the substituting amino acid is Asn, Asp, Gln, Glu, Pro or Ser;

B. when the substitution occurs in the second loop region, the substitution occurs at one of positions 94, 95, 96, 99, 101, or 105; wherein
  a. when a substitution occurs at position 94, the substituting amino acid is Ala, Gln, Gly, His, Met, Pro or Ser;
  b. when a substitution occurs at position 95, the substituting amino acid is Ala, Asn, Asp, Cys, Gln, Glu, Gly, His, Ile, Met, Pro, Ser, Thr or Val;
  c. when a substitution occurs at position 96, the substituting amino acid is Gln;

d. when a substitution occurs at position 99, the substituting amino acid is Asn, Gln, Pro or Ser;
e. when a substitution occurs at position 101, the substituting amino acid is Asn, Gln, Pro or Ser; and
f. when a substitution occurs at position 105, the substituting amino acid is Asn, Gln, Pro or Ser;

C. when the substitution occurs in the third loop region, the substitution occurs at one of positions 127, 130, 131 or 132; wherein
  a. when a substitution occurs at position 127, the substituting amino acid is Asn, Gln or Pro;
  b. when a substitution occurs at position 130, the substituting amino acid is Asn, Gln, Pro or Ser;
  c. when a substitution occurs at position 131, the substituting amino acid is Glu; and
  d. when a substitution occurs at position 132, the substituting amino acid is Asn, Gln, Pro or Ser;

D. when the substitution occurs in the fourth loop region, the substitution occurs at one of positions 153, 156, 157, 159, 161, 162, 163, or 166; wherein
  a. when a substitution occurs at position 153, the substituting amino acid is Asn, Asp, Gln, Glu, Pro or Ser;
  b. when a substitution occurs at position 156, the substituting amino acid is Asn, Asp, Gln, Glu or Pro;
  c. when a substitution occurs at position 157, the substituting amino acid is Gln;
  d. when a substitution occurs at position 159, the substituting amino acid is Asn, Gln, Pro or Ser;
  e. when a substitution occurs at position 161, the substituting amino acid is Asn, Gln, Pro or Ser;
  f. when a substitution occurs at position 162, the substituting amino acid is Gln;
  g. when a substitution occurs at position 163, the substituting amino acid is Asn, Gln, Gly, Pro or Ser; and
  h. when a substitution occurs at position 166, the substituting amino acid is His, Ile, Leu, Met or Pro;

E. when the substitution occurs in the fifth loop region, the substitution occurs at position 189; wherein the substituting amino acid is Asp or Glu; and F. when the substitution occurs in the sixth loop region, the substitution occurs at one of positions 199, 200, 201, 204, 205, 206, 207, 208, 209, 210, 211, 212, 213, 215, or 219; wherein
  a. when a substitution occurs at position 199, the substituting amino acid is Asn, Asp, Gln, Glu, Gly, His, Pro, Ser or Thr;
  b. when a substitution occurs at position 200, the substituting amino acid is Asn, Asp, Gln, Glu, Gly or Ser;
  c. when a substitution occurs at position 201, the substituting amino acid is Asn, Asp, Gln, Glu, Pro or Ser;
  d. when a substitution occurs at position 204, the substituting amino acid is Ala, Cys, Gln, Gly, His, Met, Pro or Ser;
  e. when a substitution occurs at position 205, the substituting amino acid is His, Ile, Leu, Met or Pro;
  f. when a substitution occurs at position 206, the substituting amino acid is Asp or Glu;
  g. when a substitution occurs at position 207, the substituting amino acid is Asn, Gln, Pro or Ser;
  h. when a substitution occurs at position 208, the substituting amino acid is His, Ile, Met or Pro;
  i. when a substitution occurs at position 209, the substituting amino acid is Asn, Gln, Gly or Ser;
  j. when a substitution occurs at position 210, the substituting amino acid is Asn, Gln, Pro or Ser;
  k. when a substitution occurs at position 211, the substituting amino acid is Gln or Ser;
  l. when a substitution occurs at position 212, the substituting amino acid is Asn, Gln, Pro or Ser;
  m. when a substitution occurs at position 213, the substituting amino acid is His, Ile, Leu, Met or Pro;
  n. when a substitution occurs at position 215, the substituting amino acid is Asn, Gln, Gly, Pro or Ser; and
  o. when a substitution occurs at position 219, the substituting amino acid is Asn, Asp, Gln, Glu, Gly, Pro or Ser;

whereby the subtilisin Carlsberg variant has decreased adsorption to, and increased hydrolysis of, an insoluble substrate as compared to wild-type subtilisin Carlsberg and wherein an amino acid substitution at subtilisin Carlsberg positions 58, 94, 95, 96, 99, 101, 127, 153, 156, 157, 159, 161 to 163, 166, 212 and 213 is combined with at least one further substitution at a corresponding position selected from subtilisin Carlsberg positions 59, 60, 64, 65, 104, 105,129, 131, 132, 187,189, 199 to 202, 204, 206, 209 to 211, 215 and 219.

2. The subtilisin Carlsberg variant of claim 1, wherein the substitution occurs in the first loop region.

3. The subtilisin Carlsberg variant of claim 1, wherein the substitution occurs in the second loop region.

4. The subtilisin Carlsberg variant of claim 1, wherein the substitution occurs in the third loop region.

5. The subtilisin Carlsberg variant of claim 1, wherein the substitution occurs in the fourth loop region.

6. The subtilisin Carlsberg variant of claim 1, wherein the substitution occurs in the fifth loop region.

7. The subtilisin Carlsberg variant of claim 1, wherein the substitution occurs in the sixth loop region.

8. An isolated subtilisin Carlsberg variant having a modified amino acid sequence of the Subtilisin Carlsberg wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
  A. when a substitution occurs in the first loop region, the substitution occurs at one or more of positions 58, 59, 60, 61, 62, 64 or 65; wherein
    a. when a substitution occurs at position 58, the substituting amino acid is Asn, Asp, Gln, Glu, Gly, Pro or Ser;
    b. when a substitution occurs at position 59, the substituting amino acid is Glu;
    c. when a substitution occurs at position 60, the substituting amino acid is Asn, Asp, Gln, Glu, Pro or Ser;
    d. when a substitution occurs at position 61, the substituting amino acid is Asp, Gln, Glu or Ser;
    e. when a substitution occurs at position 62, the substituting amino acid is Asn, Asp, Gln, Glu, Pro or Ser;
    f. when a substitution occurs at position 64, the substituting amino acid is Asn, Asp, Gln, Glu, Pro or Ser; and
    g. when a substitution occurs at position 65, the substituting amino acid is Asn, Asp, Gln, Glu, Gly, Pro or Ser;

B. when a substitution occurs in the second loop region, the substitution occurs at one or more of positions 94, 95, 96, 97, 98, 99, 100, 101, 102, 103, 104, 105 or 106; wherein
   a. when a substitution occurs at position 94, the substituting amino acid is Ala, Asn, Asp, Cys, Gln, Glu, Gly, His, Met, Pro, Ser or Thr;
   b. when a substitution occurs at position 95, the substituting amino acid is Ala, Asn, Asp, Cys, Gln, Glu, Gly, His, Ile, Met, Pro, Ser, Thr or Val;
   c. when a substitution occurs at position 96, the substituting amino acid is Asp, Gln, Glu, or Ser; but when position 96 is substituted the variant is not a double, triple, quadruple, quintuple, sextuple, or septuple mutation variant having substitutions at positions selected from the group consisting of 103, 154, 155, 165, 188, and 216;
   d. when a substitution occurs at position 97, the substituting amino acid is Asp or Glu; but when position 97 is substituted the variant is not a double, triple, quadruple, quintuple, sextuple, or septuple mutation variant having substitutions at positions selected from the group consisting of 103, 154, 155, 165, 188, and 216;
   e. when a substitution occurs at position 98, the substituting amino acid is Asp or Glu; but when position 98 is substituted the variant is not a double, triple, quadruple, quintuple, sextuple, or septuple mutation variant having substitutions at positions selected from the group consisting of 103, 154, 155, 165, 188, and 216;
   f. when a substitution occurs at position 99, the substituting amino acid is Asn, Asp, Gln, Glu, Pro or Ser; but when position 99 is substituted the variant is not a double, triple, quadruple, quintuple, sextuple, or septuple mutation variant having substitutions at positions selected from the group consisting of 103, 154, 155, 165, 188, and 216;
   g. when a substitution occurs at position 100, the substituting amino acid is Asp or Glu; but when position 100 is substituted the variant is not a double, triple, quadruple, quintuple, sextuple, or septuple mutation variant having substitutions at positions selected from the group consisting of 103, 154, 155, 165, 188, and 216;
   h. when a substitution occurs at position 101, the substituting amino acid is Asn, Asp, Gln, Glu, Pro or Ser; but when position 101 is substituted the variant is not a double, triple, quadruple, quintuple, sextuple, or septuple mutation variant having substitutions at positions selected from the group consisting of 103, 154, 155, 165, 188, and 216;
   i. when a substitution occurs at position 102, the substituting amino acid is Asp or Glu; but when position 102 is substituted the variant is not a double, triple, quadruple, quintuple, sextuple, or septuple mutation variant having substitutions at positions selected from the group consisting of 103, 154, 155, 165, 188, and 216;
   j. when a substitution occurs at position 103, the substituting amino acid is Ala, Asp, Cys, Gln, Glu, Gly, His, Ile, Leu, Met, Pro, Ser, Thr or Val;
   k. when a substitution occurs at position 104, the substituting amino acid is Asp or Glu;
   l. when a substitution occurs at position 105, the substituting amino acid is Asn, Asp, Gln, Glu, Pro or Ser; and
   m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, sextuple, or septuple mutation variant having substitutions at positions selected from the group consisting of 103, 154, 155, 165, 188, and 216;
C. when a substitution occurs in the third loop region, the substitution occurs at one or more of positions 125, 126, 127, 128, 129, 130, 131 or 132; wherein
   a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, quadruple, quintuple, sextuple, or septuple mutation variant having substitutions at positions selected from the group consisting of 103, 154, 155, 165, 188, and 216;
   b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;
   c. when a substitution occurs at position 127, the substituting amino acid is Asn, Asp, Gln, Glu, Pro or Ser; but when position 127 is substituted the variant is not a double, triple, quadruple, quintuple, sextuple, or septuple mutation variant having substitutions at positions selected from the group consisting of 103, 154, 155,165, 188, and 216;
   d. when a substitution occurs at position 128, the substituting amino acid is Asn, Asp, Gln, Glu, Gly, His, Pro, Ser or Thr; but when position 128 is substituted the variant is not a double, triple, quadruple, quintuple, sextuple, or septuple mutation variant having substitutions at positions selected from the group consisting of 103, 154, 155, 165, 188, and 216;
   e. when a substitution occurs at position 129, the substituting amino acid is Asp or Glu;
   f. when a substitution occurs at position 130, the substituting amino acid is Asn, Asp, Gln, Glu, Pro or Ser;
   g. when a substitution occurs at position 131, the substituting amino acid is Asp or Glu; and
   h. when a substitution occurs at position 132, the substituting amino acid is Asn, Asp, Gln, Glu, Gly, Pro or Ser;
D. when a substitution occurs in the fourth loop region, the substitution occurs at one or more of positions 153, 154, 155, 156, 157, 158, 159, 160, 161, 162, 163, 164, 165 or 166; wherein
   a. when a substitution occurs at position 153, the substituting amino acid is Asn, Asp, Gln, Glu, Pro or Ser; but when position 153 is substituted the variant is not a double, triple, quadruple, quintuple, sextuple, or septuple mutation variant having substitutions at positions selected from the group consisting of 103, 154, 155, 165, 188, and 216;
   b. when a substitution occurs at position 154, the substituting amino acid is Asp, Gln, Glu or Ser;
   c. when a substitution occurs at position 155, the substituting amino acid is Asp or Glu; but when position 155 is substituted, the variant is not a double mutation variant having a substitution at position 216, double mutation variant having a substitution at position 165, or a triple mutation variant having substitutions at positions 165 and 216;

d. when a substitution occurs at position 156, the substituting amino acid is Asn, Asp, Gln, Glu, Pro or Ser; but when position 156 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 157, the substituting amino acid is Asp, Gln, Glu or Ser; but when position 157 is substituted the variant is not a double, triple, quadruple, quintuple, sextuple, or septuple mutation variant having substitutions at positions selected from the group consisting of 103, 154, 155, 165,188, and 216;

f. when a substitution occurs at position 158, the substituting amino acid is Asp or Glu; but when position 158 is substituted the variant is not a double, triple, quadruple, quintuple, sextuple, or septuple mutation variant having substitutions at positions selected from the group consisting of 103, 154, 155, 165, 188, and 216;

g. when a substitution occurs at position 159, the substituting amino acid is Asn, Asp, Gln, Glu, Pro or Ser; but when position 159 is substituted the variant is not a double, triple, quadruple, quintuple, sextuple, or septuple mutation variant having substitutions at positions selected from the group consisting of 103, 154, 155, 165, 188, and 216;

h. when a substitution occurs at position 160, the substituting amino acid is Asp or Glu; but when position 160 is substituted the variant is not a double, triple, quadruple, quintuple, sextuple, or septuple mutation variant having substitutions at positions selected from the group consisting of 103, 154, 155, 165, 188, and 216;

i. when a substitution occurs at position 161, the substituting amino acid is Asn, Asp, Gln, Glu, Gly, Pro or Ser; but when position 161 is substituted the variant is not a double, triple, quadruple, quintuple, sextuple, or septuple mutation variant having substitutions at positions selected from the group consisting of 103, 154, 155, 165, 188, and 216;

j. when a substitution occurs at position 162, the substituting amino acid is Asp, Gln, Glu or Ser; but when position 162 is substituted the variant is not a double, triple, quadruple, quintuple, sextuple, or septuple mutation variant having substitutions at positions selected from the group consisting of 103, 154, 155, 165, 188, and 216;

k. when a substitution occurs at position 163, the substituting amino acid is Asn, Asp, Gln, Glu, Gly, Pro or Ser; but when position 163 is substituted the variant is not a double, triple, quadruple, quintuple, sextuple, or septuple mutation variant having substitutions at positions selected from the group consisting of 103, 154, 155, 165, 188, and 216;

l. when a substitution occurs at position 164, the substituting amino acid is Ala, Asn, Asp, Cys, Gln, Glu, Gly, His, Met, Pro, Ser, Thr or Val; but when position 164 is substituted the variant is not a double, triple, quadruple, quintuple, sextuple, or septuple mutation variant having substitutions at positions selected from the group consisting of 103, 154, 155, 165, 188, and 216;

m. when a substitution occurs at position 165, the substituting amino acid is Asn, Asp, Gln, Glu, Pro or Ser; but when position 165 is substituted with Asp or Glu, the variant is not a double mutation variant having a substitution of Asp or Glu at position 61; and n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, sextuple, or septuple mutation variant having substitutions at positions selected from the group consisting of 103, 154, 155, 165, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;

c. when a substitution occurs at position 188, the substituting amino acid is Ala, Asn, Asp, Cys, Gln, Glu, Gly, His, Ile, Leu, Met, Pro, Ser, Thr, Tyr or Val;

d. when a substitution occurs at position 189, the substituting amino acid is Asp or Glu;

e. when a substitution occurs at position 190, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein a. when a substitution occurs at position 199, the substituting amino acid is Asn, Asp, Gln, Glu, Gly, His, Pro, Ser or Thr;

b. when a substitution occurs at position 200, the substituting amino acid is Asn, Asp, Gln, Glu, Gly or Ser;

c. when a substitution occurs at position 201, the substituting amino acid is Asn, Asp, Gln, Glu, Pro or Ser;

d. when a substitution occurs at position 202, the substituting amino acid is Asn, Asp, Gln, Glu, Gly, His, Pro, Ser or Thr;

e. when a substitution occurs at position 203, the substituting amino acid is Asn, Asp, Gln, Glu, Pro or Ser;

f. when a substitution occurs at position 204, the substituting amino acid is Ala, Asn, Asp, Cys, Gln, Glu, Gly, His, Met, Pro, Ser or Thr;

g. when a substitution occurs at position 205, the substituting amino acid is Ala, Asn, Asp, Cys, Gln, Glu, Gly, His, Ile, Leu, Met, Pro, Ser, Thr or Val;

h. when a substitution occurs at position 206, the substituting amino acid is Asp or Glu;

i. when a substitution occurs at position 207, the substituting amino acid is Asn, Asp, Gln, Glu, Gly, Pro or Ser;

j. when a substitution occurs at position 208, the substituting amino acid is Ala, Asn, Asp, Cys, Gln, Glu, Gly, His, Ile, Leu, Met, Pro, Ser, Thr or Val;

k. when a substitution occurs at position 209, the substituting amino acid is Asn, Asp, Gln, Glu, Gly or Ser;

l. when a substitution occurs at position 210, the substituting amino acid is Asn, Asp, Gln, Glu, Gly, Pro or Ser;

m. when a substitution occurs at position 211, the substituting amino acid is Asp, Gln, Glu or Ser;

n. when a substitution occurs at position 212, the substituting amino acid is Asn, Asp, Gln, Glu, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;

o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, sextuple, or septuple mutation variant having substitutions at positions selected from the group consisting of 103, 154, 155, 165, 188, and 216;

p. when a substitution occurs at position 214, the substituting amino acid is Asn, Asp, Gln, Glu, Gly, His, Pro, Ser or Thr; but when position 214 is substituted the variant is not a double, triple, quadruple, quintuple, sextuple, or septuple mutation variant having substitutions at positions selected from the group consisting of 103, 154, 155, 165, 188, and 216;

q. when a substitution occurs at position 215, the substituting amino acid is Asn, Asp, Gln, Glu, Gly, Pro or Ser;

r. when a substitution occurs at position 216, the substituting amino acid is Ala, Asn, Asp, Cys, Gln, Glu, Gly, His, Ile, Met, Pro, Ser, Thr or Val;

but when position 216 is substituted the variant is not a double mutation variant having a substitution at position 217;

s. when a substitution occurs at position 217, the substituting amino acid is Asp, Gln, Glu or Ser;

t. when a substitution occurs at position 218, the substituting amino acid is Asn, Asp, Gln, Glu, Pro or Ser; and u. when a substitution occurs at position 219, the substituting amino acid is Asn, Asp, Gln, Glu, Gly, Pro or Ser; wherein the variant is not:

v. a double mutation variant having substitutions at positions 202 and 203;

w. a double mutation variant having substitutions at positions 202 and 216;

x. a double mutation variant having substitutions at positions 203 and 216; or y. a triple mutation variant having substitutions at positions 202, 203, and 216; and whereby the subtilisin Carlsberg variant has decreased adsorption to, and increased hydrolysis of, an insoluble substrate as compared to wild-type subtilisin Carlsberg and wherein glutamate and aspartate substitutions at both positions 207 and 213, or substitutions at either of positions 207 and 213 are combined with a serine substitution at position 217, are combined with at least one further substitution at a corresponding position selected from subtilisin Carlsberg positions 59, 60, 64, 65, 104, 105, 129, 131, 132, 187, 189, 199 to 202, 204, 206, 209 to 211 and 215.

9. The subtilisin Carlsberg variant of claim 8, wherein two or more substitutions occur in the first loop region.

10. The subtilisin Carlsberg variant of claim 8, wherein two or more substitutions occur in the second loop region.

11. The subtilisin Carlsberg variant of claim 8, wherein two or more substitutions occur in the third loop region.

12. The subtilisin Carlsberg variant of claim 8, wherein two or more substitutions occur in the fourth loop region.

13. The subtilisin Carlsberg variant of claim 8, wherein two or more substitutions occur in the fifth loop region.

14. The subtilisin Carlsberg variant of claim 8, wherein two or more substitutions occur in the sixth loop region.

15. An isolated subtilisin Carlsberg variant having a modified amino acid sequence of the Subtilisin Carlsberg wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 58, 60, 61, 62, 64 or 65; wherein a. when a substitution occurs at position 58, the substituting amino acid is Asn, Gln, Pro or Ser;

b. when a substitution occurs at position 60, the substituting amino acid is Asn, Gln, Pro or Ser;

c. when a substitution occurs at position 61, the substituting amino acid is Gln or Ser;

d. when a substitution occurs at position 62, the substituting amino acid is Asn, Asp, Gln, Glu, Pro or Ser;

e. when a substitution occurs at position 64, the substituting amino acid is Asn, Asp, Gln, Glu, Pro or Ser; and f. when a substitution occurs at position 65, the substituting amino acid is Asn, Asp, Gln, Glu, Pro or Ser;

B. when a substitution occurs in the second loop region, the substitution occurs at one or more of positions 94, 95, 96, 97, 98, 99, 100, 101, 102, 103, 104, 105 or 106; wherein a. when a substitution occurs at position 94, the substituting amino acid is Ala, Asn, Asp, Cys, Gln, Glu, Gly, His, Met, Pro, Ser or Thr;

b. when a substitution occurs at position 95, the substituting amino acid is Ala, Asn, Asp, Cys, Gln, Glu, Gly, His, Ile, Met, Pro, Ser, Thr or Val;

c. when a substitution occurs at position 96, the substituting amino acid is Asp, Gln, Glu, or Ser; but when position 96 is substituted the variant is not a double, triple, quadruple, quintuple, sextuple, or septuple mutation variant having substitutions at positions selected from the group consisting of 103, 154, 155, 165, 188, and 216;

d. when a substitution occurs at position 97, the substituting amino acid is Asp or Glu; but when position 97 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 98, the substituting amino acid is Asp or Glu; but when position 98 is substituted the variant is not a double, triple, quadruple, quintuple, sextuple, or septuple mutation variant having substitutions at positions selected from the group consisting of 103, 154, 155, 165, 188, and 216;

f. when a substitution occurs at position 99, the substituting amino acid is Asn, Asp, Gln, Glu, Pro or Ser; but when position 99 is substituted the variant is not a double, triple, quadruple, quintuple, sextuple, or septuple mutation variant having substitutions at positions selected from the group consisting of 103, 154, 155, 165,188, and 216;

g. when a substitution occurs at position 100, the substituting amino acid is Asp or Glu; but when position 100 is substituted the variant is not a double, triple, quadruple, quintuple, sextuple, or septuple mutation variant having substitutions at positions selected from the group consisting of 103, 154, 155, 165, 188, and 216;

h. when a substitution occurs at position 101, the substituting amino acid is Asn, Asp, Gln, Glu, Pro or Ser; but when position 101 is substituted the variant is not a double, triple, quadruple, quintuple, sextuple, or septuple mutation variant having substitutions at positions selected from the group consisting of 103, 154, 155, 165, 188, and 216;

i. when a substitution occurs at position 102, the substituting amino acid is Asp or Glu; but when position 102 is substituted the variant is not a double, triple, quadruple, quintuple, sextuple, or septuple mutation variant having substitutions at positions selected from the group consisting of 103, 154, 155, 165, 188, and 216;

j. when a substitution occurs at position 103, the substituting amino acid is Ala, Asp, Cys, Gln, Glu, Gly, His, Ile, Leu, Met, Pro, Ser, Thr or Val;

k. when a substitution occurs at position 104, the substituting amino acid is Asp or Glu;

l. when a substitution occurs at position 105, the substituting amino acid is Asn, Asp, Gln, Glu, Pro or Ser; and m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, sextuple, or septuple mutation variant having substitutions at positions selected from the group consisting of 103, 154, 155, 165, 188, and 216;

C. when a substitution occurs in the third loop region, the substitution occurs at one or more of positions 125, 126, 127, 128, 129, 130, 131 or 132; wherein a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, quadruple, quintuple, sextuple, or septuple mutation variant having substitutions at positions selected from the group consisting of 103, 154, 155, 165, 188, and 216;

b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;

c. when a substitution occurs at position 127, the substituting amino acid is Asn, Asp, Gln, Glu, Pro or Ser; but when position 127 is substituted the variant is not a double, triple, quadruple, quintuple, sextuple, or septuple mutation variant having substitutions at positions selected from the group consisting of 103, 154, 155, 165, 188, and 216;

d. when a substitution occurs at position 128, the substituting amino acid is Asn, Asp, Gln, Glu, Gly, His, Pro, Ser or Thr; but when position 128 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 129, the substituting amino acid is Asp or Glu;

f. when a substitution occurs at position 130, the substituting amino acid is Asn, Asp, Gln, Glu, Pro or Ser;

g. when a substitution occurs at position 131, the substituting amino acid is Asp or Glu; and h. when a substitution occurs at position 132, the substituting amino acid is Asn, Asp, Gln, Glu, Gly, Pro or Ser;

D. when a substitution occurs in the fourth loop region, the substitution occurs at one or more of positions 153, 154, 155, 156, 157, 158, 159, 160, 161, 162, 163,164, 165 or 166; wherein a. when a substitution occurs at position 153, the substituting amino acid is Asn, Asp, Gln, Glu, Pro or Ser; but when position 153 is substituted the variant is not a double, triple, quadruple, quintuple, sextuple, or septuple mutation variant having substitutions at positions selected from the group consisting of 103, 154, 155, 165, 188, and 216;

b. when a substitution occurs at position 154, the substituting amino acid is Asp, Gln, Glu or Ser;

c. when a substitution occurs at position 155, the substituting amino acid is Asp or Glu; but when position 155 is substituted, the variant is not a double mutation variant having a substitution at position 216, double mutation variant having a substitution at position 165, or a triple mutation variant having substitutions at positions 165 and 216;

l. when a substitution occurs at position 164, the substituting amino acid is Ala, Asn, Asp, Cys, Gln, Glu, Gly, His, Met, Pro, Ser, Thr or Val; but when position 164 is substituted the variant is not a double, triple, quadruple, quintuple, sextuple, or septuple mutation variant having substitutions at positions selected from the group consisting of 103, 154, 155, 165, 188, and 216;

m. when a substitution occurs at position 165, the substituting amino acid is Asn, Asp, Gln, Glu, Pro or Ser; and n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, sextuple, or septuple mutation variant having substitutions at positions selected from the group consisting of 103, 154,155, 165, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;

c. when a substitution occurs at position 188, the substituting amino acid is Ala, Asn, Asp, Cys, Gln, Glu, Gly, His, Ile, Leu, Met, Pro, Ser, Thr, Tyr or Val;

d. when a substitution occurs at position 189, the substituting amino acid is Asp or Glu;

e. when a substitution occurs at position 190, the substituting amino acid is Asp or Glu; and
F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein
   a. when a substitution occurs at position 199, the substituting amino acid is Asn, Asp, Gln, Glu, Gly, His, Pro, Ser or Thr;
   b. when a substitution occurs at position 200, the substituting amino acid is Asn, Asp, Gln, Glu, Gly or Ser;
   c. when a substitution occurs at position 201, the substituting amino acid is Asn, Asp, Gln, Glu, Pro or Ser;
   d. when a substitution occurs at position 202, the substituting amino acid is Asn, Asp, Gln, Glu, Gly, His, Pro, Ser or Thr;
   e. when a substitution occurs at position 203, the substituting amino acid is Asn, Asp, Gln, Glu, Pro or Ser;
   f. when a substitution occurs at position 204, the substituting amino acid is Ala, Asn, Asp, Cys, Gln, Glu, Gly, His, Met, Pro, Ser or Thr;
   g. when a substitution occurs at position 205, the substituting amino acid is Ala, Asn, Asp, Cys, Gln, Glu, Gly, His, Ile, Leu, Met, Pro, Ser, Thr or Val;
   h. when a substitution occurs at position 206, the substituting amino acid is Asp or Glu;
   i. when a substitution occurs at position 207, the substituting amino acid is Asn, Asp, Gln, Glu, Gly, Pro or Ser;
   j. when a substitution occurs at position 208, the substituting amino acid is Ala, Asn, Asp, Cys, Gln, Glu, Gly, His, Ile, Leu, Met, Pro, Ser, Thr or Val;
   k. when a substitution occurs at position 209, the substituting amino acid is Asn, Asp, Gln, Glu, Gly or Ser;
   l. when a substitution occurs at position 210, the substituting amino acid is Asn, Asp, Gln, Glu, Gly, Pro or Ser;
   m. when a substitution occurs at position 211, the substituting amino acid is Asp, Gln, Glu or Ser;
   n. when a substitution occurs at position 212, the substituting amino acid is Asn, Asp, Gln, Glu, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;
   o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, sextuple, or septuple mutation variant having substitutions at positions selected from the group consisting of 103, 154, 155, 165, 188, and 216;
   p. when a substitution occurs at position 214, the substituting amino acid is Asn, Asp, Gln, Glu, Gly, His, Pro, Ser or Thr; but when position 214 is substituted the variant is not a double, triple, quadruple, quintuple, sextuple, or septuple mutation variant having substitutions at positions selected from the group consisting of 103, 154, 155, 165, 188, and 216;
   q. when a substitution occurs at position 215, the substituting amino acid is Asn, Asp, Gln, Glu, Gly, Pro or Ser;
   r. when a substitution occurs at position 216, the substituting amino acid is Ala, Asn, Asp, Cys, Gln, Glu, Gly, His, Ile, Met, Pro, Ser, Thr or Val; but when position 216 is substituted the variant is not a double mutation variant having a substitution at position 217;
   s. when a substitution occurs at position 217, the substituting amino acid is Asp, Gln, Glu or Ser;
   t. when a substitution occurs at position 218, the substituting amino acid is Asn, Asp, Gln, Glu, Pro or Ser; and
   u. when a substitution occurs at position 219, the substituting amino acid is Asn, Asp, Gln, Glu, Gly, Pro or Ser; wherein the variant is not:
   v. a double mutation variant having substitutions at positions 202 and 203;
   w. a double mutation variant having substitutions at positions 202 and 216;
   x. a double mutation variant having substitutions at positions 203 and 216; or
   y. a triple mutation variant having substitutions at positions 202, 203, and 216; and
whereby the subtilisin Carlsberg variant has decreased adsorption to, and increased hydrolysis of, an insoluble substrate as compared to wild-type subtilisin Carlsberg.

16. The subtilisin Carlsberg variant of claim 15, wherein two or more substitutions occur in the first loop region.

17. The subtilisin Carlsberg variant of claim 15, wherein two or more substitutions occur in the second loop region.

18. The subtilisin Carlsberg variant of claim 15, wherein two or more substitutions occur in the third loop region.

19. The subtilisin Carlsberg variant of claim 15, wherein two or more substitutions occur in the fourth loop region.

20. The subtilisin Carlsberg variant of claim 15, wherein two or more substitutions occur in the fifth loop region.

21. The subtilisin Carlsberg variant of claim 15, wherein two or more substitutions occur in the sixth loop region.

22. An isolated subtilisin Carlsberg variant having a modified amino acid sequence of the Subtilisin Carlsberg wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
   A. when a substitution occurs in the first loop region, the substitution occurs at one or more of positions 58, 59, 60, 61, 62, 64 or 65; wherein
      a. when a substitution occurs at position 58, the substituting amino acid is Asn, Asp, Gln, Glu, Gly, Pro or Ser;
      b. when a substitution occurs at position 59, the substituting amino acid is Glu;
      c. when a substitution occurs at position 60, the substituting amino acid is Asn, Asp, Gln, Glu, Pro or Ser;
      d. when a substitution occurs at position 61, the substituting amino acid is Asp, Gln, Glu or Ser;
      e. when a substitution occurs at position 62, the substituting amino acid is Asn, Asp, Gln, Glu, Pro or Ser;
      f. when a substitution occurs at position 64, the substituting amino acid is Asn, Asp, Gln, Glu, Pro or Ser; and
      g. when a substitution occurs at position 65, the substituting amino acid is Asn, Asp, Gln, Glu, Gly, Pro or Ser;

B. when a substitution occurs in the second loop region, the substitution occurs at one or more of positions 94, 95, 96, 99, 101, 103, 105 or 106; wherein
   a. when a substitution occurs at position 94, the substituting amino acid is Ala, Cys, Gln, Gly, His, Met, Pro or Ser;
   b. when a substitution occurs at position 95, the substituting amino acid is Ala, Asn, Asp, Cys, Gln, Glu, Gly, His, Ile, Met, Pro, Ser, Thr or Val;
   c. when a substitution occurs at position 96, the substituting amino acid is Gln; but when position 96 is substituted the variant is not a double, triple, quadruple, quintuple, sextuple, or septuple mutation variant having substitutions at positions selected from the group consisting of 103, 154, 155, 165, 188, and 216;
   d. when a substitution occurs at position 99, the substituting amino acid is Asn, Gln, Pro or Ser; but when position 99 is substituted the variant is not a double, triple, quadruple, quintuple, sextuple, or septuple mutation variant having substitutions at positions selected from the group consisting of 103, 154, 155, 165, 188, and 216;
   e. when a substitution occurs at position 101, the substituting amino acid is Asn, Gln, Pro or Ser; but when position 101 is substituted the variant is not a double, triple, quadruple, quintuple, sextuple, or septuple mutation variant having substitutions at positions selected from the group consisting of 103, 154, 155, 165, 188, and 216;
   f. when a substitution occurs at position 103, the substituting amino acid is His, Ile, Leu, Met or Pro;
   g. when a substitution occurs at position 105, the substituting amino acid is Asn, Gln, Pro or Ser; and
   h. when a substitution occurs at position 106, the substituting amino acid is Ala, Cys, Gln, Gly, His, Met, Pro, Ser or Val; but when position 106 is substituted the variant is not a double, triple, quadruple, quintuple, sextuple, or septuple mutation variant having substitutions at positions selected from the group consisting of 103, 154, 155, 165, 188, and 216;
C. when a substitution occurs in the third loop region, the substitution occurs at one or more of positions 125, 126, 127, 128, 129, 130, 131 or 132; wherein
   a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, quadruple, quintuple, sextuple, or septuple mutation variant having substitutions at positions selected from the group consisting of 103, 154, 155, 165, 188, and 216;
   b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;
   c. when a substitution occurs at position 127, the substituting amino acid is Asn, Asp, Gln, Glu, Pro or Ser; but when position 127 is substituted the variant is not a double, triple, quadruple, quintuple, sextuple, or septuple mutation variant having substitutions at positions selected from the group consisting of 103, 154, 155, 165, 188, and 216;
   d. when a substitution occurs at position 128, the substituting amino acid is Asn, Asp, Gln, Glu, Gly, His, Pro, Ser or Thr; but when position 128 is substituted the variant is not a double, triple, quadruple, quintuple, sextuple, or septuple mutation variant having substitutions at positions selected from the group consisting of 103, 154, 155, 165, 188, and 216;
   e. when a substitution occurs at position 129, the substituting amino acid is Asp or Glu;
   f. when a substitution occurs at position 130, the substituting amino acid is Asn, Asp, Gln, Glu, Pro or Ser;
   g. when a substitution occurs at position 131, the substituting amino acid is Asp or Glu; and
   h. when a substitution occurs at position 132, the substituting amino acid is Asn, Asp, Gln, Glu, Gly, Pro or Ser;
D. when a substitution occurs in the fourth loop region, the substitution occurs at one or more of positions 153, 154, 155, 156, 157, 158, 159, 160, 161, 162, 163, 164, 165 or 166; wherein
   a. when a substitution occurs at position 153, the substituting amino acid is Asn, Asp, Gln, Glu, Pro or Ser; but when position 153 is substituted the variant is not a double, triple, quadruple, quintuple, sextuple, or septuple mutation variant having substitutions at positions selected from the group consisting of 103, 154, 155, 165, 188, and 216;
   b. when a substitution occurs at position 154, the substituting amino acid is Asp, Gln, Glu or Ser;
   c. when a substitution occurs at position 155, the substituting amino acid is Asp or Glu; but when position 155 is substituted, the variant is not a double mutation variant having a substitution at position 216, double mutation variant having a substitution at position 165, or a triple mutation variant having substitutions at positions 165 and 216;
   d. when a substitution occurs at position 156, the substituting amino acid is Asn, Asp, Gln, Glu, Pro or Ser; but when position 156 is substituted the variant is not a double, triple, quadruple, quintuple, sextuple, or septuple mutation variant having substitutions at positions selected from the group consisting of 103, 154, 155, 165, 188, and 216;
   e. when a substitution occurs at position 157, the substituting amino acid is Asp, Gln, Glu or Ser; but when position 157 is substituted the variant is not a double, triple, quadruple, quintuple, sextuple, or septuple mutation variant having substitutions at positions selected from the group consisting of 103, 154, 155, 165, 188, and 216;
   n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, sextuple, or septuple mutation variant having substitutions at positions selected from the group consisting of 103, 154, 155, 165, 188, and 216;
E. when a substitution occurs in the fifth loop region, the substitution occurs at one or more of positions 186, 187, 188, 189 or 190; wherein
   a. when a substitution occurs at position 186, the substituting amino acid is Asn, Asp, Gln, Glu, Gly, His, Pro, Ser or Thr;
   b. when a substitution occurs at position 187, the substituting amino acid is Asp or Glu;

c. when a substitution occurs at position 188, the substituting amino acid is Ala, Asn, Asp, Cys, Gln, Glu, Gly, His, le, Leu, Met, Pro, Ser, Thr, Tyr or Val;
d. when a substitution occurs at position 189, the substituting amino acid is Asp or Glu;
e. when a substitution occurs at position 190, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein
a. when a substitution occurs at position 199, the substituting amino acid is Asn, Asp, Gln, Glu, Gly, His, Pro, Ser or Thr;
b. when a substitution occurs at position 200, the substituting amino acid is Asn, Asp, Gln, Glu, Gly or Ser;
c. when a substitution occurs at position 201, the substituting amino acid is Asn, Asp, Gln, Glu, Pro or Ser;
d. when a substitution occurs at position 202, the substituting amino acid is Asn, Asp, Gln, Glu, Gly, His, Pro, Ser or Thr;
e. when a substitution occurs at position 203, the substituting amino acid is Asn, Asp, Gln, Glu, Pro or Ser;
f. when a substitution occurs at position 204, the substituting amino acid is Ala, Asn, Asp, Cys, Gln, Glu, Gly, His, Met, Pro, Ser or Thr;
g. when a substitution occurs at position 205, the substituting amino acid is Ala, Asn, Asp, Cys, Gln, Glu, Gly, His, Ile, Leu, Met, Pro, Ser, Thr or Val;
h. when a substitution occurs at position 206, the substituting amino acid is Asp or Glu;
i. when a substitution occurs at position 207, the substituting amino acid is Asn, Asp, Gln, Glu, Gly, Pro or Ser;
j. when a substitution occurs at position 208, the substituting amino acid is Ala, Asn, Asp, Cys, Gln, Glu, Gly, His, Ile, Leu, Met, Pro, Ser, Thr or Val;
k. when a substitution occurs at position 209, the substituting amino acid is Asn, Asp, Gln, Glu, Gly or Ser;
l. when a substitution occurs at position 210, the substituting amino acid is Asn, Asp, Gln, Glu, Gly, Pro or Ser;
m. when a substitution occurs at position 211, the substituting amino acid is Asp, Gln, Glu or Ser;
n. when a substitution occurs at position 212, the substituting amino acid is Asn, Asp, Gln, Glu, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;
o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, sextuple, or septuple mutation variant having substitutions at positions selected from the group consisting of 103, 154, 155, 165, 188, and 216;
p. when a substitution occurs at position 214, the substituting amino acid is Asn, Asp, Gln, Glu, Gly, His, Pro, Ser or Thr; but when position 214 is substituted the variant is not a double, triple, quadruple, quintuple, sextuple, or septuple mutation variant having substitutions at positions selected from the group consisting of 103, 154, 155, 165, 188, and 216;
q. when a substitution occurs at position 215, the substituting amino acid is Asn, Asp, Gln, Glu, Gly, Pro or Ser;
r. when a substitution occurs at position 216, the substituting amino acid is Ala, Asn, Asp, Cys, Gln, Glu, Gly, His, Ile, Met, Pro, Ser, Thr or Val; but when position 216 is substituted the variant is not a double mutation variant having a substitution at position 217;
s. when a substitution occurs at position 217, the substituting amino acid is Asp, Gln, Glu or Ser;
t. when a substitution occurs at position 218, the substituting amino acid is Asn, Asp, Gln, Glu, Pro or Ser; and
u. when a substitution occurs at position 219, the substituting amino acid is Asn, Asp, Gln, Glu, Gly, Pro or Ser; wherein the variant is not:
v. a double mutation variant having substitutions at positions 202 and 203;
w. a double mutation variant having substitutions at positions 202 and 216;
x. a double mutation variant having substitutions at positions 203 and 216; or
y. a triple mutation variant having substitutions at positions 202, 203, and 216; and whereby the subtilisin Carlsberg variant has decreased adsorption to, and increased hydrolysis of, an insoluble substrate as compared to wild-type subtilisin Carlsberg.

23. The subtilisin Carlsberg variant of claim 22, wherein two or more substitutions occur in the first loop region.

24. The subtilisin Carlsberg variant of claim 22, wherein two or more substitutions occur in the second loop region.

25. The subtilisin Carlsberg variant of claim 22, wherein two or more substitutions occur in the third loop region.

26. The subtilisin Carlsberg variant of claim 22, wherein two or more substitutions occur in the fourth loop region.

27. The subtilisin Carlsberg variant of claim 22, wherein two or more substitutions occur in the fifth loop region.

28. The subtilisin Carlsberg variant of claim 22, wherein two or more substitutions occur in the sixth loop region.

29. An isolated subtilisin Carlsberg variant having a modified amino acid sequence of the Subtilisin Carlsberg wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
A. when a substitution occurs in the first loop region, the substitution occurs at one or more of positions 58, 59, 60, 61, 62, 64 or 65; wherein
a. when a substitution occurs at position 58, the substituting amino acid is Asn, Asp, Gln, Glu, Gly, Pro or Ser;
b. when a substitution occurs at position 59, the substituting amino acid is Glu;
c. when a substitution occurs at position 60, the substituting amino acid is Asn, Asp, Gln, Glu, Pro or Ser;
d. when a substitution occurs at position 61, the substituting amino acid is Asp, Gln, Glu or Ser;
e. when a substitution occurs at position 62, the substituting amino acid is Asn, Asp, Gln, Glu, Pro or Ser;

f. when a substitution occurs at position 64, the substituting amino acid is Asn, Asp, Gln, Glu, Pro or Ser; and
g. when a substitution occurs at position 65, the substituting amino acid is Asn, Asp, Gln, Glu, Gly, Pro or Ser;

B. when a substitution occurs in the second loop region, the substitution occurs at one or more of positions 94, 95, 96, 97, 98, 99, 100, 101, 102, 103, 104, 105 or 106; wherein
   a. when a substitution occurs at position 94, the substituting amino acid is Ala, Asn, Asp, Cys, Gln, Glu, Gly, His, Met, Pro, Ser or Thr;
   b. when a substitution occurs at position 95, the substituting amino acid is Ala, Asn, Asp, Cys, Gln, Glu, Gly, His, Ile, Met, Pro, Ser, Thr or Val;
   c. when a substitution occurs at position 96, the substituting amino acid is Asp, Gln, Glu, or Ser; but when position 96 is substituted the variant is not a double, triple, quadruple, quintuple, sextuple, or septuple mutation variant having substitutions at positions selected from the group consisting of 103, 154, 155, 165, 188, and 216;
   d. when a substitution occurs at position 97, the substituting amino acid is Asp or Glu; but when position 97 is substituted the variant is not a double, triple, quadruple, quintuple, sextuple, or septuple mutation variant having substitutions at positions selected from the group consisting of 103, 154, 155, 165, 188, and 216;
   e. when a substitution occurs at position 98, the substituting amino acid is Asp or Glu; but when position 98 is substituted the variant is not a double, triple, quadruple, quintuple, sextuple, or septuple mutation variant having substitutions at positions selected from the group consisting of 103, 154, 155, 165, 188, and 216;
   f. when a substitution occurs at position 99, the substituting amino acid is Asn, Asp, Gln, Glu, Pro or Ser; but when position 99 is substituted the variant is not a double, triple, quadruple, quintuple, sextuple, or septuple mutation variant having substitutions at positions selected from the group consisting of 103, 154, 155, 165, 188, and 216;
   g. when a substitution occurs at position 100, the substituting amino acid is Asp or Glu; but when position 100 is substituted the variant is not a double, triple, quadruple, quintuple, sextuple, or septuple mutation variant having substitutions at positions selected from the group consisting of 103, 154, 155, 165, 188, and 216;
   h. when a substitution occurs at position 101, the substituting amino acid is Asn, Asp, Gln, Glu, Pro or Ser; but when position 101 is substituted the variant is not a double, triple, quadruple, quintuple, sextuple, or septuple mutation variant having substitutions at positions selected from the group consisting of 103, 154, 155, 165, 188, and 216;
   i. when a substitution occurs at position 102, the substituting amino acid is Asp or Glu; but when position 102 is substituted the variant is not a double, triple, quadruple, quintuple, sextuple, or septuple mutation variant having substitutions at positions selected from the group consisting of 103, 154, 155, 165, 188, and 216;
   j. when a substitution occurs at position 103, the substituting amino acid is Ala, Asp, Cys, Gln, Glu, Gly, His, Ile, Leu, Met, Pro, Ser, Thr or Val;
   k. when a substitution occurs at position 104, the substituting amino acid is Asp or Glu;
   l. when a substitution occurs at position 105, the substituting amino acid is Asn, Asp, Gln, Glu, Pro or Ser; and
   m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, sextuple, or septuple mutation variant having substitutions at positions selected from the group consisting of 103, 154, 155, 165, 188, and 216;

C. when a substitution occurs in the third loop region, the substitution occurs at one or more of positions 125, 126, 127, 128, 130, 131 or 132; wherein
   a. when a substitution occurs at position 125, the substituting amino acid is Ala, Asn, Cys, Gln, Gly, His, Met, Pro, Ser, Thr or Val; but when position 125 is substituted the variant is not a double, triple, quadruple, quintuple, sextuple, or septuple mutation variant having substitutions at positions selected from the group consisting of 103, 154, 155, 165, 188, and 216;
   b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;
   c. when a substitution occurs at position 127, the substituting amino acid is Asn, Gln or Pro; but when position 127 is substituted the variant is not a double, triple, quadruple, quintuple, sextuple, or septuple mutation variant having substitutions at positions selected from the group consisting of 103, 154, 155, 165, 188, and 216;
   d. when a substitution occurs at position 128, the substituting amino acid is Asn, Gln, Gly, His, Pro, Ser or Thr; but when position 128 is substituted the variant is not a double, triple, quadruple, quintuple, sextuple, or septuple mutation variant having substitutions at positions selected from the group consisting of 103, 154, 155, 165, 188, and 216;
   e. when a substitution occurs at position 130, the substituting amino acid is Asn, Gln, Pro or Ser;
   f. when a substitution occurs at position 131, the substituting amino acid is Glu; and
   g. when a substitution occurs at position 132, the substituting amino acid is Asn, Gln, Pro or Ser;

D. when a substitution occurs in the fourth loop region, the substitution occurs at one or more of positions 153, 154, 155, 156, 157, 158, 159, 160, 161, 162, 163, 164, 165 or 166; wherein
   a. when a substitution occurs at position 153, the substituting amino acid is Asn, Asp, Gln, Glu, Pro or Ser; but when position 153 is substituted the variant is not a double, triple, quadruple, quintuple, sextuple, or septuple mutation variant having substitutions at positions selected from the group consisting of 103, 154, 155, 165, 188, and 216;
   b. when a substitution occurs at position 154, the substituting amino acid is Asp, Gln, Glu or Ser;
   c. when a substitution occurs at position 155, the substituting amino acid is Asp or Glu; but when position 155 is substituted, the variant is not a double mutation variant having a substitution at position 216, double mutation variant having a substitution at position 165, or a triple mutation variant having substitutions at positions 165 and 216;

d. when a substitution occurs at position 156, the substituting amino acid is Asn, Asp, Gln, Glu, Pro or Ser; but when position 156 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 157, the substituting amino acid is Asp, Gln, Glu or Ser; but when position 157 is substituted the variant is not a double, triple, quadruple, quintuple, sextuple, or septuple mutation variant having substitutions at positions selected from the group consisting of 103, 154, 155, 165, 188, and 216;

f. when a substitution occurs at position 158, the substituting amino acid is Asp or Glu; but when position 158 is substituted the variant is not a double, triple, quadruple, quintuple, sextuple, or septuple mutation variant having substitutions at positions selected from the group consisting of 103, 154, 155, 165, 188, and 216;

g. when a substitution occurs at position 159, the substituting amino acid is Asn, Asp, Gln, Glu, Pro or Ser; but when position 159 is substituted the variant is not a double, triple, quadruple, quintuple, sextuple, or septuple mutation variant having substitutions at positions selected from the group consisting of 103, 154, 155, 165, 188, and 216;

h. when a substitution occurs at position 160, the substituting amino acid is Asp or Glu; but when position 160 is substituted the variant is not a double, triple, quadruple, quintuple, sextuple, or septuple mutation variant having substitutions at positions selected from the group consisting of 103, 154, 155, 165, 188, and 216;

i. when a substitution occurs at position 161, the substituting amino acid is Asn, Asp, Gln, Glu, Gly, Pro or Ser; but when position 161 is substituted the variant is not a double, triple, quadruple, quintuple, sextuple, or septuple mutation variant having substitutions at positions selected from the group consisting of 103, 154, 155, 165, 188, and 216;

j. when a substitution occurs at position 162, the substituting amino acid is Asp, Gln, Glu or Ser; but when position 162 is substituted the variant is not a double, triple, quadruple, quintuple, sextuple, or septuple mutation variant having substitutions at positions selected from the group consisting of 103, 154, 155, 165, 188, and 216;

k. when a substitution occurs at position 163, the substituting amino acid is Asn, Asp, Gln, Glu, Gly, Pro or Ser; but when position 163 is substituted the variant is not a double, triple, quadruple, quintuple, sextuple, or septuple mutation variant having substitutions at positions selected from the group consisting of 103, 154, 155, 165, 188, and 216;

l. when a substitution occurs at position 164, the substituting amino acid is Ala, Asn, Asp, Cys, Gln, Glu, Gly, His, Met, Pro, Ser, Thr or Val; but when position 164 is substituted the variant is not a double, triple, quadruple, quintuple, sextuple, or septuple mutation variant having substitutions at positions selected from the group consisting of 103, 154, 155, 165, 188, and 216;

m. when a substitution occurs at position 165, the substituting amino acid is Asn, Asp, Gln, Glu, Pro or Ser; but when position 165 is substituted with Asp or Glu, the variant is not a double mutation variant having a substitution of Asp or Glu at position 61; and n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, sextuple, or septuple mutation variant having substitutions at positions selected from the group consisting of 103, 154, 155, 165, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;

c. when a substitution occurs at position 188, the substituting amino acid is Ala, Asn, Asp, Cys, Gln, Glu, Gly, His, Ile, Leu, Met, Pro, Ser, Thr, Tyr or Val;

d. when a substitution occurs at position 189, the substituting amino acid is Asp or Glu;

e. when a substitution occurs at position 190, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein a. when a substitution occurs at position 199, the substituting amino acid is Asn, Asp, Gln, Glu, Gly, His, Pro, Ser or Thr;

b. when a substitution occurs at position 200, the substituting amino acid is Asn, Asp, Gln, Glu, Gly or Ser;

c. when a substitution occurs at position 201, the substituting amino acid is Asn, Asp, Gln, Glu, Pro or Ser;

d. when a substitution occurs at position 202, the substituting amino acid is Asn, Asp, Gln, Glu, Gly, His, Pro, Ser or Thr;

e. when a substitution occurs at position 203, the substituting amino acid is Asn, Asp, Gln, Glu, Pro or Ser;

f. when a substitution occurs at position 204, the substituting amino acid is Ala, Asn, Asp, Cys, Gln, Glu, Gly, His, Met, Pro, Ser or Thr;

g. when a substitution occurs at position 205, the substituting amino acid is Ala, Asn, Asp, Cys, Gln, Glu, Gly, His, Ile, Leu, Met, Pro, Ser, Thr or Val;

h. when a substitution occurs at position 206, the substituting amino acid is Asp or Glu;

i. when a substitution occurs at position 207, the substituting amino acid is Asn, Asp, Gln, Glu, Gly, Pro or Ser;

j. when a substitution occurs at position 208, the substituting amino acid is Ala, Asn, Asp, Cys, Gln, Glu, Gly, His, Ile, Leu, Met, Pro, Ser, Thr or Val;

k. when a substitution occurs at position 209, the substituting amino acid is Asn, Asp, Gln, Glu, Gly or Ser;

l. when a substitution occurs at position 210, the substituting amino acid is Asn, Asp, Gln, Glu, Gly, Pro or Ser;

m. when a substitution occurs at position 211, the substituting amino acid is Asp, Gln, Glu or Ser;
n. when a substitution occurs at position 212, the substituting amino acid is Asn, Asp, Gln, Glu, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;
o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, sextuple, or septuple mutation variant having substitutions at positions selected from the group consisting of 103, 154, 155, 165, 188, and 216;
p. when a substitution occurs at position 214, the substituting amino acid is Asn, Asp, Gln, Glu, Gly, His, Pro, Ser or Thr; but when position 214 is substituted the variant is not a double, triple, quadruple, quintuple, sextuple, or septuple mutation variant having substitutions at positions selected from the group consisting of 103, 154, 155, 165, 188, and 216;
q. when a substitution occurs at position 215, the substituting amino acid is Asn, Asp, Gln, Glu, Gly, Pro or Ser;
r. when a substitution occurs at position 216, the substituting amino acid is Ala, Asn, Asp, Cys, Gln, Glu, Gly, His, Ile, Met, Pro, Ser, Thr or Val; but when position 216 is substituted the variant is not a double mutation variant having a substitution at position 217;
s. when a substitution occurs at position 217, the substituting amino acid is Asp, Gln, Glu or Ser;
t. when a substitution occurs at position 218, the substituting amino acid is Asn, Asp, Gln, Glu, Pro or Ser; and
u. when a substitution occurs at position 219, the substituting amino acid is Asn, Asp, Gln, Glu, Gly, Pro or Ser; wherein the variant is not:
v. a double mutation variant having substitutions at positions 202 and 203;
w. a double mutation variant having substitutions at positions 202 and 216;
x. a double mutation variant having substitutions at positions 203 and 216; or
y. a triple mutation variant having substitutions at positions 202, 203, and 216; and
whereby the subtilisin Carlsberg variant has decreased adsorption to, and increased hydrolysis of, an insoluble substrate as compared to wild-type subtilisin Carlsberg.

30. The subtilisin Carlsberg variant of claim 29, wherein two or more substitutions occur in the first loop region.

31. The subtilisin Carlsberg variant of claim 29, wherein two or more substitutions occur in the second loop region.

32. The subtilisin Carlsberg variant of claim 29, wherein two or more substitutions occur in the third loop region.

33. The subtilisin Carlsberg variant of claim 29, wherein two or more substitutions occur in the fourth loop region.

34. The subtilisin Carlsberg variant of claim 29, wherein two or more substitutions occur in the fifth loop region.

35. The subtilisin Carlsberg variant of claim 29, wherein two or more substitutions occur in the sixth loop region.

36. An isolated subtilisin Carlsberg variant having a modified amino acid sequence of the Subtilisin Carlsberg wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
A. when a substitution occurs in the first loop region, the substitution occurs at one or more of positions 58, 59, 60, 61, 62, 64 or 65; wherein
 a. when a substitution occurs at position 58, the substituting amino acid is Asn, Asp, Gln, Glu, Gly, Pro or Ser;
 b. when a substitution occurs at position 59, the substituting amino acid is Glu;
 c. when a substitution occurs at position 60, the substituting amino acid is Asn, Asp, Gln, Glu, Pro or Ser;
 d. when a substitution occurs at position 61, the substituting amino acid is Asp, Gln, Glu or Ser;
 e. when a substitution occurs at position 62, the substituting amino acid is Asn, Asp, Gln, Glu, Pro or Ser;
 f. when a substitution occurs at position 64, the substituting amino acid is Asn, Asp, Gln, Glu, Pro or Ser; and
 g. when a substitution occurs at position 65, the substituting amino acid is Asn, Asp, Gln, Glu, Gly, Pro or Ser;
B. when a substitution occurs in the second loop region, the substitution occurs at one or more of positions 94, 95, 96, 97, 98, 99, 100, 101, 102, 103, 104, 105 or 106; wherein
 a. when a substitution occurs at position 94, the substituting amino acid is Ala, Asn, Asp, Cys, Gln, Glu, Gly, His, Met, Pro, Ser or Thr;
 b. when a substitution occurs at position 95, the substituting amino acid is Ala, Asn, Asp, Cys, Gln, Glu, Gly, His, Ile, Met, Pro, Ser, Thr or Val;
 c. when a substitution occurs at position 96, the substituting amino acid is Asp, Gln, Glu, or Ser; but when position 96 is substituted the variant is not a double, triple, quadruple, quintuple, or sextuple mutation variant having substitutions at positions selected from the group consisting of 103, 154, 165, 188, and 216;
 d. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 103, 154, 165, 188, and 216;
 e. when a substitution occurs at position 98, the substituting amino acid is Asp or Glu; but when position 98 is substituted the variant is not a double, triple, quadruple, quintuple, or sextuple mutation variant having substitutions at positions selected from the group consisting of 103, 154, 165, 188, and 216;
 f. when a substitution occurs at position 99, the substituting amino acid is Asn, Asp, Gln, Glu, Pro or Ser; but when position 99 is substituted the variant is not a double, triple, quadruple, quintuple, or sextuple mutation variant having substitutions at positions selected from the group consisting of 103, 154, 165, 188, and 216;
 g. when a substitution occurs at position 100, the substituting amino acid is Asp or Glu; but when position 100 is substituted the variant is not a double, triple, quadruple, quintuple, or sextuple mutation variant having substitutions at positions selected from the group consisting of 103, 154, 165, 188, and 216;

h. when a substitution occurs at position 101, the substituting amino acid is Asn, Asp, Gln, Glu, Pro or Ser; but when position 101 is substituted the variant is not a double, triple, quadruple, quintuple, or sextuple mutation variant having substitutions at positions selected from the group consisting of 103, 154, 165, 188, and 216;

i. when a substitution occurs at position 102, the substituting amino acid is Asp or Glu; but when position 102 is substituted the variant is not a double, triple, quadruple, quintuple, or sextuple mutation variant having substitutions at positions selected from the group consisting of 103, 154, 165, 188, and 216;

j. when a substitution occurs at position 103, the substituting amino acid is Ala, Asp, Cys, Gln, Glu, Gly, His, Ile, Leu, Met, Pro, Ser, Thr or Val;

k. when a substitution occurs at position 104, the substituting amino acid is Asp or Glu;

l. when a substitution occurs at position 105, the substituting amino acid is Asn, Asp, Gln, Glu, Pro or Ser; and m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, or sextuple mutation variant having substitutions at positions selected from the group consisting of 103, 154, 165, 188, and 216;

C. when a substitution occurs in the third loop region, the substitution occurs at one or more of positions 125, 126, 127, 128, 129, 130, 131 or 132; wherein a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, quadruple, quintuple, or sextuple mutation variant having substitutions at positions selected from the group consisting of 103, 154, 165, 188, and 216;

b. when a substitution occurs at position 126, the substituting amino acid is Asn, Asp, Gln, Glu, Pro or Ser; but when position 126 is substituted the variant is not a double, triple, quadruple, quintuple, or sextuple mutation variant having substitutions at positions selected from the group consisting of 103, 154, 165, 188, and 216;

c. when a substitution occurs at position 127, the substituting amino acid is Asn, Asp, Gln, Glu, Pro or Ser; but when position 127 is substituted the variant is not a double, triple, quadruple, quintuple, or sextuple mutation variant having substitutions at positions selected from the group consisting of 103, 154, 165, 188, and 216;

d. when a substitution occurs at position 128, the substituting amino acid is Asn, Asp, Gln, Glu, Gly, His, Pro, Ser or Thr; but when position 128 is substituted the variant is not a double, triple, quadruple, quintuple, or sextuple mutation variant having substitutions at positions selected from the group consisting of 103, 154, 165, 188, and 216;

e. when a substitution occurs at position 129, the substituting amino acid is Asp or Glu;

f. when a substitution occurs at position 130, the substituting amino acid is Asn, Asp, Gln, Glu, Pro or Ser;

g. when a substitution occurs at position 131, the substituting amino acid is Asp or Glu; and h. when a substitution occurs at position 132, the substituting amino acid is Asn, Asp, Gln, Glu, Gly, Pro or Ser;

D. when a substitution occurs in the fourth loop region, the substitution occurs at one or more of positions 153, 154, 156, 157, 159, 161, 162, 163, 164, 165 or 166; wherein a. when a substitution occurs at position 153, the substituting amino acid is Asn, Asp, Gln, Glu, Pro or Ser; but when position 153 is substituted the variant is not a double, triple, quadruple, quintuple, or sextuple mutation variant having substitutions at positions selected from the group consisting of 103, 154, 165, 188, and 216;

b. when a substitution occurs at position 154, the substituting amino acid is Gln;

c. when a substitution occurs at position 156, the substituting amino acid is Asn, Asp, Gln, Glu or Pro; but when position 156 is substituted the variant is not a double, triple, quadruple, quintuple, or sextuple mutation variant having substitutions at positions selected from the group consisting of 103, 154, 165, 188, and 216;

d. when a substitution occurs at position 157, the substituting amino acid is Gln; but when position 157 is substituted the variant is not a double, triple, quadruple, quintuple, or sextuple mutation variant having substitutions at positions selected from the group consisting of 103, 154, 165, 188, and216;

e. when a substitution occurs at position 159, the substituting amino acid is Asn, Gln, Pro or Ser; but when position 159 is substituted the variant is not a double, triple, quadruple, quintuple, or sextuple mutation variant having substitutions at positions selected from the group consisting of 103, 154, 165, 188, and 216;

f. when a substitution occurs at position 161, the substituting amino acid is Asn, Gln, Pro or Ser; but when position 161 is substituted the variant is not a double, triple, quadruple, quintuple, or sextuple mutation variant having substitutions at positions selected from the group consisting of 103, 154, 165, 188, and 216;

g. when a substitution occurs at position 162, the substituting amino acid is Gln; but when position 162 is substituted the variant is not a double, triple, quadruple, quintuple, or sextuple mutation variant having substitutions at positions selected from the group consisting of 103, 154, 165, 188, and 216;

h. when a substitution occurs at position 163, the substituting amino acid is Asn, Gln, Gly, Pro or Ser; but when position 163 is substituted the variant is not a double, triple, quadruple, quintuple, or sextuple mutation variant having substitutions at positions selected from the group consisting of 103, 154, 165, 188, and 216;

i. when a substitution occurs at position 164, the substituting amino acid is Ala, Cys, Gln, Gly, His, Met, Pro, Ser or Val; but when position 164 is substituted the variant is not a double, triple, quadruple, quintuple, or sextuple mutation variant having substitutions at positions selected from the group consisting of 103, 154, 165, 188, and 216;

j. when a substitution occurs at position 165, the substituting amino acid is Pro; and k. when a substitution occurs at position 166, the substituting amino acid is His, Ile, Leu, Met or Pro; but when position 166 is substituted the variant is not a double, triple, quadruple, quintuple, or sextuple mutation variant having substitutions at positions selected from the group consisting of 103, 154, 165, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;

c. when a substitution occurs at position 188, the substituting amino acid is Ala, Asn, Asp, Cys, Gln, Glu, Gly, His, Ile, Leu, Met, Pro, Ser, Thr, Tyr or Val;

d. when a substitution occurs at position 189, the substituting amino acid is Asp or Glu;

e. when a substitution occurs at position 190, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein a. when a substitution occurs at position 199, the substituting amino acid is Asn, Asp, Gln, Glu, Gly, His, Pro, Ser or Thr;

b. when a substitution occurs at position 200, the substituting amino acid is Asn, Asp, Gln, Glu, Gly or Ser;

c. when a substitution occurs at position 201, the substituting amino acid is Asn, Asp, Gln, Glu, Pro or Ser;

d. when a substitution occurs at position 202, the substituting amino acid is Asn, Asp, Gln, Glu, Gly, His, Pro, Ser or Thr;

e. when a substitution occurs at position 203, the substituting amino acid is Asn, Asp, Gln, Glu, Pro or Ser;

f. when a substitution occurs at position 204, the substituting amino acid is Ala, Asn, Asp, Cys, Gln, Glu, Gly, His, Met, Pro, Ser or Thr;

g. when a substitution occurs at position 205, the substituting amino acid is Ala, Asn, Asp, Cys, Gln, Glu, Gly, His, Ile, Leu, Met, Pro, Ser, Thr or Val;

h. when a substitution occurs at position 206, the substituting amino acid is Asp or Glu;

i. when a substitution occurs at position 207, the substituting amino acid is Asn, Asp, Gln, Glu, Gly, Pro or Ser;

j. when a substitution occurs at position 208, the substituting amino acid is Ala, Asn, Asp, Cys, Gln, Glu, Gly, His, Ile, Leu, Met, Pro, Ser, Thr or Val;

k. when a substitution occurs at position 209, the substituting amino acid is Asn, Asp, Gln, Glu, Gly or Ser;

l. when a substitution occurs at position 210, the substituting amino acid is Asn, Asp, Gln, Glu, Gly, Pro or Ser;

m. when a substitution occurs at position 211, the substituting amino acid is Asp, Gln, Glu or Ser;

n. when a substitution occurs at position 212, the substituting amino acid is Asn, Asp, Gln, Glu, Gly, Pro or Ser; but when position 212 is substituted the variant is not a double, triple, quadruple, quintuple, or sextuple mutation variant having substitutions at positions selected from the group consisting of 103, 154, 165, 188, and 216;

o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, or sextuple mutation variant having substitutions at positions selected from the group consisting of 103, 154, 165, 188, and 216;

p. when a substitution occurs at position 214, the substituting amino acid is Asn, Asp, Gln, Glu, Gly, His, Pro, Ser or Thr; but when position 214 is substituted the variant is not a double, triple, quadruple, quintuple, or sextuple mutation variant having substitutions at positions selected from the group consisting of 103, 154, 165, 188, and 216;

q. when a substitution occurs at position 215, the substituting amino acid is Asn, Asp, Gln, Glu, Gly, Pro or Ser;

r. when a substitution occurs at position 216, the substituting amino acid is Ala, Asn, Asp, Cys, Gln, Glu, Gly, His, Ile, Met, Pro, Ser, Thr or Val; but when position 216 is substituted the variant is not a double mutation variant having a substitution at position 217;

s. when a substitution occurs at position 217, the substituting amino acid is Asp, Gln, Glu or Ser;

t. when a substitution occurs at position 218, the substituting amino acid is Asn, Asp, Gln, Glu, Pro or Ser; and u. when a substitution occurs at position 219, the substituting amino acid is Asn, Asp, Gln, Glu, Gly, Pro or Ser; wherein the variant is not:

v. a double mutation variant having substitutions at positions 202 and 203;

w. a double mutation variant having substitutions at positions 202 and 216;

x. a double mutation variant having substitutions at positions 203 and 216; or y. a triple mutation variant having substitutions at positions 202, 203, and 216; and whereby the subtilisin Carlsberg variant has decreased adsorption to, and increased hydrolysis of, an insoluble substrate as compared to wild-type subtilisin Carlsberg.

37. The subtilisin Carlsberg variant of claim 36, wherein two or more substitutions occur in the first loop region.

38. The subtilisin Carlsberg variant of claim 36, wherein two or more substitutions occur in the second loop region.

39. The subtilisin Carlsberg variant of claim 36, wherein two or more substitutions occur in the third loop region.

40. The subtilisin Carlsberg variant of claim 36, wherein two or more substitutions occur in the fourth loop region.

41. The subtilisin Carlsberg variant of claim 36, wherein two or more substitutions occur in the fifth loop region.

42. The subtilisin Carlsberg variant of claim 36, wherein two or more substitutions occur in the sixth loop region.

43. An isolated subtilisin Carlsberg variant having a modified amino acid sequence of the Subtilisin Carlsberg wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 58, 59, 60, 61, 62, 64 or 65; wherein
  a. when a substitution occurs at position 58, the substituting amino acid is Asn, Asp, Gln, Glu, Gly, Pro or Ser;
  b. when a substitution occurs at position 59, the substituting amino acid is Glu;
  c. when a substitution occurs at position 60, the substituting amino acid is Asn, Asp, Gln, Glu, Pro or Ser;
  d. when a substitution occurs at position 61, the substituting amino acid is Asp, Gln, Glu or Ser;
  e. when a substitution occurs at position 62, the substituting amino acid is Asn, Asp, Gln, Glu, Pro or Ser;
  f. when a substitution occurs at position 64, the substituting amino acid is Asn, Asp, Gln, Glu, Pro or Ser; and
  g. when a substitution occurs at position 65, the substituting amino acid is Asn, Asp, Gln, Glu, Gly, Pro or Ser;
B. when a substitution occurs in the second loop region, the substitution occurs at one or more of positions 94, 95, 96, 97, 98, 99, 100, 101, 102, 103, 104, 105 or 106; wherein
  a. when a substitution occurs at position 94, the substituting amino acid is Ala, Asn, Asp, Cys, Gln, Glu, Gly, His, Met, Pro, Ser or Thr;
  b. when a substitution occurs at position 95, the substituting amino acid is Ala, Asn, Asp, Cys, Gln, Glu, Gly, His, Ile, Met, Pro, Ser, Thr or Val;
  c. when a substitution occurs at position 96, the substituting amino acid is Asp, Gln, Glu, or Ser; but when position 96 is substituted the variant is not a double, triple, quadruple, quintuple, or sextuple mutation variant having substitutions at positions selected from the group consisting of 103, 154, 155, 165, and 216;
  d. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 103, 154, 155, 165, and 216;
  e. when a substitution occurs at position 98, the substituting amino acid is Asp or Glu; but when position 98 is substituted the variant is not a double, triple, quadruple, quintuple, or sextuple mutation variant having substitutions at positions selected from the group consisting of 103, 154, 155, 165, and 216;
  f. when a substitution occurs at position 99, the substituting amino acid is Asn, Asp, Gln, Glu, Pro or Ser; but when position 99 is substituted the variant is not a double, triple, quadruple, quintuple, or sextuple mutation variant having substitutions at positions selected from the group consisting of 103, 154, 155, 165, and 216;
  g. when a substitution occurs at position 100, the substituting amino acid is Asp or Glu; but when position 100 is substituted the variant is not a double, triple, quadruple, quintuple, or sextuple mutation variant having substitutions at positions selected from the group consisting of 103, 154, 155, 165, and 216;
  h. when a substitution occurs at position 101, the substituting amino acid is Asn, Asp, Gln, Glu, Pro or Ser; but when position 101 is substituted the variant is not a double, triple, quadruple, quintuple, or sextuple mutation variant having substitutions at positions selected from the group consisting of 103, 154, 155, 165, and 216;
  i. when a substitution occurs at position 102, the substituting amino acid is Asp or Glu; but when position 102 is substituted the variant is not a double, triple, quadruple, quintuple, or sextuple mutation variant having substitutions at positions selected from the group consisting of 103, 154, 155, 165, and 216;
  j. when a substitution occurs at position 103, the substituting amino acid is Ala, Asp, Cys, Gln, Glu, Gly, His, Ile, Leu, Met, Pro, Ser, Thr or Val;
  k. when a substitution occurs at position 104, the substituting amino acid is Asp or Glu;
  l. when a substitution occurs at position 105, the substituting amino acid is Asn, Asp, Gln, Glu, Pro or Ser; and
  m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, or sextuple mutation variant having substitutions at positions selected from the group consisting of 103, 154, 155, 165, and 216;
C. when a substitution occurs in the third loop region, the substitution occurs at one or more of positions 125, 126, 127, 128, 129, 130, 131 or 132; wherein
  a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, quadruple, quintuple, or sextuple mutation variant having substitutions at positions selected from the group consisting of 103, 154, 155, 165, and 216;
  b. when a substitution occurs at position 126, the substituting amino acid is Asn, Asp, Gln, Glu, Pro or Ser; but when position 126 is substituted the variant is not a double, triple, quadruple, quintuple, or sextuple mutation variant having substitutions at positions selected from the group consisting of 103, 154, 155, 165, and 216;
  c. when a substitution occurs at position 127, the substituting amino acid is Asn, Asp, Gln, Glu, Pro or Ser; but when position 127 is substituted the variant is not a double, triple, quadruple, quintuple, or sextuple mutation variant having substitutions at positions selected from the group consisting of 103, 154, 155, 165, and 216;
  d. when a substitution occurs at position 128, the substituting amino acid is Asn, Asp, Gln, Glu, Gly, His, Pro, Ser or Thr; but when position 128 is substituted the variant is not a double, triple, quadruple, quintuple, or sextuple mutation variant having substitutions at positions selected from the group consisting of 103, 154, 155, 165, and 216;
  e. when a substitution occurs at position 129, the substituting amino acid is Asp or Glu;
  f. when a substitution occurs at position 130, the substituting amino acid is Asn, Asp, Gln, Glu, Pro or Ser;

g. when a substitution occurs at position 131, the substituting amino acid is Asp or Glu; and
h. when a substitution occurs at position 132, the substituting amino acid is Asn, Asp, Gln, Glu, Gly, Pro or Ser;

D. when a substitution occurs in the fourth loop region, the substitution occurs at one or more of positions 153, 154, 155, 156, 157, 158, 159, 160, 161, 162, 163, 164, 165 or 166; wherein
  a. when a substitution occurs at position 153, the substituting amino acid is Asn, Asp, Gln, Glu, Pro or Ser; but when position 153 is substituted the variant is not a double, triple, quadruple, quintuple, or sextuple mutation variant having substitutions at positions selected from the group consisting of 103, 154, 155, 165, and 216;
  b. when a substitution occurs at position 154, the substituting amino acid is Asp, Gln, Glu or Ser;
  c. when a substitution occurs at position 155, the substituting amino acid is Asp or Glu; but when position 155 is substituted, the variant is not a double mutation variant having a substitution at position 216, double mutation variant having a substitution at position 165, or a triple mutation variant having substitutions at positions 165 and 216;
  d. when a substitution occurs at position 156, the substituting amino acid is Asn, Asp, Gln, Glu, Pro or Ser; but when position 156 is substituted the variant is not a double, triple, quadruple, quintuple, or sextuple mutation variant having substitutions at positions selected from the group consisting of 103, 154, 155, 165, and 216;
  e. when a substitution occurs at position 157, the substituting amino acid is Asp, Gln, Glu, or Ser; but when position 157 is substituted the variant is not a double, triple, quadruple, quintuple, or sextuple mutation variant having substitutions at positions selected from the group consisting of 103, 154, 155, 165, and 216;
  f. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 103, 154, 155, 165, and 216;
  g. when a substitution occurs at position 159, the substituting amino acid is Asn, Asp, Gln, Glu, Pro or Ser; but when position 159 is substituted the variant is not a double, triple, quadruple, quintuple, or sextuple mutation variant having substitutions at positions selected from the group consisting of 103, 154, 155, 165, and 216;
  h. when a substitution occurs at position 160, the substituting amino acid is Asp or Glu; but when position 160 is substituted the variant is not a double, triple, quadruple, quintuple, or sextuple mutation variant having substitutions at positions selected from the group consisting of 103, 154, 155, 165, and 216;
  i. when a substitution occurs at position 161, the substituting amino acid is Asn, Asp, Gln, Glu, Gly, Pro or Ser; but when position 161 is substituted the variant is not a double, triple, quadruple, quintuple, or sextuple mutation variant having substitutions at positions selected from the group consisting of 103, 154, 155, 165, and 216;
  j. when a substitution occurs at position 162, the substituting amino acid is Asp, Gln, Glu or Ser; but when position 162 is substituted the variant is not a double, triple, quadruple, quintuple, or sextuple mutation variant having substitutions at positions selected from the group consisting of 103, 154, 155, 165, and 216;
  k. when a substitution occurs at position 163, the substituting amino acid is Asn, Asp, Gln, Glu, Gly, Pro or Ser; but when position 163 is substituted the variant is not a double, triple, quadruple, quintuple, or sextuple mutation variant having substitutions at positions selected from the group consisting of 103, 154, 155, 165, and 216;
  l. when a substitution occurs at position 164, the substituting amino acid is Ala, Asn, Asp, Cys, Gln, Glu, Gly, His, Met, Pro, Ser, Thr or Val; but when position 164 is substituted the variant is not a double, triple, quadruple, quintuple, or sextuple mutation variant having substitutions at positions selected from the group consisting of 103, 154, 155, 165, and 216;
  m. when a substitution occurs at position 165, the substituting amino acid is Asn, Asp, Gln, Glu, Pro or Ser; but when position 165 is substituted with Asp or Glu, the variant is not a double mutation variant having a substitution of Asp or Glu at position 61; and
  n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, or sextuple mutation variant having substitutions at positions selected from the group consisting of 103, 154, 155, 165, and 216;

E. when a substitution occurs in the fifth loop region, the substitution occurs at one or more of positions 186, 188 or 189; wherein
  a. when a substitution occurs at position 186, the substituting amino acid is Asn, Asp, Gln, Glu, Gly, His, Pro, Ser and Thr;
  b. when a substitution occurs at position 188, the substituting amino acid is Ala, Asn, Cys, Gln, Gly, His, Ile, Leu, Met, Pro, Ser, Thr, Tyr or Val; and
  c. when a substitution occurs at position 189, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein
  a. when a substitution occurs at position 199, the substituting amino acid is Asn, Asp, Gln, Glu, Gly, His, Pro, Ser or Thr;
  b. when a substitution occurs at position 200, the substituting amino acid is Asn, Asp, Gln, Glu, Gly or Ser;
  c. when a substitution occurs at position 201, the substituting amino acid is Asn, Asp, Gln, Glu, Pro or Ser;
  d. when a substitution occurs at position 202, the substituting amino acid is Asn, Asp, Gln, Glu, Gly, His, Pro, Ser or Thr;
  e. when a substitution occurs at position 203, the substituting amino acid is Asn, Asp, Gln, Glu, Pro or Ser;
  f. when a substitution occurs at position 204, the substituting amino acid is Ala, Asn, Asp, Cys, Gln, Glu, Gly, His, Met, Pro, Ser or Thr;

g. when a substitution occurs at position 205, the substituting amino acid is Ala, Asn, Asp, Cys, Gln, Glu, Gly, His, Ile, Leu, Met, Pro, Ser, Thr or Val;

h. when a substitution occurs at position 206, the substituting amino acid is Asp or Glu;

i. when a substitution occurs at position 207, the substituting amino acid is Asn, Asp, Gln, Glu, Gly, Pro or Ser;

j. when a substitution occurs at position 208, the substituting amino acid is Ala, Asn, Asp, Cys, Gln, Glu, Gly, His, Ile, Leu, Met, Pro, Ser, Thr or Val;

k. when a substitution occurs at position 209, the substituting amino acid is Asn, Asp, Gln, Glu, Gly or Ser;

l. when a substitution occurs at position 210, the substituting amino acid is Asn, Asp, Gln, Glu, Gly, Pro or Ser;

m. when a substitution occurs at position 211, the substituting amino acid is Asp, Gln, Glu or Ser;

n. when a substitution occurs at position 212, the substituting amino acid is Asn, Asp, Gln, Glu, Gly, Pro or Ser; but when position 212 is substituted the variant is not a double, triple, quadruple, quintuple, or sextuple mutation variant having substitutions at positions selected from the group consisting of 103, 154, 155, 165, and 216;

o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, or sextuple mutation variant having substitutions at positions selected from the group consisting of 103, 154, 155, 165, and 216;

p. when a substitution occurs at position 214, the substituting amino acid is Asn, Asp, Gln, Glu, Gly, His, Pro, Ser or Thr; but when position 214 is substituted the variant is not a double, triple, quadruple, quintuple, or sextuple mutation variant having substitutions at positions selected from the group consisting of 103, 154, 155, 165, and 216;

q. when a substitution occurs at position 215, the substituting amino acid is Asn, Asp, Gln, Glu, Gly, Pro or Ser;

r. when a substitution occurs at position 216, the substituting amino acid is Ala, Asn, Asp, Cys, Gln, Glu, Gly, His, Ile, Met, Pro, Ser, Thr or Val; but when position 216 is substituted the variant is not a double mutation variant having a substitution at position 217;

s. when a substitution occurs at position 217, the substituting amino acid is Asp, Gln, Glu or Ser;

t. when a substitution occurs at position 218, the substituting amino acid is Asn, Asp, Gln, Glu, Pro or Ser; and u. when a substitution occurs at position 219, the substituting amino acid is Asn, Asp, Gln, Glu, Gly, Pro or Ser; wherein the variant is not:

v. a double mutation variant having substitutions at positions 202 and 203;

w. a double mutation variant having substitutions at positions 202 and 216;

x. a double mutation variant having substitutions at positions 203 and 216; or y. a triple mutation variant having substitutions at positions 202, 203, and 216; and whereby the subtilisin Carlsberg variant has decreased adsorption to, and increased hydrolysis of, an insoluble substrate as compared to wild-type subtilisin Carlsberg.

44. The subtilisin Carlsberg variant of claim 43, wherein two or more substitutions occur in the first loop region.

45. The subtilisin Carlsberg variant of claim 43, wherein two or more substitutions occur in the second loop region.

46. The subtilisin Carlsberg variant of claim 43, wherein two or more substitutions occur in the third loop region.

47. The subtilisin Carlsberg variant of claim 43, wherein two or more substitutions occur in the fourth loop region.

48. The subtilisin Carlsberg variant of claim 43, wherein two or more substitutions occur in the fifth loop region.

49. The subtilisin Carlsberg variant of claim 43, wherein two or more substitutions occur in the sixth loop region.

50. An isolated subtilisin Carlsberg variant having a modified amino acid sequence of the Subtilisin Carlsberg wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 58, 59, 60, 61, 62, 64 or 65; wherein a. when a substitution occurs at position 58, the substituting amino acid is Asn, Asp, Gln, Glu, Gly, Pro or Ser;

b. when a substitution occurs at position 59, the substituting amino acid is Glu;

c. when a substitution occurs at position 60, the substituting amino acid is Asn, Asp, Gln, Glu, Pro or Ser;

d. when a substitution occurs at position 61, the substituting amino acid is Asp, Gln, Glu or Ser;

e. when a substitution occurs at position 62, the substituting amino acid is Asn, Asp, Gln, Glu, Pro or Ser;

f. when a substitution occurs at position 64, the substituting amino acid is Asn, Asp, Gln, Glu, Pro or Ser; and g. when a substitution occurs at position 65, the substituting amino acid is Asn, Asp, Gln, Glu, Gly, Pro or Ser;

B. when a substitution occurs in the second loop region, the substitution occurs at one or more of positions 94, 95, 96, 97, 98, 99, 100, 101, 102, 103, 104, 105 or 106; wherein a. when a substitution occurs at position 94, the substituting amino acid is Ala, Asn, Asp, Cys, Gln, Glu, Gly, His, Met, Pro, Ser or Thr;

b. when a substitution occurs at position 95, the substituting amino acid is Ala, Asn, Asp, Cys, Gln, Glu, Gly, His, Ile, Met, Pro, Ser, Thr or Val;

c. when a substitution occurs at position 96, the substituting amino acid is Asp, Gln, Glu, or Ser; but when position 96 is substituted the variant is not a double, triple, quadruple, quintuple, sextuple, or septuple mutation variant having substitutions at positions selected from the group consisting of 103, 154, 155, 165, 188, and 216;

d. when a substitution occurs at position 97, the substituting amino acid is Asp or Glu; but when position 97 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 98, the substituting amino acid is Asp or Glu; but when position 98 is substituted the variant is not a double, triple, quadruple, quintuple, sextuple, or septuple mutation variant having substitutions at positions selected from the group consisting of 103, 154, 155, 165, 188, and 216;

f. when a substitution occurs at position 99, the substituting amino acid is Asn, Asp, Gln, Glu, Pro or Ser; but when position 99 is substituted the variant is not a double, triple, quadruple, quintuple, sextuple, or septuple mutation variant having substitutions at positions selected from the group consisting of 103, 154, 155, 165, 188, and 216;

g. when a substitution occurs at position 100, the substituting amino acid is Asp or Glu; but when position 100 is substituted the variant is not a double, triple, quadruple, quintuple, sextuple, or septuple mutation variant having substitutions at positions selected from the group consisting of 103, 154, 155, 165, 188, and 216;

h. when a substitution occurs at position 101, the substituting amino acid is Asn, Asp, Gln, Glu, Pro or Ser; but when position 101 is substituted the variant is not a double, triple, quadruple, quintuple, sextuple, or septuple mutation variant having substitutions at positions selected from the group consisting of 103, 154, 155, 165, 188, and 216;

i. when a substitution occurs at position 102, the substituting amino acid is Asp or Glu; but when position 102 is substituted the variant is not a double, triple, quadruple, quintuple, sextuple, or septuple mutation variant having substitutions at positions selected from the group consisting of 103, 154, 155, 165, 188, and 216;

j. when a substitution occurs at position 103, the substituting amino acid is Ala, Asp, Cys, Gln, Glu, Gly, His, Ile, Leu, Met, Pro, Ser, Thr or Val;

k. when a substitution occurs at position 104, the substituting amino acid is Asp or Glu;

l. when a substitution occurs at position 105, the substituting amino acid is Asn, Asp, Gln, Glu, Pro or Ser; and m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, sextuple, or septuple mutation variant having substitutions at positions selected from the group consisting of 103, 154, 155, 165, 188, and 216;

C. when a substitution occurs in the third loop region, the substitution occurs at one or more of positions 125, 126, 127, 128, 129, 130, 131 or 132; wherein a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, quadruple, quintuple, sextuple, or septuple mutation variant having substitutions at positions selected from the group consisting of 103, 154, 155, 165, 188, and 216;

b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;

c. when a substitution occurs at position 127, the substituting amino acid is Asn, Asp, Gln, Glu, Pro or Ser; but when position 127 is substituted the variant is not a double, triple, quadruple, quintuple, sextuple, or septuple mutation variant having substitutions at positions selected from the group consisting of 103, 154, 155, 165, 188, and 216;

d. when a substitution occurs at position 128, the substituting amino acid is Asn, Asp, Gln, Glu, Gly, His, Pro, Ser or Thr; but when position 128 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 129, the substituting amino acid is Asp or Glu;

f. when a substitution occurs at position 130, the substituting amino acid is Asn, Asp, Gln, Glu, Pro or Ser;

g. when a substitution occurs at position 131, the substituting amino acid is Asp or Glu; and h. when a substitution occurs at position 132, the substituting amino acid is Asn, Asp, Gln, Glu, Gly, Pro or Ser;

D. when a substitution occurs in the fourth loop region, the substitution occurs at one or more of positions 153, 154, 155, 156, 157, 158, 159, 160, 161, 162, 163, 164, 165 or 166; wherein a. when a substitution occurs at position 153, the substituting amino acid is Asn, Asp, Gln, Glu, Pro or Ser; but when position 153 is substituted the variant is not a double, triple, quadruple, quintuple, sextuple, or septuple mutation variant having substitutions at positions selected from the group consisting of 103, 154, 155, 165, 188, and 216;

b. when a substitution occurs at position 154, the substituting amino acid is Asp, Gln, Glu or Ser;

c. when a substitution occurs at position 155, the substituting amino acid is Asp or Glu; but when position 155 is substituted, the variant is not a double mutation variant having a substitution at position 216, double mutation variant having a substitution at position 165, or a triple mutation variant having substitutions at positions 165 and 216;

d. when a substitution occurs at position 156, the substituting amino acid is Asn, Asp, Gln, Glu, Pro or Ser; but when position 156 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 157, the substituting amino acid is Asp, Gln, Glu, or Ser; but when position 157 is substituted the variant is not a double, triple, quadruple, quintuple, sextuple, or septuple mutation variant having substitutions at positions selected from the group consisting of 103, 154, 155, 165, 188, and 216;

f. when a substitution occurs at position 158, the substituting amino acid is Asp or Glu; but when position 158 is substituted the variant is not a double, triple, quadruple, quintuple, sextuple, or septuple mutation variant having substitutions at positions selected from the group consisting of 103, 154, 155, 165, 188, and 216;

g. when a substitution occurs at position 159, the substituting amino acid is Asn, Asp, Gln, Glu, Pro or Ser; but when position 159 is substituted the variant is not a double, triple, quadruple, quintuple, sextuple, or septuple mutation variant having substitutions at positions selected from the group consisting of 103, 154, 155, 165, 188, and 216;

h. when a substitution occurs at position 160, the substituting amino acid is Asp or Glu; but when position 160 is substituted the variant is not a double, triple, quadruple, quintuple, sextuple, or septuple mutation variant having substitutions at positions selected from the group consisting of 103, 154, 155, 165, 188, and 216;

i. when a substitution occurs at position 161, the substituting amino acid is Asn, Asp, Gln, Glu, Gly, Pro or Ser; but when position 161 is substituted the variant is not a double, triple, quadruple, quintuple, sextuple, or septuple mutation variant having substitutions at positions selected from the group consisting of 103, 154, 155, 165, 188, and 216;

j. when a substitution occurs at position 162, the substituting amino acid is Asp, Gln, Glu or Ser; but when position 162 is substituted the variant is not a double, triple, quadruple, quintuple, sextuple, or septuple mutation variant having substitutions at positions selected from the group consisting of 103, 154, 155, 165, 188, and 216;

k. when a substitution occurs at position 163, the substituting amino acid is Asn, Asp, Gln, Glu, Gly, Pro or Ser; but when position 163 is substituted the variant is not a double, triple, quadruple, quintuple, sextuple, or septuple mutation variant having substitutions at positions selected from the group consisting of 103, 154, 155, 165, 188, and 216;

l. when a substitution occurs at position 164, the substituting amino acid is Ala, Asn, Asp, Cys, Gln, Glu, Gly, His, Met, Pro, Ser, Thr or Val; but when position 164 is substituted the variant is not a double, triple, quadruple, quintuple, sextuple, or septuple mutation variant having substitutions at positions selected from the group consisting of 103, 154, 155, 165, 188, and 216;

m. when a substitution occurs at position 165, the substituting amino acid is Asn, Asp, Gln, Glu, Pro or Ser; but when position 165 is substituted with Asp or Glu, the variant is not a double mutation variant having a substitution of Asp or Glu at position 61; and n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, sextuple, or septuple mutation variant having substitutions at positions selected from the group consisting of 103, 154, 155, 165, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;

c. when a substitution occurs at position 188, the substituting amino acid is Ala, Asn, Asp, Cys, Gln, Glu, Gly, His, Ile, Leu, Met, Pro, Ser, Thr, Tyr or Val;

d. when a substitution occurs at position 189, the substituting amino acid is Asp or Glu;

e. when a substitution occurs at position 190, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216 or 219; wherein a. when a substitution occurs at position 199, the substituting amino acid is Asn, Asp, Gln, Glu, Gly, His, Pro, Ser or Thr;

b. when a substitution occurs at position 200, the substituting amino acid is Asn, Asp, Gln, Glu, Gly or Ser;

c. when a substitution occurs at position 201, the substituting amino acid is Asn, Asp, Gln, Glu, Pro or Ser;

d. when a substitution occurs at position 202, the substituting amino acid is Asn, Asp, Gln, Glu, Gly, His, Pro, Ser or Thr;

e. when a substitution occurs at position 203, the substituting amino acid is Asn, Gln, Pro or Ser;

f. when a substitution occurs at position 204, the substituting amino acid is Ala, Cys, Gln, Gly, His, Met, Pro or Ser;

g. when a substitution occurs at position 205, the substituting amino acid is His, Ile, Leu, Met or Pro;

h. when a substitution occurs at position 206, the substituting amino acid is Asp or Glu;

i. when a substitution occurs at position 207, the substituting amino acid is Asn, Gln, Pro or Ser;

j. when a substitution occurs at position 208, the substituting amino acid is His, Ile, Met or Pro;

k. when a substitution occurs at position 209, the substituting amino acid is Asn, Gln, Gly or Ser;

l. when a substitution occurs at position 210, the substituting amino acid is Asn, Gln, Pro or Ser;

m. when a substitution occurs at position 211, the substituting amino acid is Gln or Ser;

n. when a substitution occurs at position 212, the substituting amino acid is Asn, Gln, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;

o. when a substitution occurs at position 213, the substituting amino acid is His, Ile, Leu, Met or Pro; but when position 213 is substituted the variant is not a double, triple, quadruple, quintuple, sextuple, or septuple mutation variant having substitutions at positions selected from the group consisting of 103, 154, 155, 165, 188, and 216;

p. when a substitution occurs at position 214, the substituting amino acid is Asn, Gln, Gly, His, Pro, Ser or Thr; but when position 214 is substituted the variant is not a double, triple, quadruple, quintuple, sextuple, or septuple mutation variant having substitutions at positions selected from the group consisting of 103, 154, 155, 165, 188, and 216;

q. when a substitution occurs at position 215, the substituting amino acid is Asn, Gln, Gly, Pro or Ser;

r. when a substitution occurs at position 216, the substituting amino acid is Ala, Asn, Cys, Gln, Gly, His, Ile, Met, Pro, Ser, Thr or Val; and s. when a substitution occurs at position 219, the substituting amino acid is Asn, Asp, Gln, Glu, Gly, Pro or Ser; wherein the variant is not:

t. a double mutation variant having substitutions at positions 202 and 203;
u. a double mutation variant having substitutions at positions 202 and 216;
v. a double mutation variant having substitutions at positions 203 and 216; or
w. a triple mutation variant having substitutions at positions 202, 203, and 216; and whereby the subtilisin Carlsberg variant has decreased adsorption to, and increased hydrolysis of, an insoluble substrate as compared to wild-type subtilisin Carlsberg.

51. The subtilisin Carlsberg variant of claim 50, wherein two or more substitutions occur in the first loop region.

52. The subtilisin Carlsberg variant of claim 50, wherein two or more substitutions occur in the second loop region.

53. The subtilisin Carlsberg variant of claim 50, wherein two or more substitutions occur in the third loop region.

54. The subtilisin Carlsberg variant of claim 50, wherein two or more substitutions occur in the fourth loop region.

55. The subtilisin Carlsberg variant of claim 50, wherein two or more substitutions occur in the fifth loop region.

56. The subtilisin Carlsberg variant of claim 50, wherein two or more substitutions occur in the sixth loop region.

57. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the subtilisin Carlsberg variant of claim 22, and a cleaning composition carrier.

58. The cleaning composition of claim 57, wherein the cleaning composition is a hard surface cleaning composition.

59. The cleaning composition of claim 57, wherein the cleaning composition is a fabric cleaning composition.

60. The fabric cleaning composition of claim 59, wherein the composition is in the form of a liquid.

61. The fabric cleaning composition of claim 60, wherein the composition comprises at least about 5% surfactant and at least about 5% builder, by weight of the composition.

62. The fabric cleaning composition of claim 61 further comprising cleaning composition materials selected from the group consisting of solvents, buffers, enzymes, soil release agents, clay soil removal agents, dispersing agents, brighteners, suds supressors, fabric softeners, suds boosters, enzyme stabilizers, bleaching agents, dyes, perfumes, and mixtures thereof.

63. The fabric cleaning composition of claim 61 further comprising at least one bleaching agent.

64. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the subtilisin Carlsberg variant of claim 28, and a cleaning composition carrier.

65. An isolated mutant subtilisin Carlsberg gene encoding the subtilisin Carlsberg variant of claim 8.

* * * * *